(12) United States Patent
Schneider et al.

(10) Patent No.: US 11,969,443 B2
(45) Date of Patent: Apr. 30, 2024

(54) COMPOSITIONS AND METHODS FOR TREATING CANCER WITH SELF-DRIVING CHIMERIC ANTIGEN RECEPTORS

(71) Applicant: LENTIGEN TECHNOLOGY, INC., Gaithersburg, MD (US)

(72) Inventors: Dina Schneider, Potomac, MD (US); Boro Dropulic, Ellicott City, MD (US); Brian Robert Webster, Cologne (DE)

(73) Assignee: LENTIGEN TECHNOLOGY, INC., Gaithersburg, MD (US)

(*) Notice: Subject to any disclaimer, the term of this patent is extended or adjusted under 35 U.S.C. 154(b) by 0 days.

(21) Appl. No.: 17/436,432

(22) PCT Filed: Mar. 6, 2020

(86) PCT No.: PCT/US2020/021320
§ 371 (c)(1),
(2) Date: Sep. 3, 2021

(87) PCT Pub. No.: WO2020/181164
PCT Pub. Date: Sep. 10, 2020

(65) Prior Publication Data
US 2022/0168344 A1 Jun. 2, 2022

Related U.S. Application Data

(60) Provisional application No. 62/954,161, filed on Dec. 27, 2019, provisional application No. 62/814,759, filed on Mar. 6, 2019.

(51) Int. Cl.
| | | |
|---|---|---|
| *A61K 35/17* | (2015.01) | |
| *A61K 48/00* | (2006.01) | |
| *C07K 14/705* | (2006.01) | |
| *C07K 14/725* | (2006.01) | |
| *C07K 16/28* | (2006.01) | |
| *C12N 15/11* | (2006.01) | |
| *C12N 15/31* | (2006.01) | |

(52) U.S. Cl.
CPC .......... *A61K 35/17* (2013.01); *C07K 14/7051* (2013.01); *C07K 14/70517* (2013.01); *C07K 14/70578* (2013.01); *C07K 16/2803* (2013.01); *C07K 2317/622* (2013.01); *C07K 2319/03* (2013.01)

(58) Field of Classification Search
None
See application file for complete search history.

(56) References Cited

U.S. PATENT DOCUMENTS

2016/0017048 A1  1/2016  Dotti et al.
2021/0379149 A1* 12/2021  Pu ........................... A61K 35/17

FOREIGN PATENT DOCUMENTS

| CN | 108779162 | 11/2023 |
|---|---|---|
| WO | WO 2017062820 | * 4/2017 |
| WO | WO 2017/180989 | 10/2017 |
| WO | WO 2019025800 | * 2/2019 |

OTHER PUBLICATIONS

Warner et al., CAR T Cell Therapy for Solid Tumors: Bright Future or Dark Reality? Molecular Therapy vol. 28 No. 11 Nov. 2020, pp. 2320-2339.*
Mirzaei et al., Chimeric Antigen Receptors T cell THerapy in SOlid Tumors: Challenges and Clinical Applications, Frontiers in Immunology, 2017, pages.*
Snapgene, pGL4.52[luc2P/STAT5 RE/Hygro] Vector, 2018, pp. 1-2.*
Ajina et al., "Strategies to address chimeric antigen receptor tonic signaling," Molecular Cancer Therapeutics, Sep. 1, 2018, 17(9):1795-815.
Gomes-Silva et al., "Tonic 4-1BB costimulation in chimeric antigen receptors impedes T cell survival and is vector-dependent," Cell Reports, Oct. 3, 2017, 21(1):17-26.
GenBank ID: JX206457.1, "Reporter vector pGL4.52[luc2P/STAT5 RE/Hygro], complete sequence," dated Jul. 31, 2012, 3 pages.

* cited by examiner

*Primary Examiner* — Maria Marvich
(74) *Attorney, Agent, or Firm* — Serge Sira, Esq.; Gregory J. Hwa, Esq.; Fish & Richardson P.C.

(57) ABSTRACT

Self-driving surface antigen-regulated promoter-therapeutic payload constructs containing antigen binding domains are disclosed. Nucleic acids, recombinant expression vectors, host cells, antigen binding fragments, and pharmaceutical compositions, relating to the surface antigen-regulated promoter-therapeutic payload constructs are also disclosed. Methods of treating or preventing cancer in a subject, and methods of making self-driving surface antigen-regulated promoter-therapeutic payload constructs in T-cells are also disclosed.

5 Claims, 24 Drawing Sheets
Specification includes a Sequence Listing.

LTG2864 (AP1NFKB-CAR LTG1563-FP2AF-TGFBRIIdn)

LTG2865 (AP1NFKB-CAR LTG1563-FP2AF-PD1dn)

LTG2866 (AP1NFKB-CAR LTG1563-FP2AF-PD1dn-P2A-TGFBRIIdn)

LTG2867 (EF1a-CAR LTG1563-FP2AF-TGFBRIIdn)

LTG2868 (EF1a-CAR LTG1563-FP2AF-PD1dn)

LTG2869 (EF1a-CAR LTG1563-FP2AF-PD1dn-P2A-TGFBRIIdn)

SEQUENCE LISTING

<160> NUMBER OF SEQ ID NOS: 189

<210> SEQ ID NO 1
<211> LENGTH: 8
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 1 ttctgaga                                                            8

<210> SEQ ID NO 2
<211> LENGTH: 7
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 2 tgagtca                                                             7

<210> SEQ ID NO 3
<211> LENGTH: 7
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

-continued

```
<400> SEQUENCE: 3 tgactca                                                                  7

<210> SEQ ID NO 4
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 4
gggaatttcc                                                              10

<210> SEQ ID NO 5
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5
gggactttcc                                                              10

<210> SEQ ID NO 6
<211> LENGTH: 9
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 6 ggaatttcc                                                                9

<210> SEQ ID NO 7
<211> LENGTH: 1494
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 7
atgctgctgc tggtgaccag cctgctgctg tgcgaactgc cgcatccggc gtttctgctg        60
attccggaag tgcaattggt gcagagcggt ggaggacttg tgaaacctgg tggatccctg       120
agactttcct gtgccgcttc gggcttcacc ttctcggact actacatgtc ctggattcgc       180
caggccsctg aaagggact ggaatgggtc tcatacatca gctcctccgg ttccaccatc        240
```

(Note: line 240 reads: `caggccsctg` — actually `caggccsctg` should be `caggcccctg`)

```
tactatgccg attccgtgaa gggcagattc accatctcgc gcgacaacgc caagaacact       300
ctctatctgc aaatgaactc actgcgggct gaggacaccg cggtctacta ctgcgcccgg       360
gacctcagcg aaagtccag cggatggtcc cattacttcg attactgggg acagggaacc        420
ctggtcaccg tgtccagcgg cgggggggggc tcgggtggcg gcggctccgg cggcggcggg      480
agcaacttca tgctgactca gccccactcc gtgtccgaga gccgggaaa gaccgtgact        540 atttcgtgca cacggtcctc cgggagcatt gcgaacaact acgtgcagtg gtaccagcag       600 cggccccgata gggcccaac cactgtgatc tacgaagatg accagcggcc gtctggagtc       660
```

```
ccggaccgct tctcggggtc catcgactca tcatccaatt ccgcatcgct gacgatcagc    720
ggactgaaga tcgaggacga agccgattac tactgccagt cctacgacgg caccaactgg    780
gtctttgggg gtggaaccaa gctgactgtg ctcggagcgg ccgcaactac caccccctgcc   840 cctcggccgc cgactccggc cccaaccatc gcaagccaac ccctctcctt gcccccgaa     900 gcttgccgcc cggccgcggg tggagccgtg catacccggg ggctggactt tgcctgcgat    960
atctacattt gggccccgct ggccggcact tgcggcgtgc tcctgctgtc gctggtcatc   1020 acccttact gcaagagggg ccggaagaag ctgctttaca tcttcaagca gccgttcatg    1080
cggcccgtgc agacgactca ggaagaggac ggatgctcgt gcagattccc tgaggaggaa   1140 gagggggat gcgaactgcg cgtcaagttc tcacggtccg ccgacgcccc cgcatatcaa    1200
cagggccaga atcagctcta caacgagctg aacctgggaa ggagagagga gtacgacgtg   1260
ctggacaagc gacgcggacg cgacccggag atgggggga aaccacggcg aaaaaccct     1320 caggaaggac tgtacaacga actccagaaa gacaagatgg cggaagccta ctcagaaatc   1380
gggatgaagg gagagcggag gagggaaag ggtcacgacg ggctgtacca gggactgagc    1440
accgccacta aggataccta cgatgccttg catatgcaag cactcccacc ccgg         1494
```

<210> SEQ ID NO 8
<211> LENGTH: 498
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Met Leu Leu Leu Val Thr Ser Leu Leu Leu Cys Glu Leu Pro His Pro
1               5                   10                  15

Ala Phe Leu Leu Ile Pro Glu Val Gln Leu Val Gln Ser Gly Gly Gly
                20                  25                  30

Leu Val Lys Pro Gly Gly Ser Leu Arg Leu Ser Cys Ala Ala Ser Gly
            35                  40                  45

Phe Thr Phe Ser Asp Tyr Tyr Met Ser Trp Ile Arg Gln Ala Pro Gly
        50                  55                  60

Lys Gly Leu Glu Trp Val Ser Tyr Ile Ser Ser Gly Ser Thr Ile
65                  70                  75                  80

Tyr Tyr Ala Asp Ser Val Lys Gly Arg Phe Thr Ile Ser Arg Asp Asn
                85                  90                  95

Ala Lys Asn Thr Leu Tyr Leu Gln Met Asn Ser Leu Arg Ala Glu Asp
            100                 105                 110

Thr Ala Val Tyr Tyr Cys Ala Arg Asp Leu Ser Gly Lys Ser Ser Gly
        115                 120                 125

Trp Ser His Tyr Phe Asp Tyr Trp Gly Gln Gly Thr Leu Val Thr Val
    130                 135                 140

Ser Ser Gly Gly Gly Gly Ser Gly Gly Gly Gly Ser Gly Gly Gly Gly
145                 150                 155                 160

Ser Asn Phe Met Leu Thr Gln Pro His Ser Val Ser Glu Ser Pro Gly
                165                 170                 175

Lys Thr Val Thr Ile Ser Cys Thr Arg Ser Ser Gly Ser Ile Ala Asn
            180                 185                 190

Asn Tyr Val Gln Trp Tyr Gln Gln Arg Pro Asp Arg Ala Pro Thr Thr
        195                 200                 205

Val Ile Tyr Glu Asp Asp Gln Arg Pro Ser Gly Val Pro Asp Arg Phe
        210                 215                 220

Ser Gly Ser Ile Asp Ser Ser Asn Ser Ala Ser Leu Thr Ile Ser
225                 230                 235                 240

Gly Leu Lys Ile Glu Asp Glu Ala Asp Tyr Tyr Cys Gln Ser Tyr Asp
                245                 250                 255

Gly Thr Asn Trp Val Phe Gly Gly Thr Lys Leu Thr Val Leu Gly
                260                 265                 270

Ala Ala Ala Thr Thr Thr Pro Ala Pro Arg Pro Pro Thr Pro Ala Pro
            275                 280                 285

Thr Ile Ala Ser Gln Pro Leu Ser Leu Arg Pro Glu Ala Cys Arg Pro
290                 295                 300

Ala Ala Gly Gly Ala Val His Thr Arg Gly Leu Asp Phe Ala Cys Asp
305                 310                 315                 320

Ile Tyr Ile Trp Ala Pro Leu Ala Gly Thr Cys Gly Val Leu Leu Leu
                325                 330                 335

Ser Leu Val Ile Thr Leu Tyr Cys Lys Arg Gly Arg Lys Lys Leu Leu
                340                 345                 350

Tyr Ile Phe Lys Gln Pro Phe Met Arg Pro Val Gln Thr Thr Gln Glu
                355                 360                 365

Glu Asp Gly Cys Ser Cys Arg Phe Pro Glu Glu Glu Glu Gly Gly Cys
    370                 375                 380

Glu Leu Arg Val Lys Phe Ser Arg Ser Ala Asp Ala Pro Ala Tyr Gln
385                 390                 395                 400

Gln Gly Gln Asn Gln Leu Tyr Asn Glu Leu Asn Leu Gly Arg Arg Glu
                405                 410                 415

Glu Tyr Asp Val Leu Asp Lys Arg Arg Gly Arg Asp Pro Glu Met Gly
                420                 425                 430

Gly Lys Pro Arg Arg Lys Asn Pro Gln Glu Gly Leu Tyr Asn Glu Leu
            435                 440                 445

Gln Lys Asp Lys Met Ala Glu Ala Tyr Ser Glu Ile Gly Met Lys Gly
    450                 455                 460

Glu Arg Arg Arg Gly Lys Gly His Asp Gly Leu Tyr Gln Gly Leu Ser
465                 470                 475                 480

Thr Ala Thr Lys Asp Thr Tyr Asp Ala Leu His Met Gln Ala Leu Pro
                485                 490                 495

Pro Arg

<210> SEQ ID NO 9
<211> LENGTH: 1473
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 9
atgctgctgc tggtgaccag cctgctgctg tgcgaactgc cgcatccggc gtttctgctg      60
attccggaag tgcaacttgt cgaaagcggt ggaggtcttg tccaacctgg tgctccctg     120 aggctctcgt gtgccgcgag cggattcacc ttctcatcgt acgctatgtc ctgggtcaga     180
caggctcctg gaaagggcct ggaatgggtg gccgtgatct cctacgacgg cagcaacaag     240
tattacgccg actcagtgaa gggccggttc accatttccc gggacaacag caagaacacc     300

```
ctgtacttgc aaatgaactc cctgcgggcc gaggataccg cggtgtacta ctgcgcccac    360
ctccgctttg gatacggaat ggatgtctgg ggacagggaa ctaccgtgac cgtgtcgtcc    420
ggggggggg gaagcggcgg cggggatcg ggtggcggcg gatcccagac tgtggtcacc    480
caagagcctt cactgaccgt gtccccgggt ggcaccgtga cgctgacttg cgcgtcatct    540
accggggccg tgacctcgga ccactacccc tgctggttcc agcagaaacc cggacatcca    600
ccgagagccc tggtgtactc cactgacacc atccactcct ggactccggc ccggttctcc    660
ggaagcctcc tgggcgggaa ggccgcactg acagtgtccg gagtgcagcc cgaggatgaa    720
gccgactact actgtctgct ctactatggg ggagcacgcg tgttcggtgg cggcactcag    780
ctgaccgtgc tgggagcggc cgcaactacc accctgccc tcggccgcc gactccggcc    840
ccaaccatcg caagccaacc cctctccttg cgccccgaag cttgccgccc ggccgcgggt    900
ggagccgtgc atacccgggg gctggacttt gcctgcgata tctacatttg gccccgctg    960
gccggcactt gcggcgtgct cctgctgtcg ctggtcatca ccctttactg caagagggc   1020
cggaagaagc tgctttacat cttcaagcag ccgttcatgc ggcccgtgca gacgactcag   1080
gaagaggacg gatgctcgtg cagattccct gaggaggaag agggggatg cgaactgcgc   1140
gtcaagttct cacggtccgc cgacgcccc gcatatcaac agggccagaa tcagctctac   1200
aacgagctga acctgggaag gagagaggag tacgacgtgc tggacaagcg acgcggacgc   1260
gacccggaga tgggggggaa accacggcgg aaaaaccctc aggaaggact gtacaacgaa   1320
ctccagaaag acaagatggc ggaagcctac tcagaaatcg ggatgaaggg agagcggagg   1380
aggggaaagg gtcacgacgg gctgtaccag ggactgagca ccgccactaa ggatacctac   1440
gatgccttgc atatgcaagc actcccaccc cgg                                1473
```

<210> SEQ ID NO 10
<211> LENGTH: 491
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 10

```
Met Leu Leu Leu Val Thr Ser Leu Leu Cys Glu Leu Pro His Pro
1               5                   10                  15

Ala Phe Leu Leu Ile Pro Glu Val Gln Leu Val Glu Ser Gly Gly Gly
                20                  25                  30

Leu Val Gln Pro Gly Arg Ser Leu Arg Leu Ser Cys Ala Ala Ser Gly
            35                  40                  45

Phe Thr Phe Ser Ser Tyr Ala Met Ser Trp Val Arg Gln Ala Pro Gly
        50                  55                  60

Lys Gly Leu Glu Trp Val Ala Val Ile Ser Tyr Asp Gly Ser Asn Lys
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala His Leu Arg Phe Gly Tyr Gly Met Asp
        115                 120                 125

Val Trp Gly Gln Gly Thr Thr Val Thr Val Ser Ser Gly Gly Gly Gly
    130                 135                 140
```

```
Ser Gly Gly Gly Gly Ser Gly Gly Gly Ser Gln Thr Val Val Thr
145                 150                 155                 160

Gln Glu Pro Ser Leu Thr Val Ser Pro Gly Gly Thr Val Thr Leu Thr
                165                 170                 175

Cys Ala Ser Ser Thr Gly Ala Val Thr Ser Asp His Tyr Pro Cys Trp
            180                 185                 190

Phe Gln Gln Lys Pro Gly His Pro Pro Arg Ala Leu Val Tyr Ser Thr
        195                 200                 205

Asp Thr Ile His Ser Trp Thr Pro Ala Arg Phe Ser Gly Ser Leu Leu
    210                 215                 220

Gly Gly Lys Ala Ala Leu Thr Val Ser Gly Val Gln Pro Glu Asp Glu
225                 230                 235                 240

Ala Asp Tyr Tyr Cys Leu Leu Tyr Tyr Gly Ala Arg Val Phe Gly
                245                 250                 255

Gly Gly Thr Gln Leu Thr Val Leu Gly Ala Ala Ala Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Cys Glu Leu Arg Val Lys Phe Ser
    370                 375                 380

Arg Ser Ala Asp Ala Pro Ala Tyr Gln Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490

<210> SEQ ID NO 11
<211> LENGTH: 1467
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 11
atgctgctgc tggtgaccag cctgctgctg tgcgaactgc cgcatccggc gtttctgctg      60
```

```
attccgcaag tccaactcgt ccagtccggt gccgaagtca agaagcctgg ctcatccgtg    120
aaagtgtcct gcaaagcatc gggcggaacc ttctcctcct atgccatttc ctgggtccgc    180
caggcaccgg gccagggtct ggagtggatg ggcgggatta tccctatctt cggaactgcc    240
aaccacgccc aaaagttcca gggacgcgtg accattaccg ccgatgaatc aacctcaacc    300
gcctacatgg aactgtccag cttgaggtcc gaggacaccg ccgtgtacta ctgcgcgttc    360
atgatggtgc cggagtacta ctttgactac tggggccagg gaacccttgt gaccgtgtcg    420
tccggtggtg gcggatccgg gggggggga tctgggggcg gcggaagcga tatccagatg    480
acccagtcgc catcgagcct gtccgcttcc gtgggcgaca gagtgacgat cacttgccgg    540
gcttcacaag gcatcagaaa tgacctgggc tggtatcagc agaagcccgg agaagcgccc    600
aagcggctga tctacgcggc cagcaccctg caaaacggag tgccttcgcg gttctccggg    660
agcggctccg gaactgactt cactctgact attaacagcc tccagcccga ggatttcgcc    720
acatactact gtcagcagta caacagctac ccgtacacct tcggacaggg aactaagctc    780
gaaatcaagg cggccgcaac taccacccct gcccctcggc cgccgactcc ggccccaacc    840
atcgcaagcc aaccctctc cttgcgcccc gaagcttgcc gccggccgc gggtggagcc    900 gtgcataccc gggggctgga cttttgcctgc gatatctaca tttgggcccc gctggccggc    960
acttgcggcg tgctcctgct gtcgctggtc atcaccctt actgcaagag gggccggaag    1020
aagctgcttt acatcttcaa gcagccgttc atgcggcccg tgcagacgac tcaggaagag    1080
gacggatgct cgtgcagatt ccctgaggag aagaggggg gatgcgaact gcgcgtcaag    1140
ttctcacggt ccgccgacgc ccccgcatat caacagggcc agaatcagct ctacaacgag    1200
ctgaacctgg gaaggagaga ggagtacgac gtgctggaca gcgacgcgg acgcgacccg    1260 gagatggggg ggaaaccacg gcggaaaaac cctcaggaag gactgtacaa cgaactccag    1320
aaagacaaga tggcggaagc ctactcagaa atcgggatga agaggagag gaggagggga    1380 aagggtcacg acgggctgta ccagggactg agcaccgcca ctaaggatac ctacgatgcc    1440
ttgcatatgc aagcactccc acccccgg                                      1467
```

<210> SEQ ID NO 12
<211> LENGTH: 489
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 12

```
Met Leu Leu Leu Val Thr Ser Leu Leu Leu Cys Glu Leu Pro His Pro
1               5                   10                  15

Ala Phe Leu Leu Ile Pro Gln Val Gln Leu Val Gln Ser Gly Ala Glu
            20                  25                  30

Val Lys Lys Pro Gly Ser Ser Val Lys Val Ser Cys Lys Ala Ser Gly
        35                  40                  45

Gly Thr Phe Ser Ser Tyr Ala Ile Ser Trp Val Arg Gln Ala Pro Gly
    50                  55                  60

Gln Gly Leu Glu Trp Met Gly Gly Ile Ile Pro Ile Phe Gly Thr Ala
65                  70                  75                  80

Asn His Ala Gln Lys Phe Gln Gly Arg Val Thr Ile Thr Ala Asp Glu
                85                  90                  95
```

```
Ser Thr Ser Thr Ala Tyr Met Glu Leu Ser Ser Leu Arg Ser Glu Asp
            100                 105                 110

Thr Ala Val Tyr Tyr Cys Ala Phe Met Met Val Pro Glu Tyr Tyr Phe
        115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Asp Ile Gln Met
145                 150                 155                 160

Thr Gln Ser Pro Ser Ser Leu Ser Ala Ser Val Gly Asp Arg Val Thr
                165                 170                 175

Ile Thr Cys Arg Ala Ser Gln Gly Ile Arg Asn Asp Leu Gly Trp Tyr
            180                 185                 190

Gln Gln Lys Pro Gly Glu Ala Pro Lys Arg Leu Ile Tyr Ala Ala Ser
        195                 200                 205

Thr Leu Gln Asn Gly Val Pro Ser Arg Phe Ser Gly Ser Gly Ser Gly
    210                 215                 220

Thr Asp Phe Thr Leu Thr Ile Asn Ser Leu Gln Pro Glu Asp Phe Ala
225                 230                 235                 240

Thr Tyr Tyr Cys Gln Gln Tyr Asn Ser Tyr Pro Tyr Thr Phe Gly Gln
                245                 250                 255

Gly Thr Lys Leu Glu Ile Lys Ala Ala Ala Thr Thr Thr Pro Ala Pro
            260                 265                 270

Arg Pro Pro Thr Pro Ala Pro Thr Ile Ala Ser Gln Pro Leu Ser Leu
        275                 280                 285

Arg Pro Glu Ala Cys Arg Pro Ala Ala Gly Gly Ala Val His Thr Arg
    290                 295                 300

Gly Leu Asp Phe Ala Cys Asp Ile Tyr Ile Trp Ala Pro Leu Ala Gly
305                 310                 315                 320

Thr Cys Gly Val Leu Leu Leu Ser Leu Val Ile Thr Leu Tyr Cys Lys
                325                 330                 335

Arg Gly Arg Lys Lys Leu Leu Tyr Ile Phe Lys Gln Pro Phe Met Arg
            340                 345                 350

Pro Val Gln Thr Thr Gln Glu Glu Asp Gly Cys Ser Cys Arg Phe Pro
        355                 360                 365

Glu Glu Glu Glu Gly Gly Cys Glu Leu Arg Val Lys Phe Ser Arg Ser
    370                 375                 380

Ala Asp Ala Pro Ala Tyr Gln Gln Gly Gln Asn Gln Leu Tyr Asn Glu
385                 390                 395                 400

Leu Asn Leu Gly Arg Arg Glu Glu Tyr Asp Val Leu Asp Lys Arg Arg
                405                 410                 415

Gly Arg Asp Pro Glu Met Gly Gly Lys Pro Arg Arg Lys Asn Pro Gln
            420                 425                 430

Glu Gly Leu Tyr Asn Glu Leu Gln Lys Asp Lys Met Ala Glu Ala Tyr
        435                 440                 445

Ser Glu Ile Gly Met Lys Gly Glu Arg Arg Arg Gly Lys Gly His Asp
    450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg
                485

<210> SEQ ID NO 13
<211> LENGTH: 66
<212> TYPE: DNA
```

<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 13

```
atgctgctgc tggtgaccag cctgctgctg tgcgaactgc cgcatccggc gtttctgctg      60
attccg                                                                  66
```

<210> SEQ ID NO 14
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 14

```
Met Leu Leu Leu Val Thr Ser Leu Leu Leu Cys Glu Leu Pro His Pro
1               5                   10                  15

Ala Phe Leu Leu Ile Pro
            20
```

<210> SEQ ID NO 15
<211> LENGTH: 1500
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 15

```
atgctgctgc tggtgaccag cctgctgctg tgcgaactgc cgcatccggc gtttctgctg      60
attccgcaac tccaactcca agaatctgga ccaggcctcg tgaagccctc ccaaactctg     120
tccctgacct gtaccgtgtc gggtggaagc atttcgagcg gtggatacta ctggtcctgg     180
atcaggcaga tcctggaaaa gggactggag tggattgggt acatctacta ctccggctca     240
acctactaca acccgtcctt gaaatcgcgc gtgacgatct ccgtggacac ttcaaagaac     300
cagttcagcc tgaagctttc ctccgtgacc gcggccgata cagcggtgta ctactgcgct     360
cgggatcaga gcgtggccga ccctggtggc ggctactact actacggaat ggatgtctgg     420
ggacagggaa ccaccgtgac tgtgtccagc ggggcggcg gatccggggg gggggatcg      480 ggcggcggcg gttcgcagtc cgtgctgacc cagccaccta gcgtgtcagt ggcaccggga     540
cagaccgcct ccatttcctg cggggggaaat gacttcggta gcgctccgt gtcatggtat     600 caccagaagc cgggacaggc cccggtgctg gtcatctatg acgacaacga cagaccctcg     660
ggcatccccg aacggttttc gggaagcacc tccggagaca ctgccaccct gaccatctcc     720
cgggtcgagg tcggcgatga agccgattac tactgccaag tctgggacga cgactccgac     780
cactgggtgt tcggcggcgg aactaagctg actgtgctgg ggcggccgc aactaccacc     840 ctgccccctc ggccgccgac tccggcccca accatcgcaa gccaacccct ctccttgcgc     900
cccgaagctt gccgcccggc cgcgggtgga gccgtgcata ccgggggct ggactttgcc     960 tgcgatatct acatttgggc ccgctggcc ggcacttgcg cgtgctcct gctgtcgctg    1020 gtcatcaccc tttactgcaa gaggggccgg aagaagctgc tttacatctt caagcagccg    1080
ttcatgcggc ccgtgcagac gactcaggaa gaggacggat gctcgtgcag attccctgag    1140
```

-continued

```
gaggaagagg ggggatgcga actgcgcgtc aagttctcac ggtccgccga cgccccccgca    1200 tatcaacagg gccagaatca gctctacaac gagctgaacc tgggaaggag agaggagtac    1260
gacgtgctgg acaagcgacg cggacgcgac ccggagatgg gggggaaacc acggcggaaa    1320
aaccctcagg aaggactgta caacgaactc cagaaagaca agatggcgga agcctactca    1380
gaaatcggga tgaagggaga gcggaggagg ggaaagggtc acgacgggct gtaccaggga    1440
ctgagcaccg ccactaagga tacctacgat gccttgcata tgcaagcact cccaccccgg    1500
```

<210> SEQ ID NO 16
<211> LENGTH: 500
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

```
Met Leu Leu Leu Val Thr Ser Leu Leu Leu Cys Glu Leu Pro His Pro
1               5                   10                  15

Ala Phe Leu Leu Ile Pro Gln Leu Gln Leu Gln Glu Ser Gly Pro Gly
            20                  25                  30

Leu Val Lys Pro Ser Gln Thr Leu Ser Leu Thr Cys Thr Val Ser Gly
        35                  40                  45

Gly Ser Ile Ser Ser Gly Gly Tyr Tyr Trp Ser Trp Ile Arg Gln His
    50                  55                  60

Pro Gly Lys Gly Leu Glu Trp Ile Gly Tyr Ile Tyr Tyr Ser Gly Ser
65                  70                  75                  80

Thr Tyr Tyr Asn Pro Ser Leu Lys Ser Arg Val Thr Ile Ser Val Asp
                85                  90                  95

Thr Ser Lys Asn Gln Phe Ser Leu Lys Leu Ser Ser Val Thr Ala Ala
            100                 105                 110

Asp Thr Ala Val Tyr Tyr Cys Ala Arg Asp Gln Ser Val Ala Asp Pro
        115                 120                 125

Gly Gly Gly Tyr Tyr Tyr Gly Met Asp Val Trp Gly Gln Gly Thr
    130                 135                 140

Thr Val Thr Val Ser Ser Gly Gly Gly Ser Gly Gly Gly Gly Ser
145                 150                 155                 160

Gly Gly Gly Gly Ser Gln Ser Val Leu Thr Gln Pro Pro Ser Val Ser
                165                 170                 175

Val Ala Pro Gly Gln Thr Ala Ser Ile Ser Cys Gly Gly Asn Asp Phe
            180                 185                 190

Gly Ser Arg Ser Val Ser Trp Tyr His Gln Lys Pro Gly Gln Ala Pro
        195                 200                 205

Val Leu Val Ile Tyr Asp Asp Asn Asp Arg Pro Ser Gly Ile Pro Glu
    210                 215                 220

Arg Phe Ser Gly Ser Thr Ser Gly Asp Thr Ala Thr Leu Thr Ile Ser
225                 230                 235                 240

Arg Val Glu Val Gly Asp Glu Ala Asp Tyr Tyr Cys Gln Val Trp Asp
                245                 250                 255

Asp Asp Ser Asp His Trp Val Phe Gly Gly Gly Thr Lys Leu Thr Val
            260                 265                 270

Leu Gly Ala Ala Ala Thr Thr Thr Pro Ala Pro Arg Pro Pro Thr Pro
        275                 280                 285
```

```
Ala Pro Thr Ile Ala Ser Gln Pro Leu Ser Leu Arg Pro Glu Ala Cys
        290                 295                 300
Arg Pro Ala Ala Gly Gly Ala Val His Thr Arg Gly Leu Asp Phe Ala
305                 310                 315                 320
Cys Asp Ile Tyr Ile Trp Ala Pro Leu Ala Gly Thr Cys Gly Val Leu
                325                 330                 335
Leu Leu Ser Leu Val Ile Thr Leu Tyr Cys Lys Arg Gly Arg Lys Lys
                340                 345                 350
Leu Leu Tyr Ile Phe Lys Gln Pro Phe Met Arg Pro Val Gln Thr Thr
                355                 360                 365
Gln Glu Glu Asp Gly Cys Ser Cys Arg Phe Pro Glu Glu Glu Glu Gly
        370                 375                 380
Gly Cys Glu Leu Arg Val Lys Phe Ser Arg Ser Ala Asp Ala Pro Ala
385                 390                 395                 400
Tyr Gln Gln Gly Gln Asn Gln Leu Tyr Asn Glu Leu Asn Leu Gly Arg
                405                 410                 415
Arg Glu Glu Tyr Asp Val Leu Asp Lys Arg Arg Gly Arg Asp Pro Glu
                420                 425                 430
Met Gly Gly Lys Pro Arg Arg Lys Asn Pro Gln Glu Gly Leu Tyr Asn
                435                 440                 445
Glu Leu Gln Lys Asp Lys Met Ala Glu Ala Tyr Ser Glu Ile Gly Met
        450                 455                 460
Lys Gly Glu Arg Arg Arg Gly Lys Gly His Asp Gly Leu Tyr Gln Gly
465                 470                 475                 480
Leu Ser Thr Ala Thr Lys Asp Thr Tyr Asp Ala Leu His Met Gln Ala
                485                 490                 495
Leu Pro Pro Arg
        500

<210> SEQ ID NO 17
<211> LENGTH: 1467
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 17
atgctgctgc tggtgaccag cctgctgctg tgcgaactgc cgcatccggc gtttctgctg      60
attccgcaag ttcagctgca agaatcagga cctgggcttg tcaaaccatc tgaaaccctc     120
agcttgactt gtaccgtatc aggagggtca atttcaagct catcctacta ttggggatgg     180
atcagacaac acccgggaa agggctcgag tggataggt ccatatatta cagcggatct      240
acatactaca acccgtcatt gaagtccagg gtaacgattc cggtggacac tagcaagaat     300
cagtttagcc tcaagttgag cagtgtaact gctgcggaca cggcggtata ttattgtgct     360
cgacacctcg gtggagatgc ttttgacata tggggtcaag gacaacagt caccgttagc     420 tcaggtggag ggggtagcgg gggggcgga tctggggag gcggttcatt gcccgtactt      480
acacagccac cctctgtcag cgtcgcacct ggacaaaccg ctcgcatcac ctgtggcgga     540
aataatatag gttccaagtc tgttcattgg tatcagcaga accgggaca ggccccgtc      600 cttgtggtgt atgatgattc tgataggcca tctggtatcc cagaacggtt ttcaggtagc     660
aattcaggga atactgccac tctcactatt agcggtactc aagctatgga tgaggccgac     720
tatttttgcc agagctacga ctctagtaac ccagtcgtgt tcggggagg gacccagttg     780
```

```
accgtgctgg cggccgcaac taccacccct gccnctcggc cgccgactcc ggccccaacc    840
atcgcaagcc aaccnctctc cttgcgcccc gaagcttgcc gcccggccgc gggtggagcc    900
gtgcataccc gggggctgga ctttgcctgc gatatctaca tttgggcccc gctggccggc    960
acttgcggcg tgctcctgct gtcgctggtc atcacccttt actgcaagag gggccggaag   1020
aagctgcttt acatcttcaa gcagccgttc atgcggcccg tgcagacgac tcaggaagag   1080
gacggatgct cgtgcagatt ccctgaggag aagaggggg gatgcgaact gcgcgtcaag   1140
ttctcacggt ccgccgacgc ccccgcatat caacagggcc agaatcagct ctacaacgag   1200
ctgaacctgg aaggagaga ggagtacgac gtgctggaca gcgacgcgg acgcgacccg    1260 gagatggggg ggaaaccacg gcggaaaaac cctcaggaag gactgtacaa cgaactccag   1320
aaagacaaga tggcggaagc ctactcagaa atcgggatga aggagagcg gaggagggga   1380 aagggtcacg acgggctgta ccagggactg agcaccgcca ctaaggatac ctacgatgcc   1440
ttgcatatgc aagcactccc accccgg                                      1467
```

<210> SEQ ID NO 18
<211> LENGTH: 489
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 18

```
Met Leu Leu Leu Val Thr Ser Leu Leu Leu Cys Glu Leu Pro His Pro
1               5                   10                  15

Ala Phe Leu Leu Ile Pro Gln Val Gln Leu Gln Glu Ser Gly Pro Gly
            20                  25                  30

Leu Val Lys Pro Ser Glu Thr Leu Ser Leu Thr Cys Thr Val Ser Gly
        35                  40                  45

Gly Ser Ile Ser Ser Ser Tyr Tyr Trp Gly Trp Ile Arg Gln Pro
    50                  55                  60

Pro Gly Lys Gly Leu Glu Trp Ile Gly Ser Ile Tyr Tyr Ser Gly Ser
65                  70                  75                  80

Thr Tyr Tyr Asn Pro Ser Leu Lys Ser Arg Val Thr Ile Pro Val Asp
                85                  90                  95

Thr Ser Lys Asn Gln Phe Ser Leu Lys Leu Ser Ser Val Thr Ala Ala
            100                 105                 110

Asp Thr Ala Val Tyr Tyr Cys Ala Arg His Leu Gly Gly Asp Ala Phe
        115                 120                 125

Asp Ile Trp Gly Gln Gly Thr Thr Val Thr Val Ser Ser Gly Gly Gly
    130                 135                 140

Gly Ser Gly Gly Gly Gly Ser Gly Gly Gly Gly Ser Leu Pro Val Leu
145                 150                 155                 160

Thr Gln Pro Pro Ser Val Ser Val Ala Pro Gly Gln Thr Ala Arg Ile
                165                 170                 175

Thr Cys Gly Gly Asn Asn Ile Gly Ser Lys Ser Val His Trp Tyr Gln
            180                 185                 190

Gln Lys Pro Gly Gln Ala Pro Val Leu Val Val Tyr Asp Asp Ser Asp
        195                 200                 205

Arg Pro Ser Gly Ile Pro Glu Arg Phe Ser Gly Ser Asn Ser Gly Asn
    210                 215                 220
```

Thr Ala Thr Leu Thr Ile Ser Gly Thr Gln Ala Met Asp Glu Ala Asp
225                 230                 235                 240

Tyr Phe Cys Gln Ser Tyr Asp Ser Ser Asn Pro Val Val Phe Gly Gly
            245                 250                 255

Gly Thr Gln Leu Thr Val Leu Ala Ala Ala Thr Thr Thr Pro Ala Pro
        260                 265                 270

Arg Pro Pro Thr Pro Ala Pro Thr Ile Ala Ser Gln Pro Leu Ser Leu
        275                 280                 285

Arg Pro Glu Ala Cys Arg Pro Ala Ala Gly Gly Ala Val His Thr Arg
    290                 295                 300

Gly Leu Asp Phe Ala Cys Asp Ile Tyr Ile Trp Ala Pro Leu Ala Gly
305                 310                 315                 320

Thr Cys Gly Val Leu Leu Leu Ser Leu Val Ile Thr Leu Tyr Cys Lys
            325                 330                 335

Arg Gly Arg Lys Lys Leu Leu Tyr Ile Phe Lys Gln Pro Phe Met Arg
            340                 345                 350

Pro Val Gln Thr Thr Gln Glu Glu Asp Gly Cys Ser Cys Arg Phe Pro
        355                 360                 365

Glu Glu Glu Glu Gly Gly Cys Glu Leu Arg Val Lys Phe Ser Arg Ser
370                 375                 380

Ala Asp Ala Pro Ala Tyr Gln Gln Gly Gln Asn Gln Leu Tyr Asn Glu
385                 390                 395                 400

Leu Asn Leu Gly Arg Arg Glu Glu Tyr Asp Val Leu Asp Lys Arg Arg
            405                 410                 415

Gly Arg Asp Pro Glu Met Gly Gly Lys Pro Arg Arg Lys Asn Pro Gln
            420                 425                 430

Glu Gly Leu Tyr Asn Glu Leu Gln Lys Asp Lys Met Ala Glu Ala Tyr
        435                 440                 445

Ser Glu Ile Gly Met Lys Gly Glu Arg Arg Arg Gly Lys Gly His Asp
450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg
                485

<210> SEQ ID NO 19
<211> LENGTH: 1476
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 19
atgctgctgc tggtgaccag cctgctgctg tgcgaactgc cgcatccggc gtttctgctg      60
attccgcagg cggcccaggt acagctgcag cagtcagggg ctgaggtgaa gaagcctggg     120
tcctcggtga aggtctcctg caaggcttct ggaggcacct tcagcagcta tgctatcagc     180
tgggtgcgac aggcccctgg acaagggctt gagtggatgg gatggatcaa ccctaacagt     240
ggtggcacaa actatgcaca gaggtttcag ggcagggtca ccatgaccag gacacgtcc     300 atcagcacag cctacatgga gctgagcagg ctgagatctg acgacacggc cgtgtattac     360
tgtgcgagtt ataatgatgc ttttgatatc tggggccaag caccctggt caccgtctcc     420 tcaggaggtg gcgggtctgg tggtggcggt agcggtggtg gcggatccaa ttttatgctg     480

```
actcagcccc actctgtgtc ggagtctccg gggaagacgg taaccatctc ctgcacccgc    540
agcagtggca gcattgccag caactatgtg cagtggtacc agcagcgccc gggcagtgcc    600
cccaccattg tgatctatga ggatgatcaa agaccctctg gggtccctga tcggttctct    660
ggctccatcg acacctcctc caactctgcc tccctcacca tctctggact gcagagtgag    720
gacgaggctg actactactg tcagtcttat gagcccggca atggggtatt cggcggaggg    780
accaaggtca ccgtcctagc ggccgcaact accacccctg cccctcggcc gccgactccg    840
gccccaacca tcgcaagcca accctctcc ttgcgcccg aagcttgccg cccggccgcg    900
ggtggagccg tgcataccg ggggctggac tttgcctgcg atatctacat ttgggccccg    960
ctggccggca cttgcggcgt gctcctgctg tcgctggtca tcacccttta ctgcaagagg   1020
ggccggaaga agctgcttta catcttcaag cagccgttca tgcggcccgt gcagacgact   1080
caggaagagg acggatgctc gtgcagattc cctgaggagg aagaggggg atgcgaactg   1140 cgcgtcaagt tctcacggtc cgccgacgcc cccgcatatc aacagggcca gaatcagctc   1200
tacaacgagc tgaacctggg aaggagagag gagtacgacg tgctggacaa gacgcgga   1260 cgcgacccgg agatggggg gaaaccacgg cggaaaaacc ctcaggaagg actgtacaac   1320
gaactccaga aagacaagat ggcggaagcc tactcagaaa tcgggatgaa gggagagcgg   1380
aggaggggaa aggtcacga cgggctgtac cagggactga gcaccgccac taaggatacc   1440
tacgatgcct tgcatatgca agcactccca ccccgg                              1476
```

<210> SEQ ID NO 20
<211> LENGTH: 492
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 20

```
Met Leu Leu Leu Val Thr Ser Leu Leu Leu Cys Glu Leu Pro His Pro
1               5                   10                  15

Ala Phe Leu Leu Ile Pro Gln Ala Ala Gln Val Gln Leu Gln Gln Ser
            20                  25                  30

Gly Ala Glu Val Lys Lys Pro Gly Ser Ser Val Lys Val Ser Cys Lys
        35                  40                  45

Ala Ser Gly Gly Thr Phe Ser Ser Tyr Ala Ile Ser Trp Val Arg Gln
    50                  55                  60

Ala Pro Gly Gln Gly Leu Glu Trp Met Gly Trp Ile Asn Pro Asn Ser
65                  70                  75                  80

Gly Gly Thr Asn Tyr Ala Gln Arg Phe Gln Gly Arg Val Thr Met Thr
                85                  90                  95

Arg Asp Thr Ser Ile Ser Thr Ala Tyr Met Glu Leu Ser Arg Leu Arg
            100                 105                 110

Ser Asp Asp Thr Ala Val Tyr Tyr Cys Ala Ser Tyr Asn Asp Ala Phe
        115                 120                 125

Asp Ile Trp Gly Gln Gly Thr Leu Val Thr Val Ser Ser Gly Gly Gly
    130                 135                 140

Gly Ser Gly Gly Gly Ser Gly Gly Gly Ser Asn Phe Met Leu
145                 150                 155                 160

Thr Gln Pro His Ser Val Ser Glu Ser Pro Gly Lys Thr Val Thr Ile
                165                 170                 175
```

```
Ser Cys Thr Arg Ser Ser Gly Ser Ile Ala Ser Asn Tyr Val Gln Trp
            180                 185                 190

Tyr Gln Gln Arg Pro Gly Ser Ala Pro Thr Ile Val Ile Tyr Glu Asp
        195                 200                 205

Asp Gln Arg Pro Ser Gly Val Pro Asp Arg Phe Ser Gly Ser Ile Asp
    210                 215                 220

Thr Ser Ser Asn Ser Ala Ser Leu Thr Ile Ser Gly Leu Gln Ser Glu
225                 230                 235                 240

Asp Glu Ala Asp Tyr Tyr Cys Gln Ser Tyr Glu Pro Gly Asn Gly Val
                245                 250                 255

Phe Gly Gly Gly Thr Lys Val Thr Val Leu Ala Ala Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Lys Arg Gly Arg Lys Lys Leu Leu Tyr Ile Phe Lys Gln Pro
            340                 345                 350

Phe Met Arg Pro Val Gln Thr Thr Gln Glu Glu Asp Gly Cys Ser Cys
        355                 360                 365

Arg Phe Pro Glu Glu Glu Glu Gly Gly Cys Glu Leu Arg Val Lys Phe
    370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
        435                 440                 445

Glu Ala Tyr Ser Glu Ile Gly Met Lys Gly Glu Arg Arg Arg Gly Lys
    450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490
```

<210> SEQ ID NO 21
<211> LENGTH: 1488
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 21
atgctgctgc tggtgaccag cctgctgctg tgcgaactgc cgcatccggc gtttctgctg      60
attccgcaag aacagcttgt agagtccggc ggtagattgg tgacaccggg ggggagcctt     120
accctgtctt gtaaggcatc tgggttcgat ttcagtgcgt attatatgag ctgggttcgg     180
caggcgcccg ggaaggggct ggaatggata gccactatat acccgtcatc cggcaagact     240

```
tactacgcga cttgggtaaa cgggaggttt acgataagct cagataacgc ccaaaacacg    300
gttgatctcc aaatgaatag cttgaccgcc gctgataggg cgacctattt ctgtgcgcgg    360
gactcttacg ctgatgacgg ggccctcttc aatatatggg gaccgggaac gctcgtaacc    420
atatcatctg gaggaggtgg gagcggaggc ggagggtcag gtggggcgg gagcgaactc     480 gtacttacac aatctccaag cgtaagcgca gcgttgggga gtccagcaaa gatcacctgc    540
actttgtcaa gcgcccacaa aacggatacg atagattggt atcagcaact ccaaggtgaa    600
gcgccacgat atctcatgca ggtacagagc gacgggagtt atactaagag gcccggggtc    660
ccagacagat tcagtggcag cagttcaggt gccgacagat acctgataat accctcagtt    720
caagccgatg atgaagccga ttactactgt ggggctgact acataggtgg gtatgttttc    780
gggggcggca ctcaattgac agttacaggg gcggccgcaa ctaccacccc tgcccctcgg    840
ccgccgactc cggccccaac catcgcaagc caacccctct ccttgcgccc cgaagcttgc    900
cgcccggccg cgggtggagc cgtgcatacc cggggggctgg actttgcctg cgatatctac    960
atttgggccc cgctggccgg cacttgcggc gtgctcctgc tgtcgctggt catcacccttt   1020 tactgcaaga ggggccggaa gaagctgctt tacatcttca gcagccgtt catgcggccc    1080 gtgcagacga ctcaggaaga ggacggatgc tcgtgcagat tccctgagga ggaagagggg    1140
ggatgcgaac tgcgcgtcaa gttctcacgg tccgccgacg cccccgcata tcaacgggc    1200 cagaatcagc tctacaacga gctgaacctg gaaggagag aggagtacga cgtgctggac     1260
aagcgacgcg gacgcgaccc ggagatgggg gggaaaccac ggcggaaaaa ccctcaggaa    1320
ggactgtaca cgaactcca gaaagacaag atggcggaag cctactcaga aatcgggatg     1380
aagggagagc ggaggagggg aaagggtcac gacgggctgt accagggact gagcaccgcc    1440
actaaggata cctacgatgc cttgcatatg caagcactcc caccccgg                 1488
```

<210> SEQ ID NO 22
<211> LENGTH: 496
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 22

```
Met Leu Leu Leu Val Thr Ser Leu Leu Cys Glu Leu Pro His Pro
1               5                   10                  15

Ala Phe Leu Leu Ile Pro Gln Glu Gln Leu Val Glu Ser Gly Gly Arg
            20                  25                  30

Leu Val Thr Pro Gly Gly Ser Leu Thr Leu Ser Cys Lys Ala Ser Gly
        35                  40                  45

Phe Asp Phe Ser Ala Tyr Tyr Met Ser Trp Val Arg Gln Ala Pro Gly
    50                  55                  60

Lys Gly Leu Glu Trp Ile Ala Thr Ile Tyr Pro Ser Ser Gly Lys Thr
65                  70                  75                  80

Tyr Tyr Ala Thr Trp Val Asn Gly Arg Phe Thr Ile Ser Ser Asp Asn
                85                  90                  95

Ala Gln Asn Thr Val Asp Leu Gln Met Asn Ser Leu Thr Ala Ala Asp
            100                 105                 110

Arg Ala Thr Tyr Phe Cys Ala Arg Asp Ser Tyr Ala Asp Gly Ala
        115                 120                 125
```

-continued

Leu Phe Asn Ile Trp Gly Pro Gly Thr Leu Val Thr Ile Ser Ser Gly
    130                 135                 140

Gly Gly Gly Ser Gly Gly Gly Ser Gly Gly Gly Ser Glu Leu
145                 150                 155                 160

Val Leu Thr Gln Ser Pro Ser Val Ser Ala Ala Leu Gly Ser Pro Ala
                165                 170                 175

Lys Ile Thr Cys Thr Leu Ser Ser Ala His Lys Thr Asp Thr Ile Asp
                180                 185                 190

Trp Tyr Gln Gln Leu Gln Gly Glu Ala Pro Arg Tyr Leu Met Gln Val
                195                 200                 205

Gln Ser Asp Gly Ser Tyr Thr Lys Arg Pro Gly Val Pro Asp Arg Phe
    210                 215                 220

Ser Gly Ser Ser Ser Gly Ala Asp Arg Tyr Leu Ile Ile Pro Ser Val
225                 230                 235                 240

Gln Ala Asp Asp Glu Ala Asp Tyr Tyr Cys Gly Ala Asp Tyr Ile Gly
                245                 250                 255

Gly Tyr Val Phe Gly Gly Gly Thr Gln Leu Thr Val Thr Gly Ala Ala
                260                 265                 270

Ala Thr Thr Thr Pro Ala Pro Arg Pro Pro Thr Pro Ala Pro Thr Ile
            275                 280                 285

Ala Ser Gln Pro Leu Ser Leu Arg Pro Glu Ala Cys Arg Pro Ala Ala
    290                 295                 300

Gly Gly Ala Val His Thr Arg Gly Leu Asp Phe Ala Cys Asp Ile Tyr
305                 310                 315                 320

Ile Trp Ala Pro Leu Ala Gly Thr Cys Gly Val Leu Leu Leu Ser Leu
                325                 330                 335

Val Ile Thr Leu Tyr Cys Lys Arg Gly Arg Lys Lys Leu Leu Tyr Ile
                340                 345                 350

Phe Lys Gln Pro Phe Met Arg Pro Val Gln Thr Thr Gln Glu Glu Asp
            355                 360                 365

Gly Cys Ser Cys Arg Phe Pro Glu Glu Glu Glu Gly Gly Cys Glu Leu
    370                 375                 380

Arg Val Lys Phe Ser Arg Ser Ala Asp Ala Pro Ala Tyr Gln Gln Gly
385                 390                 395                 400

Gln Asn Gln Leu Tyr Asn Glu Leu Asn Leu Gly Arg Arg Glu Glu Tyr
                405                 410                 415

Asp Val Leu Asp Lys Arg Arg Gly Arg Asp Pro Glu Met Gly Gly Lys
                420                 425                 430

Pro Arg Arg Lys Asn Pro Gln Glu Gly Leu Tyr Asn Glu Leu Gln Lys
            435                 440                 445

Asp Lys Met Ala Glu Ala Tyr Ser Glu Ile Gly Met Lys Gly Glu Arg
    450                 455                 460

Arg Arg Gly Lys Gly His Asp Gly Leu Tyr Gln Gly Leu Ser Thr Ala
465                 470                 475                 480

Thr Lys Asp Thr Tyr Asp Ala Leu His Met Gln Ala Leu Pro Pro Arg
                485                 490                 495

<210> SEQ ID NO 23
<211> LENGTH: 1464
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 23

```
atgctgctgc tggtgaccag cctgctgctg tgcgaactgc cgcatccggc gtttctgctg      60
attccggaag tgcaactcgt cgaaactgga gccgaagtga aaaagcctgg agcgtccgtc     120
aaagtgtcgt gcaaggcctc cggctacacc ttcacgacct actacgtgca ctgggtcaga     180
caggctccgg gtcaagggct ggagtggatg ggcatcatta cccctccgg tggaagcacc      240
tcctatgcgc aaaagttcca gggtcgcgtc accatgactc gcgataccct cacttccact     300
gtgtacatgg aactgagctc cctgaggtcc gaggacaccg ccgtgtacta ctgcgcacgg     360
gatggaggct gggcggcta cgaggcttgg ggacagggca ccctcgtgac tgtgtcaagc     420
ggaggggtg atccggagg gggaggatca ggcggtggtg aagcgatat ccagcttacc       480
cagtcgcctt ccgcgctgtc tgcatcggcc ggcgacagag tgacaattac ctgtcaagcc    540
agccaggaca tctccaacta tctgaactgg taccagcaga agcccggaaa ggctccgaag    600
ctgctgatct acgacgccag caacctggaa cggggcgtgc catcacggtt ctcgggatca    660
gggtcgggca ctgagttcac cttcaccatc tcctccctcc aacccgagga cattgccacc    720
tactactgcc agcagtacga caacctcccg atcacctttg gcagggggac tcgcctggaa    780
atcaaggcgg ccgcaactac cacccctgcc ctcggccgc cgactccggc cccaaccatc     840
gcaagccaac ccctctcctt gcgccccgaa gcttgccgcc cggccgcggg tggagccgtg    900
catacccggg ggctggactt tgcctgcgat atctacattt gggccccgct ggccggcact    960
tgcggcgtgc tcctgctgtc gctggtcatc accctttact gcaagagggg ccggaagaag   1020
ctgctttaca tcttcaagca gccgttcatg cggcccgtgc agacgactca ggaagaggac   1080
ggatgctcgt gcagattccc tgaggaggaa gagggggat gcgaactgcg cgtcaagttc    1140
tcacggtccg ccgacgcccc cgcatatcaa cagggccaga tcagctcta caacgagctg    1200
aacctgggaa ggagagagga gtacgacgtg ctggacaagc gacgcggacg cgacccggag   1260
atggggggga aaccacggcg gaaaaaccct caggaaggac tgtacaacga actccagaaa   1320
gacaagatgg cggaagccta ctcagaaatc gggatgaagg gagagcggag gaggggaaag   1380
ggtcacgacg gcctgtacca gggactgagc accgccacta aggataccta cgatgccttg   1440
catatgcaag cactcccacc ccgg                                          1464
```

<210> SEQ ID NO 24
<211> LENGTH: 488
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 24

```
Met Leu Leu Leu Val Thr Ser Leu Leu Leu Cys Glu Leu Pro His Pro
1               5                   10                  15

Ala Phe Leu Leu Ile Pro Glu Val Gln Leu Val Glu Thr Gly Ala Glu
            20                  25                  30

Val Lys Lys Pro Gly Ala Ser Val Lys Val Ser Cys Lys Ala Ser Gly
        35                  40                  45

Tyr Thr Phe Thr Thr Tyr Tyr Val His Trp Val Arg Gln Ala Pro Gly
    50                  55                  60

Gln Gly Leu Glu Trp Met Gly Ile Ile Asn Pro Ser Gly Gly Ser Thr
65                  70                  75                  80
```

-continued

```
Ser Tyr Ala Gln Lys Phe Gln Gly Arg Val Thr Met Thr Arg Asp Thr
                85                  90                  95
Ser Thr Ser Thr Val Tyr Met Glu Leu Ser Ser Leu Arg Ser Glu Asp
            100                 105                 110
Thr Ala Val Tyr Tyr Cys Ala Arg Asp Gly Leu Gly Gly Tyr Glu
        115                 120                 125
Ala Trp Gly Gln Gly Thr Leu Val Thr Val Ser Ser Gly Gly Gly Gly
    130                 135                 140
Ser Gly Gly Gly Gly Ser Gly Gly Gly Gly Ser Asp Ile Gln Leu Thr
145                 150                 155                 160
Gln Ser Pro Ser Ala Leu Ser Ala Ser Ala Gly Asp Arg Val Thr Ile
                165                 170                 175
Thr Cys Gln Ala Ser Gln Asp Ile Ser Asn Tyr Leu Asn Trp Tyr Gln
            180                 185                 190
Gln Lys Pro Gly Lys Ala Pro Lys Leu Leu Ile Tyr Asp Ala Ser Asn
        195                 200                 205
Leu Glu Arg Gly Val Pro Ser Arg Phe Ser Gly Ser Gly Ser Gly Thr
    210                 215                 220
Glu Phe Thr Phe Thr Ile Ser Ser Leu Gln Pro Glu Asp Ile Ala Thr
225                 230                 235                 240
Tyr Tyr Cys Gln Gln Tyr Asp Asn Leu Pro Ile Thr Phe Gly Gln Gly
                245                 250                 255
Thr Arg Leu Glu Ile Lys Ala Ala Ala Thr Thr Thr Pro Ala Pro Arg
            260                 265                 270
Pro Pro Thr Pro Ala Pro Thr Ile Ala Ser Gln Pro Leu Ser Leu Arg
        275                 280                 285
Pro Glu Ala Cys Arg Pro Ala Ala Gly Gly Ala Val His Thr Arg Gly
    290                 295                 300
Leu Asp Phe Ala Cys Asp Ile Tyr Ile Trp Ala Pro Leu Ala Gly Thr
305                 310                 315                 320
Cys Gly Val Leu Leu Leu Ser Leu Val Ile Thr Leu Tyr Cys Lys Arg
                325                 330                 335
Gly Arg Lys Lys Leu Leu Tyr Ile Phe Lys Gln Pro Phe Met Arg Pro
            340                 345                 350
Val Gln Thr Thr Gln Glu Glu Asp Gly Cys Ser Cys Arg Phe Pro Glu
        355                 360                 365
Glu Glu Glu Gly Gly Cys Glu Leu Arg Val Lys Phe Ser Arg Ser Ala
    370                 375                 380
Asp Ala Pro Ala Tyr Gln Gln Gly Gln Asn Gln Leu Tyr Asn Glu Leu
385                 390                 395                 400
Asn Leu Gly Arg Arg Glu Glu Tyr Asp Val Leu Asp Lys Arg Arg Gly
                405                 410                 415
Arg Asp Pro Glu Met Gly Gly Lys Pro Arg Arg Lys Asn Pro Gln Glu
            420                 425                 430
Gly Leu Tyr Asn Glu Leu Gln Lys Asp Lys Met Ala Glu Ala Tyr Ser
        435                 440                 445
Glu Ile Gly Met Lys Gly Glu Arg Arg Arg Gly Lys Gly His Asp Gly
    450                 455                 460
Leu Tyr Gln Gly Leu Ser Thr Ala Thr Lys Asp Thr Tyr Asp Ala Leu
465                 470                 475                 480
His Met Gln Ala Leu Pro Pro Arg
                485
```

```
<210> SEQ ID NO 25
<211> LENGTH: 1503
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 25
```

| | |
|---|---|
| atgctgctgc tggtgaccag cctgctgctg tgcgaactgc cgcatccggc gtttctgctg | 60 |
| attccggaag tgcaattggt ccagagcgga ggaggacttg tgaagccagg cggatccctg | 120 |
| agattgtcat gcgccgcatc ggggttcacc ttttcctcct actccatgaa ctgggtcaga | 180 |
| caggcgcccg aaagggact tgaatgggtg tcgtccattt cctcctcctc gtcctacatc | 240 |
| tactacgccg actccgtgaa gggccgcttc accatctccc gggacaacgc caagaacagc | 300 |
| ctgtatctcc aaatgaactc cctgcgggcc gaagatactg ctgtgtatta ctgcgctcgg | 360 |
| gacttcccgt acgactcatc gggctattac tcggacgcgt tcgatatctg gggccaggga | 420 |
| actatggtca ccgtcagctc tggtggcggt ggttccggag ggggtggatc cggtggcgga | 480 |
| ggatcagaga ttgtgctgac ccagtccccg ctgtcactgc ccgtgactcc gggagagcct | 540 |
| gcctcgatct cgtgtcggtc cagccagtcc ctgctgcact cgaatgggta caactacctc | 600 |
| gattggtacc tccaaaagcc tgggcagtca ccccaactgc tgatctacct cgggagcaac | 660 |
| agagccagcg gagtgcctga ccgctttagc ggttccggat ccggcaccga cttcaccctg | 720 |
| aaaatcagcc gggtggaagc cgaggatgtc ggcgtgtact actgcatgca ggcactgcag | 780 |
| actctggggt acaccttcgg ccagggcacg aagctcgaga tcaaggcggc cgcaactacc | 840 |
| accccctgccc ctcggccgcc gactccggcc ccaaccatcg caagccaacc cctctccttg | 900 |
| cgccccgaag cttgccgccc ggccgcgggt ggagccgtgc atacccgggg ctggactttt | 960 |
| gcctgcgata tctacatttg gcccccgctg ccggcactt cggcgtgct cctgctgtcg | 1020 |
| ctggtcatca ccctttactg caagaggggc cggaagaagc tgctttacat cttcaagcag | 1080 |
| ccgttcatgc ggcccgtgca gacgactcag gaagaggacg gatgctcgtg cagattccct | 1140 |
| gaggaggaag agggggatg cgaactgcgc gtcaagttct cacggtccgc cgacgccccc | 1200 |
| gcatatcaac agggccagaa tcagctctac aacgagctga acctgggaag gagagaggag | 1260 |
| tacgacgtgc tggacaagcg acgcggacgc gacccggaga tggggggaa accacggcgg | 1320 |
| aaaaaccctc aggaaggact gtacaacgaa ctccagaaag acaagatggc ggaagcctac | 1380 |
| tcagaaatcg ggatgaaggg agagcggagg aggggaaagg gtcacgacgg gctgtaccag | 1440 |
| ggactgagca ccgccactaa ggatacctac gatgccttgc atatgcaagc actcccaccc | 1500 |
| cgg | 1503 |

```
<210> SEQ ID NO 26
<211> LENGTH: 501
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Met Leu Leu Leu Val Thr Ser Leu Leu Leu Cys Glu Leu Pro His Pro
1               5                   10                  15

Ala Phe Leu Leu Ile Pro Glu Val Gln Leu Val Gln Ser Gly Gly Gly
```

```
                20                  25                  30
Leu Val Lys Pro Gly Gly Ser Leu Arg Leu Ser Cys Ala Ala Ser Gly
            35                  40                  45
Phe Thr Phe Ser Ser Tyr Ser Met Asn Trp Val Arg Gln Ala Pro Gly
        50                  55                  60
Lys Gly Leu Glu Trp Val Ser Ser Ile Ser Ser Ser Ser Ser Tyr Ile
65                  70                  75                  80
Tyr Tyr Ala Asp Ser Val Lys Gly Arg Phe Thr Ile Ser Arg Asp Asn
                85                  90                  95
Ala Lys Asn Ser Leu Tyr Leu Gln Met Asn Ser Leu Arg Ala Glu Asp
            100                 105                 110
Thr Ala Val Tyr Tyr Cys Ala Arg Asp Phe Pro Tyr Asp Ser Ser Gly
            115                 120                 125
Tyr Tyr Ser Asp Ala Phe Asp Ile Trp Gly Gln Gly Thr Met Val Thr
        130                 135                 140
Val Ser Ser Gly Gly Gly Gly Ser Gly Gly Gly Gly Ser Gly Gly Gly
145                 150                 155                 160
Gly Ser Glu Ile Val Leu Thr Gln Ser Pro Leu Ser Leu Pro Val Thr
                165                 170                 175
Pro Gly Glu Pro Ala Ser Ile Ser Cys Arg Ser Ser Gln Ser Leu Leu
            180                 185                 190
His Ser Asn Gly Tyr Asn Tyr Leu Asp Trp Tyr Leu Gln Lys Pro Gly
            195                 200                 205
Gln Ser Pro Gln Leu Leu Ile Tyr Leu Gly Ser Asn Arg Ala Ser Gly
        210                 215                 220
Val Pro Asp Arg Phe Ser Gly Ser Gly Ser Gly Thr Asp Phe Thr Leu
225                 230                 235                 240
Lys Ile Ser Arg Val Glu Ala Glu Asp Val Gly Val Tyr Tyr Cys Met
                245                 250                 255
Gln Ala Leu Gln Thr Leu Gly Tyr Thr Phe Gly Gln Gly Thr Lys Leu
            260                 265                 270
Glu Ile Lys Ala Ala Ala Thr Thr Thr Pro Ala Pro Arg Pro Pro Thr
            275                 280                 285
Pro Ala Pro Thr Ile Ala Ser Gln Pro Leu Ser Leu Arg Pro Glu Ala
        290                 295                 300
Cys Arg Pro Ala Ala Gly Gly Ala Val His Thr Arg Gly Leu Asp Phe
305                 310                 315                 320
Ala Cys Asp Ile Tyr Ile Trp Ala Pro Leu Ala Gly Thr Cys Gly Val
                325                 330                 335
Leu Leu Leu Ser Leu Val Ile Thr Leu Tyr Cys Lys Arg Gly Arg Lys
            340                 345                 350
Lys Leu Leu Tyr Ile Phe Lys Gln Pro Phe Met Arg Pro Val Gln Thr
            355                 360                 365
Thr Gln Glu Glu Asp Gly Cys Ser Cys Arg Phe Pro Glu Glu Glu Glu
        370                 375                 380
Gly Gly Cys Glu Leu Arg Val Lys Phe Ser Arg Ser Ala Asp Ala Pro
385                 390                 395                 400
Ala Tyr Gln Gln Gly Gln Asn Gln Leu Tyr Asn Glu Leu Asn Leu Gly
                405                 410                 415
Arg Arg Glu Glu Tyr Asp Val Leu Asp Lys Arg Arg Gly Arg Asp Pro
            420                 425                 430
Glu Met Gly Gly Lys Pro Arg Arg Lys Asn Pro Gln Glu Gly Leu Tyr
            435                 440                 445
```

Asn Glu Leu Gln Lys Asp Lys Met Ala Glu Ala Tyr Ser Glu Ile Gly
            450                 455                 460

Met Lys Gly Glu Arg Arg Gly Lys Gly His Asp Gly Leu Tyr Gln
465                 470                 475                 480

Gly Leu Ser Thr Ala Thr Lys Asp Thr Tyr Asp Ala Leu His Met Gln
                485                 490                 495

Ala Leu Pro Pro Arg
            500

<210> SEQ ID NO 27
<211> LENGTH: 72
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 27
atctacatct gggcgcccct tggccgggact tgtggggtcc ttctcctgtc actggttatc      60
accctttact gc                                                          72

<210> SEQ ID NO 28
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Ile Trp Ala Pro Leu Ala Gly Thr Cys Gly Val Leu Leu Leu Ser Leu
1               5                   10                  15

Val Ile Thr Leu Tyr Cys
            20

<210> SEQ ID NO 29
<211> LENGTH: 135
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 29
accacgacgc cagcgccgcg accaccaaca ccggcgccca ccatcgcgtc gcagcccctg      60
tccctgcgcc cagaggcgtg ccggccagcg gcgggggggcg cagtgcacac gagggggctg    120
gacttcgcct gtgat                                                     135

<210> SEQ ID NO 30
<211> LENGTH: 47
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr
        35                  40                  45

<210> SEQ ID NO 31
<211> LENGTH: 42
<212> TYPE: PRT
<213> ORGANISM: Homo sapiens

<400> SEQUENCE: 31

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
            35                  40

<210> SEQ ID NO 32
<211> LENGTH: 106
<212> TYPE: PRT
<213> ORGANISM: Homo sapiens

<400> SEQUENCE: 32

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 33
<211> LENGTH: 126
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 33
aaacggggca gaaagaaact cctgtatata ttcaaacaac catttatgag accagtacaa      60
actactcaag aggaagatgg ctgtagctgc cgatttccag aagaagaaga aggaggatgt     120
gaactg                                                                126

<210> SEQ ID NO 34
<211> LENGTH: 42
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"

<400> SEQUENCE: 34

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 35
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 35
agagtgaagt tcagcaggag cgcagacgcc cccgcgtaca agcagggcca gaaccagctc       60
tataacgagc tcaatctagg acgaagagag gagtacgatg ttttggacaa gagacgtggc      120
cgggaccctg agatgggggg aaagccgaga aggaagaacc ctcaggaagg cctgtacaat      180
gaactgcaga agataagat ggcggaggcc tacagtgaga ttgggatgaa aggcgagcgc       240
cggaggggca aggggcacga tggcctttac cagggtctca gtacagccac caaggacacc      300
tacgacgccc ttcacatgca ggccctgccc cctcgc                               336

<210> SEQ ID NO 36
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 37
<211> LENGTH: 726
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

-continued

<400> SEQUENCE: 37

```
gacatccaga tgacacagac tacatcctcc ctgtctgcct ctctgggaga cagagtcacc    60
atcagttgca gggcaagtca ggacattagt aaatatttaa attggtatca gcagaaacca   120
gatggaactg ttaaactcct gatctaccat acatcaagat tacactcagg agtcccatca   180
aggttcagtg gcagtgggtc tggaacagat tattctctca ccattagcaa cctggagcaa   240
gaagatattg ccacttactt ttgccaacag ggtaatacgc ttccgtacac gttcggaggg   300
gggaccaagc tggagatcac aggtggcggt ggctcgggcg gtggtgggtc gggtggcggc   360
ggatctgagg tgaaactgca ggagtcagga cctggcctgg tggcgccctc acagagcctg   420
tccgtcacat gcactgtctc agggggtctca ttacccgact atggtgtaag ctggattcgc   480
cagcctccac gaaagggtct ggagtggctg gagtaatat ggggtagtga aaccacatac    540
tataattcag ctctcaaatc cagactgacc atcatcaagg acaactccaa gagccaagtt   600
ttcttaaaaa tgaacagtct gcaaactgat gacacagcca tttactactg tgccaaacat   660
tattactacg gtggtagcta tgctatggac tactggggcc aaggaacctc agtcaccgtc   720
tcctca                                                             726
```

<210> SEQ ID NO 38
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 38

```
Asp Ile Gln Met Thr Gln Thr Thr Ser Ser Leu Ser Ala Ser Leu Gly
1               5                   10                  15
Asp Arg Val Thr Ile Ser Cys Arg Ala Ser Gln Asp Ile Ser Lys Tyr
            20                  25                  30
Leu Asn Trp Tyr Gln Gln Lys Pro Asp Gly Thr Val Lys Leu Leu Ile
        35                  40                  45
Tyr His Thr Ser Arg Leu His Ser Gly Val Pro Ser Arg Phe Ser Gly
    50                  55                  60
Ser Gly Ser Gly Thr Asp Tyr Ser Leu Thr Ile Ser Asn Leu Glu Gln
65                  70                  75                  80
Glu Asp Ile Ala Thr Tyr Phe Cys Gln Gln Gly Asn Thr Leu Pro Tyr
                85                  90                  95
Thr Phe Gly Gly Gly Thr Lys Leu Glu Ile Thr Gly Gly Gly Gly Ser
            100                 105                 110
Gly Gly Gly Gly Ser Gly Gly Gly Ser Glu Val Lys Leu Gln Glu
        115                 120                 125
Ser Gly Pro Gly Leu Val Ala Pro Ser Gln Ser Leu Ser Val Thr Cys
    130                 135                 140
Thr Val Ser Gly Val Ser Leu Pro Asp Tyr Gly Val Ser Trp Ile Arg
145                 150                 155                 160
Gln Pro Pro Arg Lys Gly Leu Glu Trp Leu Gly Val Ile Trp Gly Ser
                165                 170                 175
Glu Thr Thr Tyr Tyr Asn Ser Ala Leu Lys Ser Arg Leu Thr Ile Ile
            180                 185                 190
Lys Asp Asn Ser Lys Ser Gln Val Phe Leu Lys Met Asn Ser Leu Gln
        195                 200                 205
```

Thr Asp Asp Thr Ala Ile Tyr Tyr Cys Ala Lys His Tyr Tyr Tyr Gly
            210                 215                 220

Gly Ser Tyr Ala Met Asp Tyr Trp Gly Gln Gly Thr Ser Val Thr Val
225                 230                 235                 240

Ser Ser

<210> SEQ ID NO 39
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 39
atgctgctgc tggtgaccag cctgctgctg tgcgaactgc cgcatccggc gtttctgctg      60
attccg                                                                66

<210> SEQ ID NO 40
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 41
<211> LENGTH: 85
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 41
ggctctgaaa gtgctgttgg aacaagaaaa gaccttcttc accttgctcg tgttgctggg      60
gtacctgtcc tgcaaagtca cctgt                                           85

<210> SEQ ID NO 42
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Met Ala Leu Lys Val Leu Leu Glu Gln Glu Lys Thr Phe Phe Thr Leu
1               5                   10                  15

Leu Val Leu Leu Gly Tyr Leu Ser Cys Lys Val Thr Cys
            20                  25

<210> SEQ ID NO 43

<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 43

```
atggcgctgc cggtgaccgc gctgctgctg ccgctggcgc tgctgctgca tgcggcgcgc    60
ccg                                                                  63
```

<210> SEQ ID NO 44
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 44

```
Met Ala Leu Pro Val Thr Ala Leu Leu Leu Pro Leu Ala Leu Leu Leu
1               5                   10                  15

His Ala Ala Arg Pro
            20
```

<210> SEQ ID NO 45
<211> LENGTH: 123
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 45

```
cggtcgaaga ggtccagact cttgcactcc gactacatga acatgactcc tagaaggccc    60
ggacccacta gaaagcacta ccagccgtac gcccctcctc gggatttcgc cgcataccgg   120
tcc                                                                 123
```

<210> SEQ ID NO 46
<211> LENGTH: 41
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 46

```
Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
            35                  40
```

<210> SEQ ID NO 47
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic polynucleotide"

<400> SEQUENCE: 47

```
agagtgaagt tcagccgctc agccgatgca ccggcctacc agcagggaca gaaccagctc    60
tacaacgagc tcaacctggg tcggcgggaa gaatatgacg tgctggacaa acggcgcggc   120
agagatccgg agatgggggg aaagccgagg aggaagaacc ctcaagaggg cctgtacaac   180
gaactgcaga aggacaagat ggcggaagcc tactccgaga tcggcatgaa gggagaacgc   240
cggagaggga agggtcatga cggactgtac cagggcctgt caactgccac taaggacact   300
tacgatgcgc tccatatgca agctttgccc ccgcgg                             336
```

<210> SEQ ID NO 48
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 48

```
Arg Val Lys Phe Ser Arg Ser Ala Asp Ala Pro Ala Tyr Gln Gln Gly
1               5                   10                  15
Gln Asn Gln Leu Tyr Asn Glu Leu Asn Leu Gly Arg Arg Glu Glu Tyr
            20                  25                  30
Asp Val Leu Asp Lys Arg Arg Gly Arg Asp Pro Glu Met Gly Gly Lys
        35                  40                  45
Pro Arg Arg Lys Asn Pro Gln Glu Gly Leu Tyr Asn Glu Leu Gln Lys
    50                  55                  60
Asp Lys Met Ala Glu Ala Tyr Ser Glu Ile Gly Met Lys Gly Glu Arg
65                  70                  75                  80
Arg Arg Gly Lys Gly His Asp Gly Leu Tyr Gln Gly Leu Ser Thr Ala
                85                  90                  95
Thr Lys Asp Thr Tyr Asp Ala Leu His Met Gln Ala Leu Pro Pro Arg
            100                 105                 110
```

<210> SEQ ID NO 49
<211> LENGTH: 201
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 49

```
gcggccgcgg tcggattcca agacatggaa tgcgtgccct gcggcgaccc gccacctcct    60
tacgagccgc actgcgcatc gaaggtcaac ctcgtgaaga tcgcgagcac cgcgtcctca   120
ccccgggata ctgctctggc cgccgtgatt tgttccgcct tggccaccgt gcttctggcc   180
ctgctgatcc tctgtgtgat c                                             201
```

<210> SEQ ID NO 50
<211> LENGTH: 67
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 50

Ala Ala Ala Val Gly Phe Gln Asp Met Glu Cys Val Pro Cys Gly Asp
1               5                   10                  15

Pro Pro Pro Pro Tyr Glu Pro His Cys Ala Ser Lys Val Asn Leu Val
            20                  25                  30

Lys Ile Ala Ser Thr Ala Ser Ser Pro Arg Asp Thr Ala Leu Ala Ala
        35                  40                  45

Val Ile Cys Ser Ala Leu Ala Thr Val Leu Leu Ala Leu Leu Ile Leu
    50                  55                  60

Cys Val Ile
65

<210> SEQ ID NO 51
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 51
gccgccgtga tttgttccgc cttggccacc gtgcttctgg ccctgctgat cctctgtgtg      60
atc                                                                   63

<210> SEQ ID NO 52
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Ala Ala Val Ile Cys Ser Ala Leu Ala Thr Val Leu Leu Ala Leu Leu
1               5                   10                  15

Ile Leu Cys Val Ile
            20

<210> SEQ ID NO 53
<211> LENGTH: 138
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 53
gcggccgcgg tcggattcca agacatggaa tgcgtgccct gcggcgaccc gccacctcct      60
tacgagccgc actgcgcatc gaaggtcaac ctcgtgaaga tcgcgagcac cgcgtcctca     120
ccccgggata ctgctctg                                                  138

<210> SEQ ID NO 54
<211> LENGTH: 46
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 54

Ala Ala Ala Val Gly Phe Gln Asp Met Glu Cys Val Pro Cys Gly Asp
1               5                   10                  15

Pro Pro Pro Pro Tyr Glu Pro His Cys Ala Ser Lys Val Asn Leu Val
            20                  25                  30

Lys Ile Ala Ser Thr Ala Ser Ser Pro Arg Asp Thr Ala Leu
        35                  40                  45

<210> SEQ ID NO 55
<211> LENGTH: 80
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 55
tacgagcctc actgcgccag caaagtcaac ttggtgaaga tcgcgagcac tgcctcgtcc    60
cctcgggaca ctgctctggc                                                80

<210> SEQ ID NO 56
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Tyr Glu Pro His Cys Ala Ser Lys Val Asn Leu Val Lys Ile Ala Ser
1               5                   10                  15

Thr Ala Ser Ser Pro Arg Asp Thr Ala Leu
            20                  25

<210> SEQ ID NO 57
<211> LENGTH: 222
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 57
gcggccgcgc cgccccctcg gcccccgact cctgccccga cgatcgcttc ccaacctctc    60
tcgctgcgcc cggaagcatg ccggcccgcc gccggtggcg ctgtccacac tcgcggactg   120
gactttgata ccgcactggc ggccgtgatc tgtagcgccc tggccaccgt gctgctggcg   180
ctgctcatcc tttgcgtgat ctactgcaag cggcagccta gg                      222

<210> SEQ ID NO 58
<211> LENGTH: 74
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 58

Ala Ala Ala Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Asp Thr Ala Leu Ala Ala
        35                  40                  45

Val Ile Cys Ser Ala Leu Ala Thr Val Leu Leu Ala Leu Leu Ile Leu
    50                  55                  60

Cys Val Ile Tyr Cys Lys Arg Gln Pro Arg
65                  70

<210> SEQ ID NO 59
<211> LENGTH: 123
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 59
cggtcgaaga ggtccagact cttgcactcc gactacatga acatgactcc tagaaggccc        60
ggacccacta gaaagcacta ccagccgtac gcccctcctc gggatttcgc cgcataccgg       120
tcc                                                                    123

<210> SEQ ID NO 60
<211> LENGTH: 41
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 60

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 61
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 61
cgcgtgaaat tagccgcag cgcggatgcg ccggcgtatc agcagggcca gaaccagctg         60
tataacgaac tgaacctggg ccgccgcgaa gaatatgatg tgctggataa cgccgcggc        120 cgcgatccgg aaatgggcgg caaaccgcgc cgcaaaaacc cgcaggaagg cctgtataac       180
gaactgcaga agataaaat ggcggaagcg tatagcgaaa ttggcatgaa aggcgaacgc        240
cgccgcggca aaggccatga tggcctgtat cagggcctga gcaccgcgac caaagatacc       300
tatgatgcgc tgcatatgca ggcgctgccg ccgcgc                                 336

<210> SEQ ID NO 62
<211> LENGTH: 112

<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 62

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 63
<211> LENGTH: 93
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 63
cgcgcgaaac gcagcggcag cggcgcgacc aactttagcc tgctgaaaca ggcgggcgat      60
gtggaagaaa acccgggccc gcgagcaaag agg                                  93

<210> SEQ ID NO 64
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 64

Arg Ala Lys Arg Ser Gly Ser Gly Ala Thr Asn Phe Ser Leu Leu Lys
1               5                   10                  15

Gln Ala Gly Asp Val Glu Glu Asn Pro Gly Pro Arg Ala Lys Arg
            20                  25                  30

<210> SEQ ID NO 65
<211> LENGTH: 78
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 65
agagctaaac gctctgggtc tggtgaagga cgaggtagcc ttcttacgtg cggagacgtg      60
gaggaaaacc caggaccc                                                   78

<210> SEQ ID NO 66
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 66

Arg Ala Lys Arg Ser Gly Ser Gly Glu Gly Arg Gly Ser Leu Leu Thr
1               5                   10                  15

Cys Gly Asp Val Glu Glu Asn Pro Gly Pro
            20                  25

<210> SEQ ID NO 67
<211> LENGTH: 1005
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 67

```
aggaaggttt gcaatggaat cggtataggg gagtttaagg attcacttag cataaacgct    60
actaatatta aacacttcaa aaactgtacg agtataagtg gagatcttca cattttgccg   120
gttgcattcc gaggcgattc attcacccac acgccaccgc ttgacccaca agaattggat   180
attcttaaaa ccgttaaaga ataacggggt ttttgctca ttcaagcgtg gccagaaaat   240
cgcactgacc tccatgcttt cgagaacctg gagattataa gaggacgaac taagcagcat   300
ggtcaattct cccttgctgt ggtcagcctg aacatcacca gtcttggttt gcggtccctc   360
aaggaaattt cagatggaga tgtcatcata agcggcaaca agaatttgtg ctatgcaaat   420
accataaact ggaaaaaact gtttggcact tccggccaga aaaccaagat tatttcaaat   480
cggggtgaga acagctgcaa agccaccggc caggtttgtc atgccttgtg ctctccggaa   540
ggctgttggg ggccagaacc cagggactgc gtcagttgca gaaacgtctc aagaggccgc   600
gaatgcgttg acaagtgtaa cctccttgag ggtgagccac gagagtttgt tgagaacagc   660
gagtgtatac aatgtcaccc tgaatgtttg ccccaggcta tgaatataac ctgcacaggc   720
cgcgggcctg ataactgcat ccagtgtgct cattacatag atggacctca ctgtgtgaaa   780
acctgcccgg ccggagttat gggagaaaac aacactctgg tgtggaaata cgctgatgca   840
ggccacgtgt gccaccttg tcacccgaat tgtacatatg ggtgtaccgg tcctggactt   900
gaaggttgcc ctaccaatgg ccctaaaata cccagtatcg caactggcat ggtaggcgct   960
cttctcttgc tcttggtagt tgctctcggc ataggtcttt ttatg              1005
```

<210> SEQ ID NO 68
<211> LENGTH: 335
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 68

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Cys Asn Leu
        195                 200                 205

Leu Glu Gly Glu Pro Arg Glu Phe Val Glu Asn Ser Glu Cys Ile Gln
    210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255

His Cys Val Lys Thr Cys Pro Ala Gly Val Met Gly Glu Asn Asn Thr
            260                 265                 270

Leu Val Trp Lys Tyr Ala Asp Ala Gly His Val Cys His Leu Cys His
        275                 280                 285

Pro Asn Cys Thr Tyr Gly Cys Thr Gly Pro Gly Leu Glu Gly Cys Pro
    290                 295                 300

Thr Asn Gly Pro Lys Ile Pro Ser Ile Ala Thr Gly Met Val Gly Ala
305                 310                 315                 320

Leu Leu Leu Leu Leu Val Val Ala Leu Gly Ile Gly Leu Phe Met
                325                 330                 335

<210> SEQ ID NO 69
<211> LENGTH: 1482
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 69
atgcttcttt tggtgacttc ccttttgctg tgcgagttgc cacaccccgc cttcctgctt     60
attccccagg tacagctcca gcagagtggc ccagggctcg tgaagccaag ccagacgctg    120
tccctgactt gtgcaatttc aggggattca gtttcatcaa atagcgcggc gtggaattgg    180

-continued

| | |
|---|---|
| attcgacaat ctccttcccg agggttggaa tggcttggac gaacatatta cagatccaaa | 240 |
| tggtataacg actatgcggt atcagtaaag tcaagaataa ccattaaccc cgacacaagc | 300 |
| aagaaccaat tctctttgca gcttaactct gtcacgccag aagacacggc agtctattat | 360 |
| tgcgctcgcg aggtaacggg tgacctggaa gacgcttttg acatttgggg gcagggtacg | 420 |
| atggtgacag tcagttcagg gggcggtggg agtggggggag ggggtagcgg ggggggaggg | 480 |
| tcagacattc agatgaccca gtccccttca tccttgtctg cctccgtcgg tgacagggtg | 540 |
| acaataacat gcagagcaag ccaaacaatc tggagctatc tcaactggta ccagcagcga | 600 |
| ccaggaaaag cgccaaacct gctgatttac gctgcttcct ccctccaatc aggcgtgcct | 660 |
| agtagattta gcggtagggg ctccggcacc gattttacgc tcactataag ctctcttcaa | 720 |
| gcagaagatt ttgcgactta ttactgccag cagtcctata gtatacctca gactttcgga | 780 |
| cagggtacca agttggagat taaggcggcc gcaactacca cccctgcccc tcggccgccg | 840 |
| actccggccc caaccatcgc aagccaaccc tctccttgc gccccgaagc ttgccgcccg | 900 |
| gccgcgggtg gagccgtgca tacccggggg ctggactttg cctgcgatat ctacatttgg | 960 |
| gccccgctgg ccggcacttg cggcgtgctc ctgctgtcgc tggtcatcac cctttactgc | 1020 |
| aagagggggcc ggaagaagct gctttacatc ttcaagcagc cgttcatgcg gcccgtgcag | 1080 |
| acgactcagg aagaggacgg atgctcgtgc agattccctg aggaggaaga gggggatgc | 1140 |
| gaactgcgcg tcaagttctc acggtccgcc gacgcccccg catatcaaca gggccagaat | 1200 |
| cagctctaca cgagctgaa cctgggaagg agagaggagt acgacgtgct ggacaagcga | 1260 |
| cgcggacgcg acccggagat gggggggaaa ccacggcgga aaaaccctca ggaaggactg | 1320 |
| tacaacgaac tccagaaaga caagatggcg gaagcctact cagaaatcgg gatgaaggga | 1380 |
| gagcggagga ggggaaaggg tcacgacggg ctgtaccagg gactgagcac cgccactaag | 1440 |
| gatacctacg atgccttgca tatgcaagca ctcccacccc gg | 1482 |

<210> SEQ ID NO 70
<211> LENGTH: 494
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 70

Met Leu Leu Leu Val Thr Ser Leu Leu Cys Glu Leu Pro His Pro
1               5                   10                  15

Ala Phe Leu Leu Ile Pro Gln Val Gln Leu Gln Gln Ser Gly Pro Gly
                20                  25                  30

Leu Val Lys Pro Ser Gln Thr Leu Ser Leu Thr Cys Ala Ile Ser Gly
            35                  40                  45

Asp Ser Val Ser Ser Asn Ser Ala Ala Trp Asn Trp Ile Arg Gln Ser
        50                  55                  60

Pro Ser Arg Gly Leu Glu Trp Leu Gly Arg Thr Tyr Tyr Arg Ser Lys
65                  70                  75                  80

Trp Tyr Asn Asp Tyr Ala Val Ser Val Lys Ser Arg Ile Thr Ile Asn
                85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Arg Glu Val Thr Gly Asp
        115                 120                 125

Leu Glu Asp Ala Phe Asp Ile Trp Gly Gln Gly Thr Met Val Thr Val
130                 135                 140

Ser Ser Gly Gly Gly Ser Gly Gly Gly Ser Gly Gly Gly Gly
145                 150                 155                 160

Ser Asp Ile Gln Met Thr Gln Ser Pro Ser Ser Leu Ser Ala Ser Val
                165                 170                 175

Gly Asp Arg Val Thr Ile Thr Cys Arg Ala Ser Gln Thr Ile Trp Ser
            180                 185                 190

Tyr Leu Asn Trp Tyr Gln Gln Arg Pro Gly Lys Ala Pro Asn Leu Leu
        195                 200                 205

Ile Tyr Ala Ala Ser Ser Leu Gln Ser Gly Val Pro Ser Arg Phe Ser
210                 215                 220

Gly Arg Gly Ser Gly Thr Asp Phe Thr Leu Thr Ile Ser Ser Leu Gln
225                 230                 235                 240

Ala Glu Asp Phe Ala Thr Tyr Tyr Cys Gln Gln Ser Tyr Ser Ile Pro
                245                 250                 255

Gln Thr Phe Gly Gln Gly Thr Lys Leu Glu Ile Lys Ala Ala Ala Thr
                260                 265                 270

Thr Thr Pro Ala Pro Arg Pro Pro Thr Pro Ala Pro Thr Ile Ala Ser
            275                 280                 285

Gln Pro Leu Ser Leu Arg Pro Glu Ala Cys Arg Pro Ala Ala Gly Gly
290                 295                 300

Ala Val His Thr Arg Gly Leu Asp Phe Ala Cys Asp Ile Tyr Ile Trp
305                 310                 315                 320

Ala Pro Leu Ala Gly Thr Cys Gly Val Leu Leu Leu Ser Leu Val Ile
                325                 330                 335

Thr Leu Tyr Cys Lys Arg Gly Arg Lys Lys Leu Leu Tyr Ile Phe Lys
                340                 345                 350

Gln Pro Phe Met Arg Pro Val Gln Thr Thr Gln Glu Glu Asp Gly Cys
                355                 360                 365

Ser Cys Arg Phe Pro Glu Glu Glu Glu Gly Gly Cys Glu Leu Arg Val
            370                 375                 380

Lys Phe Ser Arg Ser Ala Asp Ala Pro Ala Tyr Gln Gln Gly Gln Asn
385                 390                 395                 400

Gln Leu Tyr Asn Glu Leu Asn Leu Gly Arg Arg Glu Glu Tyr Asp Val
                405                 410                 415

Leu Asp Lys Arg Arg Gly Arg Asp Pro Glu Met Gly Gly Lys Pro Arg
            420                 425                 430

Arg Lys Asn Pro Gln Glu Gly Leu Tyr Asn Glu Leu Gln Lys Asp Lys
        435                 440                 445

Met Ala Glu Ala Tyr Ser Glu Ile Gly Met Lys Gly Glu Arg Arg Arg
    450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg
                485                 490

<210> SEQ ID NO 71
<211> LENGTH: 1485
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 71

```
atgcttctcc tggtcaccct cctgctcctc tgcgaactgc ctcaccctgc cttccttctg    60
attcctgaca ctgacattca gatgactcag accacctctt ccttgtccgc gtcactggga   120
gacagagtga ccatctcgtg tcgcgcaagc caggatatct ccaagtacct gaactggtac   180
caacagaagc ccgacgggac tgtgaagctg ctgatctacc acacctcacg cctgcacagc   240
ggagtgccaa gcagattctc cggctccggc tcgggaaccg attactcgct taccattagc   300
aacctcgagc aggaggacat cgctacctac ttctgccagc aaggaaatac cctgccctac   360
accttcggcg gaggaaccaa attggaaatc accggctcca cgagcggctc cgggaagcct   420
ggttccgggg aaggctccac taagggtgaa gtgaagctcc aggagtccgg ccccggcctg   480
gtggcgccgt cgcaatcact ctctgtgacc tgtaccgtgt cgggagtgtc cctgcctgat   540
tacggcgtga gctggattcg gcagccgccg cggaagggcc tggaatggct gggtgtcatc   600
tggggatccg agactaccta ctacaactcg gccctgaagt cccgcctgac tatcatcaaa   660
gacaactcga agtcccaggt ctttctgaag atgaactccc tgcaaactga cgacaccgcc   720
atctattact gtgctaagca ctactactac ggtggaagct atgctatgga ctactggggc   780
caggggacat ccgtgacagt cagctccgcg gccgcaacta ccacccctgc ccctcggccg   840
ccgactccgg ccccaaccat cgcaagccaa cccctctcct gcgcccccga agcttgccgc   900
ccggccgcgg gtggagccgt gcataccccgg gggctggact ttgcctgcga tatctacatt   960
tgggcccgc tggccggcac ttgcggcgtg ctcctgctgt cgctggtcat caccctttac  1020
tgcaagaggg gccggaagaa gctgctttac atcttcaagc agccgttcat gcggcccgtg  1080
cagacgactc aggaagagga cggatgctcg tgcagattcc ctgaggagga gaggggggga  1140
tgcgaactgc gcgtcaagtt ctcacggtcc gccgacgccc ccgcatatca acagggccag  1200
aatcagctct acaacgagct gaacctggga aggagagagg agtacgacgt gctggacaag  1260
cgacgcggac gcgacccgga gatggggggg aaaccacggc ggaaaaaccc tcaggaagga  1320
ctgtacaacg aactccagaa agacaagatg gcggaagcct actcagaaat cgggatgaag  1380
ggagagcgga ggaggggaaa gggtcacgac gggctgtacc agggactgag caccgccact  1440
aaggatacct acgatgcctt gcatatgcaa gcactcccac cccgg               1485
```

<210> SEQ ID NO 72
<211> LENGTH: 495
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 72

```
Met Leu Leu Leu Val Thr Ser Leu Leu Cys Glu Leu Pro His Pro
1               5                   10                  15

Ala Phe Leu Leu Ile Pro Asp Thr Asp Ile Gln Met Thr Gln Thr Thr
            20                  25                  30

Ser Ser Leu Ser Ala Ser Leu Gly Asp Arg Val Thr Ile Ser Cys Arg
        35                  40                  45

Ala Ser Gln Asp Ile Ser Lys Tyr Leu Asn Trp Tyr Gln Gln Lys Pro
    50                  55                  60

Asp Gly Thr Val Lys Leu Leu Ile Tyr His Thr Ser Arg Leu His Ser
65                  70                  75                  80
```

-continued

```
Gly Val Pro Ser Arg Phe Ser Gly Ser Gly Thr Asp Tyr Ser
                85                  90                  95

Leu Thr Ile Ser Asn Leu Glu Gln Glu Asp Ile Ala Thr Tyr Phe Cys
                100                 105                 110

Gln Gln Gly Asn Thr Leu Pro Tyr Thr Phe Gly Gly Gly Thr Lys Leu
                115                 120                 125

Glu Ile Thr Gly Ser Thr Ser Gly Ser Gly Lys Pro Gly Ser Gly Glu
        130                 135                 140

Gly Ser Thr Lys Gly Glu Val Lys Leu Gln Glu Ser Gly Pro Gly Leu
145                 150                 155                 160

Val Ala Pro Ser Gln Ser Leu Ser Val Thr Cys Thr Val Ser Gly Val
                165                 170                 175

Ser Leu Pro Asp Tyr Gly Val Ser Trp Ile Arg Gln Pro Pro Arg Lys
                180                 185                 190

Gly Leu Glu Trp Leu Gly Val Ile Trp Gly Ser Glu Thr Thr Tyr Tyr
                195                 200                 205

Asn Ser Ala Leu Lys Ser Arg Leu Thr Ile Ile Lys Asp Asn Ser Lys
        210                 215                 220

Ser Gln Val Phe Leu Lys Met Asn Ser Leu Gln Thr Asp Asp Thr Ala
225                 230                 235                 240

Ile Tyr Tyr Cys Ala Lys His Tyr Tyr Gly Gly Ser Tyr Ala Met
                245                 250                 255

Asp Tyr Trp Gly Gln Gly Thr Ser Val Thr Val Ser Ser Ala Ala Ala
                260                 265                 270

Thr Thr Thr Pro Ala Pro Arg Pro Pro Thr Pro Ala Pro Thr Ile Ala
                275                 280                 285

Ser Gln Pro Leu Ser Leu Arg Pro Glu Ala Cys Arg Pro Ala Ala Gly
        290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
                325                 330                 335

Ile Thr Leu Tyr Cys Lys Arg Gly Arg Lys Lys Leu Leu Tyr Ile Phe
                340                 345                 350

Lys Gln Pro Phe Met Arg Pro Val Gln Thr Thr Gln Glu Glu Asp Gly
                355                 360                 365

Cys Ser Cys Arg Phe Pro Glu Glu Glu Glu Gly Gly Cys Glu Leu Arg
        370                 375                 380

Val Lys Phe Ser Arg Ser Ala Asp Ala Pro Ala Tyr Gln Gln Gly Gln
385                 390                 395                 400

Asn Gln Leu Tyr Asn Glu Leu Asn Leu Gly Arg Arg Glu Glu Tyr Asp
                405                 410                 415

Val Leu Asp Lys Arg Arg Gly Arg Asp Pro Glu Met Gly Gly Lys Pro
                420                 425                 430

Arg Arg Lys Asn Pro Gln Glu Gly Leu Tyr Asn Glu Leu Gln Lys Asp
        435                 440                 445

Lys Met Ala Glu Ala Tyr Ser Glu Ile Gly Met Lys Gly Glu Arg Arg
450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg
                485                 490                 495
```

<210> SEQ ID NO 73
<211> LENGTH: 1470
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 73

```
atgcttctcc tggtcacctc cctgctcctc tgcgaactgc ctcaccctgc cttccttctg      60
attcctgaca ttcagatgac tcagaccacc tcttccttgt ccgcgtcact gggagacaga     120
gtgaccatct cgtgtcgcgc aagccaggat atctccaagt acctgaactg gtaccaacag     180
aagcccgacg ggactgtgaa gctgctgatc taccacacct cacgcctgca cagcggagtg     240
ccaagcagat tctccggctc cggctcggga accgattact cgcttaccat tagcaacctc     300
gagcaggagg acatcgctac ctacttctgc cagcaaggaa ataccctgcc ctacaccttc     360
ggcggaggaa ccaaattgga aatcaccggc ggaggaggct ccggggagg aggttccggg       420
ggcggggt tccgaagtgaa gctccaggag tccggccccg gctggtggc gccgtcgcaa        480
tcactctctg tgacctgtac cgtgtcggga gtgtccctgc ctgattacgg cgtgagctgg     540
attcggcagc cgccgcggaa gggcctggaa tggctgggtg tcatctgggg atccgagact     600
acctactaca actcggccct gaagtccgc ctgactatca tcaaagacaa ctcgaagtcc      660
caggtctttc tgaagatgaa ctccctgcaa actgacgaca ccgccatcta ttactgtgct     720
aagcactact actacggtgg aagctatgct atggactact gggggcaagg cacttcggtg     780
actgtgtcaa gcgcggccgc aactaccacc cctgcccctc ggccgccgac tccggcccca     840
accatcgcaa gccaacccct ctccttgcgc cccgaagctt gccgcccggc cgcgggtgga     900
gccgtgcata cccgggggct ggactttgcc tgcgatatct acatttgggc cccgctggcc     960
ggcacttgcg gcgtgctcct gctgtcgctg gtcatcaccc tttactgcaa gaggggccgg    1020
aagaagctgc tttacatctt caagcagccg ttcatgcggc ccgtgcagac gactcaggaa    1080
gaggacggat gctcgtgcag attccctgag gaggaagagg ggggatgcga actgcgcgtc    1140
aagttctcac ggtccgccga cgccccccgca tatcaacagg gccagaatca gctctacaac    1200
gagctgaacc tgggaaggag agaggagtac gacgtgctgg acaagcgacg cggacgcgac    1260
ccggagatgg gggggaaacc acggcggaaa aaccctcagg aaggactgta caacgaactc    1320
cagaaagaca gatggcggaa agcctactca gaaatcggga tgaagggaga gcggaggagg    1380
ggaaagggtc acgacgggct gtaccaggga ctgagcaccg ccactaagga tacctacgat    1440
gccttgcata tgcaagcact cccaccccgg                                     1470
```

<210> SEQ ID NO 74
<211> LENGTH: 490
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 74

```
Met Leu Leu Leu Val Thr Ser Leu Leu Cys Glu Leu Pro His Pro
1               5                   10                  15
Ala Phe Leu Leu Ile Pro Asp Ile Gln Met Thr Gln Thr Thr Ser Ser
            20                  25                  30
```

```
Leu Ser Ala Ser Leu Gly Asp Arg Val Thr Ile Ser Cys Arg Ala Ser
            35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
                100                 105                 110

Gly Asn Thr Leu Pro Tyr Thr Phe Gly Gly Gly Thr Lys Leu Glu Ile
            115                 120                 125

Thr Gly Gly Gly Gly Ser Gly Gly Gly Gly Ser Gly Gly Gly Gly Ser
130                 135                 140

Glu Val Lys Leu Gln Glu Ser Gly Pro Gly Leu Val Ala Pro Ser Gln
145                 150                 155                 160

Ser Leu Ser Val Thr Cys Thr Val Ser Gly Val Ser Leu Pro Asp Tyr
                165                 170                 175

Gly Val Ser Trp Ile Arg Gln Pro Pro Arg Lys Gly Leu Glu Trp Leu
            180                 185                 190

Gly Val Ile Trp Gly Ser Glu Thr Thr Tyr Tyr Asn Ser Ala Leu Lys
            195                 200                 205

Ser Arg Leu Thr Ile Ile Lys Asp Asn Ser Lys Ser Gln Val Phe Leu
    210                 215                 220

Lys Met Asn Ser Leu Gln Thr Asp Asp Thr Ala Ile Tyr Tyr Cys Ala
225                 230                 235                 240

Lys His Tyr Tyr Tyr Gly Gly Ser Tyr Ala Met Asp Tyr Trp Gly Gln
                245                 250                 255

Gly Thr Ser Val Thr Val Ser Ser Ala Ala Ala Thr Thr Thr Pro Ala
            260                 265                 270

Pro Arg Pro Pro Thr Pro Ala Pro Thr Ile Ala Ser Gln Pro Leu Ser
            275                 280                 285

Leu Arg Pro Glu Ala Cys Arg Pro Ala Ala Gly Gly Ala Val His Thr
            290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
            355                 360                 365

Pro Glu Glu Glu Glu Gly Gly Cys Glu Leu Arg Val Lys Phe Ser Arg
            370                 375                 380

Ser Ala Asp Ala Pro Ala Tyr Gln Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
            435                 440                 445
```

Tyr Ser Glu Ile Gly Met Lys Gly Glu Arg Arg Gly Lys Gly His
450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490

<210> SEQ ID NO 75
<211> LENGTH: 1467
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 75

```
atgctgctgc tggtgaccag cctgctgctg tgcgaactgc gcatccggc gtttctgctg      60
attccggata ttcagatgac ccagaccacc agcagcctga gcgcgagcct gggcgatcgc    120
gtgaccatta gctgccgcgc gagccaggat attagcaaat atctgaactg gtatcagcag    180
aaaccggatg gcaccgtgaa actgctgatt tatcatacca gccgcctgca tagcggcgtg    240
ccgagccgct ttagcggcag cggcagcggc accgattata gcctgaccat tagcaacctg    300
gaacaggaag atattgcgac ctatttttgc cagcagggca caccctgcc gtataccttt    360
ggcggcggca ccaaactgga aattaccggc ggcggcggca gcggcggcgg cggcagcggc    420
ggcggcggca gcgaagtgaa actgcaggaa agcggcccgg gcctggtggc gccgagccag    480
agcctgagcg tgacctgcac cgtgagcggc gtgagcctgc cggattatgg cgtgagctgg    540
attcgccagc cgccgcgcaa aggcctggaa tggctgggcg tgatttgggg cagcgaaacc    600
acctattata cagcgcgct gaaaagccgc ctgaccatta ttaaagataa cagcaaaagc    660
caggtgtttc tgaaaatgaa cagcctgcag accgatgata ccgcgattta ttattgcgcg    720
aaacattatt attatggcgg cagctatgcg atggattatt ggggccaggg caccagcgtg    780
accgtgagca gcgcggcggc gccggcgccg cgcccgccga ccccggcgcc gaccattgcg    840
agccagccgc tgagcctgcg cccggaagcg tgccgcccgg cggcgggcgg cgcggtgcat    900
acccgcggcc tggattttgt gcagccgatg gcgctgattg tgctgggcgg cgtggcgggc    960
ctgctgctgt ttattggcct gggcattttt ttttgcgtgc gctgccgcc cgccgcaaa   1020
aaactgctgt atatttttaa acagccgttt atgcgcccgg tgcagaccac ccaggaagaa   1080
gatggctgca gctgccgctt tccggaagaa gaagaaggcg gctgcgaact gcgcgtgaaa   1140
tttagccgca gcgcggatgc gccggcgtat cagcagggcc agaaccagct gtataacgaa   1200
ctgaacctgg gccgccgcga agaatatgat gtgctggata acgccgcgg ccgcgatccg   1260
gaaatgggcg gcaaaccgcg ccgcaaaaac ccgcaggaag gcctgtataa cgaactgcag   1320
aaagataaaa tggcggaagc gtatagcgaa attggcatga aggcgaacg ccgccgcggc   1380
aaaggccatg atggcctgta tcagggcctg agcaccgcga ccaaagatac ctatgatgcg   1440
ctgcatatgc aggcgctgcc gccgcgc                                      1467
```

<210> SEQ ID NO 76
<211> LENGTH: 489
<212> TYPE: PRT
<213> ORGANISM: Artificial Sequence
<220> FEATURE:
<221> NAME/KEY: source
<223> OTHER INFORMATION: /note="Description of Artificial Sequence:

-continued

Synthetic polypeptide"

<400> SEQUENCE: 76

Met Leu Leu Leu Val Thr Ser Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Gly Gly Gly Ser Gly Gly Gly Ser Gly Gly Gly Gly Ser
    130                 135                 140

Glu Val Lys Leu Gln Glu Ser Gly Pro Gly Leu Val Ala Pro Ser Gln
145                 150                 155                 160

Ser Leu Ser Val Thr Cys Thr Val Ser Gly Val Ser Leu Pro Asp Tyr
                165                 170                 175

Gly Val Ser Trp Ile Arg Gln Pro Pro Arg Lys Gly Leu Glu Trp Leu
            180                 185                 190

Gly Val Ile Trp Gly Ser Glu Thr Thr Tyr Tyr Asn Ser Ala Leu Lys
        195                 200                 205

Ser Arg Leu Thr Ile Ile Lys Asp Asn Ser Lys Ser Gln Val Phe Leu
    210                 215                 220

Lys Met Asn Ser Leu Gln Thr Asp Asp Thr Ala Ile Tyr Tyr Cys Ala
225                 230                 235                 240

Lys His Tyr Tyr Tyr Gly Gly Ser Tyr Ala Met Asp Tyr Trp Gly Gln
                245                 250                 255

Gly Thr Ser Val Thr Val Ser Ser Ala Ala Ala Pro Ala Pro Arg Pro
            260                 265                 270

Pro Thr Pro Ala Pro Thr Ile Ala Ser Gln Pro Leu Ser Leu Arg Pro
        275                 280                 285

Glu Ala Cys Arg Pro Ala Ala Gly Gly Ala Val His Thr Arg Gly Leu
    290                 295                 300

Asp Phe Val Gln Pro Met Ala Leu Ile Val Leu Gly Gly Val Ala Gly
305                 310                 315                 320

Leu Leu Leu Phe Ile Gly Leu Gly Ile Phe Phe Cys Val Arg Cys Arg
                325                 330                 335

Pro Arg Arg Lys Lys Leu Leu Tyr Ile Phe Lys Gln Pro Phe Met Arg
            340                 345                 350

Pro Val Gln Thr Thr Gln Glu Glu Asp Gly Cys Ser Cys Arg Phe Pro
        355                 360                 365

Glu Glu Glu Glu Gly Gly Cys Glu Leu Arg Val Lys Phe Ser Arg Ser
    370                 375                 380

Ala Asp Ala Pro Ala Tyr Gln Gln Gly Gln Asn Gln Leu Tyr Asn Glu
385                 390                 395                 400

| | | | | | | | | | | | |
|---|---|---|---|---|---|---|---|---|---|---|---|
|Leu|Asn|Leu|Gly|Arg|Arg|Glu|Glu|Tyr|Asp|Val|Leu|Asp|Lys|Arg|Arg|
| | | | |405| | | | |410| | | | |415| |

Gly Arg Asp Pro Glu Met Gly Gly Lys Pro Arg Arg Lys Asn Pro Gln
            420                 425                 430

Glu Gly Leu Tyr Asn Glu Leu Gln Lys Asp Lys Met Ala Glu Ala Tyr
        435                 440                 445

Ser Glu Ile Gly Met Lys Gly Glu Arg Arg Arg Gly Lys Gly His Asp
450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg
                485

<210> SEQ ID NO 77
<211> LENGTH: 1467
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 77

```
atgctgctgc tggtcaccag cctgctgctg tgcgagctcc ctcacccgc ctttctgctt      60
atcccggaca ttcagatgac acagaccacc tcgagcttgt ccgcgtcgct gggcgatcgc    120
gtgaccatct cctgccgggc ctcccaagac atttcaaagt atctcaactg gtaccagcag    180
aagccggacg gaaccgtgaa actgctgatc taccatacca gccgcctgca ctccggcgtg    240
ccgtcccgct ctccggatc gggttccgga actgactact cactgactat ctccaacttg    300
gaacaagagg acatcgccac ttacttctgt caacaaggaa ataccccttcc ctacaccttc    360
ggggggggta ccaagctgga gatcactggg ggcggaggct ccggtggagg cggatccggc    420
ggtggaggga gcgaagtcaa gctgcaggaa tcaggaccag gactcgtggc gccatcccag    480
tccctgtcgg tgacctgtac tgtctccgga gtcagcctcc ccgattacgg agtgtcatgg    540
attaggcaac cccaagaaa agggctgaa tggctcggag tgatctgggg ctccgaaaacc    600
acctactaca actcggcgct gaagtcccgg ctgaccatca tcaaggacaa ctccaagagc    660
caagtgttct tgaagatgaa cagcttgcag accgacgata ccgcaatcta ctactgtgcc    720
aagcactatt actacggggg gtcttacgcc atggactact ggggacaggg cacctccgtg    780
actgtgtcgt ccgcggccgc gcccgcccct cggcccccga ctcctgcccc gacgatcgct    840
tcccaacctc tctcgctgcg cccggaagca tgccggcccg ccgccggtgg cgctgtccac    900
actcgcggac tggactttga taccgcactg cgggccgtga tctgtagcgc cctggccacc    960
gtgctgctgg cgctgctcat cctttgcgtg atctactgca agcggcagcc taggcgaaag   1020
aagctcctct acattttcaa gcaacccttc atgcgccccg tgcaaaccac caggaggag   1080
gatgatgct catgccggtt ccctgaggaa gaagagggcg ttgcgagct cagagtgaaa   1140
ttcagccggt cggctgacgc cccggcgtac cagcagggcc agaaccagct gtacaatgag   1200
ctcaacctgg ggcgccgcga agagtacgac gtgctggaca gaggagagg cagagatccg   1260
gaaatgggcg gaaagccaag gcggaagaac ccgcaggaag gtctttacaa cgaactgcag   1320
aaggacaaga tggccgaggc ctactccgag attggatga agggagaaag acggagggga   1380
aagggacatg acggacttta ccagggcctg agcactgcca cgaaggacac ctatgatgcc   1440
ctgcacatgc aggcgctgcc gcctcgg                                       1467
```

<210> SEQ ID NO 78
<211> LENGTH: 489
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 78

```
Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Gly Gly Gly Ser Gly Gly Gly Ser Gly Gly Gly Gly Ser
    130                 135                 140

Glu Val Lys Leu Gln Glu Ser Gly Pro Gly Leu Val Ala Pro Ser Gln
145                 150                 155                 160

Ser Leu Ser Val Thr Cys Thr Val Ser Gly Val Ser Leu Pro Asp Tyr
                165                 170                 175

Gly Val Ser Trp Ile Arg Gln Pro Pro Arg Lys Gly Leu Glu Trp Leu
            180                 185                 190

Gly Val Ile Trp Gly Ser Glu Thr Thr Tyr Tyr Asn Ser Ala Leu Lys
        195                 200                 205

Ser Arg Leu Thr Ile Ile Lys Asp Asn Ser Lys Ser Gln Val Phe Leu
    210                 215                 220

Lys Met Asn Ser Leu Gln Thr Asp Asp Thr Ala Ile Tyr Tyr Cys Ala
225                 230                 235                 240

Lys His Tyr Tyr Tyr Gly Gly Ser Tyr Ala Met Asp Tyr Trp Gly Gln
                245                 250                 255

Gly Thr Ser Val Thr Val Ser Ser Ala Ala Ala Pro Ala Pro Arg Pro
            260                 265                 270

Pro Thr Pro Ala Pro Thr Ile Ala Ser Gln Pro Leu Ser Leu Arg Pro
        275                 280                 285

Glu Ala Cys Arg Pro Ala Ala Gly Gly Ala Val His Thr Arg Gly Leu
    290                 295                 300

Asp Phe Asp Thr Ala Leu Ala Val Ile Cys Ser Ala Leu Ala Thr
305                 310                 315                 320

Val Leu Leu Ala Leu Leu Ile Leu Cys Val Ile Tyr Cys Lys Arg Gln
                325                 330                 335

Pro Arg Arg Lys Lys Leu Leu Tyr Ile Phe Lys Gln Pro Phe Met Arg
            340                 345                 350
```

```
Pro Val Gln Thr Thr Gln Glu Glu Asp Gly Cys Ser Cys Arg Phe Pro
            355                 360                 365

Glu Glu Glu Gly Gly Cys Glu Leu Arg Val Lys Phe Ser Arg Ser
    370                 375                 380

Ala Asp Ala Pro Ala Tyr Gln Gln Gly Gln Asn Gln Leu Tyr Asn Glu
385                 390                 395                 400

Leu Asn Leu Gly Arg Arg Glu Glu Tyr Asp Val Leu Asp Lys Arg Arg
                405                 410                 415

Gly Arg Asp Pro Glu Met Gly Gly Lys Pro Arg Arg Lys Asn Pro Gln
            420                 425                 430

Glu Gly Leu Tyr Asn Glu Leu Gln Lys Asp Lys Met Ala Glu Ala Tyr
        435                 440                 445

Ser Glu Ile Gly Met Lys Gly Glu Arg Arg Arg Gly Lys Gly His Asp
    450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg
                485

<210> SEQ ID NO 79
<211> LENGTH: 36
<212> TYPE: DNA
<213> ORGANISM: Homo sapiens

<400> SEQUENCE: 79
gagagcaaat acgggccgcc atgtcccccg tgtccg                              36

<210> SEQ ID NO 80
<211> LENGTH: 12
<212> TYPE: PRT
<213> ORGANISM: Homo sapiens

<400> SEQUENCE: 80

Glu Ser Lys Tyr Gly Pro Pro Cys Pro Pro Cys Pro
1               5                   10

<210> SEQ ID NO 81
<211> LENGTH: 327
<212> TYPE: DNA
<213> ORGANISM: Homo sapiens

<400> SEQUENCE: 81
gcaccaccag ttgctggccc tagtgtcttc ttgttccctc ccaagcccaa agacaccttg     60
atgatttcca gaactcctga ggttacctgc gttgtcgtag atgtttctca ggaggaccca    120
gaggtccaat ttaactggta cgttgatggg gtggaagttc acaatgcgaa gacaaagccg    180
cgggaagaac aatttcagtc cacttaccgg gttgtcagcg ttctgacggt attgcatcaa    240
gactggctta tggaaaagga atataagtgt aaggtgtcca caaaggtttt gccgagcagt    300
attgagaaga ccatatcaaa ggcgaag                                       327

<210> SEQ ID NO 82
<211> LENGTH: 109
<212> TYPE: PRT
<213> ORGANISM: Homo sapiens

<400> SEQUENCE: 82

Ala Pro Pro Val Ala Gly Pro Ser Val Phe Leu Phe Pro Pro Lys Pro
1               5                   10                  15
```

Lys Asp Thr Leu Met Ile Ser Arg Thr Pro Glu Val Thr Cys Val Val
                20                  25                  30

Val Asp Val Ser Gln Glu Asp Pro Glu Val Gln Phe Asn Trp Tyr Val
            35                  40                  45

Asp Gly Val Glu Val His Asn Ala Lys Thr Lys Pro Arg Glu Glu Gln
        50                  55                  60

Phe Gln Ser Thr Tyr Arg Val Val Ser Val Leu Thr Val Leu His Gln
65                  70                  75                  80

Asp Trp Leu Asn Gly Lys Glu Tyr Lys Cys Lys Val Ser Asn Lys Gly
                85                  90                  95

Leu Pro Ser Ser Ile Glu Lys Thr Ile Ser Lys Ala Lys
            100                 105

<210> SEQ ID NO 83
<211> LENGTH: 321
<212> TYPE: DNA
<213> ORGANISM: Homo sapiens

<400> SEQUENCE: 83
gggcagccgc gcgagccaca agtttacact tgccgccat ctcaagagga aatgactaaa      60
aaccaggtat ccttgacatg cctcgtaaaa ggatttatc catctgatat tgctgtggaa     120
tgggagtcta acgggcagcc ggaaaataat tacaaaacta caccacctgt gctcgattca     180
gatggaagtt tcttccttta cagtagactt acggtgaca aatctaggtg gcaggaaggg     240
aatgtgttta gttgtagtgt aatgcacgag gcacttcata accactatac acagaagtca     300
ctgagtttga gtcttggcaa a                                                321

<210> SEQ ID NO 84
<211> LENGTH: 107
<212> TYPE: PRT
<213> ORGANISM: Homo sapiens

<400> SEQUENCE: 84

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
        50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105

<210> SEQ ID NO 85
<211> LENGTH: 684
<212> TYPE: DNA
<213> ORGANISM: Homo sapiens

<400> SEQUENCE: 85
gagagcaaat acggccgcc atgtcccccg tgtccggcac caccagttgc tggccctagt       60
gtcttcttgt tccctcccaa gcccaaagac accttgatga tttccagaac tcctgaggtt    120

-continued

```
acctgcgttg tcgtagatgt ttctcaggag gacccagagg tccaatttaa ctggtacgtt    180 gatgggtgg aagttcacaa tgcgaagaca aagccgcggg aagaacaatt tcagtccact    240
taccgggttg tcagcgttct gacggtattg catcaagact ggcttaatgg aaaggaatat    300
aagtgtaagg tgtccaacaa aggtttgccg agcagtattg agaagaccat atcaaaggcg    360 aagggcagc cgcgcgagcc acaagtttac actttgccgc catctcaaga ggaaatgact    420
aaaaaccagg tatccttgac atgcctcgta aaaggatttt atccatctga tattgctgtg    480
gaatgggagt ctaacgggca gccggaaaat aattacaaaa ctacaccacc tgtgctcgat    540
tcagatggaa gtttcttcct ttacagtaga cttacggtgg acaaatctag gtggcaggaa    600
gggaatgtgt ttagttgtag tgtaatgcac gaggcacttc ataaccacta tacacagaag    660
tcactgagtt tgagtcttgg caaa                                           684
```

<210> SEQ ID NO 86
<211> LENGTH: 228
<212> TYPE: PRT
<213> ORGANISM: Homo sapiens

<400> SEQUENCE: 86

```
Glu Ser Lys Tyr Gly Pro Pro Cys Pro Pro Cys Pro Ala Pro Pro Val
 1               5                  10                  15

Ala Gly Pro Ser Val Phe Leu Phe Pro Pro Lys Pro Lys Asp Thr Leu
                20                  25                  30

Met Ile Ser Arg Thr Pro Glu Val Thr Cys Val Val Val Asp Val Ser
            35                  40                  45

Gln Glu Asp Pro Glu Val Gln Phe Asn Trp Tyr Val Asp Gly Val Glu
        50                  55                  60

Val His Asn Ala Lys Thr Lys Pro Arg Glu Glu Gln Phe Gln Ser Thr
    65                  70                  75                  80

Tyr Arg Val Val Ser Val Leu Thr Val Leu His Gln Asp Trp Leu Asn
                    85                  90                  95

Gly Lys Glu Tyr Lys Cys Lys Val Ser Asn Lys Gly Leu Pro Ser Ser
               100                 105                 110

Ile Glu Lys Thr Ile Ser Lys Ala Lys Gly Gln Pro Arg Glu Pro Gln
           115                 120                 125

Val Tyr Thr Leu Pro Pro Ser Gln Glu Glu Met Thr Lys Asn Gln Val
       130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                   165                 170                 175

Pro Val Leu Asp Ser Asp Gly Ser Phe Phe Leu Tyr Ser Arg Leu Thr
               180                 185                 190

Val Asp Lys Ser Arg Trp Gln Glu Gly Asn Val Phe Ser Cys Ser Val
           195                 200                 205

Met His Glu Ala Leu His Asn His Tyr Thr Gln Lys Ser Leu Ser Leu
       210                 215                 220

Ser Leu Gly Lys
225
```

<210> SEQ ID NO 87
<211> LENGTH: 732
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic polynucleotide"

<400> SEQUENCE: 87

```
gaggtccagc tggtacagtc tgggggaggc ttggtacagc ctgggggtc cctgagactc      60 tcctgtgcag cctctggatt cacctttgat gattatgcca tgcactgggt ccggcaagct     120
ccagggaagg gcctggagtg ggtctcaggt attagttgga atagtggtag cataggctat     180
gcggactctg tgaagggccg attcaccatc tccagagaca acgccaagaa ctccctgtat     240
ctgcaaatga acagtctgag agctgaggac acggccttgt attactgtgc aaaagattta     300
tcgtcagtgg ctggaccctt taactactgg ggccagggca ccctggtcac cgtctcctca     360
ggaggtggcg gtctggtgg aggcggtagc ggcggtggcg gatcctcttc tgagctgact     420
caggaccctg ctgtgtctgt ggccttggga cagacagtca ggatcacatg ccaaggagac     480
agcctcagaa gctattatgc aagctggtac cagcagaagc caggacaggc ccctgtactt     540
gtcatctatg gtaaaaacaa ccggccctca gggatcccag accgattctc tggctccagc     600
tcaggaaaca cagcttcctt gaccatcact ggggctcagg cggaggatga ggctgactat     660
tactgtaact cccgggacag cagtggtaac catctggtat tcggcggagg cacccagctg     720
accgtcctcg gt                                                         732
```

<210> SEQ ID NO 88
<211> LENGTH: 244
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 88

```
Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Leu Ser Ser Val Ala Gly Pro Phe Asn Tyr Trp Gly Gln
            100                 105                 110

Gly Thr Leu Val Thr Val Ser Gly Gly Gly Gly Ser Gly Gly Gly
        115                 120                 125

Gly Ser Gly Gly Gly Gly Ser Ser Glu Leu Thr Gln Asp Pro Ala
    130                 135                 140

Val Ser Val Ala Leu Gly Gln Thr Val Arg Ile Thr Cys Gln Gly Asp
145                 150                 155                 160

Ser Leu Arg Ser Tyr Tyr Ala Ser Trp Tyr Gln Gln Lys Pro Gly Gln
                165                 170                 175

Ala Pro Val Leu Val Ile Tyr Gly Lys Asn Asn Arg Pro Ser Gly Ile
            180                 185                 190
```

```
Pro Asp Arg Phe Ser Gly Ser Ser Gly Asn Thr Ala Ser Leu Thr
        195                 200                 205

Ile Thr Gly Ala Gln Ala Glu Asp Glu Ala Asp Tyr Tyr Cys Asn Ser
    210                 215                 220

Arg Asp Ser Ser Gly Asn His Leu Val Phe Gly Gly Gly Thr Gln Leu
225             230                 235                 240

Thr Val Leu Gly

<210> SEQ ID NO 89
<211> LENGTH: 1476
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 89
atgctgctgc tggtgaccag cctgctgctg tgcgaactgc cgcatccggc gtttctgctg      60
attccggagg tccagctggt acagtctggg ggaggcttgg tacagcctgg ggggtccctg     120
agactctcct gtgcagcctc tggattcacc tttgatgatt atgccatgca ctgggtccgg     180
caagctccag ggaagggcct ggagtgggtc tcaggtatta gttggaatag tggtagcata     240
ggctatgcgg actctgtgaa gggccgattc accatctcca gagacaacgc caagaactcc     300
ctgtatctgc aaatgaacag tctgagagct gaggacacgg ccttgtatta ctgtgcaaaa     360
gatttatcgt cagtggctgg acccttt aac tactggggcc agggcaccct ggtcaccgtc     420
tcctcaggag gtggcgggtc tggtggaggc ggtagcggcg tggcggatc ctcttctgag     480 ctgactcagg accctgctgt gtctgtggcc ttgggacaga cagtcaggat cacatgccaa     540
ggagacagcc tcagaagcta ttatgcaagc tggtaccagc agaagccagg acaggcccct     600
gtacttgtca tctatggtaa aaacaaccgg ccctcaggga tcccagaccg attctctggc     660
tccagctcag gaaacacagc ttccttgacc atcactgggg ctcaggcgga ggatgaggct     720
gactattact gtaactcccg ggacagcagt ggtaaccatc tggtattcgg cggaggcacc     780
cagctgaccg tcctcggtgc ggccgcaact accacccctg cccctcggcc gccgactccg     840
gccccaacca tcgcaagcca ccccctctcc ttgcgcccg aagcttgccg cccggccgcg     900
ggtggagccg tgcatacccg ggggctggac tttgcctgcg atatctacat ttgggccccg     960
ctggccggca cttgcggcgt gctcctgctg tcgctggtca tcaccctttta ctgcaagagg    1020 ggccggaaga gctgcttta catcttcaag cagccgttca tgcgcccgt gcagacgact    1080 caggaagagg acggatgctc gtgcagattc cctgaggagg aagagggggg atgcgaactg    1140
cgcgtcaagt tctcacggtc cgccgacgcc ccgcatatc aacagggcca gaatcagctc    1200
tacaacgagc tgaacctggg aaggagagag gagtacgacg tgctggacaa gcgacgcgga    1260
cgcgacccgg agatgggggg gaaaccacgg cggaaaaacc ctcaggaagg actgtacaac    1320
gaactccaga agacaagat ggcggaagcc tactcagaaa tcgggatgaa gggagagcgg    1380
aggaggggaa aggtcacga cgggctgtac cagggactga gcaccgccac taaggatacc    1440
tacgatgcct tgcatatgca agcactccca ccccgg                              1476

<210> SEQ ID NO 90
<211> LENGTH: 492
<212> TYPE: PRT
<213> ORGANISM: Artificial Sequence
```

-continued

```
<220> FEATURE:
<221> NAME/KEY: source
<223> OTHER INFORMATION: /note="Description of Artificial Sequence:
      Synthetic polypeptide"

<400> SEQUENCE: 90

Met Leu Leu Leu Val Thr Ser Leu Leu Leu Cys Glu Leu Pro His Pro
1               5                   10                  15

Ala Phe Leu Leu Ile Pro Glu Val Gln Leu Val Gln Ser Gly Gly Gly
            20                  25                  30

Leu Val Gln Pro Gly Gly Ser Leu Arg Leu Ser Cys Ala Ala Ser Gly
        35                  40                  45

Phe Thr Phe Asp Asp Tyr Ala Met His Trp Val Arg Gln Ala Pro Gly
    50                  55                  60

Lys Gly Leu Glu Trp Val Ser Gly Ile Ser Trp Asn Ser Gly Ser Ile
65                  70                  75                  80

Gly Tyr Ala Asp Ser Val Lys Gly Arg Phe Thr Ile Ser Arg Asp Asn
                85                  90                  95

Ala Lys Asn Ser Leu Tyr Leu Gln Met Asn Ser Leu Arg Ala Glu Asp
            100                 105                 110

Thr Ala Leu Tyr Tyr Cys Ala Lys Asp Leu Ser Val Ala Gly Pro
        115                 120                 125

Phe Asn Tyr Trp Gly Gln Gly Thr Leu Val Thr Val Ser Ser Gly Gly
    130                 135                 140

Gly Gly Ser Gly Gly Gly Ser Gly Gly Gly Ser Ser Ser Glu
145                 150                 155                 160

Leu Thr Gln Asp Pro Ala Val Ser Val Ala Leu Gly Gln Thr Val Arg
                165                 170                 175

Ile Thr Cys Gln Gly Asp Ser Leu Arg Ser Tyr Tyr Ala Ser Trp Tyr
            180                 185                 190

Gln Gln Lys Pro Gly Gln Ala Pro Val Leu Val Ile Tyr Gly Lys Asn
        195                 200                 205

Asn Arg Pro Ser Gly Ile Pro Asp Arg Phe Ser Gly Ser Ser Ser Gly
    210                 215                 220

Asn Thr Ala Ser Leu Thr Ile Thr Gly Ala Gln Ala Glu Asp Glu Ala
225                 230                 235                 240

Asp Tyr Tyr Cys Asn Ser Arg Asp Ser Ser Gly Asn His Leu Val Phe
                245                 250                 255

Gly Gly Gly Thr Gln Leu Thr Val Leu Gly Ala Ala Ala Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Lys Arg Gly Arg Lys Lys Leu Leu Tyr Ile Phe Lys Gln Pro
            340                 345                 350

Phe Met Arg Pro Val Gln Thr Thr Gln Glu Glu Asp Gly Cys Ser Cys
        355                 360                 365

Arg Phe Pro Glu Glu Glu Glu Gly Gly Cys Glu Leu Arg Val Lys Phe
    370                 375                 380
```

```
Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Tyr Asp Val Leu Asp
            405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
            435                 440                 445

Glu Ala Tyr Ser Glu Ile Gly Met Lys Gly Glu Arg Arg Arg Gly Lys
            450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490
```

<210> SEQ ID NO 91
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 91

```
gaggtgcagc tggtggagtc tgggggaggc ttggtacagc ctggagggtc cctgagactc      60
tcctgtgcag cctctggatt caccttcagt agctatggca tgagctgggt ccgccaggct     120
ccaagacaag ggcttgagtg ggtggccaac ataaagcaag atggaagtga aaatactat      180 gcggactcag tgaagggccg attcaccatc tccagagaca attccaagaa cacgctgtat     240
ctgcaaatga acagcctgag agccgaggac acagccacgt attactgtgc gaaagaaaat     300
gtggactggg gccagggcac cctggtcacc gtctcctca                            339
```

<210> SEQ ID NO 92
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 92

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Arg Gln Gly Leu Glu Trp Val
        35                  40                  45

Ala Asn Ile Lys Gln Asp Gly Ser Glu Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Lys Glu Asn Val Asp Trp Gly Gln Gly Thr Leu Val Thr Val Ser
            100                 105                 110

Ser
```

<210> SEQ ID NO 93
<211> LENGTH: 1083
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 93

```
atgctgctgc tggtgaccag cctgctgctg tgcgaactgc cgcatccggc gtttctgctg      60
attccggagg tgcagctggt ggagtctggg ggaggcttgg tacagcctgg agggtccctg     120
agactctcct gtgcagcctc tggattcacc ttcagtagct atggcatgag ctgggtccgc     180
caggctccaa gacaagggct tgagtgggtg gccaacataa agcaagatgg aagtgagaaa     240
tactatgcgg actcagtgaa gggccgattc accatctcca gagacaattc caagaacacg     300
ctgtatctgc aaatgaacag cctgagagcc gaggacacag ccacgtatta ctgtgcgaaa     360
gaaaatgtgg actggggcca gggcaccctg gtcaccgtct cctcagcggc cgcaactacc     420
accccctgccc ctcggccgcc gactccggcc ccaaccatcg caagccaacc cctctccttg     480
cgccccgaag cttgccgccc ggccgcgggt ggagccgtgc atacccgggg gctggacttt     540
gcctgcgata tctacatttg gcccccgctg ccggcactt cgggcgtgct cctgctgtcg     600
ctggtcatca cccttctactg caagagggc cggaagaagc tgctttacat cttcaagcag     660
ccgttcatgc ggcccgtgca gacgactcag gaagaggacg gatgctcgtg cagattccct     720
gaggaggaag agggggatg cgaactgcgc gtcaagttct cacggtccgc cgacgccccc     780
gcatatcaac agggccagaa tcagctctac aacgagctga acctgggaag agagagggag     840
tacgacgtgc tggacaagcg acgcggacgc gaccccggaga tggggggaa accacggcgg     900
aaaaaccctc aggaaggact gtacaacgaa ctccagaaag acaagatggc ggaagcctac     960
tcagaaatcg ggatgaaggg agagcggagg agggggaagg gtcacgacgg gctgtaccag    1020
ggactgagca ccgccactaa ggataccttac gatgccttgc atatgcaagc actcccaccc    1080
cgg                                                                  1083
```

<210> SEQ ID NO 94
<211> LENGTH: 361
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 94

```
Met Leu Leu Leu Val Thr Ser Leu Leu Leu Cys Glu Leu Pro His Pro
1               5                   10                  15

Ala Phe Leu Leu Ile Pro Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Ser Tyr Gly Met Ser Trp Val Arg Gln Ala Pro Arg
    50                  55                  60

Gln Gly Leu Glu Trp Val Ala Asn Ile Lys Gln Asp Gly Ser Glu Lys
65                  70                  75                  80

Tyr Tyr Ala Asp Ser Val Lys Gly Arg Phe Thr Ile Ser Arg Asp Asn
```

```
                        85                  90                  95
        Ser Lys Asn Thr Leu Tyr Leu Gln Met Asn Ser Leu Arg Ala Glu Asp
                    100                 105                 110

Thr Ala Thr Tyr Tyr Cys Ala Lys Glu Asn Val Asp Trp Gly Gln Gly
                    115                 120                 125

Thr Leu Val Thr Val Ser Ser Ala Ala Ala Thr Thr Pro Ala Pro
                    130                 135                 140

Arg Pro Pro Thr Pro Ala Pro Thr Ile Ala Ser Gln Pro Leu Ser Leu
        145                 150                 155                 160

Arg Pro Glu Ala Cys Arg Pro Ala Ala Gly Gly Ala Val His Thr Arg
                        165                 170                 175

Gly Leu Asp Phe Ala Cys Asp Ile Tyr Ile Trp Ala Pro Leu Ala Gly
                        180                 185                 190

Thr Cys Gly Val Leu Leu Leu Ser Leu Val Ile Thr Leu Tyr Cys Lys
                        195                 200                 205

Arg Gly Arg Lys Lys Leu Leu Tyr Ile Phe Lys Gln Pro Phe Met Arg
            210                 215                 220

Pro Val Gln Thr Thr Gln Glu Glu Asp Gly Cys Ser Cys Arg Phe Pro
        225                 230                 235                 240

Glu Glu Glu Glu Gly Gly Cys Glu Leu Arg Val Lys Phe Ser Arg Ser
                        245                 250                 255

Ala Asp Ala Pro Ala Tyr Gln Gln Gly Gln Asn Gln Leu Tyr Asn Glu
                    260                 265                 270

Leu Asn Leu Gly Arg Arg Glu Glu Tyr Asp Val Leu Asp Lys Arg Arg
                275                 280                 285

Gly Arg Asp Pro Glu Met Gly Gly Lys Pro Arg Arg Lys Asn Pro Gln
            290                 295                 300

Glu Gly Leu Tyr Asn Glu Leu Gln Lys Asp Lys Met Ala Glu Ala Tyr
        305                 310                 315                 320

Ser Glu Ile Gly Met Lys Gly Glu Arg Arg Gly Lys Gly His Asp
                        325                 330                 335

Gly Leu Tyr Gln Gly Leu Ser Thr Ala Thr Lys Asp Thr Tyr Asp Ala
                    340                 345                 350

Leu His Met Gln Ala Leu Pro Pro Arg
                    355                 360

<210> SEQ ID NO 95
<211> LENGTH: 2283
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 95
atgctccttc tcgtgacctc cctgcttctc tgcgaactgc cccatcctgc cttcctgctg      60
attcccgaca ttcagatgac tcagaccacc tcctccctgt ccgcctccct gggcgaccgc     120
gtgaccatct catgccgcgc cagccaggac atctcgaagt acctcaactg gtaccagcag     180
aagcccgacg gaaccgtgaa gctcctgatc taccacacct cccggctgca cagcggagtg     240
ccgtctagat tctcgggttc ggggtcggga actgactact cccttactat ttccaacctg     300
gagcaggagg atattgccac ctacttctgc caacaaggaa acaccctgcc gtacactttt     360
ggcgggggaa ccaagctgga aatcactggc agcacatccg gttccgggaa gcccggctcc     420
```

| | | |
|---|---|---|
| ggagagggca gcaccaaggg ggaagtcaag ctgcaggaat caggacctgg cctggtggcc | 480 | |
| ccgagccagt cactgtccgt gacttgtact gtgtccggag tgtcgctccc ggattacgga | 540 | |
| gtgtcctgga tcaggcagcc acctcggaaa ggattggaat ggctcggagt catctggggt | 600 | |
| tccgaaacca cctattacaa ctcggcactg aaatccaggc tcaccattat caaggataac | 660 | |
| tccaagtcac aagtgttcct gaagatgaat agcctgcaga ctgacgacac ggcgatctac | 720 | |
| tattgcgcca agcactacta ctacggcgga tcctacgcta tggactactg gggccagggg | 780 | |
| accagcgtga ccgtgtcatc cggaggcggc ggcagcggcg ggggagggtc cggaggggt | 840 | |
| ggttctggtg gaggaggatc gggaggcggt ggcagcgagg tgcagttgca acagtcagga | 900 | |
| gctgaactgg tcaagccagg agccagcgtg aagatgagct gcaaggcctc cggttacacc | 960 | |
| ttcacctcct acaacatgca ctgggtgaaa cagaccccgg acaagggct cgaatggatt | 1020 | |
| ggcgccatct accccgggaa tggcgatact tcgtacaacc agaagttcaa gggaaaggcc | 1080 | |
| accctgaccg ccgacaagag ctcctccacc gcgtatatgc agttgagctc cctgacctcc | 1140 | |
| gaggactccg ccgactacta ctgcgcacgg tccaactact atggaagctc gtactggttc | 1200 | |
| ttcgatgtct ggggggccgg caccactgtg accgtcagct cggggggcgg aggatccggt | 1260 | |
| ggaggcggaa gcggggtgg aggatccgac attgtgctga ctcagtcccc ggcaatcctg | 1320 | |
| tcggcctcac cgggcgaaaa ggtcacgatg acttgtagag cgtcgtccag cgtgaactac | 1380 | |
| atggattggt accaaaagaa gcctggatcg tcacccaagc cttggatcta cgctacatct | 1440 | |
| aacctggcct ccggcgtgcc agcgcggttc agcgggtccg gctcgggcac ctcatactcg | 1500 | |
| ctgaccatct cccgcgtgga ggctgaggac gccgcgacct actactgcca gcagtggtcc | 1560 | |
| ttcaacccgc cgactttgg aggcggtact aagctggaga tcaaagcggc cgcaactacc | 1620 | |
| accccctgccc ctcggccgcc gactccgcc ccaaccatcg caagccaacc cctctccttg | 1680 | |
| cgccccgaag cttgccgccc ggccgcgggt ggagccgtgc atacccgggg gctggacttt | 1740 | |
| gcctgcgata tctacatttg gccccgctg gccggcactt cgcgcgtgct cctgctgtcg | 1800 | |
| ctggtcatca ccctttactg caagaggggc cggaagaagc tgctttacat cttcaagcag | 1860 | |
| ccgttcatgc ggcccgtgca gacgactcag gaagaggacg gatgctcgtg cagattccct | 1920 | |
| gaggaggaag agggggatg cgaactgcgc gtcaagttct cacggtccgc cgacgccccc | 1980 | |
| gcatatcaac agggccagaa tcagctctac aacgagctga acctgggaag gagagaggag | 2040 | |
| tacgacgtgc tggacaagcg acgcggacgc gacccggaga tgggggggaa accacggcgg | 2100 | |
| aaaaaccctc aggaaggact gtacaacgaa ctccagaaag acaagatggc ggaagcctac | 2160 | |
| tcagaaatcg ggatgaaggg agagcggagg aggggaaagg gtcacgacgg gctgtaccag | 2220 | |
| ggactgagca ccgccactaa ggatacctac gatgccttgc atatgcaagc actcccaccc | 2280 | |
| cgg | 2283 | |

<210> SEQ ID NO 96
<211> LENGTH: 761
<212> TYPE: PRT
<213> ORGANISM: Artificial Sequence
<220> FEATURE:
<221> NAME/KEY: source
<223> OTHER INFORMATION: /note="Description of Artificial Sequence:
   Synthetic polypeptide"

<400> SEQUENCE: 96

Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
                20                  25                  30

Leu Ser Ala Ser Leu Gly Asp Arg Val Thr Ile Ser Cys Arg Ala Ser
            35                  40                  45

Gln Asp Ile Ser Lys Tyr Leu Asn Trp Tyr Gln Gln Lys Pro Asp Gly
        50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Ser Thr Ser Gly Ser Gly Lys Pro Gly Ser Gly Glu Gly Ser
130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
        195                 200                 205

Ala Leu Lys Ser Arg Leu Thr Ile Ile Lys Asp Asn Ser Lys Ser Gln
210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Gly Gly Ser Tyr Ala Met Asp Tyr
                245                 250                 255

Trp Gly Gln Gly Thr Ser Val Thr Val Ser Ser Gly Gly Gly Gly Ser
            260                 265                 270

Gly Gly Gly Gly Ser Gly Gly Gly Ser Gly Gly Gly Gly Ser Gly
        275                 280                 285

Gly Gly Gly Ser Glu Val Gln Leu Gln Gln Ser Gly Ala Glu Leu Val
290                 295                 300

Lys Pro Gly Ala Ser Val Lys Met Ser Cys Lys Ala Ser Gly Tyr Thr
305                 310                 315                 320

Phe Thr Ser Tyr Asn Met His Trp Val Lys Gln Thr Pro Gly Gln Gly
                325                 330                 335

Leu Glu Trp Ile Gly Ala Ile Tyr Pro Gly Asn Gly Asp Thr Ser Tyr
            340                 345                 350

Asn Gln Lys Phe Lys Gly Lys Ala Thr Leu Thr Ala Asp Lys Ser Ser
        355                 360                 365

Ser Thr Ala Tyr Met Gln Leu Ser Ser Leu Thr Ser Glu Asp Ser Ala
370                 375                 380

Asp Tyr Tyr Cys Ala Arg Ser Asn Tyr Gly Ser Ser Tyr Trp Phe
385                 390                 395                 400

Phe Asp Val Trp Gly Ala Gly Thr Thr Val Thr Val Ser Ser Gly Gly
                405                 410                 415

Gly Gly Ser Gly Gly Gly Gly Ser Gly Gly Gly Gly Ser Asp Ile Val
            420                 425                 430

Leu Thr Gln Ser Pro Ala Ile Leu Ser Ala Ser Pro Gly Glu Lys Val 435                 440                 445
Thr Met Thr Cys Arg Ala Ser Ser Val Asn Tyr Met Asp Trp Tyr
        450                 455                 460
Gln Lys Lys Pro Gly Ser Ser Pro Lys Pro Trp Ile Tyr Ala Thr Ser
465                 470                 475                 480
Asn Leu Ala Ser Gly Val Pro Ala Arg Phe Ser Gly Ser Gly Ser Gly
                485                 490                 495
Thr Ser Tyr Ser Leu Thr Ile Ser Arg Val Glu Ala Glu Asp Ala Ala
                500                 505                 510
Thr Tyr Tyr Cys Gln Gln Trp Ser Phe Asn Pro Pro Thr Phe Gly Gly
                515                 520                 525
Gly Thr Lys Leu Glu Ile Lys Ala Ala Ala Thr Thr Thr Pro Ala Pro
        530                 535                 540
Arg Pro Pro Thr Pro Ala Pro Thr Ile Ala Ser Gln Pro Leu Ser Leu
545                 550                 555                 560
Arg Pro Glu Ala Cys Arg Pro Ala Ala Gly Gly Ala Val His Thr Arg
                565                 570                 575
Gly Leu Asp Phe Ala Cys Asp Ile Tyr Ile Trp Ala Pro Leu Ala Gly
                580                 585                 590
Thr Cys Gly Val Leu Leu Leu Ser Leu Val Ile Thr Leu Tyr Cys Lys
                595                 600                 605
Arg Gly Arg Lys Lys Leu Leu Tyr Ile Phe Lys Gln Pro Phe Met Arg
        610                 615                 620
Pro Val Gln Thr Thr Gln Glu Glu Asp Gly Cys Ser Cys Arg Phe Pro
625                 630                 635                 640
Glu Glu Glu Glu Gly Gly Cys Glu Leu Arg Val Lys Phe Ser Arg Ser
                645                 650                 655
Ala Asp Ala Pro Ala Tyr Gln Gln Gly Gln Asn Gln Leu Tyr Asn Glu
                660                 665                 670
Leu Asn Leu Gly Arg Arg Glu Glu Tyr Asp Val Leu Asp Lys Arg Arg
        675                 680                 685
Gly Arg Asp Pro Glu Met Gly Gly Lys Pro Arg Arg Lys Asn Pro Gln
        690                 695                 700
Glu Gly Leu Tyr Asn Glu Leu Gln Lys Asp Lys Met Ala Glu Ala Tyr
705                 710                 715                 720
Ser Glu Ile Gly Met Lys Gly Glu Arg Arg Arg Gly Lys Gly His Asp
                725                 730                 735
Gly Leu Tyr Gln Gly Leu Ser Thr Ala Thr Lys Asp Thr Tyr Asp Ala
                740                 745                 750
Leu His Met Gln Ala Leu Pro Pro Arg
        755                 760

<210> SEQ ID NO 97
<211> LENGTH: 2283
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 97
atgctccttc tcgtgacctc cctgcttctc tgcgaactgc ccatcctgc cttcctgctg      60 attcccgagg tgcagttgca acagtcagga gctgaactgg tcaagccagg agccagcgtg     120
aagatgagct gcaaggcctc cggttacacc ttcacctcct acaacatgca ctgggtgaaa    180

```
cagaccccgg gacaagggct cgaatggatt ggcgccatct accccgggaa tggcgatact    240
tcgtacaacc agaagttcaa gggaaaggcc accctgaccg ccgacaagag ctcctccacc    300
gcgtatatgc agttgagctc cctgacctcc gaggactccg ccgactacta ctgcgcacgg    360
tccaactact atggaagctc gtactggttc ttcgatgtct gggggggccgg caccactgtg   420 accgtcagct ccggggggcgg aggatccggt ggaggcggaa gcggggggtgg aggatccgac  480 attgtgctga ctcagtcccc ggcaatcctg tcggcctcac cgggcgaaaa ggtcacgatg    540
acttgtagag cgtcgtccag cgtgaactac atggattggt accaaaagaa gcctggatcg    600
tcacccaagc cttggatcta cgctacatct aacctggcct ccggcgtgcc agcgcggttc    660
agcgggtccg gctcgggcac ctcatactcg ctgaccatct cccgcgtgga ggctgaggac    720
gccgcgacct actactgcca gcagtggtcc ttcaacccgc cgacttttgg aggcggtact    780
aagctggaga tcaaaggagg cggcggcagc ggcgggggag ggtccggagg gggtggttct    840
ggtggaggag gatcgggagg cggtggcagc gacattcaga tgactcagac cacctcctcc    900
ctgtccgcct ccctgggcga ccgcgtgacc atctcatgcc gcgccagcca ggacatctcg    960
aagtacctca actggtacca gcagaagccc gacggaaccg tgaagctcct gatctaccac   1020
acctcccggc tgcacagcgg agtgccgtct agattctcgg gttcggggtc gggaactgac   1080
tactccctta ctatttccaa cctggagcag gaggatattg ccacctactt ctgccaacaa   1140
ggaaacaccc tgccgtacac ttttggcggg ggaaccaagc tggaaatcac tggcagcaca   1200
tccggttccg ggaagcccgg ctccggagag ggcagcacca agggggaagt caagctgcag   1260
gaatcaggac ctggcctggt ggccccgagc cagtcactgt ccgtgacttg tactgtgtcc   1320
ggagtgtcgc tcccggatta cggagtgtcc tggatcaggc agccacctcg gaaaggattg   1380
gaatggctcg gagtcatctg gggttccgaa accacctatt acaactcggc actgaaatcc   1440
aggctcacca ttatcaagga taactccaag tcacaagtgt tcctgaagat gaatagcctg   1500
cagactgacg acacggcgat ctactattgc gccaagcact actactacgg cggatcctac   1560
gctatggact actggggcca ggggaccagc gtgaccgtgt catccgcggc cgcaactacc   1620 accccctgccc ctcggccgcc gactccggcc ccaaccatcg caagccaacc cctctccttg   1680
cgccccgaag cttgccgccc ggccgcgggt ggagccgtgc ataccgggg gctggacttt    1740 gcctgcgata tctacatttg gcccccgctg ccggcactt cgcgcgtgct cctgctgtcg    1800
ctggtcatca cccttactg caagagggc cggaagaagc tgctttacat cttcaagcag    1860
ccgttcatgc ggcccgtgca gacgactcag gaagaggacg gatgctcgtg cagattccct    1920
gaggaggaag aggggggatg cgaactgcgc gtcaagttct cacggtccgc cgacgccccc    1980
gcatatcaac agggccagaa tcagctctac aacgagctga acctgggaag agagaggag    2040 tacgacgtgc tggacaagcg acgcggacgc gacccggaga tggggggaa accacggcgg   2100 aaaaaccctc aggaaggact gtacaacgaa ctccagaaag acaagatggc ggaagcctac   2160
tcagaaatcg ggatgaaggg agagcggagg aggggaaagg gtcacgacgg gctgtaccag   2220
ggactgagca ccgccactaa ggatacctac gatgccttgc atatgcaagc actcccaccc   2280
cgg                                                                 2283
```

<210> SEQ ID NO 98
<211> LENGTH: 761
<212> TYPE: PRT
<213> ORGANISM: Artificial Sequence
<220> FEATURE:

<221> NAME/KEY: source
<223> OTHER INFORMATION: /note="Description of Artificial Sequence: Synthetic polypeptide"

<400> SEQUENCE: 98

```
Met Leu Leu Leu Val Thr Ser Leu Leu Leu Cys Glu Leu Pro His Pro
1               5                   10                  15

Ala Phe Leu Leu Ile Pro Glu Val Gln Leu Gln Gln Ser Gly Ala Glu
            20                  25                  30

Leu Val Lys Pro Gly Ala Ser Val Lys Met Ser Cys Lys Ala Ser Gly
        35                  40                  45

Tyr Thr Phe Thr Ser Tyr Asn Met His Trp Val Lys Gln Thr Pro Gly
50                  55                  60

Gln Gly Leu Glu Trp Ile Gly Ala Ile Tyr Pro Gly Asn Gly Asp Thr
65                  70                  75                  80

Ser Tyr Asn Gln Lys Phe Lys Gly Lys Ala Thr Leu Thr Ala Asp Lys
                85                  90                  95

Ser Ser Ser Thr Ala Tyr Met Gln Leu Ser Ser Leu Thr Ser Glu Asp
            100                 105                 110

Ser Ala Asp Tyr Tyr Cys Ala Arg Ser Asn Tyr Tyr Gly Ser Ser Tyr
        115                 120                 125

Trp Phe Phe Asp Val Trp Gly Ala Gly Thr Thr Val Thr Val Ser Ser
130                 135                 140

Gly Gly Gly Gly Ser Gly Gly Gly Ser Gly Gly Gly Gly Ser Asp
145                 150                 155                 160

Ile Val Leu Thr Gln Ser Pro Ala Ile Leu Ser Ala Ser Pro Gly Glu
                165                 170                 175

Lys Val Thr Met Thr Cys Arg Ala Ser Ser Ser Val Asn Tyr Met Asp
            180                 185                 190

Trp Tyr Gln Lys Lys Pro Gly Ser Ser Pro Lys Pro Trp Ile Tyr Ala
        195                 200                 205

Thr Ser Asn Leu Ala Ser Gly Val Pro Ala Arg Phe Ser Gly Ser Gly
210                 215                 220

Ser Gly Thr Ser Tyr Ser Leu Thr Ile Ser Arg Val Glu Ala Glu Asp
225                 230                 235                 240

Ala Ala Thr Tyr Tyr Cys Gln Gln Trp Ser Phe Asn Pro Pro Thr Phe
                245                 250                 255

Gly Gly Gly Thr Lys Leu Glu Ile Lys Gly Gly Gly Ser Gly Gly
            260                 265                 270

Gly Gly Ser Gly Gly Gly Ser Gly Gly Gly Ser Gly Gly Gly
        275                 280                 285

Gly Ser Asp Ile Gln Met Thr Gln Thr Thr Ser Ser Leu Ser Ala Ser
290                 295                 300

Leu Gly Asp Arg Val Thr Ile Ser Cys Arg Ala Ser Gln Asp Ile Ser
305                 310                 315                 320

Lys Tyr Leu Asn Trp Tyr Gln Gln Lys Pro Asp Gly Thr Val Lys Leu
                325                 330                 335

Leu Ile Tyr His Thr Ser Arg Leu His Ser Gly Val Pro Ser Arg Phe
            340                 345                 350

Ser Gly Ser Gly Ser Gly Thr Asp Tyr Ser Leu Thr Ile Ser Asn Leu
        355                 360                 365

Glu Gln Glu Asp Ile Ala Thr Tyr Phe Cys Gln Gln Gly Asn Thr Leu
370                 375                 380

Pro Tyr Thr Phe Gly Gly Gly Thr Lys Leu Glu Ile Thr Gly Ser Thr
```

```
                385                 390                 395                 400
        Ser Gly Ser Gly Lys Pro Gly Ser Gly Glu Gly Ser Thr Lys Gly Glu
                        405                 410                 415

Val Lys Leu Gln Glu Ser Gly Pro Gly Leu Val Ala Pro Ser Gln Ser
                        420                 425                 430

Leu Ser Val Thr Cys Thr Val Ser Gly Val Ser Leu Pro Asp Tyr Gly
                        435                 440                 445

Val Ser Trp Ile Arg Gln Pro Pro Arg Lys Gly Leu Glu Trp Leu Gly
                        450                 455                 460

Val Ile Trp Gly Ser Glu Thr Thr Tyr Tyr Asn Ser Ala Leu Lys Ser
        465                 470                 475                 480

Arg Leu Thr Ile Ile Lys Asp Asn Ser Lys Ser Gln Val Phe Leu Lys
                        485                 490                 495

Met Asn Ser Leu Gln Thr Asp Asp Thr Ala Ile Tyr Tyr Cys Ala Lys
                        500                 505                 510

His Tyr Tyr Tyr Gly Gly Ser Tyr Ala Met Asp Tyr Trp Gly Gln Gly
                        515                 520                 525

Thr Ser Val Thr Val Ser Ser Ala Ala Ala Thr Thr Pro Ala Pro
                        530                 535                 540

Arg Pro Pro Thr Pro Ala Pro Thr Ile Ala Ser Gln Pro Leu Ser Leu
        545                 550                 555                 560

Arg Pro Glu Ala Cys Arg Pro Ala Ala Gly Gly Ala Val His Thr Arg
                        565                 570                 575

Gly Leu Asp Phe Ala Cys Asp Ile Tyr Ile Trp Ala Pro Leu Ala Gly
                        580                 585                 590

Thr Cys Gly Val Leu Leu Leu Ser Leu Val Ile Thr Leu Tyr Cys Lys
                        595                 600                 605

Arg Gly Arg Lys Lys Leu Leu Tyr Ile Phe Lys Gln Pro Phe Met Arg
                        610                 615                 620

Pro Val Gln Thr Thr Gln Glu Glu Asp Gly Cys Ser Cys Arg Phe Pro
        625                 630                 635                 640

Glu Glu Glu Glu Gly Gly Cys Glu Leu Arg Val Lys Phe Ser Arg Ser
                        645                 650                 655

Ala Asp Ala Pro Ala Tyr Gln Gln Gly Gln Asn Gln Leu Tyr Asn Glu
                        660                 665                 670

Leu Asn Leu Gly Arg Arg Glu Glu Tyr Asp Val Leu Asp Lys Arg Arg
                        675                 680                 685

Gly Arg Asp Pro Glu Met Gly Gly Lys Pro Arg Arg Lys Asn Pro Gln
                        690                 695                 700

Glu Gly Leu Tyr Asn Glu Leu Gln Lys Asp Lys Met Ala Glu Ala Tyr
        705                 710                 715                 720

Ser Glu Ile Gly Met Lys Gly Glu Arg Arg Arg Gly Lys Gly His Asp
                        725                 730                 735

Gly Leu Tyr Gln Gly Leu Ser Thr Ala Thr Lys Asp Thr Tyr Asp Ala
                        740                 745                 750

Leu His Met Gln Ala Leu Pro Pro Arg
                        755                 760

<210> SEQ ID NO 99
<211> LENGTH: 797
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic polynucleotide"

<400> SEQUENCE: 99

```
atggcactgc ccgtgaccgc cctgcttctg ccgcttgcac ttctgctgca cgccgctagg      60
ccccaagtca ccctcaaaga gtcagggcca ggaatcctca agccctcaca gactctgtct     120
cttacttgct cattcagcgg attcagcctt tccacctctg gtatgggcgt ggggtggatt     180
aggcaaccta gcggaaaggg gcttgaatgg ctggcccaca tctggtggga cgacgacaag     240
tactacaacc cctcactgaa gtcccagctc actatttcca agatacttc ccggaatcag      300
gtgttcctca agattacctc tgtcgacacc gctgataccg ccacttacta ttgttcacgc     360
agaccgagag gtaccatgga cgcaatggac tactggggac agggcaccag cgtgaccgtg     420
tcatctggcg gtggagggtc aggaggtgga ggtagcggag gcggtgggtc cgacattgtc     480
atgacccagg ccgccagcag cctgagcgct tcactgggcg acagggtgac catcagctgt     540
cgcgcatcac aagatatctc taagtatctt aattggtacc agcaaaagcc ggatggaacc     600
gtgaagctgc tgatctacta cacctcacgg ctgcattctg gagtgcctag ccgctttagc     660
ggatctgggt ccggtactga ctacagcctc accattagaa accttgaaca ggaggacatc     720
gcaacttatt tctgccaaca ggtctatact ctgccgtgga ccttcggcgg aggtaccaaa     780
ctggagatta agtccgg                                                    797
```

<210> SEQ ID NO 100
<211> LENGTH: 265
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 100

```
Met Ala Leu Pro Val Thr Ala Leu Leu Leu Pro Leu Ala Leu Leu Leu
1               5                   10                  15

His Ala Ala Arg Pro Gln Val Thr Leu Lys Glu Ser Gly Pro Gly Ile
                20                  25                  30

Leu Lys Pro Ser Gln Thr Leu Ser Leu Thr Cys Ser Phe Ser Gly Phe
            35                  40                  45

Ser Leu Ser Thr Ser Gly Met Gly Val Gly Trp Ile Arg Gln Pro Ser
        50                  55                  60

Gly Lys Gly Leu Glu Trp Leu Ala His Ile Trp Trp Asp Asp Asp Lys
65                  70                  75                  80

Tyr Tyr Asn Pro Ser Leu Lys Ser Gln Leu Thr Ile Ser Lys Asp Thr
                85                  90                  95

Ser Arg Asn Gln Val Phe Leu Lys Ile Thr Ser Val Asp Thr Ala Asp
            100                 105                 110

Thr Ala Thr Tyr Tyr Cys Ser Arg Arg Pro Arg Gly Thr Met Asp Ala
        115                 120                 125

Met Asp Tyr Trp Gly Gln Gly Thr Ser Val Thr Val Ser Ser Gly Gly
    130                 135                 140

Gly Gly Ser Gly Gly Gly Gly Ser Gly Gly Gly Gly Ser Asp Ile Val
145                 150                 155                 160

Met Thr Gln Ala Ala Ser Ser Leu Ser Ala Ser Leu Gly Asp Arg Val
                165                 170                 175

Thr Ile Ser Cys Arg Ala Ser Gln Asp Ile Ser Lys Tyr Leu Asn Trp
            180                 185                 190
```

Tyr Gln Gln Lys Pro Asp Gly Thr Val Lys Leu Leu Ile Tyr Tyr Thr
            195                 200                 205

Ser Arg Leu His Ser Gly Val Pro Ser Arg Phe Ser Gly Ser Gly Ser
    210                 215                 220

Gly Thr Asp Tyr Ser Leu Thr Ile Arg Asn Leu Glu Gln Glu Asp Ile
225                 230                 235                 240

Ala Thr Tyr Phe Cys Gln Gln Val Tyr Thr Leu Pro Trp Thr Phe Gly
                245                 250                 255

Gly Gly Thr Lys Leu Glu Ile Lys Ser
            260                 265

<210> SEQ ID NO 101
<211> LENGTH: 1170
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 101

| | | | | |
|---|---|---|---|---|
| atggcactgc | ccgtgaccgc | cctgcttctg | ccgcttgcac | ttctgctgca | cgccgctagg | 60 |
| ccccaagtca | ccctcaaaga | gtcagggcca | ggaatcctca | gccctcacag | actctgtct | 120 |
| cttacttgct | cattcagcgg | attcagcctt | tccacctctg | gtatgggcgt | ggggtggatt | 180 |
| aggcaaccta | gcggaaaggg | gcttgaatgg | ctggcccaca | tctggtggga | cgacgacaag | 240 |
| tactacaacc | cctcactgaa | gtcccagctc | actatttcca | agatacttc | ccggaatcag | 300 |
| gtgttcctca | agattaccct | gtcgacacc | gctgataccg | ccacttacta | ttgttcacgc | 360 |
| agaccgagag | gtaccatgga | cgcaatggac | tactggggac | agggcaccag | cgtgaccgtg | 420 |
| tcatctggcg | gtggagggtc | aggaggtgga | ggtagcggag | gcggtgggtc | cgacattgtc | 480 |
| atgacccagg | ccgccagcag | cctgagcgct | tcactgggcg | acagggtgac | catcagctgt | 540 |
| cgcgcatcac | aagatatctc | taagtatctt | aattggtacc | agcaaaagcc | ggatggaacc | 600 |
| gtgaagctgc | tgatctacta | cacctcacgg | ctgcattctg | gagtgcctag | ccgcttagc | 660 |
| ggcacttgcg | gcgtgctcct | gctgtcgctg | gtcatcaccc | tttactgcaa | gaggggccgg | 720 |
| aagaagctgc | tttacatctt | caagcagccg | ttcatgcggc | ccgtgcagac | gactcaggaa | 780 |
| gaggacggat | gctcgtgcag | attccctgag | gaggaagagg | ggggatgcga | actgcgcgtc | 840 |
| aagttctcac | ggtccgccga | cgcccccgca | tatcaacagg | ccagaatca | gctctacaac | 900 |
| gagctgaacc | tgggaaggag | agaggagtac | gacgtgctgg | acaagcgacg | cggacgcgac | 960 |
| ccggagatgg | gggggaaacc | acggcggaaa | aaccctcagg | aaggactgta | caacgaactc | 1020 |
| cagaaagaca | agatggcgga | agcctactca | gaaatcggga | tgaagggaga | gcggaggagg | 1080 |
| ggaaagggtc | acgacgggct | gtaccaggga | ctgagcaccg | ccactaagga | tacctacgat | 1140 |
| gccttgcata | tgcaagcact | cccaccccgg | | | | 1170 |

<210> SEQ ID NO 102
<211> LENGTH: 490
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 102

```
Met Ala Leu Pro Val Thr Ala Leu Leu Leu Pro Leu Ala Leu Leu Leu
1               5                   10                  15

His Ala Ala Arg Pro Gln Val Thr Leu Lys Glu Ser Gly Pro Gly Ile
            20                  25                  30

Leu Lys Pro Ser Gln Thr Leu Ser Leu Thr Cys Ser Phe Ser Gly Phe
        35                  40                  45

Ser Leu Ser Thr Ser Gly Met Gly Val Gly Trp Ile Arg Gln Pro Ser
    50                  55                  60

Gly Lys Gly Leu Glu Trp Leu Ala His Ile Trp Trp Asp Asp Asp Lys
65                  70                  75                  80

Tyr Tyr Asn Pro Ser Leu Lys Ser Gln Leu Thr Ile Ser Lys Asp Thr
                85                  90                  95

Ser Arg Asn Gln Val Phe Leu Lys Ile Thr Ser Val Asp Thr Ala Asp
            100                 105                 110

Thr Ala Thr Tyr Tyr Cys Ser Arg Arg Pro Arg Gly Thr Met Asp Ala
        115                 120                 125

Met Asp Tyr Trp Gly Gln Gly Thr Ser Val Thr Val Ser Ser Gly Gly
    130                 135                 140

Gly Gly Ser Gly Gly Gly Ser Gly Gly Gly Ser Asp Ile Val
145                 150                 155                 160

Met Thr Gln Ala Ala Ser Ser Leu Ser Ala Ser Leu Gly Asp Arg Val
                165                 170                 175

Thr Ile Ser Cys Arg Ala Ser Gln Asp Ile Ser Lys Tyr Leu Asn Trp
            180                 185                 190

Tyr Gln Gln Lys Pro Asp Gly Thr Val Lys Leu Leu Ile Tyr Tyr Thr
        195                 200                 205

Ser Arg Leu His Ser Gly Val Pro Ser Arg Phe Ser Gly Ser Gly Ser
    210                 215                 220

Gly Thr Asp Tyr Ser Leu Thr Ile Arg Asn Leu Glu Gln Glu Asp Ile
225                 230                 235                 240

Ala Thr Tyr Phe Cys Gln Gln Val Tyr Thr Leu Pro Trp Thr Phe Gly
                245                 250                 255

Gly Gly Thr Lys Leu Glu Ile Lys Ala Ala Ala Thr Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
        355                 360                 365

Pro Glu Glu Glu Glu Gly Gly Cys Glu Leu Arg Val Lys Phe Ser Arg
    370                 375                 380

Ser Ala Asp Ala Pro Ala Tyr Gln Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415
```

Arg Gly Arg Asp Pro Glu Met Gly Gly Lys Pro Arg Lys Asn Pro
         420                 425                 430

Gln Glu Gly Leu Tyr Asn Glu Leu Gln Lys Asp Lys Met Ala Glu Ala
             435                 440                 445

Tyr Ser Glu Ile Gly Met Lys Gly Glu Arg Arg Arg Gly Lys Gly His
         450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490

<210> SEQ ID NO 103
<211> LENGTH: 2366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 103
tgagctctga gtcagtgact cagtgagtca gtgactcagt gagtcagtga ctcagctcga      60
ggatctcgct agcgggaatt tccggggact tccgggaat ttccgggac tttccgggaa      120 tttccagatc tggcctcggc ggccaagctt agacactaga gggtatataa tggaagctcg      180
acttccagct tggcaatccg gtactgttgg taaaggcgcg ccccaccatg ctgctgctgg      240
tcaccagcct gctgctgtgc gagctccctc accccgcctt tctgcttatc ccggacattc      300
agatgacaca gaccaccctc gagcttgtcc gtcgctggg cgatcgcgtg accatctcct      360
gccgggcctc ccaagacatt tcaaagtatc tcaactggta ccagcagaag ccggacggaa      420
ccgtgaaact gctgatctac cataccagcc gcctgcactc cggcgtgccg tcccgcttct      480
ccggatcggg ttccggaact gactactcac tgactatctc caacttggaa caagaggaca      540
tcgccactta cttctgtcaa caaggaaata cccttcccta ccttcgggg ggggtacca      600 agctggagat cactgggggc ggaggctccg gtggaggcgg atccggcggt ggagggagcg      660
aagtcaagct gcaggaatca ggaccaggac tcgtggcgcc atcccagtcc ctgtcggtga      720
cctgtactgt ctccggagtc agcctccccg attacggagt gcatggatt aggcaacccc      780 caagaaaagg gctggaatgg ctcggagtga tctgggctc cgaaaccacc tactacaact      840
cggcgctgaa gtcccggctg accatcatca ggacaactc aagagccaa gtgttcttga      900 agatgaacag cttgcagacc gacgataccg caatctacta ctgtgccaag cactattact      960 acgggggggtc ttacgccatg gactactggg gacagggcac ctccgtgact gtgtcgtccg     1020
cggccgctac cacaaccct gcgccccggc ctcctacccc gcacccacg attgcttctc     1080 aacctctttc actccgacct gaggcttgta gacctgcagc cggggtgcc gtccacacac     1140 ggggactcga cttcgcttgt gatatatata tttgggcgcc cctggccggc acttgtggag     1200
ttcttttgct ctctcttgtt atcacattgt actgcaagcg aggtaggaag aaattgcttt     1260
acatttttaa gcagccgttc atgcgaccag tacagactac tcaagaagaa gatgggtgct     1320
cttgtcggtt cccggaagaa gaagagggtg gttgcgagtt gagggtgaag ttctcccgct     1380
ctgccgacgc accggcatat cagcagggac aaaaccagct ctacaacgaa ttgaacctgg     1440
gtcggcggga agaatatgac gtgctcgata gcggcgggg tcgcgaccca gaaatgggag     1500
gcaaaccgcg caggaaaaat ccacaggagg gactttataa cgaacttcaa aaggataaga     1560

```
tggcagaggc atacagcgaa atcgggatga aaggcgagag aagaaggggg aaagggcacg  1620
atggtcttta ccaggggctt tctaccgcga cgaaggatac ctacgatgct ctccatatgc  1680
aagcacttcc tcctagacgg gcaaagcggg gctcagggc gactaactttt tcactgttga   1740
agcaggccgg ggatgtggag gagaatcctg gtcctagagc taagcgagta gacatgggaa  1800
gagggctgct ccgaggcttg tggccgttgc atattgtatt gtggacgcgg atagcgagta  1860
caatcccgcc tcacgtgcaa aaatcagtta ataacgacat gatcgttact gacaacaatg  1920
gcgcagttaa atttccgcag ctttgtaaat tctgtgatgt aagattttca acgtgcgata  1980
accagaaaag ctgtatgtcc aactgcagca tcacatcaat ctgtgaaaaa ccccaagagg  2040
tatgtgtggc cgtctggcga aagaatgacg aaaatatcac actggagacc gtttgtcacg  2100
atcctaaact cccttatcat gactttattc tggaagacgc agcgtcaccg aagtgtataa  2160
tgaaagagaa gaagaagcct ggagagacgt ttttcatgtg cagttgctcc tcagatgagt  2220
gtaatgacaa catcatttttt tccgaggagt acaatacgag taacccagac ctcctgctgg  2280
ttattttcca ggtaaccggc atcagtttgt tgcccccact gggtgttgca atcagtgtaa  2340
taatcatatt ttattgttac cgggtg                                        2366
```

<210> SEQ ID NO 104
<211> LENGTH: 713
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 104

```
Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Gly Gly Gly Ser Gly Gly Gly Ser Gly Gly Gly Gly Ser
130                 135                 140

Glu Val Lys Leu Gln Glu Ser Gly Pro Gly Leu Val Ala Pro Ser Gln
145                 150                 155                 160

Ser Leu Ser Val Thr Cys Thr Val Ser Gly Val Ser Leu Pro Asp Tyr
                165                 170                 175

Gly Val Ser Trp Ile Arg Gln Pro Pro Arg Lys Gly Leu Glu Trp Leu
            180                 185                 190

Gly Val Ile Trp Gly Ser Glu Thr Thr Tyr Tyr Asn Ser Ala Leu Lys
        195                 200                 205
```

```
Ser Arg Leu Thr Ile Ile Lys Asp Asn Ser Lys Ser Gln Val Phe Leu
    210                 215                 220

Lys Met Asn Ser Leu Gln Thr Asp Asp Thr Ala Ile Tyr Tyr Cys Ala
225                 230                 235                 240

Lys His Tyr Tyr Tyr Gly Gly Ser Tyr Ala Met Asp Tyr Trp Gly Gln
            245                 250                 255

Gly Thr Ser Val Thr Val Ser Ser Ala Ala Ala Thr Thr Thr Pro Ala
            260                 265                 270

Pro Arg Pro Pro Thr Pro Ala Pro Thr Ile Ala Ser Gln Pro Leu Ser
            275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
            325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
            355                 360                 365

Pro Glu Glu Glu Glu Gly Gly Cys Glu Leu Arg Val Lys Phe Ser Arg
    370                 375                 380

Ser Ala Asp Ala Pro Ala Tyr Gln Gln Gly Gln Asn Gln Leu Tyr Asn
385                 390                 395                 400

Glu Leu Asn Leu Gly Arg Arg Glu Glu Tyr Asp Val Leu Asp Lys Arg
            405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
            435                 440                 445

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg Arg Ala Lys Arg Gly Ser
            485                 490                 495

Gly Ala Thr Asn Phe Ser Leu Leu Lys Gln Ala Gly Asp Val Glu Glu
            500                 505                 510

Asn Pro Gly Pro Arg Ala Lys Arg Val Asp Met Gly Arg Gly Leu Leu
            515                 520                 525

Arg Gly Leu Trp Pro Leu His Ile Val Leu Trp Thr Arg Ile Ala Ser
    530                 535                 540

Thr Ile Pro Pro His Val Gln Lys Ser Val Asn Asn Asp Met Ile Val
545                 550                 555                 560

Thr Asp Asn Asn Gly Ala Val Lys Phe Pro Gln Leu Cys Lys Phe Cys
            565                 570                 575

Asp Val Arg Phe Ser Thr Cys Asp Asn Gln Lys Ser Cys Met Ser Asn
            580                 585                 590

Cys Ser Ile Thr Ser Ile Cys Glu Lys Pro Gln Glu Val Cys Val Ala
            595                 600                 605

Val Trp Arg Lys Asn Asp Glu Asn Ile Thr Leu Glu Thr Val Cys His
    610                 615                 620

Asp Pro Lys Leu Pro Tyr His Asp Phe Ile Leu Glu Asp Ala Ala Ser
```

```
             625                 630                 635                 640
Pro Lys Cys Ile Met Lys Glu Lys Lys Lys Pro Gly Glu Thr Phe Phe
                    645                 650                 655
Met Cys Ser Cys Ser Ser Asp Glu Cys Asn Asp Asn Ile Ile Phe Ser
                660                 665                 670
Glu Glu Tyr Asn Thr Ser Asn Pro Asp Leu Leu Leu Val Ile Phe Gln
            675                 680                 685
Val Thr Gly Ile Ser Leu Leu Pro Pro Leu Gly Val Ala Ile Ser Val
        690                 695                 700
Ile Ile Ile Phe Tyr Cys Tyr Arg Val
705             710
```

<210> SEQ ID NO 105
<211> LENGTH: 2390
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 105

| | | | | | |
|---|---|---|---|---|---|
| tgagctctga | gtcagtgact | cagtgagtca | gtgactcagt | gagtcagtga | ctcagctcga | 60 |
| ggatctcgct | agcgggaatt | ccggggact | tccggggaat | tccggggac | tttccgggaa | 120 |
| tttccagatc | tggcctcggc | ggccaagctt | agacactaga | gggtatataa | tggaagctcg | 180 |
| acttccagct | tggcaatccg | gtactgttgg | taaaggcgcg | ccccaccatg | ctgctgctgg | 240 |
| tcaccagcct | gctgctgtgc | gagctccctc | accccgcctt | tctgcttatc | ccggacattc | 300 |
| agatgacaca | gaccacctcg | agcttgtccg | cgtcgctggg | cgatcgcgtg | accatctcct | 360 |
| gccgggcctc | ccaagacatt | tcaaagtatc | tcaactggta | ccagcagaag | ccggacggaa | 420 |
| ccgtgaaact | gctgatctac | cataccagcc | gcctgcactc | cggcgtgccg | tcccgcttct | 480 |
| ccggatcggg | ttccggaact | gactactcac | tgactatctc | caacttggaa | caagaggaca | 540 |
| tcgccactta | cttctgtcaa | caaggaaata | cccttcccta | caccttcggg | ggggtaccaa | 600 |
| agctggagat | cactgggggc | ggaggctccg | gtggaggcgg | atccggcggt | ggagggagcg | 660 |
| aagtcaagct | gcaggaatca | ggaccaggac | tcgtggcgcc | atcccagtcc | ctgtcggtga | 720 |
| cctgtactgt | ctccggagtc | agcctccccg | attacgagt | gtcatggatt | aggcaacccc | 780 |
| caagaaaagg | gctggaatgg | ctcggagtga | tctgggctc | cgaaaccacc | tactacaact | 840 |
| cggcgctgaa | gtcccggctg | accatcatca | aggacaactc | caagagccaa | gtgttcttga | 900 |
| agatgaacag | cttgcagacc | gacgataccg | caatctacta | ctgtgccaag | cactattact | 960 |
| acggggggtc | ttacgccatg | gactactggg | gacagggcac | ctccgtgact | gtgtcgtccg | 1020 |
| cggccgctac | cacaaccct | gcgccccggc | ctcctacccc | cgcacccacg | attgcttctc | 1080 |
| aacctctttc | actccgacct | gaggcttgta | gacctgcagc | cggggtgcc | gtccacacac | 1140 |
| ggggactcga | cttcgcttgt | gatatatata | tttgggcgcc | cctggccggc | acttgtggag | 1200 |
| ttcttttgct | ctctcttgtt | atcacattgt | actgcaagcg | aggtaggaag | aaattgcttt | 1260 |
| acattttaa | gcagccgttc | atgcgaccag | tacgactac | tcaagaagaa | gatgggtgct | 1320 |
| cttgtcggtt | cccggaagaa | gaagagggtg | gttgcgagtt | gagggtgaag | ttctcccgct | 1380 |
| ctgccgacgc | accggcatat | cagcaggac | aaaaccagct | ctacaacgaa | ttgaacctgg | 1440 |
| gtcggcggga | agaatatgac | gtgctcgata | agcggcgggg | tcgcgaccca | gaaatgggag | 1500 |

```
gcaaaccgcg caggaaaaat ccacaggagg gactttataa cgaacttcaa aaggataaga    1560
tggcagaggc atacagcgaa atcgggatga aaggcgagag aagaaggggg aaagggcacg    1620 atggtctta  ccaggggctt tctaccgcga cgaaggatac ctacgatgct ctccatatgc    1680
aagcacttcc tcctagacgg gcaaagcggg gctcaggggc gactaacttt tcactgttga    1740
agcaggccgg ggatgtggag gagaatcctg gtcctagagc taagcgagta gacatgcaaa    1800
taccacaagc gccgtggccc gtcgtctggg ctgttcttca gcttggctgg agacctggct    1860
ggtttctcga ttctccagat aggccctgga acccaccgac gttcagtccg gcacttctcg    1920
tggtcacaga gggggacaac gccactttta cgtgctcctt tagcaacacc tccgagtcct    1980
tcgtactgaa ttggtatcgc atgagtccgt ccaatcagac ggacaagttg gccgcgtttc    2040
ctgaagatag gtcacaacct ggccaagact gtcggttccg ggtcacccag ttgccgaatg    2100
ggagggactt tcatatgagc gtcgttcggg caagaaggaa cgattctgga acgtatttgt    2160
gcggggccat tagccttgcg ccaaaagcgc agataaagga gtcccttcgg gcagaacttc    2220
gcgtgacaga gcgacgcgct gaagttccga ctgcccatcc ctctccgagc ccacgaccag    2280
ccggacaatt tcagactctt gtggtgggtg tggtaggcgg cctgctcgga agcttggtct    2340
tgctggtgtg ggtcctggct gtgatttgca gtcgagcagc ccgcggcacc               2390
```

<210> SEQ ID NO 106
<211> LENGTH: 721
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 106

```
Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Gly Gly Gly Ser Gly Gly Gly Gly Ser Gly Gly Gly Gly Ser
    130                 135                 140

Glu Val Lys Leu Gln Glu Ser Gly Pro Gly Leu Val Ala Pro Ser Gln
145                 150                 155                 160

Ser Leu Ser Val Thr Cys Thr Val Ser Gly Val Ser Leu Pro Asp Tyr
                165                 170                 175

Gly Val Ser Trp Ile Arg Gln Pro Pro Arg Lys Gly Leu Glu Trp Leu
            180                 185                 190

Gly Val Ile Trp Gly Ser Glu Thr Thr Tyr Tyr Asn Ser Ala Leu Lys
```

-continued

```
                195                 200                 205
Ser Arg Leu Thr Ile Ile Lys Asp Asn Ser Lys Ser Gln Val Phe Leu
210                 215                 220

Lys Met Asn Ser Leu Gln Thr Asp Asp Thr Ala Ile Tyr Tyr Cys Ala
225                 230                 235                 240

Lys His Tyr Tyr Tyr Gly Gly Ser Tyr Ala Met Asp Tyr Trp Gly Gln
                245                 250                 255

Gly Thr Ser Val Thr Val Ser Ser Ala Ala Thr Thr Thr Pro Ala
                260                 265                 270

Pro Arg Pro Pro Thr Pro Ala Pro Thr Ile Ala Ser Gln Pro Leu Ser
                275                 280                 285

Leu Arg Pro Glu Ala Cys Arg Pro Ala Ala Gly Gly Ala Val His Thr
                290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
                340                 345                 350

Arg Pro Val Gln Thr Thr Gln Glu Glu Asp Gly Cys Ser Cys Arg Phe
                355                 360                 365

Pro Glu Glu Glu Gly Gly Cys Glu Leu Arg Val Lys Phe Ser Arg
370                 375                 380

Ser Ala Asp Ala Pro Ala Tyr Gln Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
                420                 425                 430

Gln Glu Gly Leu Tyr Asn Glu Leu Gln Lys Asp Lys Met Ala Glu Ala
                435                 440                 445

Tyr Ser Glu Ile Gly Met Lys Gly Glu Arg Arg Arg Gly Lys Gly His
450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg Arg Ala Lys Arg Gly Ser
                485                 490                 495

Gly Ala Thr Asn Phe Ser Leu Leu Lys Gln Ala Gly Asp Val Glu Glu
                500                 505                 510

Asn Pro Gly Pro Arg Ala Lys Arg Val Asp Met Gln Ile Pro Gln Ala
                515                 520                 525

Pro Trp Pro Val Val Trp Ala Val Leu Gln Leu Gly Trp Arg Pro Gly
                530                 535                 540

Trp Phe Leu Asp Ser Pro Asp Arg Pro Trp Asn Pro Pro Thr Phe Ser
545                 550                 555                 560

Pro Ala Leu Leu Val Val Thr Glu Gly Asp Asn Ala Thr Phe Thr Cys
                565                 570                 575

Ser Phe Ser Asn Thr Ser Glu Ser Phe Val Leu Asn Trp Tyr Arg Met
                580                 585                 590

Ser Pro Ser Asn Gln Thr Asp Lys Leu Ala Ala Phe Pro Glu Asp Arg
                595                 600                 605

Ser Gln Pro Gly Gln Asp Cys Arg Phe Arg Val Thr Gln Leu Pro Asn
                610                 615                 620
```

Gly Arg Asp Phe His Met Ser Val Val Arg Ala Arg Asn Asp Ser
625                 630                 635                 640

Gly Thr Tyr Leu Cys Gly Ala Ile Ser Leu Ala Pro Lys Ala Gln Ile
            645                 650                 655

Lys Glu Ser Leu Arg Ala Glu Leu Arg Val Thr Glu Arg Ala Glu
        660                 665                 670

Val Pro Thr Ala His Pro Ser Pro Ser Pro Arg Pro Ala Gly Gln Phe
            675                 680                 685

Gln Thr Leu Val Val Gly Val Gly Gly Leu Leu Gly Ser Leu Val
        690                 695                 700

Leu Leu Val Trp Val Leu Ala Val Ile Cys Ser Arg Ala Ala Arg Gly
705                 710                 715                 720

Thr

<210> SEQ ID NO 107
<211> LENGTH: 3050
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 107
tgagctctga gtcagtgact cagtgagtca gtgactcagt gagtcagtga ctcagctcga      60
ggatctcgct agcgggaatt ccgggggact tccggggaat tccggggac tttccgggaa     120 tttccagatc tggcctcggc ggccaagctt agacactaga gggtatataa tggaagctcg    180
acttccagct tggcaatccg gtactgttgg taaaggcgcg ccccaccatg ctgctgctgg    240
tcaccagcct gctgctgtgc gagctccctc accccgcctt tctgcttatc ccggacattc    300
agatgacaca gaccacctcg agcttgtccg cgtcgctggg cgatcgcgtg accatctcct    360
gccgggcctc ccaagacatt tcaaagtatc tcaactggta ccagcagaag ccggacggaa    420
ccgtgaaact gctgatctac cataccagcc gcctgcactc cggcgtgccg tcccgcttct    480
ccggatcggg ttccggaact gactactcac tgactatctc caacttggaa caagaggaca    540
tcgccactta cttctgtcaa caaggaaata cccttcccta caccttcggg gggggtacca    600
agctggagat cactggggc ggaggctccg gtggaggcgg atccggcggt ggaggagcg     660 aagtcaagct gcaggaatca ggaccaggac tcgtggcgcc atcccagtcc ctgtcggtga    720
cctgtactgt ctccggagtc agcctccccg attacggagt gcatggatt aggcaacccc    780 caagaaaagg gctggaatgg ctcggagtga tctgggctc cgaaaccacc tactacaact    840
cggcgctgaa gtcccggctg accatcatca aggacaactc caagagccaa gtgttcttga    900
agatgaacag cttgcagacc gacgataccg caatctacta ctgtgccaag cactattact    960
acggggggtc ttacgccatg gactactggg gacagggcac ctccgtgact gtgtcgtccg   1020
cggccgctac cacaaccct gcgccccggc ctcctacccc cgcacccacg attgcttctc    1080 aacctcttc actccgacct gaggcttgta gacctgcagc cgggggtgcc gtccacacac    1140
ggggactcga cttcgcttgt gatatatata tttgggcgcc cctggccggc acttgtggag   1200
ttcttttgct ctctcttgtt atcacattgt actgcaagcg aggtaggaag aaattgcttt   1260
acatttttaa gcagccgttc atgcgaccag tacagactac tcaagaagaa gatgggtgct   1320
cttgtcggtt cccggaagaa gaagagggtg gttgcgagtt gagggtgaag ttctcccgct   1380

```
ctgccgacgc accggcatat cagcagggac aaaaccagct ctacaacgaa ttgaacctgg    1440
gtcggcggga agaatatgac gtgctcgata agcggcgggg tcgcgaccca gaaatgggag    1500
gcaaaccgcg caggaaaaat ccacaggagg gactttataa cgaacttcaa aaggataaga    1560
tggcagaggc atacagcgaa atcgggatga aaggcgagag aagaagggggg aaagggcacg    1620 atggtctttta ccaggggctt tctaccgcga cgaaggatac ctacgatgct ctccatatgc    1680
aagcacttcc tcctagacgg gcaaagcggg gctcaggggc gactaacttt tcactgttga    1740
agcaggccgg ggatgtggag gagaatcctg gtcctagagc taagcgagta gacatgcaaa    1800
taccacaagc gccgtggccc gtcgtctggg ctgttcttca gcttggctgg agacctggct    1860
ggtttctcga ttctccagat aggccctgga acccaccgac gttcagtccg gcacttctcg    1920
tggtcacaga gggggacaac gccactttta cgtgctcctt tagcaacacc tccgagtcct    1980
tcgtactgaa ttggtatcgc atgagtccgt ccaatcagac ggacaagttg gccgcgtttc    2040
ctgaagatag gtcacaacct ggccaagact gtcggttccg ggtcacccag ttgccgaatg    2100
ggagggactt tcatatgagc gtcgttcggg caagaaggaa cgattctgga acgtatttgt    2160
gcggggccat tagccttgcg ccaaaagcgc agataaagga gtcccttcgg gcagaacttc    2220
gcgtgacaga gcgacgcgct gaagttccga ctgcccatcc ctctccgagc ccacgaccag    2280
ccggacaatt tcagactctt gtggtgggtg tggtaggcgg cctgctcgga agcttggtct    2340
tgctggtgtg ggtcctggct gtgatttgca gtcgagcagc ccgcggcacc cgggctaaac    2400
ggagcggctc cggggcaacc aactttagtc tgctgaaaca ggcaggagat gtggaggaaa    2460
acccaggacc agctagcatg ggaagagggc tgctccgagg cttgtggccg ttgcatattg    2520
tattgtggac gcggatagcg agtacaatcc cgcctcacgt gcaaaaatca gttaataacg    2580
acatgatcgt tactgacaac aatggcgcag ttaaatttcc gcagctttgt aaattctgtg    2640
atgtaagatt ttcaacgtgc gataaccaga aaagctgtat gtccaactgc agcatcacat    2700
caatctgtga aaaccccaa gaggtatgtg tggccgtctg gcgaaagaat gacgaaaata    2760
tcacactgga gaccgtttgt cacgatccta aactccctta tcatgacttt attctggaag    2820
acgcagcgtc accgaagtgt ataatgaaag agaagaagaa gcctggagag cgttttttca    2880
tgtgcagttg ctcctcagat gagtgtaatg acaacatcat ttttttccgag gagtacaata    2940 cgagtaaccc agacctcctg ctggttattt tccaggtaac cggcatcagt ttgttgcccc    3000
cactgggtgt tgcaatcagt gtaataatca tattttattg ttaccgggtg              3050

<210> SEQ ID NO 108
<211> LENGTH: 941
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 108

Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60
```

```
Thr Val Lys Leu Leu Ile Tyr His Thr Ser Arg Leu His Ser Gly Val
 65                  70                  75                  80

Pro Ser Arg Phe Ser Gly Ser Gly Ser Gly Thr Asp Tyr Ser Leu Thr
                 85                  90                  95

Ile Ser Asn Leu Glu Gln Glu Asp Ile Ala Thr Tyr Phe Cys Gln Gln
                100                 105                 110

Gly Asn Thr Leu Pro Tyr Thr Phe Gly Gly Gly Thr Lys Leu Glu Ile
                115                 120                 125

Thr Gly Gly Gly Gly Ser Gly Gly Gly Gly Ser Gly Gly Gly Gly Ser
130                 135                 140

Glu Val Lys Leu Gln Glu Ser Gly Pro Gly Leu Val Ala Pro Ser Gln
145                 150                 155                 160

Ser Leu Ser Val Thr Cys Thr Val Ser Gly Val Ser Leu Pro Asp Tyr
                165                 170                 175

Gly Val Ser Trp Ile Arg Gln Pro Pro Arg Lys Gly Leu Glu Trp Leu
                180                 185                 190

Gly Val Ile Trp Gly Ser Glu Thr Thr Tyr Tyr Asn Ser Ala Leu Lys
                195                 200                 205

Ser Arg Leu Thr Ile Ile Lys Asp Asn Ser Lys Ser Gln Val Phe Leu
210                 215                 220

Lys Met Asn Ser Leu Gln Thr Asp Asp Thr Ala Ile Tyr Tyr Cys Ala
225                 230                 235                 240

Lys His Tyr Tyr Tyr Gly Gly Ser Tyr Ala Met Asp Tyr Trp Gly Gln
                245                 250                 255

Gly Thr Ser Val Thr Val Ser Ser Ala Ala Thr Thr Thr Pro Ala
                260                 265                 270

Pro Arg Pro Pro Thr Pro Ala Pro Thr Ile Ala Ser Gln Pro Leu Ser
                275                 280                 285

Leu Arg Pro Glu Ala Cys Arg Pro Ala Ala Gly Gly Ala Val His Thr
290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
                340                 345                 350

Arg Pro Val Gln Thr Thr Gln Glu Glu Asp Gly Cys Ser Cys Arg Phe
                355                 360                 365

Pro Glu Glu Glu Glu Gly Gly Cys Glu Leu Arg Val Lys Phe Ser Arg
                370                 375                 380

Ser Ala Asp Ala Pro Ala Tyr Gln Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
                420                 425                 430

Gln Glu Gly Leu Tyr Asn Glu Leu Gln Lys Asp Lys Met Ala Glu Ala
                435                 440                 445

Tyr Ser Glu Ile Gly Met Lys Gly Glu Arg Arg Arg Gly Lys Gly His
                450                 455                 460

Asp Gly Leu Tyr Gln Gly Leu Ser Thr Ala Thr Lys Asp Thr Tyr Asp
465                 470                 475                 480
```

Ala Leu His Met Gln Ala Leu Pro Pro Arg Ala Lys Arg Gly Ser
            485                 490                 495

Gly Ala Thr Asn Phe Ser Leu Leu Lys Gln Ala Gly Asp Val Glu Glu
        500                 505                 510

Asn Pro Gly Pro Arg Ala Lys Arg Val Asp Met Gln Ile Pro Gln Ala
            515                 520                 525

Pro Trp Pro Val Val Trp Ala Val Leu Gln Leu Gly Trp Arg Pro Gly
        530                 535                 540

Trp Phe Leu Asp Ser Pro Asp Arg Pro Trp Asn Pro Thr Phe Ser
545                 550                 555                 560

Pro Ala Leu Leu Val Val Thr Glu Gly Asp Asn Ala Thr Phe Thr Cys
            565                 570                 575

Ser Phe Ser Asn Thr Ser Glu Ser Phe Val Leu Asn Trp Tyr Arg Met
        580                 585                 590

Ser Pro Ser Asn Gln Thr Asp Lys Leu Ala Ala Phe Pro Glu Asp Arg
        595                 600                 605

Ser Gln Pro Gly Gln Asp Cys Arg Phe Arg Val Thr Gln Leu Pro Asn
    610                 615                 620

Gly Arg Asp Phe His Met Ser Val Val Arg Ala Arg Arg Asn Asp Ser
625                 630                 635                 640

Gly Thr Tyr Leu Cys Gly Ala Ile Ser Leu Ala Pro Lys Ala Gln Ile
            645                 650                 655

Lys Glu Ser Leu Arg Ala Glu Leu Arg Val Thr Glu Arg Arg Ala Glu
        660                 665                 670

Val Pro Thr Ala His Pro Ser Pro Ser Pro Arg Pro Ala Gly Gln Phe
        675                 680                 685

Gln Thr Leu Val Val Gly Val Val Gly Gly Leu Leu Gly Ser Leu Val
        690                 695                 700

Leu Leu Val Trp Val Leu Ala Val Ile Cys Ser Arg Ala Ala Arg Gly
705                 710                 715                 720

Thr Arg Ala Lys Arg Ser Gly Ser Gly Ala Thr Asn Phe Ser Leu Leu
            725                 730                 735

Lys Gln Ala Gly Asp Val Glu Glu Asn Pro Gly Pro Ala Ser Met Gly
            740                 745                 750

Arg Gly Leu Leu Arg Gly Leu Trp Pro Leu His Ile Val Leu Trp Thr
        755                 760                 765

Arg Ile Ala Ser Thr Ile Pro Pro His Val Gln Lys Ser Val Asn Asn
        770                 775                 780

Asp Met Ile Val Thr Asp Asn Asn Gly Ala Val Lys Phe Pro Gln Leu
785                 790                 795                 800

Cys Lys Phe Cys Asp Val Arg Phe Ser Thr Cys Asp Asn Gln Lys Ser
            805                 810                 815

Cys Met Ser Asn Cys Ser Ile Thr Ser Ile Cys Glu Lys Pro Gln Glu
            820                 825                 830

Val Cys Val Ala Val Trp Arg Lys Asn Asp Glu Asn Ile Thr Leu Glu
        835                 840                 845

Thr Val Cys His Asp Pro Lys Leu Pro Tyr His Asp Phe Ile Leu Glu
    850                 855                 860

Asp Ala Ala Ser Pro Lys Cys Ile Met Lys Glu Lys Lys Lys Pro Gly
865                 870                 875                 880

Glu Thr Phe Phe Met Cys Ser Cys Ser Ser Asp Glu Cys Asn Asp Asn
            885                 890                 895

Ile Ile Phe Ser Glu Glu Tyr Asn Thr Ser Asn Pro Asp Leu Leu Leu

```
              900            905             910
Val Ile Phe Gln Val Thr Gly Ile Ser Leu Leu Pro Pro Leu Gly Val
            915                 920                 925

Ala Ile Ser Val Ile Ile Ile Phe Tyr Cys Tyr Arg Val
        930                 935                 940
```

<210> SEQ ID NO 109
<211> LENGTH: 2342
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 109

| | | | | | |
|---|---|---|---|---|---|
| ggtacctgag | ctcagttctg | agaaaagtag | ttctgagaaa | agtagttctg | agaaaagtag | 60 |
| ttctgagaaa | agtagttctg | agaaaagtct | cgaggatatc | aagatctggc | ctcggcggcc | 120 |
| aagcttagac | actagagggt | atataatgga | agctcgactt | ccagcttggc | aatccggtac | 180 |
| tgttggtaaa | ggcgcgcccc | accatgctgc | tgctggtcac | cagcctgctg | ctgtgcgagc | 240 |
| tccctcaccc | cgccttttctg | cttatcccgg | acattcagat | gacacagacc | acctcgagct | 300 |
| tgtccgcgtc | gctgggcgat | cgcgtgacca | tctcctgccg | ggcctcccaa | gacatttcaa | 360 |
| agtatctcaa | ctggtaccag | cagaagccgg | acggaaccgt | gaaactgctg | atctaccata | 420 |
| ccagccgcct | gcactccggc | gtgccgtccc | gcttctccgg | atcgggttcc | ggaactgact | 480 |
| actcactgac | tatctccaac | ttggaacaag | gacatcgc | cacttacttc | tgtcaacaag | 540 |
| gaaataccct | tccctacacc | ttcgggggg | gtaccaagct | ggagatcact | ggggcggag | 600 |
| gctccggtgg | aggcggatcc | ggcggtgag | ggagcgaagt | caagctgcag | gaatcaggac | 660 |
| caggactcgt | ggcgccatcc | cagtccctgt | cggtgacctg | tactgtctcc | ggagtcagcc | 720 |
| tccccgatta | cggagtgtca | tggattaggc | aaccccaag | aaaagggctg | aatggctcg | 780 |
| gagtgatctg | ggctccgaa | accacctact | acaactcggc | gctgaagtcc | cggctgacca | 840 |
| tcatcaagga | caactccaag | agccaagtgt | tcttgaagat | aacagcttg | cagaccgacg | 900 |
| ataccgcaat | ctactactgt | gccaagcact | attactacgg | ggggtcttac | gccatggact | 960 |
| actggggaca | gggcacctcc | gtgactgtgt | cgtccgcggc | cgctaccaca | accctgcgc | 1020 |
| cccggcctcc | taccccgca | cccacgattg | cttctcaacc | tctttcactc | cgacctgagg | 1080 |
| cttgtagacc | tgcagccggg | ggtgccgtcc | acacacgggg | actcgacttc | gcttgtgata | 1140 |
| tatatatttg | ggcgcccctg | gccggcactt | gtggagttct | tttgctctct | cttgttatca | 1200 |
| cattgtactg | caagcgaggt | aggaagaaat | tgctttacat | ttttaagcag | ccgttcatgc | 1260 |
| gaccagtaca | gactactcaa | gaagaagatg | ggtgctcttg | tcggttcccg | gaagaagaag | 1320 |
| agggtggttg | cgagttgagg | gtgaagttct | cccgctctgc | cgacgcaccg | gcatatcagc | 1380 |
| agggacaaaa | ccagctctac | aacgaattga | acctgggtcg | gcgggaagaa | tatgacgtgc | 1440 |
| tcgataagcg | gcggggtcgc | gacccagaaa | tgggaggcaa | accgcgcagg | aaaaatccac | 1500 |
| aggagggact | ttataacgaa | cttcaaaagg | ataagatggc | agaggcatac | agcgaaatcg | 1560 |
| ggatgaaagg | cgagagaaga | aggggaaag | ggcacgatgg | tctttaccag | ggctttctca | 1620 |
| ccgcgacgaa | ggatacctac | gatgctctcc | atatgcaagc | acttcctcct | agacgggcaa | 1680 |
| agcggggctc | aggggcgact | aacttttcac | tgttgaagca | ggccggggat | gtggaggaga | 1740 |
| atcctggtcc | tagagctaag | cgagtagaca | tgggaagagg | gctgctccga | ggcttgtggc | 1800 |

| | |
|---|---|
| cgttgcatat tgtattgtgg acgcggatag cgagtacaat cccgcctcac gtgcaaaaat | 1860 |
| cagttaataa cgacatgatc gttactgaca acaatggcgc agttaaattt ccgcagcttt | 1920 |
| gtaaattctg tgatgtaaga ttttcaacgt gcgataacca gaaaagctgt atgtccaact | 1980 |
| gcagcatcac atcaatctgt gaaaaacccc aagaggtatg tgtggccgtc tggcgaaaga | 2040 |
| atgacgaaaa tatcacactg gagaccgttt gtcacgatcc taaactccct tatcatgact | 2100 |
| ttattctgga agacgcagcg tcaccgaagt gtataatgaa agagaagaag aagcctggag | 2160 |
| agacgttttt catgtgcagt tgctcctcag atgagtgtaa tgacaacatc attttttccg | 2220 |
| aggagtacaa tacgagtaac ccagacctcc tgctggttat tttccaggta accggcatca | 2280 |
| gtttgttgcc cccactgggt gttgcaatca gtgtaataat catattttat tgttaccggg | 2340 |
| tg | 2342 |

<210> SEQ ID NO 110
<211> LENGTH: 2366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 110

| | |
|---|---|
| ggtacctgag ctcagttctg agaaaagtag ttctgagaaa agtagttctg agaaaagtag | 60 |
| ttctgagaaa agtagttctg agaaaagtct cgaggatatc aagatctggc ctcggcggcc | 120 |
| aagcttagac actagagggt atataatgga agctcgactt ccagcttggc aatccggtac | 180 |
| tgttggtaaa ggcgcgcccc accatgctgc tgctggtcac cagcctgctg ctgtgcgagc | 240 |
| tccctcaccc cgcctttctg cttatcccgg acattcagat gacacagacc acctcgagct | 300 |
| tgtccgcgtc gctgggcgat cgcgtgacca tctcctgccg ggcctcccaa gacatttcaa | 360 |
| agtatctcaa ctggtaccag cagaagccgg acggaaccgt gaaactgctg atctaccata | 420 |
| ccagccgcct gcactccggc gtgccgtccc gcttctccgg atcgggttcc ggaactgact | 480 |
| actcactgac tatctccaac ttggaacaag aggacatcgc cacttacttc tgtcaacaag | 540 |
| gaaataccct tccctacacc ttcggggggg gtaccaagct ggagatcact ggggggcggag | 600 |
| gctccggtgg aggcggatcc ggcggtggag ggagcgaagt caagctgcag gaatcaggac | 660 |
| caggactcgt ggcgccatcc cagtccctgt cggtgacctg tactgtctcc ggagtcagcc | 720 |
| tccccgatta cggagtgtca tggattaggc aaccccaag aaaagggctg gaatggctcg | 780 |
| gagtgatctg gggctccgaa accacctact acaactcggc gctgaagtcc cggctgacca | 840 |
| tcatcaagga caactccaag agccaagtgt tcttgaagat gaacagcttg cagaccgacg | 900 |
| ataccgcaat ctactactgt gccaagcact attactacgg ggggtcttac gccatggact | 960 |
| actggggaca gggcacctcc gtgactgtgt cgtccgcggc cgctaccaca acccctgcgc | 1020 |
| cccggcctcc taccccgca cccacgattg cttctcaacc tctttcactc gacctgaggc | 1080 |
| cttgtagacc tgcagccggg ggtgccgtcc acacacgggg actcgacttc gcttgtgata | 1140 |
| tatatatttg ggcgcccctg gccggcactt gtggagttct tttgctctct cttgttatca | 1200 |
| cattgtactg caagcgaggt aggaagaaat tgctttacat ttttaagcag ccgttcatgc | 1260 |
| gaccagtaca gactactcaa gaagaagatg ggtgctcttg tcggttcccg gaagaagaag | 1320 |
| agggtggttg cgagttgagg gtgaagttct cccgctctgc cgacgcaccg gcatatcagc | 1380 |

| | |
|---|---|
| agggacaaaa ccagctctac aacgaattga acctgggtcg gcgggaagaa tatgacgtgc | 1440 |
| tcgataagcg gcggggtcgc gacccagaaa tgggaggcaa accgcgcagg aaaaatccac | 1500 |
| aggagggact ttataacgaa cttcaaaagg ataagatggc agaggcatac agcgaaatcg | 1560 |
| ggatgaaagg cgagagaaga aggggggaaag ggcacgatgg tctttaccag gggcttttcta | 1620 |
| ccgcgacgaa ggatacctac gatgctctcc atatgcaagc acttcctcct agacgggcaa | 1680 |
| agcggggctc aggggcgact aacttttcac tgttgaagca ggccggggat gtggaggaga | 1740 |
| atcctggtcc tagagctaag cgagtagaca tgcaaatacc acaagcgccg tggcccgtcg | 1800 |
| tctgggctgt tcttcagctt ggctggagac ctggctggtt tctcgattct ccagataggc | 1860 |
| cctggaaccc accgacgttc agtccggcac ttctcgtggt cacagagggg gacaacgcca | 1920 |
| cttttacgtg ctcctttagc aacacctccg agtccttcgt actgaattgg tatcgcatga | 1980 |
| gtccgtccaa tcagacggac aagttggccg cgtttcctga agataggtca caacctggcc | 2040 |
| aagactgtcg gttccgggtc acccagttgc cgaatgggag ggactttcat atgagcgtcg | 2100 |
| ttcgggcaag aaggaacgat tctggaacgt atttgtgcgg ggccattagc cttgcgccaa | 2160 |
| aagcgcagat aaaggagtcc cttcgggcag aacttcgcgt gacagagcga cgcgctgaag | 2220 |
| ttccgactgc ccatccctct ccgagcccac gaccagccgg acaatttcag actcttgtgg | 2280 |
| tgggtgtggt aggcggcctg ctcggaagct tggtcttgct ggtgtgggtc ctggctgtga | 2340 |
| tttgcagtcg agcagcccgc ggcacc | 2366 |

<210> SEQ ID NO 111
<211> LENGTH: 3026
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 111

| | |
|---|---|
| ggtacctgag ctcagttctg agaaaagtag ttctgagaaa agtagttctg agaaaagtag | 60 |
| ttctgagaaa agtagttctg agaaaagtct cgaggatatc aagatctggc ctcggcggcc | 120 |
| aagcttagac actagagggt atataatgga agctcgactt ccagcttggc aatccggtac | 180 |
| tgttggtaaa ggcgcgcccc accatgctgc tgctggtcac cagcctgctg ctgtgcgagc | 240 |
| tccctcaccc cgcctttctg cttatcccgg acattcagat gacacagacc acctcgagct | 300 |
| tgtccgcgtc gctgggcgat cgcgtgacca tctcctgccg ggcctcccaa gacatttcaa | 360 |
| agtatctcaa ctggtaccag cagaagccgg acggaaccgt gaaactgctg atctaccata | 420 |
| ccagccgcct gcactccggc gtgccgtccc gcttctccgg atcgggttcc ggaactgact | 480 |
| actcactgac tatctccaac ttggaacaag aggacatcgc cacttacttc tgtcaacaag | 540 |
| gaaatacccct tccctacacc ttcgggggg gtaccaagct ggagatcact ggggggcggag | 600 |
| gctccggtgg aggcggatcc ggcggtgagg ggagcgaagt caagctgcag gaatcaggac | 660 |
| caggactcgt ggcgccatcc cagtccctgt cggtgacctg tactgtctcc ggagtcagcc | 720 |
| tccccgatta cggagtgtca tggattaggc aaccccaag aaaagggctg aatggctcg | 780 |
| gagtgatctg gggctccgaa accacctact acaactcggc gctgaagtcc cggctgacca | 840 |
| tcatcaagga caactccaag agccaagtgt tcttgaagat gaacagcttg cagaccgacg | 900 |
| ataccgcaat ctactactgt gccaagcact attactacgg ggggtcttac gccatggact | 960 |
| actggggaca gggcaccctcc gtgactgtgt cgtccgcggc cgctaccaca ccccctgcgc | 1020 |

```
cccggcctcc taccccccgca cccacgattg cttctcaacc tctttcactc cgacctgagg   1080
cttgtagacc tgcagccggg ggtgccgtcc acacacgggg actcgacttc gcttgtgata   1140
tatatatttg ggcgcccctg gccggcactt gtggagttct tttgctctct cttgttatca   1200
cattgtactg caagcgaggt aggaagaaat tgctttacat ttttaagcag ccgttcatgc   1260
gaccagtaca gactactcaa gaagaagatg ggtgctcttg tcggttcccg gaagaagaag   1320 aggggtggttg cgagttgagg gtgaagttct cccgctctgc cgacgcaccg gcatatcagc   1380
agggacaaaa ccagctctac aacgaattga acctgggtcg gcgggaagaa tatgacgtgc   1440
tcgataagcg gcggggtcgc gacccagaaa tgggaggcaa accgcgcagg aaaaatccac   1500
aggagggact ttataacgaa cttcaaaagg ataagatggc agaggcatac agcgaaatcg   1560
ggatgaaagg cgagagaaga aggggggaaag ggcacgatgg tctttaccag gggctttcta   1620
ccgcgacgaa ggatacctac gatgctctcc atatgcaagc acttcctcct agacgggcaa   1680 agcgggctc aggggcgact aacttttcac tgttgaagca ggccggggat gtggaggaga   1740
atcctggtcc tagagctaag cgagtagaca tgcaaatacc acaagcgccg tggcccgtcg   1800
tctgggctgt tcttcagctt ggctggagac ctggctggtt tctcgattct ccagataggc   1860
cctggaaccc accgacgttc agtccggcac ttctcgtggt cacagagggg gacaacgcca   1920
cttttacgtg ctcctttagc aacacctccg agtccttcgt actgaattgg tatcgcatga   1980
gtccgtccaa tcagacggac aagttggccg cgtttcctga agataggtca caacctggcc   2040
aagactgtcg gttccgggtc acccagttgc cgaatgggag ggactttcat atgagcgtcg   2100
ttcgggcaag aaggaacgat tctggaacgt atttgtgcgg ggccattagc cttgcgccaa   2160
aagcgcagat aaaggagtcc cttcgggcag aacttcgcgt gacagagcga cgcgctgaag   2220
ttccgactgc ccatccctct ccgagcccac gaccagccgg acaatttcag actcttgtgg   2280
tgggtgtggt aggcggcctg ctcggaagct tggtcttgct ggtgtgggtc ctggctgtga   2340
tttgcagtcg agcagcccgc ggcacccggg ctaaacggag cggctccggg gcaaccaact   2400
ttagtctgct gaaacaggca ggagatgtgg aggaaaaccc aggaccagct agcatgggaa   2460
gagggctgct ccgaggcttg tggccgttgc atattgtatt gtggacgcgg atagcgagta   2520
caatcccgcc tcacgtgcaa aaatcagtta ataacgacat gatcgttact gacaacaatg   2580
gcgcagttaa atttccgcag ctttgtaaat tctgtgatgt aagattttca acgtgcgata   2640
accagaaaag ctgtatgtcc aactgcagca tcacatcaat ctgtgaaaaa ccccaagagg   2700
tatgtgtggc cgtctggcga aagaatgacg aaaatatcac actggagacc gtttgtcacg   2760
atcctaaact cccttatcat gactttattc tggaagacgc agcgtcaccg aagtgtataa   2820
tgaaagagaa gaagaagcct ggagagacgt ttttcatgtg cagttgctcc tcagatgagt   2880
gtaatgacaa catcattttt tccgaggagt acaatacgag taacccagac ctcctgctgg   2940
ttatttccca ggtaaccggc atcagtttgt tgcccccact gggtgttgca atcagtgtaa   3000
taatcatatt ttattgttac cgggtg                                        3026
```

<210> SEQ ID NO 112
<211> LENGTH: 245
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 112

```
Asp Ile Gln Met Thr Gln Thr Thr Ser Ser Leu Ser Ala Ser Leu Gly
1               5                   10                  15
Asp Arg Val Thr Ile Ser Cys Arg Ala Ser Gln Asp Ile Ser Lys Tyr
            20                  25                  30
Leu Asn Trp Tyr Gln Gln Lys Pro Asp Gly Thr Val Lys Leu Leu Ile
        35                  40                  45
Tyr His Thr Ser Arg Leu His Ser Gly Val Pro Ser Arg Phe Ser Gly
    50                  55                  60
Ser Gly Ser Gly Thr Asp Tyr Ser Leu Thr Ile Ser Asn Leu Glu Gln
65                  70                  75                  80
Glu Asp Ile Ala Thr Tyr Phe Cys Gln Gln Gly Asn Thr Leu Pro Tyr
                85                  90                  95
Thr Phe Gly Gly Gly Thr Lys Leu Glu Ile Thr Gly Ser Thr Ser Gly
            100                 105                 110
Ser Gly Lys Pro Gly Ser Gly Glu Gly Ser Thr Lys Gly Glu Val Lys
        115                 120                 125
Leu Gln Glu Ser Gly Pro Gly Leu Val Ala Pro Ser Gln Ser Leu Ser
    130                 135                 140
Val Thr Cys Thr Val Ser Gly Val Ser Leu Pro Asp Tyr Gly Val Ser
145                 150                 155                 160
Trp Ile Arg Gln Pro Pro Arg Lys Gly Leu Glu Trp Leu Gly Val Ile
                165                 170                 175
Trp Gly Ser Glu Thr Thr Tyr Tyr Asn Ser Ala Leu Lys Ser Arg Leu
            180                 185                 190
Thr Ile Ile Lys Asp Asn Ser Lys Ser Gln Val Phe Leu Lys Met Asn
        195                 200                 205
Ser Leu Gln Thr Asp Asp Thr Ala Ile Tyr Tyr Cys Ala Lys His Tyr
    210                 215                 220
Tyr Tyr Gly Gly Ser Tyr Ala Met Asp Tyr Trp Gly Gln Gly Thr Ser
225                 230                 235                 240
Val Thr Val Ser Ser
                245
```

```
<210> SEQ ID NO 113
<211> LENGTH: 729
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 113

```
gaggtgcagt tgcaacagtc aggagctgaa ctggtcaagc caggagccag cgtgaagatg      60
agctgcaagg cctccggtta caccttcacc tcctacaaca tgcactgggt gaaacagacc     120
ccgggacaag ggctcgaatg gattggcgcc atctaccccg gaatggcga  tacttcgtac     180
aaccagaagt tcaagggaaa ggccaccctg accgccgaca gagctcctc  caccgcgtat     240
atgcagttga gctccctgac ctccgaggac tccgccgact actactgcgc acggtccaac     300
tactatggaa gctcgtactg gttcttcgat gtctgggggg ccggcaccac tgtgaccgtc     360
agctccgggg gcggaggatc cggtggaggc ggaagcgggg gtggaggatc cgacattgtg     420
ctgactcagt ccccggcaat cctgtcggcc tcaccgggcg aaaaggtcac gatgacttgt     480
agagcgtcgt ccagcgtgaa ctacatggat tggtaccaaa agaagcctgg atcgtcaccc     540
```

```
aagccttgga tctacgctac atctaacctg gcctccggcg tgccagcgcg gttcagcggg    600
tccggctcgg gcacctcata ctcgctgacc atctcccgcg tggaggctga ggacgccgcg    660
acctactact gccagcagtg gtccttcaac ccgccgactt ttggaggcgg tactaagctg    720
gagatcaaa                                                            729
```

<210> SEQ ID NO 114
<211> LENGTH: 243
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 114

```
Glu Val Gln Leu Gln Gln Ser Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Asp Tyr Tyr Cys
                85                  90                  95

Ala Arg Ser Asn Tyr Tyr Gly Ser Ser Tyr Trp Phe Phe Asp Val Trp
            100                 105                 110

Gly Ala Gly Thr Thr Val Thr Val Ser Ser Gly Gly Gly Gly Ser Gly
        115                 120                 125

Gly Gly Gly Ser Gly Gly Gly Ser Asp Ile Val Leu Thr Gln Ser
    130                 135                 140

Pro Ala Ile Leu Ser Ala Ser Pro Gly Glu Lys Val Thr Met Thr Cys
145                 150                 155                 160

Arg Ala Ser Ser Val Asn Tyr Met Asp Trp Tyr Gln Lys Lys Pro
                165                 170                 175

Gly Ser Ser Pro Lys Pro Trp Ile Tyr Ala Thr Ser Asn Leu Ala Ser
            180                 185                 190

Gly Val Pro Ala Arg Phe Ser Gly Ser Gly Ser Gly Thr Ser Tyr Ser
        195                 200                 205

Leu Thr Ile Ser Arg Val Glu Ala Glu Asp Ala Ala Thr Tyr Tyr Cys
    210                 215                 220

Gln Gln Trp Ser Phe Asn Pro Pro Thr Phe Gly Gly Gly Thr Lys Leu
225                 230                 235                 240

Glu Ile Lys
```

<210> SEQ ID NO 115
<211> LENGTH: 1491
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 115

```
atgctgctgc tggtgaccag cctgctgctg tgcgaactgc cgcatccggc gtttctgctg      60
attccgcaag tgcaactcgt ccaatccggt gccgaagtca agaagcctgg ttcctccgtg     120
aaagtgtcgt gcaaagccag cggcgggact tttagctcct acgcgatcag ctgggtcaga     180
caggcccctg gacaaggcct cgagtggatg gcgggcatca ttccgatttt cggtaccgcc     240
aactacgccc agaagttcca gggacgcgtg accattacta ccgacgagag cacctcaacc     300
gcatacatgg aactgtccag cctgcgctcc gaggacacgg ctgtgtacta ttgcgccaga     360
cggggatggg gaggattctc ctccggctcc gcattcgaca tctggggaca gggcactatg     420
gtcactgtgt catccggggg aggaggatca ggcggtggag atccggtgg tggcggatcc     480
aacttcatgc tgacccagcc ccactcagtg tcggaatcgc ccggcaacac cgtgactatc     540
agctgcaccg gatccagcgg gaccatcggc tctaatttcg tgcagtggta ccagcagtcc     600
ccagggagag ctccgaccct gttgatctac gaggacacaa agcggccaag cggagtgccg     660
cctagattcg ccggctccgt ggattcctcg tccaactcgg cgtcgctgac catcagcgga     720
ctcaagactg aagatgaagc cgactactac tgtcagtcct acgactcgag caactgggtg     780
tttggggggcg ggactaagct gaccgtgctt ggagcggccg caactaccac ccctgcccct     840
cggccgccga ctccggcccc aaccatcgca agccaacccc tctccttgcg ccccgaagct     900
tgccgccccg gccgcgggtgg agccgtgcat cccgggggc tggactttgc ctgcgatatc     960
tacatttggg ccccgctggc cggcacttgc ggcgtgctcc tgctgtcgct ggtcatcacc    1020
ctttactgca agagggggccg gaagaagctg ctttacatct tcaagcagcc gttcatgcgg    1080
cccgtgcaga cgactcagga agaggacgga tgctcgtgca gattccctga ggaggaagag    1140
gggggatgcg aactgcgcgt caagttctca cggtccgccg acgcccccgc atatcaacag    1200
ggccagaatc agctctacaa cgagctgaac ctggaagga gagggagta cgacgtgctg    1260
gacaagcgac gcggacgcga cccggagatg ggggggaaac cacggcggaa aaaccctcag    1320
gaaggactgt acaacgaact ccagaaagac aagatggcgg aagcctactc agaaatcggg    1380
atgaagggag agcggaggag gggaaagggt cacgacgggc tgtaccaggg actgagcacc    1440
gccactaagg ataccctacga tgccttgcat atgcaagcac tcccacccg g             1491
```

<210> SEQ ID NO 116
<211> LENGTH: 497
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 116

Met Leu Leu Leu Val Thr Ser Leu Leu Cys Glu Leu Pro His Pro
1               5                   10                  15

Ala Phe Leu Leu Ile Pro Gln Val Gln Leu Val Gln Ser Gly Ala Glu
            20                  25                  30

Val Lys Lys Pro Gly Ser Ser Val Lys Val Ser Cys Lys Ala Ser Gly
        35                  40                  45

Gly Thr Phe Ser Ser Tyr Ala Ile Ser Trp Val Arg Gln Ala Pro Gly
    50                  55                  60

Gln Gly Leu Glu Trp Met Gly Gly Ile Ile Pro Ile Phe Gly Thr Ala
65                  70                  75                  80

Asn Tyr Ala Gln Lys Phe Gln Gly Arg Val Thr Ile Thr Thr Asp Glu

-continued

```
                85                  90                  95
Ser Thr Ser Thr Ala Tyr Met Glu Leu Ser Ser Leu Arg Ser Glu Asp
                    100                 105                 110

Thr Ala Val Tyr Tyr Cys Ala Arg Arg Gly Trp Gly Gly Phe Ser Ser
            115                 120                 125

Gly Ser Ala Phe Asp Ile Trp Gly Gln Gly Thr Met Val Thr Val Ser
        130                 135                 140

Ser Gly Gly Gly Gly Ser Gly Gly Gly Gly Ser Gly Gly Gly Gly Ser
145                 150                 155                 160

Asn Phe Met Leu Thr Gln Pro His Ser Val Ser Glu Ser Pro Gly Asn
                165                 170                 175

Thr Val Thr Ile Ser Cys Thr Gly Ser Ser Gly Thr Ile Gly Ser Asn
            180                 185                 190

Phe Val Gln Trp Tyr Gln Gln Ser Pro Gly Arg Ala Pro Thr Leu Leu
        195                 200                 205

Ile Tyr Glu Asp Thr Lys Arg Pro Ser Gly Val Pro Pro Arg Phe Ala
    210                 215                 220

Gly Ser Val Asp Ser Ser Asn Ser Ala Ser Leu Thr Ile Ser Gly
225                 230                 235                 240

Leu Lys Thr Glu Asp Glu Ala Asp Tyr Tyr Cys Gln Ser Tyr Asp Ser
                245                 250                 255

Ser Asn Trp Val Phe Gly Gly Gly Thr Lys Leu Thr Val Leu Gly Ala
            260                 265                 270

Ala Ala Thr Thr Thr Pro Ala Pro Arg Pro Pro Thr Pro Ala Pro Thr
        275                 280                 285

Ile Ala Ser Gln Pro Leu Ser Leu Arg Pro Glu Ala Cys Arg Pro Ala
    290                 295                 300

Ala Gly Gly Ala Val His Thr Arg Gly Leu Asp Phe Ala Cys Asp Ile
305                 310                 315                 320

Tyr Ile Trp Ala Pro Leu Ala Gly Thr Cys Gly Val Leu Leu Leu Ser
                325                 330                 335

Leu Val Ile Thr Leu Tyr Cys Lys Arg Gly Arg Lys Lys Leu Leu Tyr
            340                 345                 350

Ile Phe Lys Gln Pro Phe Met Arg Pro Val Gln Thr Thr Gln Glu Glu
        355                 360                 365

Asp Gly Cys Ser Cys Arg Phe Pro Glu Glu Glu Glu Gly Gly Cys Glu
    370                 375                 380

Leu Arg Val Lys Phe Ser Arg Ser Ala Asp Ala Pro Ala Tyr Gln Gln
385                 390                 395                 400

Gly Gln Asn Gln Leu Tyr Asn Glu Leu Asn Leu Gly Arg Arg Glu Glu
                405                 410                 415

Tyr Asp Val Leu Asp Lys Arg Arg Gly Arg Asp Pro Glu Met Gly Gly
            420                 425                 430

Lys Pro Arg Arg Lys Asn Pro Gln Glu Gly Leu Tyr Asn Glu Leu Gln
        435                 440                 445

Lys Asp Lys Met Ala Glu Ala Tyr Ser Glu Ile Gly Met Lys Gly Glu
    450                 455                 460

Arg Arg Arg Gly Lys Gly His Asp Gly Leu Tyr Gln Gly Leu Ser Thr
465                 470                 475                 480

Ala Thr Lys Asp Thr Tyr Asp Ala Leu His Met Gln Ala Leu Pro Pro
                485                 490                 495

Arg
```

<210> SEQ ID NO 117
<211> LENGTH: 1479
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 117

```
atgctgctgc tggtgaccag cctgctgctg tgcgaactgc cgcatccggc gtttctgctg      60
attccggaag tccaattggt gcagagcgga tccgaactta agaaacctgg cgcgagcgtg     120
aaagtgtcct gcaaggcctc cggagggact ttctcgtcgt acgccattag ctgggtccgc     180
caagctcctg gccaaggcct ggagtggatg gcgggatta tccccatctt cgggactgcg     240
aactacgccc agaagtttca gggccgggtc actatcaccg ccgacgaatc aacctcgacc     300
gcctacatgg aactgtcctc gcttcggtcc gaggatactg ccgtgtacta ttgtgcctca     360
acggccagac gcggatggga caccgctggt ccgctcgatt actggggcca gggaaccctc     420
gtgaccgtca gctccggagg aggaggctcc ggtggtggag atccggggg tggtggatcc     480
gacatccaaa tgacccagtc cccctcgtcc ctgagcgcct tgtgggcga cagagtgaca     540
attgcatgca gggcctcaca gactatctcc cgctacctga actggtacca gcagaagcca     600
ggaaaggccc ctaagctgct catctacgct gcgtcctcgc tccaatccgg ggtgtcctca     660
cggttttccg gatcgggttc cggcaccgag ttcaccctga ccatcagcag cctgcagccc     720
gaggacttcg caacctactt ctgccagcaa acctactccc cgccgattac gttcggacag     780
gggactcggc tggaaatcaa ggcggccgca actaccaccc tgcccctcg ccgccgact     840
ccggccccaa ccatcgcaag ccaacccctc tccttgcgcc ccgaagcttg ccgcccggcc     900
gcgggtggag ccgtgcatac ccggggggctg actttgcct gcgatatcta catttgggcc     960
ccgctggccg gcacttgcgg cgtgctcctg ctgtcgctgg tcatcaccct ttactgcaag    1020
agggggccgga agaagctgct ttacatcttc aagcagccgt tcatgcggcc cgtgcagacg    1080
actcaggaag aggacggatg ctcgtgcaga ttccctgagg aggaagaggg gggatgcgaa    1140
ctgcgcgtca gttctcacg gtccgccgac gccccgcat atcaacaggg ccagaatcag    1200
ctctacaacg agctgaacct gggaaggaga gaggagtacg acgtgctgga caagcgacgc    1260
ggacgcgacc cggagatggg ggggaaacca cggcggaaaa accctcagga aggactgtac    1320
aacgaactcc agaaagacaa gatggcggaa gcctactcag aaatcgggat gaagggagag    1380
cggaggaggg gaaagggtca cgacgggctg taccagggac tgagcaccgc cactaaggat    1440
acctacgatg ccttgcatat gcaagcactc ccaccccgg                           1479
```

<210> SEQ ID NO 118
<211> LENGTH: 493
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 118

```
Met Leu Leu Leu Val Thr Ser Leu Leu Cys Glu Leu Pro His Pro
1               5                   10                  15

Ala Phe Leu Leu Ile Pro Glu Val Gln Leu Val Gln Ser Gly Ser Glu
            20                  25                  30
```

```
Leu Lys Lys Pro Gly Ala Ser Val Lys Val Ser Cys Lys Ala Ser Gly
        35                  40                  45

Gly Thr Phe Ser Ser Tyr Ala Ile Ser Trp Val Arg Gln Ala Pro Gly
        50                  55                  60

Gln Gly Leu Glu Trp Met Gly Gly Ile Ile Pro Ile Phe Gly Thr Ala
 65                  70                  75                  80

Asn Tyr Ala Gln Lys Phe Gln Gly Arg Val Thr Ile Thr Ala Asp Glu
                    85                  90                  95

Ser Thr Ser Thr Ala Tyr Met Glu Leu Ser Ser Leu Arg Ser Glu Asp
                100                 105                 110

Thr Ala Val Tyr Tyr Cys Ala Ser Thr Ala Arg Arg Gly Trp Asp Thr
                115                 120                 125

Ala Gly Pro Leu Asp Tyr Trp Gly Gln Gly Thr Leu Val Thr Val Ser
        130                 135                 140

Ser Gly Gly Gly Gly Ser Gly Gly Gly Gly Ser Gly Gly Gly Gly Ser
145                 150                 155                 160

Asp Ile Gln Met Thr Gln Ser Pro Ser Ser Leu Ser Ala Ser Val Gly
                165                 170                 175

Asp Arg Val Thr Ile Ala Cys Arg Ala Ser Gln Thr Ile Ser Arg Tyr
                180                 185                 190

Leu Asn Trp Tyr Gln Gln Lys Pro Gly Lys Ala Pro Lys Leu Leu Ile
        195                 200                 205

Tyr Ala Ala Ser Ser Leu Gln Ser Gly Val Ser Ser Arg Phe Ser Gly
        210                 215                 220

Ser Gly Ser Gly Thr Glu Phe Thr Leu Thr Ile Ser Ser Leu Gln Pro
225                 230                 235                 240

Glu Asp Phe Ala Thr Tyr Phe Cys Gln Gln Thr Tyr Ser Pro Pro Ile
                245                 250                 255

Thr Phe Gly Gln Gly Thr Arg Leu Glu Ile Lys Ala Ala Ala Thr Thr
                260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
        290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
                340                 345                 350

Pro Phe Met Arg Pro Val Gln Thr Thr Gln Glu Glu Asp Gly Cys Ser
        355                 360                 365

Cys Arg Phe Pro Glu Glu Glu Glu Gly Gly Cys Glu Leu Arg Val Lys
        370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
                420                 425                 430

Lys Asn Pro Gln Glu Gly Leu Tyr Asn Glu Leu Gln Lys Asp Lys Met
        435                 440                 445
```

Ala Glu Ala Tyr Ser Glu Ile Gly Met Lys Gly Glu Arg Arg Arg Gly
            450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490

<210> SEQ ID NO 119
<211> LENGTH: 1473
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 119

```
atgctgctgc tggtgaccag cctgctgctg tgcgaactgc cgcatccggc gtttctgctg        60
attccggaag tgcaactcgt cgaaacaggg cagaagtga aaacccagg ctcaagcgtg         120 aaagtgtcgt gcaaggcttc gggcggaact ctgtccaact acgccatctc ctgggtccgc       180
caagctccgg aaagggcct cgagtggatg gcggaatca ttcccatttt cgggaccgcc         240
aactacgcgc aaaagttcca gggccgggtc actatcaccg cggacgaaag caccagcacc      300
gcctacatgg aactgtcctc cctgcgctcc gaggacactg ccgtgtacta ttgcgcccgg       360
aggtcatcgt ggtaccccga gggctgcttc cagcactggg gacagggcac tctcgtgacc      420
gtgtcgtcgg tggtggtgg atcaggaggg ggaggatccg gaggaggcgg aagcgatatt       480
cagctgaccc agtcaccgag ctccctgtcc gcctccaccg agacagagt gaccatcacg       540 tgtcgggcct cccaagggat ctcctcctac ctggcctggt accagcagaa gcctggaaag      600
gcaccgaagt tgctgatcta cgccgcgagc acccttcagt ccggagtgcc tagccgcttc       660
tcgggttccg gctctggcac tgacttcact ctgaccatta gctgcctgca gtccgaggat      720
tttgccacct actactgcca gcagtactat agctacccc tgaccttcgg gggcggaacc      780
aagctcgaca tcaaggcggc cgcaactacc accctgccc tcggccgcc gactccggcc       840 ccaaccatcg caagccaacc cctctccttg cgccccgaag cttgccgcc ggccgcgggt      900 ggagccgtgc ataccgggg gctggacttt gcctgcgata tctacatttg gccccgctg       960 gccggcactt gcggcgtgct cctgctgtcg ctggtcatca cccttactg caagaggggc      1020 cggaagaagc tgctttacat cttcaagcag ccgttcatgc ggcccgtgca gacgactcag      1080
gaagaggacg gatgctcgtg cagattccct gaggaggaag aggggggatg cgaactgcgc      1140
gtcaagttct cacggtccgc cgacgccccc gcatatcaac agggccagaa tcagctctac      1200
aacgagctga acctgggaag agagaggag tacgacgtgc tggacaagcg acgcggacgc       1260
gacccggaga tggggggaa accacggcgg aaaaaccctc aggaaggact gtacaacgaa       1320
ctccagaaag acaagatggc ggaagcctac tcagaaatcg gatgaaggg agagcggagg      1380 agggaaagg gtcacgacgg gctgtaccag ggactgagca ccgccactaa ggatacctac      1440
gatgccttgc atatgcaagc actcccaccc cgg                                  1473
```

<210> SEQ ID NO 120
<211> LENGTH: 491
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"

<400> SEQUENCE: 120

```
Met Leu Leu Leu Val Thr Ser Leu Leu Leu Cys Glu Leu Pro His Pro
1               5                   10                  15

Ala Phe Leu Leu Ile Pro Glu Val Gln Leu Val Glu Thr Gly Ala Glu
            20                  25                  30

Val Lys Asn Pro Gly Ser Ser Val Lys Val Ser Cys Lys Ala Ser Gly
        35                  40                  45

Gly Thr Leu Ser Asn Tyr Ala Ile Ser Trp Val Arg Gln Ala Pro Gly
    50                  55                  60

Lys Gly Leu Glu Trp Met Gly Gly Ile Ile Pro Ile Phe Gly Thr Ala
65                  70                  75                  80

Asn Tyr Ala Gln Lys Phe Gln Gly Arg Val Thr Ile Thr Ala Asp Glu
            85                  90                  95

Ser Thr Ser Thr Ala Tyr Met Glu Leu Ser Ser Leu Arg Ser Glu Asp
        100                 105                 110

Thr Ala Val Tyr Tyr Cys Ala Arg Arg Ser Ser Trp Tyr Pro Glu Gly
    115                 120                 125

Cys Phe Gln His Trp Gly Gln Gly Thr Leu Val Thr Val Ser Ser Gly
130                 135                 140

Gly Gly Ser Gly Gly Gly Gly Ser Gly Gly Gly Ser Asp Ile
145                 150                 155                 160

Gln Leu Thr Gln Ser Pro Ser Ser Leu Ser Ala Ser Thr Gly Asp Arg
            165                 170                 175

Val Thr Ile Thr Cys Arg Ala Ser Gln Gly Ile Ser Ser Tyr Leu Ala
        180                 185                 190

Trp Tyr Gln Gln Lys Pro Gly Lys Ala Pro Lys Leu Leu Ile Tyr Ala
    195                 200                 205

Ala Ser Thr Leu Gln Ser Gly Val Pro Ser Arg Phe Ser Gly Ser Gly
210                 215                 220

Ser Gly Thr Asp Phe Thr Leu Thr Ile Ser Cys Leu Gln Ser Glu Asp
225                 230                 235                 240

Phe Ala Thr Tyr Tyr Cys Gln Gln Tyr Ser Tyr Pro Leu Thr Phe
            245                 250                 255

Gly Gly Gly Thr Lys Leu Asp Ile Lys Ala Ala Ala Thr Thr Thr Pro
        260                 265                 270

Ala Pro Arg Pro Pro Thr Pro Ala Pro Thr Ile Ala Ser Gln Pro Leu
    275                 280                 285

Ser Leu Arg Pro Glu Ala Cys Arg Pro Ala Ala Gly Gly Ala Val His
290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
            325                 330                 335

Cys Lys Arg Gly Arg Lys Lys Leu Leu Tyr Ile Phe Lys Gln Pro Phe
        340                 345                 350

Met Arg Pro Val Gln Thr Thr Gln Glu Glu Asp Gly Cys Ser Cys Arg
    355                 360                 365

Phe Pro Glu Glu Glu Glu Gly Gly Cys Glu Leu Arg Val Lys Phe Ser
370                 375                 380

Arg Ser Ala Asp Ala Pro Ala Tyr Gln Gln Gly Gln Asn Gln Leu Tyr
385                 390                 395                 400
```

Asn Glu Leu Asn Leu Gly Arg Arg Glu Tyr Asp Val Leu Asp Lys
            405                 410                 415

Arg Arg Gly Arg Asp Pro Glu Met Gly Gly Lys Pro Arg Lys Asn
        420                 425                 430

Pro Gln Glu Gly Leu Tyr Asn Glu Leu Gln Lys Asp Lys Met Ala Glu
    435                 440                 445

Ala Tyr Ser Glu Ile Gly Met Lys Gly Glu Arg Arg Gly Lys Gly
450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
            485                 490

<210> SEQ ID NO 121
<211> LENGTH: 1476
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 121

```
atgctgctgc tggtgaccag cctgctgctg tgcgaactgc gcatccggc gtttctgctg      60
attccggaag tgcaactcgt ccaatctggt gccgaagtca agaagcctgg ctcaagcgtg    120
aaagtgtcct gcaaagcgtc gggagggacc ttcagctcct acgccatttc ctgggtccgc    180
caagcaccag acagggcct ggagtggatg gcgcggcatca tcccgatctt cgggactgcc    240
aactacgccc agaagttcca ggggagagtg accattaccg ccgacgagtc gaccagcacg    300
gcctacatgg aactgtccag cctgcgctcc gaggacactg ccgtgtacta ctgcgcgagg    360
gccagactcg gtggagcgtt cgacatctgg ggacagggca ccatggtcac cgtgtcatcc    420
ggtggcggag gatccggtgg tggcggatca ggagggggag gatcccagtc cgtgctgact    480
cagcctccct ccgtgagcgc tgcaccggga cagaaggtca ccatctcatg ctcgggggga    540
agctccaaca tcgggaacca ctacgtgtcc tggtaccaac agttgcctgg tccgctcca    600
aagctgctga tctatgacga taacaagcgg ccgtccggaa tccccgaccg gttctcgggg    660
tctagatccg gaaccagcgc aactctcggc attaccggac tgcagagcgg cgatgaggcc    720
gactactact gtggcacatg ggactcgtcg ctggctgccc acgtgtttgg cactggcacc    780
aaggtcaccg tgcttggagc ggccgcaact accacccctg ccctcggcc gccgactccg    840
gccccaacca tcgcaagcca acccctctcc ttgcgccccg aagcttgccg cccggccgcg    900
ggtgagccg tgcataccccg ggctggac tttgcctgcg atatctacat ttggccccg    960
ctggccggca cttgcggcgt gctcctgctg tcgctggtca tcaccttta ctgcaagagg    1020
ggccggaaga gctgctttta catcttcaag cagccgttca tgcggccgt gcagacgact   1080
caggaagagg acggatgctc cgtgcagatt cctgaggagg aagaggggggg atgcgaactg   1140
cgcgtcaagt tctcacggtc cgccgacgcc cccgcatatc aacagggcca gaatcagctc   1200
tacaacgagc tgaacctggg aaggagaga gagtacgacg tgctggacaa gacgcgcgga   1260
cgcgacccgg agatgggggg gaaaccacgg cggaaaaacc ctcaggaagg actgtacaac   1320
gaactccaga agacaagat ggcggaagcc tactcagaaa tcgggatgaa gggagagcgg   1380
aggaggggaa agggtcacga cgggctgtac caggggactga gcaccgccac taaggatacc   1440
tacgatgcct tgcatatgca agcactccca ccccgg                           1476
```

<210> SEQ ID NO 122
<211> LENGTH: 492
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 122

```
Met Leu Leu Leu Val Thr Ser Leu Leu Leu Cys Glu Leu Pro His Pro
1               5                   10                  15

Ala Phe Leu Leu Ile Pro Glu Val Gln Leu Val Gln Ser Gly Ala Glu
            20                  25                  30

Val Lys Lys Pro Gly Ser Ser Val Lys Val Ser Cys Lys Ala Ser Gly
        35                  40                  45

Gly Thr Phe Ser Ser Tyr Ala Ile Ser Trp Val Arg Gln Ala Pro Gly
    50                  55                  60

Gln Gly Leu Glu Trp Met Gly Gly Ile Ile Pro Ile Phe Gly Thr Ala
65                  70                  75                  80

Asn Tyr Ala Gln Lys Phe Gln Gly Arg Val Thr Ile Thr Ala Asp Glu
                85                  90                  95

Ser Thr Ser Thr Ala Tyr Met Glu Leu Ser Ser Leu Arg Ser Glu Asp
            100                 105                 110

Thr Ala Val Tyr Tyr Cys Ala Arg Ala Arg Leu Gly Gly Ala Phe Asp
        115                 120                 125

Ile Trp Gly Gln Gly Thr Met Val Thr Val Ser Ser Gly Gly Gly Gly
    130                 135                 140

Ser Gly Gly Gly Gly Ser Gly Gly Gly Gly Ser Gln Ser Val Leu Thr
145                 150                 155                 160

Gln Pro Pro Ser Val Ser Ala Ala Pro Gly Gln Lys Val Thr Ile Ser
                165                 170                 175

Cys Ser Gly Gly Ser Ser Asn Ile Gly Asn His Tyr Val Ser Trp Tyr
            180                 185                 190

Gln Gln Leu Pro Gly Ala Ala Pro Lys Leu Leu Ile Tyr Asp Asp Asn
        195                 200                 205

Lys Arg Pro Ser Gly Ile Pro Asp Arg Phe Ser Gly Ser Arg Ser Gly
    210                 215                 220

Thr Ser Ala Thr Leu Gly Ile Thr Gly Leu Gln Ser Gly Asp Glu Ala
225                 230                 235                 240

Asp Tyr Tyr Cys Gly Thr Trp Asp Ser Ser Leu Ala Ala His Val Phe
                245                 250                 255

Gly Thr Gly Thr Lys Val Thr Val Leu Gly Ala Ala Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Lys Arg Gly Arg Lys Lys Leu Leu Tyr Ile Phe Lys Gln Pro
            340                 345                 350
```

```
Phe Met Arg Pro Val Gln Thr Thr Gln Glu Glu Asp Gly Cys Ser Cys
            355                 360                 365

Arg Phe Pro Glu Glu Glu Gly Gly Cys Glu Leu Arg Val Lys Phe
370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
        435                 440                 445

Glu Ala Tyr Ser Glu Ile Gly Met Lys Gly Glu Arg Arg Arg Gly Lys
    450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490
```

<210> SEQ ID NO 123
<211> LENGTH: 1491
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 123

```
atgctgctgc tggtgaccag cctgctgctg tgcgaactgc cgcatccggc gtttctgctg      60
attccggaag tgcaacttgt ccagagcgga gccgaagtga agaaacctgg atcctccgtc     120
aaagtgtcgt gcaaggcttc gggcggaacc ttctcctcgt acgcgatctc atgggtcaga     180
caggcacccg acagggact ggagtggatg gcggcatca ttcccatctt cggcaccgct       240
aattacgccc agaagtttca ggggagagtg accatcaccg ccgacgagtc cacctccact    300
gcctacatgg aactgtcctc actgaggtcc gaggatactg ccgtgtacta ctgcgcgtcg    360 caaaagggg gtggatggtc cattgacgcc ttcgatattt ggggacaggg gacgatggtc     420
acagtgtcat ccggcggtgg tggatccggt ggtggcggat ccgaggagg aggcagccag     480 tccgtgctga cccagccgcc tagcgtgtcg ccgcatctg gcagcgcgt gaccatttcc      540 tgttccgggt cctcgtccaa catcggcaac aactacgcct cctggtacca acagctcccg    600
ggaatggccc ctaagctgct gatctacgag gacaacaagc ggccatccgg gatctcagac    660
cggttcagcg gatcccagtc cggcacttcc gcgagcctcg ccatcaccgg actgcaggct    720
gaggacgaag ccgactacta ctgccaatca tatgacagct cgctcagcgg cgatgtggtg    780
ttcggcggtg gcactaagct gaccgtgttg gagcggccg caactaccac ccctgcccct    840
cggccgccga ctccggcccc aaccatcgca agccaacccc tctccttgcg ccccgaagct    900
tgccgcccgg ccgcgggtgg agccgtgcat acccggggc tggactttgc ctgcgatatc    960
tacatttggg ccccgctggc cggcacttgc ggcgtgctcc tgctgtcgct ggtcatcacc   1020
ctttactgca gaggggccg gaagaagctg ctttacatct tcaagcagcc gttcatgcgg    1080
cccgtgcaga cgactcagga agaggacgga tgctcgtgca gattccctga ggaggaagag   1140
gggggatgcg aactgcgcgt caagttctca cggtccgccg acgccccgc atatcaacag    1200
```

-continued

```
ggccagaatc agctctacaa cgagctgaac ctgggaagga gagaggagta cgacgtgctg   1260
gacaagcgac gcggacgcga cccggagatg ggggggaaac cacggcggaa aaaccctcag   1320
gaaggactgt acaacgaact ccagaaagac aagatggcgg aagcctactc agaaatcggg   1380
atgaagggag agcggaggag gggaaagggt cacgacgggc tgtaccaggg actgagcacc   1440
gccactaagg atacctacga tgccttgcat atgcaagcac tcccaccccg g            1491
```

<210> SEQ ID NO 124
<211> LENGTH: 497
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 124

```
Met Leu Leu Leu Val Thr Ser Leu Leu Cys Glu Leu Pro His Pro
1               5                   10                  15

Ala Phe Leu Leu Ile Pro Glu Val Gln Leu Val Gln Ser Gly Ala Glu
                20                  25                  30

Val Lys Lys Pro Gly Ser Ser Val Lys Val Ser Cys Lys Ala Ser Gly
            35                  40                  45

Gly Thr Phe Ser Ser Tyr Ala Ile Ser Trp Val Arg Gln Ala Pro Gly
    50                  55                  60

Gln Gly Leu Glu Trp Met Gly Gly Ile Ile Pro Ile Phe Gly Thr Ala
65                  70                  75                  80

Asn Tyr Ala Gln Lys Phe Gln Gly Arg Val Thr Ile Thr Ala Asp Glu
                85                  90                  95

Ser Thr Ser Thr Ala Tyr Met Glu Leu Ser Ser Leu Arg Ser Glu Asp
            100                 105                 110

Thr Ala Val Tyr Tyr Cys Ala Ser Gln Lys Gly Gly Gly Trp Ser Ile
        115                 120                 125

Asp Ala Phe Asp Ile Trp Gly Gln Gly Thr Met Val Thr Val Ser Ser
    130                 135                 140

Gly Gly Gly Gly Ser Gly Gly Gly Ser Gly Gly Gly Gly Ser Gln
145                 150                 155                 160

Ser Val Leu Thr Gln Pro Pro Ser Val Ser Ala Ala Ser Gly Gln Arg
                165                 170                 175

Val Thr Ile Ser Cys Ser Gly Ser Ser Ser Asn Ile Gly Asn Asn Tyr
            180                 185                 190

Ala Ser Trp Tyr Gln Gln Leu Pro Gly Met Ala Pro Lys Leu Leu Ile
        195                 200                 205

Tyr Glu Asp Asn Lys Arg Pro Ser Gly Ile Ser Asp Arg Phe Ser Gly
    210                 215                 220

Ser Gln Ser Gly Thr Ser Ala Ser Leu Ala Ile Thr Gly Leu Gln Ala
225                 230                 235                 240

Glu Asp Glu Ala Asp Tyr Tyr Cys Gln Ser Tyr Asp Ser Ser Leu Ser
                245                 250                 255

Gly Asp Val Val Phe Gly Gly Gly Thr Lys Leu Thr Val Leu Gly Ala
            260                 265                 270

Ala Ala Thr Thr Thr Pro Ala Pro Arg Pro Pro Thr Pro Ala Pro Thr
        275                 280                 285

Ile Ala Ser Gln Pro Leu Ser Leu Arg Pro Glu Ala Cys Arg Pro Ala
    290                 295                 300
```

Ala Gly Gly Ala Val His Thr Arg Gly Leu Asp Phe Ala Cys Asp Ile
305                 310                 315                 320

Tyr Ile Trp Ala Pro Leu Ala Gly Thr Cys Gly Val Leu Leu Leu Ser
            325                 330                 335

Leu Val Ile Thr Leu Tyr Cys Lys Arg Gly Lys Lys Leu Leu Tyr
                340                 345                 350

Ile Phe Lys Gln Pro Phe Met Arg Pro Val Gln Thr Thr Gln Glu Glu
            355                 360                 365

Asp Gly Cys Ser Cys Arg Phe Pro Glu Glu Glu Gly Gly Cys Glu
        370                 375                 380

Leu Arg Val Lys Phe Ser Arg Ser Ala Asp Ala Pro Ala Tyr Gln Gln
385                 390                 395                 400

Gly Gln Asn Gln Leu Tyr Asn Glu Leu Asn Leu Gly Arg Arg Glu Glu
                405                 410                 415

Tyr Asp Val Leu Asp Lys Arg Arg Gly Arg Asp Pro Glu Met Gly Gly
                420                 425                 430

Lys Pro Arg Arg Lys Asn Pro Gln Glu Gly Leu Tyr Asn Glu Leu Gln
            435                 440                 445

Lys Asp Lys Met Ala Glu Ala Tyr Ser Glu Ile Gly Met Lys Gly Glu
        450                 455                 460

Arg Arg Arg Gly Lys Gly His Asp Gly Leu Tyr Gln Gly Leu Ser Thr
465                 470                 475                 480

Ala Thr Lys Asp Thr Tyr Asp Ala Leu His Met Gln Ala Leu Pro Pro
                485                 490                 495

Arg

<210> SEQ ID NO 125
<211> LENGTH: 1479
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 125
atgctgctgc tggtgaccag cctgctgctg tgcgaactgc cgcatccggc gtttctgctg     60
attccgcaag tccagttgca acaatgggga gcaggccttc tgaaaccgtc cgagacactg    120
agcctgacgt gcgccgtcta tggcggatcg ttctccggat actactggtc gtggatcaga    180
cagcctccgg gaaagggtct ggaatggatc ggcgaaatca accacagcgg cagcaccaat    240
tacaacccgt cactgaagtc aagggtcacc attagcgtgg acacttccaa gaaccagttc    300
tccctgaaac tgtcgagcgt gaccgctgcc gatactgccg tgtactactg tgcccgcggc    360
caagtcaagt atagctcaag cctcggctac tggggccagg gaaccctcgt gaccgtgtcc    420
tcgggtggag gaggctccgg tggtggagga ccggtggcg gaggatcgca gtccgtgctg    480
acccagcctc cctccgtgtc tgctgccct gggcaaaagg tcaccatttc gtgctccggc    540
tcatcgtcca acatcgggaa caactttgtg tcctggtacc agcagctgcc cggtactgcc    600
ccaaagctgc tgatctacga ggacaacaag cgcccatccg ggattccgga tcggttcagc    660
ggatcacggt ccggaactag cgcgaccctg gggatcaccg gctccagac tggcgacgaa    720 gcggactact actgcggaac ttgggactcc tccttggggg cctgggtgtt cggcggaggg    780
accaagctca ccgtgcttgg agcggccgca actaccaccc ctgcccctcg gccgccgact    840
ccggccccaa ccatcgcaag ccaacccctc tccttgcgcc ccgaagcttg ccgcccggcc    900

```
gcgggtggag ccgtgcatac ccgggggctg gactttgcct gcgatatcta catttgggcc    960
ccgctggccg gcacttgcgg cgtgctcctg ctgtcgctgg tcatcaccct ttactgcaag   1020
aggggccgga agaagctgct ttacatcttc aagcagccgt tcatgcggcc cgtgcagacg   1080
actcaggaag aggacggatg ctcgtgcaga ttccctgagg aggaagaggg gggatgcgaa   1140
ctgcgcgtca agttctcacg gtccgccgac gcccccgcat atcaacaggg ccagaatcag   1200
ctctacaacg agctgaacct ggaaggagag gaggagtacg acgtgctgga caagcgacgc   1260
ggacgcgacc cggagatggg ggggaaacca cggcggaaaa accctcagga aggactgtac   1320
aacgaactcc agaaagacaa gatggcgaa gcctactcag aaatcgggat gaagggagag   1380
cggaggaggg gaaagggtca cgacgggctg taccagggac tgagcaccgc cactaaggat   1440
acctacgatg ccttgcatat gcaagcactc ccaccccgg                          1479
```

<210> SEQ ID NO 126
<211> LENGTH: 493
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 126

```
Met Leu Leu Leu Val Thr Ser Leu Leu Leu Cys Glu Leu Pro His Pro
1               5                   10                  15

Ala Phe Leu Leu Ile Pro Gln Val Gln Leu Gln Gln Trp Gly Ala Gly
            20                  25                  30

Leu Leu Lys Pro Ser Glu Thr Leu Ser Leu Thr Cys Ala Val Tyr Gly
        35                  40                  45

Gly Ser Phe Ser Gly Tyr Tyr Trp Ser Trp Ile Arg Gln Pro Pro Gly
    50                  55                  60

Lys Gly Leu Glu Trp Ile Gly Glu Ile Asn His Ser Gly Ser Thr Asn
65                  70                  75                  80

Tyr Asn Pro Ser Leu Lys Ser Arg Val Thr Ile Ser Val Asp Thr Ser
                85                  90                  95

Lys Asn Gln Phe Ser Leu Lys Leu Ser Ser Val Thr Ala Ala Asp Thr
            100                 105                 110

Ala Val Tyr Tyr Cys Ala Arg Gly Gln Val Lys Tyr Ser Ser Ser Leu
        115                 120                 125

Gly Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Gln Ser Val Leu
145                 150                 155                 160

Thr Gln Pro Pro Ser Val Ser Ala Ala Pro Gly Gln Lys Val Thr Ile
                165                 170                 175

Ser Cys Ser Gly Ser Ser Ser Asn Ile Gly Asn Asn Phe Val Ser Trp
            180                 185                 190

Tyr Gln Gln Leu Pro Gly Thr Ala Pro Lys Leu Leu Ile Tyr Glu Asp
        195                 200                 205

Asn Lys Arg Pro Ser Gly Ile Pro Asp Arg Phe Ser Gly Ser Arg Ser
    210                 215                 220

Gly Thr Ser Ala Thr Leu Gly Ile Thr Gly Leu Gln Thr Gly Asp Glu
225                 230                 235                 240

Ala Asp Tyr Tyr Cys Gly Thr Trp Asp Ser Ser Leu Gly Ala Trp Val
```

```
            245                 250                 255
Phe Gly Gly Thr Lys Leu Thr Val Leu Gly Ala Ala Ala Thr Thr
            260                 265                 270

Thr Pro Ala Pro Arg Pro Pro Thr Pro Ala Pro Thr Ile Ala Ser Gln
                275                 280                 285

Pro Leu Ser Leu Arg Pro Glu Ala Cys Arg Pro Ala Ala Gly Gly Ala
            290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
                340                 345                 350

Pro Phe Met Arg Pro Val Gln Thr Thr Gln Glu Glu Asp Gly Cys Ser
                355                 360                 365

Cys Arg Phe Pro Glu Glu Glu Glu Gly Gly Cys Glu Leu Arg Val Lys
            370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
            435                 440                 445

Ala Glu Ala Tyr Ser Glu Ile Gly Met Lys Gly Glu Arg Arg Arg Gly
            450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490

<210> SEQ ID NO 127
<211> LENGTH: 1467
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 127
atgctgctgc tggtgaccag cctgctgctg tgcgaactgc cgcatccggc gtttctgctg      60
attccgcaag tccaactcgt cgaaactggt ggtggcctcg tgaagcctgg aggatccctg     120 cgccttttcct gtgccgcttc cggctttact ttctcgtcgt actccatgaa ctgggtcaga     180
caggctcccg aaagggcct ggaatgggtg tcctccatct cgtcctcatc ctcctacatc      240
tattacgcgg actccgtgaa gggcagattc accatttccc gggacaacgc caagaacagc     300
ttgtacctcc aaatgaactc cctgcgggca gaggacaccg ccgtgtacta ctgcgcgagg     360 gatgggatt tctggagcgg agccatcgac tactggggcc aggaactctc gtgaccgtc      420 agctccggtg gtggtggaag cggaggcgga ggttctgggg ggaggatc agacattcag      480 ctgacccagt cgccatcctc cctgagcgcc tcagtggggg accgcgtgac tattacatgc     540
caggcctccc aagatatctc gaactacctg aactggtatc agcagaagcc tggaaaggcc     600
```

```
ccgaagctgt tgatctacga tgccagcaac ctggagactg ggtgccttc ccggttctcg    660
ggatcaggct cgggcaccga tttcaccttc acgatcagca gcctgcagcc cgaggacatt    720
gcaacctact actgccagca gtacgacaat ctgccgcttt ttggggagg caccaagctg    780
gaaatcaaag cggccgcaac taccacccct gcccctcggc cgccgactcc ggccccaacc    840
atcgcaagcc aaccctctc cttgcgcccc gaagcttgcc gccggccgc gggtggagcc    900
gtgcataccc gggggctgga ctttgcctgc gatatctaca tttgggcccc gctggccggc    960
acttgcggcg tgctcctgct gtcgctggtc atccccttt actgcaagag gggccggaag   1020
aagctgcttt acatcttcaa gcagccgttc atgcggcccg tgcagacgac tcaggaagag   1080
gacggatgct cgtgcagatt ccctgaggag gaagaggggg gatgcgaact gcgcgtcaag   1140
ttctcacggt ccgccgacgc ccccgcatat caacagggcc agaatcagct ctacaacgag   1200
ctgaacctgg aaggagaga ggagtacgac gtgctggaca agcgacgcgg acgcgacccg   1260
gagatggggg ggaaaccacg gcggaaaaac cctcaggaag gactgtacaa cgaactccag   1320
aaagacaaga tggcggaagc ctactcagaa atcgggatga aggagagcg gaggaggga   1380
aagggtcacg acgggctgta ccagggactg agcaccgcca ctaaggatac ctacgatgcc   1440
ttgcatatgc aagcactccc accccgg                                       1467
```

<210> SEQ ID NO 128
<211> LENGTH: 489
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 128

```
Met Leu Leu Leu Val Thr Ser Leu Leu Leu Cys Glu Leu Pro His Pro
1               5                   10                  15
Ala Phe Leu Leu Ile Pro Gln Val Gln Leu Val Glu Thr Gly Gly Gly
            20                  25                  30
Leu Val Lys Pro Gly Gly Ser Leu Arg Leu Ser Cys Ala Ala Ser Gly
        35                  40                  45
Phe Thr Phe Ser Ser Tyr Ser Met Asn Trp Val Arg Gln Ala Pro Gly
    50                  55                  60
Lys Gly Leu Glu Trp Val Ser Ile Ser Ser Ser Ser Tyr Ile
65                  70                  75                  80
Tyr Tyr Ala Asp Ser Val Lys Gly Arg Phe Thr Ile Ser Arg Asp Asn
                85                  90                  95
Ala Lys Asn Ser Leu Tyr Leu Gln Met Asn Ser Leu Arg Ala Glu Asp
            100                 105                 110
Thr Ala Val Tyr Tyr Cys Ala Arg Asp Gly Asp Phe Trp Ser Gly Ala
        115                 120                 125
Ile Asp Tyr Trp Gly Gln Gly Thr Leu Val Thr Val Ser Ser Gly Gly
    130                 135                 140
Gly Gly Ser Gly Gly Gly Gly Ser Gly Gly Gly Gly Ser Asp Ile Gln
145                 150                 155                 160
Leu Thr Gln Ser Pro Ser Ser Leu Ser Ala Ser Val Gly Asp Arg Val
                165                 170                 175
Thr Ile Thr Cys Gln Ala Ser Gln Asp Ile Ser Asn Tyr Leu Asn Trp
            180                 185                 190
Tyr Gln Gln Lys Pro Gly Lys Ala Pro Lys Leu Leu Ile Tyr Asp Ala
```

```
              195                 200                 205
Ser Asn Leu Glu Thr Gly Val Pro Ser Arg Phe Ser Gly Ser Gly Ser
210                 215                 220

Gly Thr Asp Phe Thr Phe Thr Ile Ser Ser Leu Gln Pro Glu Asp Ile
225                 230                 235                 240

Ala Thr Tyr Tyr Cys Gln Gln Tyr Asp Asn Leu Pro Leu Phe Gly Gly
                245                 250                 255

Gly Thr Lys Leu Glu Ile Lys Ala Ala Ala Thr Thr Pro Ala Pro
                260                 265                 270

Arg Pro Pro Thr Pro Ala Pro Thr Ile Ala Ser Gln Pro Leu Ser Leu
                275                 280                 285

Arg Pro Glu Ala Cys Arg Pro Ala Ala Gly Gly Ala Val His Thr Arg
290                 295                 300

Gly Leu Asp Phe Ala Cys Asp Ile Tyr Ile Trp Ala Pro Leu Ala Gly
305                 310                 315                 320

Thr Cys Gly Val Leu Leu Leu Ser Leu Val Ile Thr Leu Tyr Cys Lys
                325                 330                 335

Arg Gly Arg Lys Lys Leu Leu Tyr Ile Phe Lys Gln Pro Phe Met Arg
                340                 345                 350

Pro Val Gln Thr Thr Gln Glu Glu Asp Gly Cys Ser Cys Arg Phe Pro
                355                 360                 365

Glu Glu Glu Glu Gly Gly Cys Glu Leu Arg Val Lys Phe Ser Arg Ser
370                 375                 380

Ala Asp Ala Pro Ala Tyr Gln Gln Gly Gln Asn Gln Leu Tyr Asn Glu
385                 390                 395                 400

Leu Asn Leu Gly Arg Arg Glu Glu Tyr Asp Val Leu Asp Lys Arg Arg
                405                 410                 415

Gly Arg Asp Pro Glu Met Gly Gly Lys Pro Arg Arg Lys Asn Pro Gln
                420                 425                 430

Glu Gly Leu Tyr Asn Glu Leu Gln Lys Asp Lys Met Ala Glu Ala Tyr
                435                 440                 445

Ser Glu Ile Gly Met Lys Gly Glu Arg Arg Arg Gly Lys Gly His Asp
450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg
                485

<210> SEQ ID NO 129
<211> LENGTH: 1467
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 129
atgctgctgc tggtgaccag cctgctgctg tgcgaactgc cgcatccggc gtttctgctg      60
attccggagg tgcaattggt gcagtcaggt ggtggagtgg tgcagccagg aagatccctt     120
agactctcgt gtgcggcgtc aggctttacc ttctcctcgt actccatgaa ctgggtcaga     180
caggcaccgg gaaagggact ggaatgggtg tcctccatct cgtcctcctc ctcctacatc     240
tactacgccg atagcgtgaa gggccggttc accatttcgc gcgacaacgc caagaacacc     300
ctgtacctcc aaatgaattc gctgcgggcc gaagataccg ctgtctatta ctgcgcccgc     360
```

```
gacaactggg gctcgctgga ctattggggc cagggaaccc tcgtcaccgt gtcaagcgga    420
gggggtggat ccggaggcgg aggatccggt ggagggggaa gcgacattca gatgactcag    480
agcccgtcct ccctgtctgc ctccgtgggg gatcgcgtga ccatcacatg ccaggcctca    540
caagacatca gcaattacct gaactggtac cagcagaagc ctggaaaggc ccccaagctg    600
ctgatctacg atgccagcaa cctggagact ggggtgcctt caaggttctc cggttccgga    660
agcggcactg acttcacctt cactatctcg agcctgcaac ccgaggacat tgccacctac    720
tactgccagc agtacgacaa ccttccgcac atgtacacgt tcggccaggg caccaagctc    780
gaaatcaaag cggccgcaac taccacccct gcccctcggc cgccgactcc ggccccaacc    840
atcgcaagcc aaccccctctc cttgcgcccc gaagcttgcc gcccggccgc gggtggagcc    900
gtgcataccc gggggctgga ctttgcctgc gatatctaca tttgggcccc gctggccggc    960
acttgcggcg tgctcctgct gtcgctggtc atcacccttt actgcaagag gggccggaag    1020
aagctgcttt acatcttcaa gcagccgttc atgcggcccg tgcagacgac tcaggaagag    1080
gacggatgct cgtgcagatt ccctgaggag gaagaggggg gatgcgaact gcgcgtcaag    1140
ttctcacggt ccgccgacgc ccccgcatat caacagggcc agaatcagct ctacaacgag    1200
ctgaacctgg aaggagaga ggagtacgac gtgctggaca gcgacgcgg acgcgacccg    1260 gagatggggg ggaaaccacg gcggaaaaac cctcaggaag gactgtacaa cgaactccag    1320
aaagacaaga tggcggaagc ctactcagaa atcgggatga agggagagcg gaggagggga    1380
aagggtcacg acgggctgta ccagggactg agcaccgcca ctaaggatac ctacgatgcc    1440
ttgcatatgc aagcactccc accccgg                                       1467
```

<210> SEQ ID NO 130
<211> LENGTH: 489
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 130

```
Met Leu Leu Leu Val Thr Ser Leu Leu Cys Glu Leu Pro His Pro
1               5                   10                  15

Ala Phe Leu Leu Ile Pro Glu Val Gln Leu Val Gln Ser Gly Gly
                20                  25                  30

Val Val Gln Pro Gly Arg Ser Leu Arg Leu Ser Cys Ala Ala Ser Gly
            35                  40                  45

Phe Thr Phe Ser Ser Tyr Ser Met Asn Trp Val Arg Gln Ala Pro Gly
        50                  55                  60

Lys Gly Leu Glu Trp Val Ser Ser Ile Ser Ser Ser Ser Tyr Ile
65                  70                  75                  80

Tyr Tyr Ala Asp Ser Val Lys Gly Arg Phe Thr Ile Ser Arg Asp Asn
                85                  90                  95

Ala Lys Asn Thr Leu Tyr Leu Gln Met Asn Ser Leu Arg Ala Glu Asp
            100                 105                 110

Thr Ala Val Tyr Tyr Cys Ala Arg Asp Asn Trp Gly Ser Leu Asp Tyr
        115                 120                 125

Trp Gly Gln Gly Thr Leu Val Thr Val Ser Ser Gly Gly Gly Gly Ser
    130                 135                 140

Gly Gly Gly Gly Ser Gly Gly Gly Gly Ser Asp Ile Gln Met Thr Gln
```

```
                145                 150                 155                 160
Ser Pro Ser Ser Leu Ser Ala Ser Val Gly Asp Arg Val Thr Ile Thr
                    165                 170                 175

Cys Gln Ala Ser Gln Asp Ile Ser Asn Tyr Leu Asn Trp Tyr Gln Gln
                    180                 185                 190

Lys Pro Gly Lys Ala Pro Lys Leu Leu Ile Tyr Asp Ala Ser Asn Leu
                    195                 200                 205

Glu Thr Gly Val Pro Ser Arg Phe Ser Gly Ser Gly Ser Gly Thr Asp
    210                 215                 220

Phe Thr Phe Thr Ile Ser Ser Leu Gln Pro Glu Asp Ile Ala Thr Tyr
225                 230                 235                 240

Tyr Cys Gln Gln Tyr Asp Asn Leu Pro His Met Tyr Thr Phe Gly Gln
                245                 250                 255

Gly Thr Lys Leu Glu Ile Lys Ala Ala Thr Thr Thr Pro Ala Pro
                260                 265                 270

Arg Pro Pro Thr Pro Ala Pro Thr Ile Ala Ser Gln Pro Leu Ser Leu
            275                 280                 285

Arg Pro Glu Ala Cys Arg Pro Ala Ala Gly Gly Ala Val His Thr Arg
    290                 295                 300

Gly Leu Asp Phe Ala Cys Asp Ile Tyr Ile Trp Ala Pro Leu Ala Gly
305                 310                 315                 320

Thr Cys Gly Val Leu Leu Leu Ser Leu Val Ile Thr Leu Tyr Cys Lys
                325                 330                 335

Arg Gly Arg Lys Lys Leu Leu Tyr Ile Phe Lys Gln Pro Phe Met Arg
                340                 345                 350

Pro Val Gln Thr Thr Gln Glu Glu Asp Gly Cys Ser Cys Arg Phe Pro
            355                 360                 365

Glu Glu Glu Glu Gly Gly Cys Glu Leu Arg Val Lys Phe Ser Arg Ser
    370                 375                 380

Ala Asp Ala Pro Ala Tyr Gln Gln Gly Gln Asn Gln Leu Tyr Asn Glu
385                 390                 395                 400

Leu Asn Leu Gly Arg Arg Glu Glu Tyr Asp Val Leu Asp Lys Arg Arg
                405                 410                 415

Gly Arg Asp Pro Glu Met Gly Gly Lys Pro Arg Arg Lys Asn Pro Gln
                420                 425                 430

Glu Gly Leu Tyr Asn Glu Leu Gln Lys Asp Lys Met Ala Glu Ala Tyr
            435                 440                 445

Ser Glu Ile Gly Met Lys Gly Glu Arg Arg Arg Gly Lys Gly His Asp
    450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg
                485

<210> SEQ ID NO 131
<211> LENGTH: 2293
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 131
atgctcttgc tcgtgacttc tttgcttttg tgcgaacttc cgcacccagc cttccttttg    60
```

-continued

| | |
|---|---|
| ataccctcagg tacagcttca acaaagcgga ccgggacttg ttaagcattc ccaaacccttt | 120 |
| tctctcacgt gtgcaattag cggcgatagt gtatcctcta attctgcggc ctggaactgg | 180 |
| atacgacaat caccaagccg gggactcgag tggttgggcc gaacctacta tcggtccaaa | 240 |
| tggtataatg actacgcagt atccgtgaaa tctcgcatta cgatcaatcc agacacctcc | 300 |
| aaaaatcaat tttctctgca gttgaatagc gtgactcccg aggacacggc cgtttactat | 360 |
| tgcgcccagg aagttgaacc ccacgatgca tttgatattt ggggccaggg aaccatggtg | 420 |
| acagtgagta gtgggggtgg aggatctgga ggaggcggta gcggcggggg cggcagtgat | 480 |
| atccagatga cgcagtcacc ttccagcgtg tatgcgagtg tggggacaa ggtcaccata | 540 |
| acctgtcgcg ctagccaaga tgtcagcggg tggctggctt ggtaccagca gaaaccaggt | 600 |
| ttggctcctc agcttttgat ctcaggagca agcacgcttc agggtgaggt cccaagtcgc | 660 |
| tttagtggct ctggctccgg gacagacttc acgttgacga tcagcagttt gcagcctgag | 720 |
| gatttcgcga cctactactg ccagcaagcg aaatattttc cgtacacttt cggtcagggg | 780 |
| accaaattgg agatcaaagg tggggtggt tcaggcggcg gaggctcagg cggcggcggt | 840 |
| agcggaggag gcggaagcgg gggtggcgga tcagaagtgc aactcgttca gagtggcgcg | 900 |
| gaggttaaga aacccggtgc atctgtaaag gttagctgta aggcatcagg atacactttt | 960 |
| accagctatt acatgcattg ggtgagacag gctcccggtc aggggctcga atggatgggg | 1020 |
| ttgatcaacc cgagtggtgg ttcaacatct tacgcccaga gtttcagggg ccgagtaaca | 1080 |
| atgactcggg acacgtctac ctcaactgtg tatatggagc tttccagcct gcgctcagag | 1140 |
| gatacagcag tctattactg cgcacggtca gacagaggta taacggccac tgatgcgttc | 1200 |
| gatatctggg gacaagggac tatggtaact gtgtcttccg gaggaggagg tagtggaggg | 1260 |
| ggaggaagcg gtgggggggg ctcacagtcc gttttgactc agccaccaag cgtctcagtc | 1320 |
| gcaccggggc gaatggcgaa aattacttgc ggcgggagcg acataggcaa caagaatgtg | 1380 |
| cattggtacc aacagaaacc aggtcaagca cctgttctcg tggtgtatga tgactacgat | 1440 |
| cgcccaagcg ggatcccgga gcggttctct ggatcaaatt ctggtgatgc agccactctg | 1500 |
| acaatatcaa cggtggaagt cggtgacgag gctgattact tctgccaagt atgggatggc | 1560 |
| agcggagatc cctactggat gttttggagga ggtactcaac tgacagttct gggcgcggcc | 1620 |
| gcaacgacca ctcctgcacc ccgccctccg actccggccc caaccattgc cagccagccc | 1680 |
| ctgtccctgc ggccggaagc ctgcagaccg gctgccggcg gagccgtcca taccegggga | 1740 |
| ctggatttcg cctgcgatat ctatatctgg gcaccactcg ccggaacctg tggagtgctg | 1800 |
| ctgctgtccc ttgtgatcac cctgtactgc aagcgcggac ggaagaaact cttgtacatc | 1860 |
| ttcaagcagc cgttcatgcg ccctgtgcaa accacccaag aagaggacgg gtgctcctgc | 1920 |
| cggttcccgg aagaggaaga gggcggctgc gaactgcgcg tgaagttttc ccggtccgcc | 1980 |
| gacgctccgg cgtaccagca ggggcaaaac cagctgtaca cgaacttaa cctcggtcgc | 2040 |
| cgggaagaat atgacgtgct ggacaagcgg cggggaagag atcccgagat gggtggaaag | 2100 |
| ccgcggcgga agaaccctca ggagggcttg tacaacgagc tgcaaaagga caaaatggcc | 2160 |
| gaagcctact ccgagattgg catgaaggga gagcgcagac gcgggaaggg acacgatgga | 2220 |
| ctgtaccagg gactgtcaac cgcgactaag gacacttacg acgccctgca catgcaggcc | 2280 |
| ctgccccgc gct | 2293 |

<210> SEQ ID NO 132
<211> LENGTH: 764

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 132
```

Met Leu Leu Leu Val Thr Ser Leu Leu Leu Cys Glu Leu Pro His Pro
1               5                   10                  15

Ala Phe Leu Leu Ile Pro Gln Val Gln Leu Gln Gln Ser Gly Pro Gly
            20                  25                  30

Leu Val Lys His Ser Gln Thr Leu Ser Leu Thr Cys Ala Ile Ser Gly
        35                  40                  45

Asp Ser Val Ser Ser Asn Ser Ala Ala Trp Asn Trp Ile Arg Gln Ser
    50                  55                  60

Pro Ser Arg Gly Leu Glu Trp Leu Gly Arg Thr Tyr Tyr Arg Ser Lys
65                  70                  75                  80

Trp Tyr Asn Asp Tyr Ala Val Ser Val Lys Ser Arg Ile Thr Ile Asn
                85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Gln Glu Val Glu Pro His
        115                 120                 125

Asp Ala Phe Asp Ile Trp Gly Gln Gly Thr Met Val Thr Val Ser Ser
    130                 135                 140

Gly Gly Gly Gly Ser Gly Gly Gly Ser Gly Gly Gly Gly Ser Asp
145                 150                 155                 160

Ile Gln Met Thr Gln Ser Pro Ser Ser Val Tyr Ala Ser Val Gly Asp
                165                 170                 175

Lys Val Thr Ile Thr Cys Arg Ala Ser Gln Asp Val Ser Gly Trp Leu
            180                 185                 190

Ala Trp Tyr Gln Gln Lys Pro Gly Leu Ala Pro Gln Leu Leu Ile Ser
        195                 200                 205

Gly Ala Ser Thr Leu Gln Gly Glu Val Pro Ser Arg Phe Ser Gly Ser
    210                 215                 220

Gly Ser Gly Thr Asp Phe Thr Leu Thr Ile Ser Ser Leu Gln Pro Glu
225                 230                 235                 240

Asp Phe Ala Thr Tyr Tyr Cys Gln Gln Ala Lys Tyr Phe Pro Tyr Thr
                245                 250                 255

Phe Gly Gln Gly Thr Lys Leu Glu Ile Lys Gly Gly Gly Gly Ser Gly
            260                 265                 270

Gly Gly Ser Gly Gly Gly Ser Gly Gly Gly Ser Gly Gly
        275                 280                 285

Gly Gly Ser Glu Val Gln Leu Val Gln Ser Gly Ala Glu Val Lys Lys
    290                 295                 300

Pro Gly Ala Ser Val Lys Val Ser Cys Lys Ala Ser Gly Tyr Thr Phe
305                 310                 315                 320

Thr Ser Tyr Tyr Met His Trp Val Arg Gln Ala Pro Gly Gln Gly Leu
                325                 330                 335

Glu Trp Met Gly Leu Ile Asn Pro Ser Gly Gly Ser Thr Ser Tyr Ala
            340                 345                 350

Gln Lys Phe Gln Gly Arg Val Thr Met Thr Arg Asp Thr Ser Thr Ser
        355                 360                 365

Thr Val Tyr Met Glu Leu Ser Ser Leu Arg Ser Glu Asp Thr Ala Val

```
             370                 375                 380
Tyr Tyr Cys Ala Arg Ser Asp Arg Gly Ile Thr Ala Thr Asp Ala Phe
385                 390                 395                 400

Asp Ile Trp Gly Gln Gly Thr Met Val Thr Val Ser Ser Gly Gly Gly
                405                 410                 415

Gly Ser Gly Gly Gly Ser Gly Gly Gly Ser Gln Ser Val Leu
            420                 425                 430

Thr Gln Pro Pro Ser Val Ser Val Ala Pro Gly Arg Met Ala Lys Ile
            435                 440                 445

Thr Cys Gly Gly Ser Asp Ile Gly Asn Lys Asn Val His Trp Tyr Gln
450                 455                 460

Gln Lys Pro Gly Gln Ala Pro Val Leu Val Val Tyr Asp Asp Tyr Asp
465                 470                 475                 480

Arg Pro Ser Gly Ile Pro Glu Arg Phe Ser Gly Ser Asn Ser Gly Asp
                485                 490                 495

Ala Ala Thr Leu Thr Ile Ser Thr Val Glu Val Gly Asp Glu Ala Asp
                500                 505                 510

Tyr Phe Cys Gln Val Trp Asp Gly Ser Gly Asp Pro Tyr Trp Met Phe
                515                 520                 525

Gly Gly Gly Thr Gln Leu Thr Val Leu Gly Ala Ala Ala Thr Thr Thr
530                 535                 540

Pro Ala Pro Arg Pro Pro Thr Pro Ala Pro Thr Ile Ala Ser Gln Pro
545                 550                 555                 560

Leu Ser Leu Arg Pro Glu Ala Cys Arg Pro Ala Ala Gly Gly Ala Val
                565                 570                 575

His Thr Arg Gly Leu Asp Phe Ala Cys Asp Ile Tyr Ile Trp Ala Pro
                580                 585                 590

Leu Ala Gly Thr Cys Gly Val Leu Leu Leu Ser Leu Val Ile Thr Leu
                595                 600                 605

Tyr Cys Lys Arg Gly Arg Lys Lys Leu Leu Tyr Ile Phe Lys Gln Pro
                610                 615                 620

Phe Met Arg Pro Val Gln Thr Thr Gln Glu Glu Asp Gly Cys Ser Cys
625                 630                 635                 640

Arg Phe Pro Glu Glu Glu Glu Gly Gly Cys Glu Leu Arg Val Lys Phe
                645                 650                 655

Ser Arg Ser Ala Asp Ala Pro Ala Tyr Gln Gln Gly Gln Asn Gln Leu
                660                 665                 670

Tyr Asn Glu Leu Asn Leu Gly Arg Arg Glu Glu Tyr Asp Val Leu Asp
                675                 680                 685

Lys Arg Arg Gly Arg Asp Pro Glu Met Gly Gly Lys Pro Arg Arg Lys
690                 695                 700

Asn Pro Gln Glu Gly Leu Tyr Asn Glu Leu Gln Lys Asp Lys Met Ala
705                 710                 715                 720

Glu Ala Tyr Ser Glu Ile Gly Met Lys Gly Glu Arg Arg Arg Gly Lys
                725                 730                 735

Gly His Asp Gly Leu Tyr Gln Gly Leu Ser Thr Ala Thr Lys Asp Thr
                740                 745                 750

Tyr Asp Ala Leu His Met Gln Ala Leu Pro Pro Arg
                755                 760

<210> SEQ ID NO 133
<211> LENGTH: 1476
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic polynucleotide"

<400> SEQUENCE: 133
atgcttcttt tggtgacttc ccttttgctg tgcgagttgc cacacccgc cttcctgctt      60 attccccagg tacagcttca acagagtggg ccgggactgg tgaaacactc ccaaacactt    120
tctctgacgt gcgctatatc aggtgactct gtttcatcta attctgctgc gtggaactgg    180
attcgacaat ctcccagtcg cgggttggaa tggctgggac gaacatatta tcggtctaag    240
tggtataacg attatgctgt atctgttaaa tctcgaatta cgattaatcc tgacacctcc    300
aagaaccagt tctccctcca gttgaactca gtcacaccgg aagacactgc ggtctactat    360
tgcgctcaag aagtcgagcc acatgatgca ttcgacatct ggggccaggg aacgatggtc    420
accgtcagca gtggcggcgg cggatctggg ggtggcggtt ctggcggtgg aggatcagac    480
atacaaatga cgcagagtcc ctcaagtgtg tacgcgagtg tggggataaa ggtaactatt    540
acgtgcagag cgtcacagga tgttagtgga tggcttgcct ggtatcagca aagccaggc    600 cttgctccac agctccttat cagtggtgct tctacacttc agggcgaggt tccgagtaga    660
ttctctggtt ctggatctgg tactgacttc actcttacaa tttcttcttt gcaaccagaa    720
gactttgcga cttattactg ccaacaggcc aaatacttcc cttatacatt tggccaaggt    780
accaagttgg agataaaggc ggccgcaact accaccccctg cccctcggcc gccgactccg    840
gccccaacca tcgcaagcca acccctctcc ttgcgcccccg aagcttgccg cccggccgcg    900
ggtggagccg tgcatacccg ggggctggac tttgcctgcg atatctacat ttgggccccg    960
ctggccggca cttgcggcgt gctcctgctg tcgctggtca tcacccttta ctgcaagagg   1020
ggccggaaga agctgcttta catcttcaag cagccgttca tgcggcccgt gcagacgact   1080
caggaagagg acggatgctc gtgcagattc cctgaggagg aagaggggggg atgcgaactg   1140 cgcgtcaagt tctcacggtc cgccgacgcc ccgcatatc aacagggcca gaatcagctc    1200
tacaacgagc tgaacctggg aaggagagag gagtacgacg tgctggacaa gcgacgcgga   1260
cgcgacccgg agatgggggg gaaaccacgg cggaaaaacc ctcaggaagg actgtacaac   1320
gaactccaga aagacaagat ggcggaagcc tactcagaaa tcgggatgaa gggagagcgg   1380 aggagggggaa agggtcacga cgggctgtac cagggactga gcaccgccac taaggatacc   1440
tacgatgcct tgcatatgca agcactccca ccccgg                             1476

<210> SEQ ID NO 134
<211> LENGTH: 492
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 134

Met Leu Leu Leu Val Thr Ser Leu Leu Cys Glu Leu Pro His Pro
1               5                   10                  15

Ala Phe Leu Leu Ile Pro Gln Val Gln Leu Gln Gln Ser Gly Pro Gly
            20                  25                  30

Leu Val Lys His Ser Gln Thr Leu Ser Leu Thr Cys Ala Ile Ser Gly
        35                  40                  45

Asp Ser Val Ser Ser Asn Ser Ala Ala Trp Asn Trp Ile Arg Gln Ser
```

```
                50                  55                  60
Pro Ser Arg Gly Leu Glu Trp Leu Gly Arg Thr Tyr Tyr Arg Ser Lys
65                  70                  75                  80

Trp Tyr Asn Asp Tyr Ala Val Ser Val Lys Ser Arg Ile Thr Ile Asn
                85                  90                  95

Pro Asp Thr Ser Lys Asn Gln Phe Ser Leu Gln Leu Asn Ser Val Thr
                100                 105                 110

Pro Glu Asp Thr Ala Val Tyr Tyr Cys Ala Gln Glu Val Glu Pro His
                115                 120                 125

Asp Ala Phe Asp Ile Trp Gly Gln Gly Thr Met Val Thr Val Ser Ser
                130                 135                 140

Gly Gly Gly Gly Ser Gly Gly Gly Ser Gly Gly Gly Gly Ser Asp
145                 150                 155                 160

Ile Gln Met Thr Gln Ser Pro Ser Ser Val Tyr Ala Ser Val Gly Asp
                165                 170                 175

Lys Val Thr Ile Thr Cys Arg Ala Ser Gln Asp Val Ser Gly Trp Leu
                180                 185                 190

Ala Trp Tyr Gln Gln Lys Pro Gly Leu Ala Pro Gln Leu Leu Ile Ser
                195                 200                 205

Gly Ala Ser Thr Leu Gln Gly Glu Val Pro Ser Arg Phe Ser Gly Ser
210                 215                 220

Gly Ser Gly Thr Asp Phe Thr Leu Thr Ile Ser Ser Leu Gln Pro Glu
225                 230                 235                 240

Asp Phe Ala Thr Tyr Tyr Cys Gln Gln Ala Lys Tyr Phe Pro Tyr Thr
                245                 250                 255

Phe Gly Gln Gly Thr Lys Leu Glu Ile Lys Ala Ala Ala Thr Thr Thr
                260                 265                 270

Pro Ala Pro Arg Pro Pro Thr Pro Ala Pro Thr Ile Ala Ser Gln Pro
                275                 280                 285

Leu Ser Leu Arg Pro Glu Ala Cys Arg Pro Ala Ala Gly Gly Ala Val
290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Lys Arg Gly Arg Lys Lys Leu Leu Tyr Ile Phe Lys Gln Pro
                340                 345                 350

Phe Met Arg Pro Val Gln Thr Thr Gln Glu Glu Asp Gly Cys Ser Cys
                355                 360                 365

Arg Phe Pro Glu Glu Glu Glu Gly Gly Cys Glu Leu Arg Val Lys Phe
370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
                420                 425                 430

Asn Pro Gln Glu Gly Leu Tyr Asn Glu Leu Gln Lys Asp Lys Met Ala
                435                 440                 445

Glu Ala Tyr Ser Glu Ile Gly Met Lys Gly Glu Arg Arg Arg Gly Lys
                450                 455                 460

Gly His Asp Gly Leu Tyr Gln Gly Leu Ser Thr Ala Thr Lys Asp Thr
465                 470                 475                 480
```

Tyr Asp Ala Leu His Met Gln Ala Leu Pro Pro Arg
            485                 490

<210> SEQ ID NO 135
<211> LENGTH: 1476
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 135

| | |
|---|---|
| atgttgctgc tcgtgacctc gctccttctg tgcgagctgc cccatccggc ttttctgctc | 60 |
| atccctcaag tgcagctgca gcagtccggt cctggactgg tcaagccgtc ccagactctg | 120 |
| agcctgactt gcgccattag cgggaactca gtctcgtcca attcggcggc ctggaactgg | 180 |
| atccggcagt caccatcaag gggcctggaa tggctcgggc gcacttacta ccggtccaaa | 240 |
| tggtataacg actacgccgt gtccgtgaag tcccggatca ccattaaccc cgacacctcg | 300 |
| aagaaccagt tctcactcca actgaacagc gtgaccccccg aggataccgc ggtgtactac | 360 |
| tgcgcacaag aagtggaacc gcaggacgcc ttcgacattt ggggacaggg aacgatggtc | 420 |
| acagtgtcgt ccggtggagg aggttccgga ggcggtggat ctggaggcgg aggttcggat | 480 |
| atccagatga cccagagccc ctcctcggtg tccgcatccg tgggcgataa ggtcaccatt | 540 |
| acctgtagag cgtcccagga cgtgtccgga tggctggcct ggtaccagca gaagccaggc | 600 |
| ttggctcctc aactgctgat ctttggcgcc agcactcttc aggggaggt gccatcacgc | 660 |
| ttctccggag gtggttccgg caccgacttc accctgacca tcagcagcct ccagcctgag | 720 |
| gacttcgcca cttactactg ccaacaggcc aagtacttcc cctatacctt cggacaaggc | 780 |
| actaagctgg aaatcaaggc ggccgcaact accaccccctg cccctcggcc gccgactccg | 840 |
| gccccaacca tcgcaagcca acccctctcc ttgcgccccg aagcttgccg cccggccgcg | 900 |
| ggtggagccg tgcatacccg ggggctggac tttgcctgcg atatctacat ttgggccccg | 960 |
| ctggccggca cttgcggcgt gctcctgctg tcgctggtca tcacccttta ctgcaagagg | 1020 |
| ggccggaaga agctgcttta catcttcaag cagccgttca tgcggcccgt gcagacgact | 1080 |
| caggaagagg acgatgctc gtgcagattc cctgaggagg aagaggggg atgcgaactg | 1140 |
| cgcgtcaagt tctcacggtc cgccgacgcc cccgcatatc aacagggcca gaatcagctc | 1200 |
| tacaacgagc tgaacctggg aaggagagag gagtacgacg tgctggacaa gcgacgcgga | 1260 |
| cgcgacccgg agatggggg gaaccacggg cggaaaaacc ctcaggaagg actgtacaac | 1320 |
| gaactccaga agacaagat ggcggaagcc tactcagaaa tcgggatgaa gggagagcgg | 1380 |
| aggagggaa agggtcacga cgggctgtac cagggactga gcaccgccac taaggatacc | 1440 |
| tacgatgcct tgcatatgca agcactccca ccccgg | 1476 |

<210> SEQ ID NO 136
<211> LENGTH: 492
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 136

Met Leu Leu Leu Val Thr Ser Leu Leu Leu Cys Glu Leu Pro His Pro

-continued

```
1               5                   10                  15
Ala Phe Leu Leu Ile Pro Gln Val Gln Leu Gln Gln Ser Gly Pro Gly
                20                  25                  30
Leu Val Lys Pro Ser Gln Thr Leu Ser Leu Thr Cys Ala Ile Ser Gly
                35                  40                  45
Asn Ser Val Ser Ser Asn Ser Ala Ala Trp Asn Trp Ile Arg Gln Ser
 50                      55                      60
Pro Ser Arg Gly Leu Glu Trp Leu Gly Arg Thr Tyr Tyr Arg Ser Lys
 65                  70                  75                  80
Trp Tyr Asn Asp Tyr Ala Val Ser Val Lys Ser Arg Ile Thr Ile Asn
                 85                  90                  95
Pro Asp Thr Ser Lys Asn Gln Phe Ser Leu Gln Leu Asn Ser Val Thr
                100                 105                 110
Pro Glu Asp Thr Ala Val Tyr Tyr Cys Ala Gln Glu Val Glu Pro Gln
                115                 120                 125
Asp Ala Phe Asp Ile Trp Gly Gln Gly Thr Met Val Thr Val Ser Ser
            130                 135                 140
Gly Gly Gly Gly Ser Gly Gly Gly Ser Gly Gly Gly Gly Ser Asp
145                 150                 155                 160
Ile Gln Met Thr Gln Ser Pro Ser Ser Val Ser Ala Ser Val Gly Asp
                165                 170                 175
Lys Val Thr Ile Thr Cys Arg Ala Ser Gln Asp Val Ser Gly Trp Leu
                180                 185                 190
Ala Trp Tyr Gln Gln Lys Pro Gly Leu Ala Pro Gln Leu Leu Ile Phe
            195                 200                 205
Gly Ala Ser Thr Leu Gln Gly Glu Val Pro Ser Arg Phe Ser Gly Gly
        210                 215                 220
Gly Ser Gly Thr Asp Phe Thr Leu Thr Ile Ser Ser Leu Gln Pro Glu
225                 230                 235                 240
Asp Phe Ala Thr Tyr Tyr Cys Gln Gln Ala Lys Tyr Phe Pro Tyr Thr
                245                 250                 255
Phe Gly Gln Gly Thr Lys Leu Glu Ile Lys Ala Ala Ala Thr Thr Thr
                260                 265                 270
Pro Ala Pro Arg Pro Pro Thr Pro Ala Pro Thr Ile Ala Ser Gln Pro
            275                 280                 285
Leu Ser Leu Arg Pro Glu Ala Cys Arg Pro Ala Ala Gly Gly Ala Val
        290                 295                 300
His Thr Arg Gly Leu Asp Phe Ala Cys Asp Ile Tyr Ile Trp Ala Pro
305                 310                 315                 320
Leu Ala Gly Thr Cys Gly Val Leu Leu Leu Ser Leu Val Ile Thr Leu
                325                 330                 335
Tyr Cys Lys Arg Gly Arg Lys Lys Leu Leu Tyr Ile Phe Lys Gln Pro
                340                 345                 350
Phe Met Arg Pro Val Gln Thr Thr Gln Glu Glu Asp Gly Cys Ser Cys
            355                 360                 365
Arg Phe Pro Glu Glu Glu Glu Gly Gly Cys Glu Leu Arg Val Lys Phe
        370                 375                 380
Ser Arg Ser Ala Asp Ala Pro Ala Tyr Gln Gln Gly Gln Asn Gln Leu
385                 390                 395                 400
Tyr Asn Glu Leu Asn Leu Gly Arg Arg Glu Glu Tyr Asp Val Leu Asp
                405                 410                 415
Lys Arg Arg Gly Arg Asp Pro Glu Met Gly Gly Lys Pro Arg Arg Lys
                420                 425                 430
```

```
Asn Pro Gln Glu Gly Leu Tyr Asn Glu Leu Gln Lys Asp Lys Met Ala
            435                 440                 445

Glu Ala Tyr Ser Glu Ile Gly Met Lys Gly Glu Arg Arg Gly Lys
    450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490

<210> SEQ ID NO 137
<211> LENGTH: 190
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 137
ggtacctgag ctcagttctg agaaaagtag ttctgagaaa agtagttctg agaaaagtag      60
ttctgagaaa agtagttctg agaaaagtct cgaggatatc aagatctggc ctcggcggcc    120
aagcttagac actagagggt atataatgga agctcgactt ccagcttggc aatccggtac    180
tgttggtaaa                                                            190

<210> SEQ ID NO 138
<211> LENGTH: 214
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 138
tgagctctga gtcagtgact cagtgagtca gtgactcagt gagtcagtga ctcagctcga     60
ggatctcgct agcgggaatt ccggggact tccggaat ttccgggac tttccgggaa       120 tttccagatc tggcctcggc ggccaagctt agacactaga gggtatataa tggaagctcg    180
acttccagct tggcaatccg gtactgttgg taaa                                 214

<210> SEQ ID NO 139
<211> LENGTH: 1670
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 139
ggtacctgag ctcagttctg agaaaagtag ttctgagaaa agtagttctg agaaaagtag      60
ttctgagaaa agtagttctg agaaaagtct cgaggatatc aagatctggc ctcggcggcc    120
aagcttagac actagagggt atataatgga agctcgactt ccagcttggc aatccggtac    180
tgttggtaaa ggcgcgcccc accatgctgc tgctggtcac cagcctgctg ctgtgcgagc    240
tccctcaccc cgccttttctg cttatcccgg acattcagat gacacagacc acctcgagct    300
tgtccgcgtc gctgggcgat cgcgtgacca tctcctgccg ggcctcccaa gacatttcaa    360
agtatctcaa ctggtaccag cagaagccgg acggaaccgt gaaactgctg atctaccata    420
```

| | |
|---|---:|
| ccagccgcct gcactccggc gtgccgtccc gcttctccgg atcgggttcc ggaactgact | 480 |
| actcactgac tatctccaac ttggaacaag aggacatcgc cacttacttc tgtcaacaag | 540 |
| gaaataccct tccctacacc ttcggggggg gtaccaagct ggagatcact ggggggcggag | 600 |
| gctccggtgg aggcggatcc ggcggtggag ggagcgaagt caagctgcag gaatcaggac | 660 |
| caggactcgt ggcgccatcc cagtccctgt cggtgacctg tactgtctcc ggagtcagcc | 720 |
| tccccgatta cggagtgtca tggattaggc aacccccaag aaaagggctg aatggctcg | 780 |
| gagtgatctg gggctccgaa accacctact acaactcggc gctgaagtcc cggctgacca | 840 |
| tcatcaagga caactccaag agccaagtgt tcttgaagat gaacagcttg cagaccgacg | 900 |
| ataccgcaat ctactactgt gccaagcact attactacgg ggggtcttac gccatggact | 960 |
| actggggaca gggcacctcc gtgactgtgt cgtccgcggc cgcgcccgcc cctcggcccc | 1020 |
| cgactcctgc cccgacgatc gcttcccaac ctctctcgct gcgcccggaa gcatgccggc | 1080 |
| ccgccgccgg tggcgctgtc cacactcgcg gactggactt tgataccgca ctggcggccg | 1140 |
| tgatctgtag cgccctggcc accgtgctgc tggcgctgct catcctttgc gtgatctact | 1200 |
| gcaagcggca gcctaggcga agaagctc tctacatttt caagcaaccc ttcatgcgcc | 1260 |
| ccgtgcaaac cacccaggag gaggatggat gctcatgccg gttccctgag gaagaagagg | 1320 |
| gcggttgcga gctcagagtg aaattcagcc ggtcggctga cgccccggcg taccagcagg | 1380 |
| gccagaacca gctgtacaat gagctcaacc tggggcgccg cgaagagtac gacgtgctgg | 1440 |
| acaagaggag aggcagagat ccggaaatgg gcggaaagcc aaggcggaag aacccgcagg | 1500 |
| aaggtctta caacgaactg cagaaggaca agatggccga ggcctactcc gagattggga | 1560 |
| tgaagggaga agacggagg ggaaagggac atgacggact ttaccagggc ctgagcactg | 1620 |
| ccacgaagga cacctatgat gccctgcaca tgcaggcgct gccgcctcgg | 1670 |

<210> SEQ ID NO 140
<211> LENGTH: 1694
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 140

| | |
|---|---:|
| tgagctctga gtcagtgact cagtgagtca gtgactcagt gagtcagtga ctcagctcga | 60 |
| ggatctcgct agcgggaatt tccggggact ttccggggaat ttccggggac tttccgggaa | 120 |
| tttccagatc tggcctcggc ggccaagctt agacactaga gggtatataa tggaagctcg | 180 |
| acttccagct tggcaatccg gtactgttgg taaaggcgcg ccccaccatg ctgctgctgg | 240 |
| tcaccagcct gctgctgtgc gagctccctc accccgcctt tctgcttatc ccggacattc | 300 |
| agatgacaca gaccacctcg agcttgtccg cgtcgctggg cgatcgcgtg accatctcct | 360 |
| gccgggcctc ccaagacatt tcaaagtatc tcaactggta ccagcagaag ccggacggaa | 420 |
| ccgtgaaact gctgatctac cataccagcc gcctgcactc cggcgtgccg tcccgcttct | 480 |
| ccggatcggg ttccgaact gactactcac tgactatctc caacttggaa caagaggaca | 540 |
| tcgccactta cttctgtcaa caaggaaata cccttcccta ccttcgggg ggggtacca | 600 |
| agctggagat cactggggc ggaggctccg gtggaggcgg atccggcggt ggagggagcg | 660 |
| aagtcaagct gcaggaatca ggaccaggac tcgtggcgcc atcccagtcc ctgtcggtga | 720 |
| cctgtactgt ctccggagtc agcctccccg attacggagt gtcatggatt aggcaacccc | 780 |

```
caagaaaagg gctggaatgg ctcggagtga tctggggctc cgaaaccacc tactacaact    840
cggcgctgaa gtcccggctg accatcatca aggacaactc caagagccaa gtgttcttga    900
agatgaacag cttgcagacc gacgataccg caatctacta ctgtgccaag cactattact    960
acggggggtc ttacgccatg gactactggg acagggcac ctccgtgact gtgtcgtccg   1020
cggccgcgcc cgcccctcgg ccccgactc ctgccccgac gatcgcttcc caacctctct   1080
cgctgcgccc ggaagcatgc cggcccgccg ccggtggcgc tgtccacact cgcggactgg   1140
actttgatac cgcactggcg gccgtgatct gtagcgccct ggccaccgtg ctgctggcgc   1200
tgctcatcct ttgcgtgatc tactgcaagc ggcagcctag gcgaaagaag ctcctctaca   1260
ttttcaagca acccttcatg cgccccgtgc aaaccaccca ggaggaggat ggatgctcat   1320
gccggttccc tgaggaagaa gagggcggtt gcgagctcag agtgaaattc agccggtcgg   1380
ctgacgcccc ggcgtaccag cagggccaga accagctgta caatgagctc aacctggggc   1440
gccgcgaaga gtacgacgtg ctggacaaga ggagaggcag agatccggaa atgggcggaa   1500
agccaaggcg gaagaacccg caggaaggtc tttacaacga actgcagaag gacaagatgg   1560
ccgaggccta ctccgagatt gggatgaagg agaaagacg gaggggaaag ggacatgacg   1620
gactttacca gggcctgagc actgccacga aggacaccta tgatgccctg cacatgcagg   1680
cgctgccgcc tcgg                                                      1694

<210> SEQ ID NO 141
<211> LENGTH: 735
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 141
gacattcaga tgactcagac cacctcctcc ctgtccgcct ccctgggcga ccgcgtgacc     60
atctcatgcc gcgccagcca ggacatctcg aagtacctca actggtacca gcagaagccc    120
gacggaaccg tgaagctcct gatctaccac acctcccggc tgcacagcgg agtgccgtct    180
agattctcgg gttcggggtc gggaactgac tactcccta ctatttccaa cctggagcag    240
gaggatattg ccacctactt ctgccaacaa ggaaacaccc tgccgtacac ttttggcggg    300
ggaaccaagc tggaaatcac tgcagcaca tccggttccg ggaagcccgg ctccggagag    360
ggcagcacca aggggggaagt caagctgcag gaatcaggac ctggcctggt ggccccgagc    420
cagtcactgt ccgtgacttg tactgtgtcc ggagtgtcgc tcccggatta cggagtgtcc    480
tggatcaggc agccacctcg gaaaggattg gaatggctcg gagtcatctg gggttccgaa    540
accacctatt acaactcggc actgaaatcc aggctcacca ttatcaagga taactccaag    600
tcacaagtgt tcctgaagat gaatagcctg cagactgacg acacggcgat ctactattgc    660
gccaagcact actactacgg cggatcctac gctatggact actggggcca ggggaccagc    720
gtgaccgtgt catcc                                                     735

<210> SEQ ID NO 142
<211> LENGTH: 1473
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic polynucleotide"

<400> SEQUENCE: 142

| | | | | | |
|---|---|---|---|---|---|
| atgctccttc | tcgtgacctc | cctgcttctc | tgcgaactgc | cccatcctgc | cttcctgctg | 60 |
| attcccgagg | tgcagttgca | acagtcagga | gctgaactgg | tcaagccagg | agccagcgtg | 120 |
| aagatgagct | gcaaggcctc | cggttacacc | ttcacctcct | acaacatgca | ctgggtgaaa | 180 |
| cagaccccgg | gacaagggct | cgaatggatt | ggcgccatct | accccgggaa | tggcgatact | 240 |
| tcgtacaacc | agaagttcaa | gggaaaggcc | accctgaccg | ccgacaagag | ctcctccacc | 300 |
| gcgtatatgc | agttgagctc | cctgacctcc | gaggactccg | ccgactacta | ctgcgcacgg | 360 |
| tccaactact | atggaagctc | gtactggttc | ttcgatgtct | gggggccgg | caccactgtg | 420 |
| accgtcagct | ccggggggcgg | aggatccggt | ggaggcggaa | gcggggggtgg | aggatccgac | 480 |
| attgtgctga | ctcagtcccc | ggcaatcctg | tcggcctcac | cgggcgaaaa | ggtcacgatg | 540 |
| acttgtagag | cgtcgtccag | cgtgaactac | atggattggt | accaaaagaa | gcctggatcg | 600 |
| tcacccaagc | cttggatcta | cgctacatct | aacctggcct | ccggcgtgcc | agcgcggttc | 660 |
| agcgggtccg | gctcgggcac | ctcatactcg | ctgaccatct | cccgcgtgga | ggctgaggac | 720 |
| gccgcgacct | actactgcca | gcagtggtcc | ttcaacccgc | cgacttttgg | aggcggtact | 780 |
| aagctggaga | tcaaagcggc | cgcaactacc | accctgccc | ctcggccgcc | gactccggcc | 840 |
| ccaaccatcg | caagccaacc | cctctccttg | cgccccgaag | cttgccgccc | ggccgcgggt | 900 |
| ggagccgtgc | atacccgggg | gctggacttt | gcctgcgata | tctacatttg | gccccgctg | 960 |
| gccggcactt | gcggcgtgct | cctgctgtcg | ctggtcatca | ccctttactg | caagagggc | 1020 |
| cggaagaagc | tgctttacat | cttcaagcag | ccgttcatgc | ggcccgtgca | gacgactcag | 1080 |
| gaagaggacg | gatgctcgtg | cagattccct | gaggaggaag | aggggggatg | cgaactgcgc | 1140 |
| gtcaagttct | cacggtccgc | cgacgccccc | gcatatcaac | agggccagaa | tcagctctac | 1200 |
| aacgagctga | acctgggaag | gagagaggag | tacgacgtgc | tggacaagcg | acgcggacgc | 1260 |
| gacccggaga | tgggggggaa | accacggcgg | aaaaaccctc | aggaaggact | gtacaacgaa | 1320 |
| ctccagaaag | acaagatggc | ggaagcctac | tcagaaatcg | gatgaaggg | agagcggagg | 1380 |
| aggggaaagg | gtcacgacgg | gctgtaccag | ggactgagca | ccgccactaa | ggatacctac | 1440 |
| gatgccttgc | atatgcaagc | actcccaccc | cgg | | | 1473 |

<210> SEQ ID NO 143
<211> LENGTH: 491
<212> TYPE: PRT
<213> ORGANISM: Artificial Sequence
<220> FEATURE:
<221> NAME/KEY: source
<223> OTHER INFORMATION: /note="Description of Artificial Sequence:
   Synthetic polypeptide"

<400> SEQUENCE: 143

```
Met Leu Leu Leu Val Thr Ser Leu Leu Cys Glu Leu Pro His Pro
1               5                   10                  15

Ala Phe Leu Leu Ile Pro Glu Val Gln Leu Gln Gln Ser Gly Ala Glu
            20                  25                  30

Leu Val Lys Pro Gly Ala Ser Val Lys Met Ser Cys Lys Ala Ser Gly
        35                  40                  45

Tyr Thr Phe Thr Ser Tyr Asn Met His Trp Val Lys Gln Thr Pro Gly
    50                  55                  60

Gln Gly Leu Glu Trp Ile Gly Ala Ile Tyr Pro Gly Asn Gly Asp Thr
```

```
            65                  70                  75                  80
Ser Tyr Asn Gln Lys Phe Lys Gly Lys Ala Thr Leu Thr Ala Asp Lys
                85                  90                  95

Ser Ser Ser Thr Ala Tyr Met Gln Leu Ser Ser Leu Thr Ser Glu Asp
                100                 105                 110

Ser Ala Asp Tyr Tyr Cys Ala Arg Ser Asn Tyr Tyr Gly Ser Ser Tyr
                115                 120                 125

Trp Phe Phe Asp Val Trp Gly Ala Gly Thr Thr Val Thr Val Ser Ser
            130                 135                 140

Gly Gly Gly Gly Ser Gly Gly Gly Ser Gly Gly Gly Gly Ser Asp
145                 150                 155                 160

Ile Val Leu Thr Gln Ser Pro Ala Ile Leu Ser Ala Ser Pro Gly Glu
                165                 170                 175

Lys Val Thr Met Thr Cys Arg Ala Ser Ser Ser Val Asn Tyr Met Asp
                180                 185                 190

Trp Tyr Gln Lys Lys Pro Gly Ser Ser Pro Lys Pro Trp Ile Tyr Ala
                195                 200                 205

Thr Ser Asn Leu Ala Ser Gly Val Pro Ala Arg Phe Ser Gly Ser Gly
            210                 215                 220

Ser Gly Thr Ser Tyr Ser Leu Thr Ile Ser Arg Val Glu Ala Glu Asp
225                 230                 235                 240

Ala Ala Thr Tyr Tyr Cys Gln Gln Trp Ser Phe Asn Pro Pro Thr Phe
                245                 250                 255

Gly Gly Gly Thr Lys Leu Glu Ile Lys Ala Ala Ala Thr Thr Thr Pro
                260                 265                 270

Ala Pro Arg Pro Pro Thr Pro Ala Pro Thr Ile Ala Ser Gln Pro Leu
                275                 280                 285

Ser Leu Arg Pro Glu Ala Cys Arg Pro Ala Ala Gly Gly Ala Val His
                290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
                340                 345                 350

Met Arg Pro Val Gln Thr Thr Gln Glu Glu Asp Gly Cys Ser Cys Arg
                355                 360                 365

Phe Pro Glu Glu Glu Glu Gly Gly Cys Glu Leu Arg Val Lys Phe Ser
                370                 375                 380

Arg Ser Ala Asp Ala Pro Ala Tyr Gln Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
                420                 425                 430

Pro Gln Glu Gly Leu Tyr Asn Glu Leu Gln Lys Asp Lys Met Ala Glu
                435                 440                 445

Ala Tyr Ser Glu Ile Gly Met Lys Gly Glu Arg Arg Arg Gly Lys Gly
                450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490
```

<210> SEQ ID NO 144
<211> LENGTH: 750
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 144

```
gaagtgcaat tggtgcagag cggtggagga cttgtgaaac ctggtggatc cctgagactt      60
tcctgtgccg cttcgggctt caccttctcg gactactaca tgtcctggat tcgccaggcc     120
cctggaaagg gactggaatg ggtgtcatac atcagctcct ccggttccac catctactat     180
gccgattccg tgaagggcag attcaccatc tcgcgcgaca acgccaagaa cactctctat     240
ctgcaaatga actcactgcg ggctgaggac accgcggtct actactgcgc ccgggacctc     300
agcggaaagt ccagcggatg gtcccattac ttcgattact ggggacaggg aaccctggtc     360
accgtgtcca gcggcggggg gggctcgggt ggcggcggct ccggcggcgg cgggagcaac     420
ttcatgctga ctcagcccca ctccgtgtcc gagagcccgg gaaagaccgt gactatttcg     480
tgcacacggt cctccgggag cattgcgaac aactacgtgc agtggtacca gcagcggccc     540
gatagggccc caaccactgt gatctacgaa gatgaccagc ggccgtctgg agtcccggac     600
cgcttctcgg ggtccatcga ctcatcatcc aattccgcat cgctgacgat cagcggactg     660
aagatcgagg acgaagccga ttactactgc cagtcctacg acggcaccaa ctgggtcttt     720
gggggtggaa ccaagctgac tgtgctcgga                                      750
```

<210> SEQ ID NO 145
<211> LENGTH: 250
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 145

```
Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Ser Gly Lys Ser Ser Gly Trp Ser His Tyr Phe Asp
            100                 105                 110

Tyr Trp Gly Gln Gly Thr Leu Val Thr Val Ser Ser Gly Gly Gly Gly
        115                 120                 125

Ser Gly Gly Gly Gly Ser Gly Gly Gly Gly Ser Asn Phe Met Leu Thr
    130                 135                 140

Gln Pro His Ser Val Ser Glu Ser Pro Gly Lys Thr Val Thr Ile Ser
```

```
                145                 150                 155                 160
Cys Thr Arg Ser Ser Gly Ser Ile Ala Asn Asn Tyr Val Gln Trp Tyr
                    165                 170                 175

Gln Gln Arg Pro Asp Arg Ala Pro Thr Thr Val Ile Tyr Glu Asp Asp
                180                 185                 190

Gln Arg Pro Ser Gly Val Pro Asp Arg Phe Ser Gly Ser Ile Asp Ser
            195                 200                 205

Ser Ser Asn Ser Ala Ser Leu Thr Ile Ser Gly Leu Lys Ile Glu Asp
        210                 215                 220

Glu Ala Asp Tyr Tyr Cys Gln Ser Tyr Asp Gly Thr Asn Trp Val Phe
225                 230                 235                 240

Gly Gly Gly Thr Lys Leu Thr Val Leu Gly
                245                 250

<210> SEQ ID NO 146
<211> LENGTH: 729
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 146
gaagtgcaac ttgtcgaaag cggtggaggt cttgtccaac tggtcgctc cctgaggctc      60 tcgtgtgccg cgagcggatt caccttctca tcgtacgcta tgtcctgggt cagacaggct     120
cctggaaagg gctggaatg gtggccgtg atctcctacg acggcagcaa caagtattac     180
gccgactcag tgaagggccg gttcaccatt tcccgggaca cagcaagaa cacctgtac     240 ttgcaaatga actccctgcg ggccgaggat accgcgtgt actactgcgc ccacctccgc     300
tttggatacg gaatggatgt ctggggacag ggaactaccg tgaccgtgtc gtccgggggg    360
gggggaagcg gcggcggggg atcgggtggc ggcggatccc agactgtggt cacccaagag    420
ccttcactga ccgtgtcccc gggtggcacc gtgacgctga cttgcgcgtc atctaccggg    480
gccgtgacct cggaccacta cccctgctgg ttccagcaga aacccggaca tccaccgaga    540
gccctggtgt actccactga caccatccac tcctggactc cggcccggtt ctccggaagc    600
ctcctgggcg ggaaggccgc actgacagtg tccggagtgc agcccgagga tgaagccgac    660
tactactgtc tgctctacta tggggagca gcgtgttcg gtggcggcac tcagctgacc     720
gtgctggga                                                             729

<210> SEQ ID NO 147
<211> LENGTH: 243
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 147

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45
```

Ala Val Ile Ser Tyr Asp Gly Ser Asn Lys Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala His Leu Arg Phe Gly Tyr Gly Met Asp Val Trp Gly Gln Gly Thr
            100                 105                 110

Thr Val Thr Val Ser Ser Gly Gly Gly Ser Gly Gly Gly Gly Ser
            115                 120                 125

Gly Gly Gly Gly Ser Gln Thr Val Val Thr Gln Glu Pro Ser Leu Thr
130                 135                 140

Val Ser Pro Gly Gly Thr Val Thr Leu Thr Cys Ala Ser Ser Thr Gly
145                 150                 155                 160

Ala Val Thr Ser Asp His Tyr Pro Cys Trp Phe Gln Gln Lys Pro Gly
                165                 170                 175

His Pro Pro Arg Ala Leu Val Tyr Ser Thr Asp Thr Ile His Ser Trp
            180                 185                 190

Thr Pro Ala Arg Phe Ser Gly Ser Leu Leu Gly Gly Lys Ala Ala Leu
            195                 200                 205

Thr Val Ser Gly Val Gln Pro Glu Asp Glu Ala Asp Tyr Tyr Cys Leu
210                 215                 220

Leu Tyr Tyr Gly Gly Ala Arg Val Phe Gly Gly Gly Thr Gln Leu Thr
225                 230                 235                 240

Val Leu Gly

<210> SEQ ID NO 148
<211> LENGTH: 723
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 148
caagtccaac tcgtccagtc cggtgccgaa gtcaagaagc tggctcatc cgtgaaagtg      60 tcctgcaaag catcgggcgg aaccttctcc tcctatgcca tttcctgggt ccgccaggca     120
ccgggccagg gtctggagtg gatgggcggg attatcccta tcttcggaac tgccaaccac     180
gcccaaaagt tccagggacg cgtgaccatt accgccgatg aatcaacctc aaccgcctac     240
atggaactgt ccagcttgag gtccgaggac accgccgtgt actactgcgc gttcatgatg     300
gtgccggagt actactttga ctactggggc cagggaaccc ttgtgaccgt gtcgtccggt     360
ggtggcggat ccggggggggg gggatctggg ggcggcggaa gcgatatcca gatgacccag     420
tcgccatcga gcctgtccgc ttccgtgggc gacagagtga cgatcacttg ccgggcttca     480
caaggcatca gaaatgacct gggctggtat cagcagaagc cggagaagc gcccaagcgg     540 ctgatctacg cggccagcac cctgcaaaac ggagtgcctt cgcggttctc cgggagcggc     600
tccggaactg acttcactct gactattaac agcctccagc ccgaggattt cgccacatac     660
tactgtcagc agtacaacag ctacccgtac accttcggac agggaactaa gctcgaaatc     720
aag                                                                    723

<210> SEQ ID NO 149
<211> LENGTH: 241

<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 149

```
Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
Ala Ile Ser Trp Val Arg Gln Ala Pro Gly Gln Gly Leu Glu Trp Met
        35                  40                  45
Gly Gly Ile Ile Pro Ile Phe Gly Thr Ala Asn His Ala Gln Lys Phe
    50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Phe Met Met Val Pro Glu Tyr Tyr Phe Asp Tyr Trp Gly Gln Gly
            100                 105                 110
Thr Leu Val Thr Val Ser Ser Gly Gly Gly Ser Gly Gly Gly Gly
        115                 120                 125
Ser Gly Gly Gly Gly Ser Asp Ile Gln Met Thr Gln Ser Pro Ser Ser
    130                 135                 140
Leu Ser Ala Ser Val Gly Asp Arg Val Thr Ile Thr Cys Arg Ala Ser
145                 150                 155                 160
Gln Gly Ile Arg Asn Asp Leu Gly Trp Tyr Gln Gln Lys Pro Gly Glu
                165                 170                 175
Ala Pro Lys Arg Leu Ile Tyr Ala Ala Ser Thr Leu Gln Asn Gly Val
            180                 185                 190
Pro Ser Arg Phe Ser Gly Ser Gly Ser Gly Thr Asp Phe Thr Leu Thr
        195                 200                 205
Ile Asn Ser Leu Gln Pro Glu Asp Phe Ala Thr Tyr Tyr Cys Gln Gln
    210                 215                 220
Tyr Asn Ser Tyr Pro Tyr Thr Phe Gly Gln Gly Thr Lys Leu Glu Ile
225                 230                 235                 240
Lys
```

<210> SEQ ID NO 150
<211> LENGTH: 756
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 150

| | |
|---|---:|
| caactccaac tccaagaatc tggaccaggc ctcgtgaagc cctcccaaac tctgtccctg | 60 |
| acctgtaccg tgtcgggtgg aagcatttcg agcggtggat actactggtc ctggatcagg | 120 |
| cagcatcctg gaaagggact ggagtggatt gggtacatct actactccgg ctcaacctac | 180 |
| tacaacccgt ccttgaaatc gcgcgtgacg atctccgtgg acacttcaaa gaaccagttc | 240 |
| agcctgaagc tttcctccgt gaccgcggcc gatacagcgg tgtactactg cgctcgggat | 300 |
| cagagcgtgg ccgaccctgg tggcggctac tactactacg gaatggatgt ctggggacag | 360 |

-continued

```
ggaaccaccg tgactgtgtc cagcggggc ggcggatccg ggggggggg atcgggcggc    420 ggcggttcgc agtccgtgct gacccagcca cctagcgtgt cagtggcacc gggacagacc    480
gcctccattt cctgcggggg aaatgacttc ggtagccgct ccgtgtcatg gtatcaccag    540
aagccgggac aggccccggt gctggtcatc tatgacgaca acgacagacc ctcgggcatc    600
cccgaacggt tttcgggaag cacctccgga gacactgcca ccctgaccat ctcccgggtc    660
gaggtcggcg atgaagccga ttactactgc aagtctggg acgacgactc cgaccactgg    720
gtgttcggcg gcggaactaa gctgactgtg ctgggg                              756
```

```
<210> SEQ ID NO 151
<211> LENGTH: 252
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 151

```
Gln Leu Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Gln Ser Val Ala Asp Pro Gly Gly Gly Tyr Tyr Tyr
            100                 105                 110

Tyr Gly Met Asp Val Trp Gly Gln Gly Thr Thr Val Thr Val Ser Ser
        115                 120                 125

Gly Gly Gly Gly Ser Gly Gly Gly Ser Gly Gly Gly Ser Gln
130                 135                 140

Ser Val Leu Thr Gln Pro Pro Ser Val Ser Val Ala Pro Gly Gln Thr
145                 150                 155                 160

Ala Ser Ile Ser Cys Gly Gly Asn Asp Phe Gly Ser Arg Ser Val Ser
            165                 170                 175

Trp Tyr His Gln Lys Pro Gly Gln Ala Pro Val Leu Val Ile Tyr Asp
        180                 185                 190

Asp Asn Asp Arg Pro Ser Gly Ile Pro Glu Arg Phe Ser Gly Ser Thr
    195                 200                 205

Ser Gly Asp Thr Ala Thr Leu Thr Ile Ser Arg Val Glu Val Gly Asp
210                 215                 220

Glu Ala Asp Tyr Tyr Cys Gln Val Trp Asp Asp Ser Asp His Trp
225                 230                 235                 240

Val Phe Gly Gly Gly Thr Lys Leu Thr Val Leu Gly
                245                 250
```

```
<210> SEQ ID NO 152
<211> LENGTH: 723
<212> TYPE: DNA
```

<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 152

```
caggtgcagc tgcaggagtc cggcccagga ctggtgaagc cttcggagac cctgtccctc      60
acctgcactg tctctggtgg ctccatcagc agtagtagtt actactgggg ctggatccgc     120
cagcccccag ggaaggggct ggagtggatt gggagtatct attatagtgg gagcacctac     180
tacaacccgt ccctcaagag tcgagtcacc atacccgtag acacgtccaa gaaccagttc     240
tccctgaagc tgagctctgt gaccgccgca gacacggctg tgtattactg tgcgagacac     300
ctgggggtg atgctttga tatctggggc caagggacca cggtcaccgt ctcctcagga     360
ggtggcgggt ctggtggtgg cggtagcggt ggaggcggat ccctgcctgt gctgactcag     420
ccccctcgg tgtcagtggc cccaggacag acggccagga ttacctgtgg ggggaacaac     480
attggaagta aaagtgtgca ctggtaccag cagaagccag gccaggcccc tgtgctggtc     540
gtctatgatg atagcgaccg gccctcaggg atccctgagc gattctctgg ctccaactct     600
gggaacacag ccactctgac catcagcggg acccaggcta tggatgaggc tgactacttc     660
tgtcagtctt atgatagcag caatcccgtg gtattcggcg agggacccca gctcaccgtt     720
tta                                                                  723
```

<210> SEQ ID NO 153
<211> LENGTH: 241
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 153

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Pro Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Leu Gly Gly Asp Ala Phe Asp Ile Trp Gly Gln Gly
            100                 105                 110

Thr Thr Val Thr Val Ser Ser Gly Gly Gly Ser Gly Gly Gly Gly
        115                 120                 125

Ser Gly Gly Gly Gly Ser Leu Pro Val Leu Thr Gln Pro Pro Ser Val
    130                 135                 140

Ser Val Ala Pro Gly Gln Thr Ala Arg Ile Thr Cys Gly Gly Asn Asn
145                 150                 155                 160

Ile Gly Ser Lys Ser Val His Trp Tyr Gln Gln Lys Pro Gly Gln Ala
                165                 170                 175
```

```
Pro Val Leu Val Val Tyr Asp Asp Ser Asp Arg Pro Ser Gly Ile Pro
            180                 185                 190

Glu Arg Phe Ser Gly Ser Asn Ser Gly Asn Thr Ala Thr Leu Thr Ile
        195                 200                 205

Ser Gly Thr Gln Ala Met Asp Glu Ala Asp Tyr Phe Cys Gln Ser Tyr
    210                 215                 220

Asp Ser Ser Asn Pro Val Val Phe Gly Gly Gly Thr Gln Leu Thr Val
225                 230                 235                 240

Leu
```

<210> SEQ ID NO 154
<211> LENGTH: 732
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 154

```
caggcggccc aggtacagct gcagcagtca ggggctgagg tgaagaagcc tgggtcctcg      60
gtgaaggtct cctgcaaggc ttctggaggc accttcagca gctatgctat cagctgggtg     120
cgacaggccc ctggacaagg gcttgagtgg atgggatgga tcaaccctaa cagtggtggc     180
acaaactatg cacagaggtt tcagggcagg gtcaccatga ccaggacac gtccatcagc      240
acagcctaca tggagctgag caggctgaga tctgacgaca cggccgtgta ttactgtgcg     300
agttataatg atgcttttga tatctggggc caaggcaccc tggtcaccgt ctcctcagga     360
ggtggcgggt ctggtggtgg cggtagcggt ggtggcggat ccaatttat gctgactcag     420
cccccactctg tgtcggagtc tccggggaag acggtaacca tctcctgcac ccgcagcagt     480
ggcagcattg ccagcaacta tgtgcagtgg taccagcagc gcccgggcag tgcccccacc     540
attgtgatct atgaggatga tcaaagaccc tctggggtcc ctgatcggtt ctctggctcc     600
atcgacacct cctccaactc tgcctccctc accatctctg gactgcagag tgaggacgag     660
gctgactact actgtcagtc ttatgagccc ggcaatgggg tattcggcgg agggaccaag     720
gtcaccgtcc ta                                                         732
```

<210> SEQ ID NO 155
<211> LENGTH: 244
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 155

```
Gln Ala Ala Gln Val Gln Leu Gln Gln Ser Gly Ala Glu Val Lys Lys
1               5                   10                  15

Pro Gly Ser Ser Val Lys Val Ser Cys Lys Ala Ser Gly Gly Thr Phe
            20                  25                  30

Ser Ser Tyr Ala Ile Ser Trp Val Arg Gln Ala Pro Gly Gln Gly Leu
        35                  40                  45

Glu Trp Met Gly Trp Ile Asn Pro Asn Ser Gly Gly Thr Asn Tyr Ala
    50                  55                  60

Gln Arg Phe Gln Gly Arg Val Thr Met Thr Arg Asp Thr Ser Ile Ser
65                  70                  75                  80
```

```
Thr Ala Tyr Met Glu Leu Ser Arg Leu Arg Ser Asp Asp Thr Ala Val
             85                  90                  95
Tyr Tyr Cys Ala Ser Tyr Asn Asp Ala Phe Asp Ile Trp Gly Gln Gly
            100                 105                 110
Thr Leu Val Thr Val Ser Ser Gly Gly Gly Ser Gly Gly Gly Gly
            115                 120                 125
Ser Gly Gly Gly Gly Ser Asn Phe Met Leu Thr Gln Pro His Ser Val
130                 135                 140
Ser Glu Ser Pro Gly Lys Thr Val Thr Ile Ser Cys Thr Arg Ser Ser
145                 150                 155                 160
Gly Ser Ile Ala Ser Asn Tyr Val Gln Trp Tyr Gln Gln Arg Pro Gly
            165                 170                 175
Ser Ala Pro Thr Ile Val Ile Tyr Glu Asp Asp Gln Arg Pro Ser Gly
            180                 185                 190
Val Pro Asp Arg Phe Ser Gly Ser Ile Asp Thr Ser Ser Asn Ser Ala
            195                 200                 205
Ser Leu Thr Ile Ser Gly Leu Gln Ser Glu Asp Glu Ala Asp Tyr Tyr
            210                 215                 220
Cys Gln Ser Tyr Glu Pro Gly Asn Gly Val Phe Gly Gly Gly Thr Lys
225                 230                 235                 240
Val Thr Val Leu
```

<210> SEQ ID NO 156
<211> LENGTH: 744
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 156

```
caagaacagc ttgtagagtc cggcggtaga ttggtgacac cggggggag ccttaccctg      60
tcttgtaagg catctgggtt cgatttcagt gcgtattata tgagctgggt tcggcaggcg    120
cccgggaagg ggctggaatg gatagccact atataccgt catccggcaa gacttactac     180
gcgacttggg taaacgggag gtttacgata agctcagata acgcccaaaa cacggttgat    240
ctccaaatga atagcttgac cgccgctgat agggcgacct atttctgtgc gcggactct    300
tacgctgatg acggggccct cttcaatata tggggaccgg gaacgctcgt aaccatatca    360
tctggaggag gtgggagcgg aggcggaggg tcaggtgggg cgggagcga actcgtactt     420
acacaatctc caagcgtaag cgcagcgttg gggagtccag caaagatcac ctgcactttg    480
tcaagcgccc acaaaacgga tacgatagat tggtatcagc aactccaagg tgaagcgcca    540
cgatatctca tgcaggtaca gagcgacggg agttatacta agaggcccgg ggtcccagac    600
agattcagtg gcagcagttc aggtgccgac agatacctga taatacccte agttcaagcc    660
gatgatgaag ccgattacta ctgtggggct gactacatag gtgggtatgt tttcggggc    720
ggcactcaat tgacagttac aggg                                           744
```

<210> SEQ ID NO 157
<211> LENGTH: 248
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 157

```
Gln Glu Gln Leu Val Glu Ser Gly Gly Arg Leu Val Thr Pro Gly Gly
1               5                   10                  15
Ser Leu Thr Leu Ser Cys Lys Ala Ser Gly Phe Asp Phe Ser Ala Tyr
            20                  25                  30
Tyr Met Ser Trp Val Arg Gln Ala Pro Gly Lys Gly Leu Glu Trp Ile
        35                  40                  45
Ala Thr Ile Tyr Pro Ser Ser Gly Lys Thr Tyr Tyr Ala Thr Trp Val
    50                  55                  60
Asn Gly Arg Phe Thr Ile Ser Ser Asp Asn Ala Gln Asn Thr Val Asp
65                  70                  75                  80
Leu Gln Met Asn Ser Leu Thr Ala Ala Asp Arg Ala Thr Tyr Phe Cys
                85                  90                  95
Ala Arg Asp Ser Tyr Ala Asp Gly Ala Leu Phe Asn Ile Trp Gly
            100                 105                 110
Pro Gly Thr Leu Val Thr Ile Ser Ser Gly Gly Gly Ser Gly Gly
        115                 120                 125
Gly Gly Ser Gly Gly Gly Ser Glu Leu Val Leu Thr Gln Ser Pro
    130                 135                 140
Ser Val Ser Ala Ala Leu Gly Ser Pro Ala Lys Ile Thr Cys Thr Leu
145                 150                 155                 160
Ser Ser Ala His Lys Thr Asp Thr Ile Asp Trp Tyr Gln Gln Leu Gln
                165                 170                 175
Gly Glu Ala Pro Arg Tyr Leu Met Gln Val Gln Ser Asp Gly Ser Tyr
            180                 185                 190
Thr Lys Arg Pro Gly Val Pro Asp Arg Phe Ser Gly Ser Ser Ser Gly
        195                 200                 205
Ala Asp Arg Tyr Leu Ile Ile Pro Ser Val Gln Ala Asp Asp Glu Ala
    210                 215                 220
Asp Tyr Tyr Cys Gly Ala Asp Tyr Ile Gly Gly Tyr Val Phe Gly Gly
225                 230                 235                 240
Gly Thr Gln Leu Thr Val Thr Gly
                245
```

<210> SEQ ID NO 158
<211> LENGTH: 720
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 158

```
gaagtgcaac tcgtcgaaac tggagccgaa gtgaaaaagc tggagcgtc cgtcaaagtg      60
tcgtgcaagg cctccggcta caccttcacg acctactacg tgcactgggt cagacaggct    120
ccgggtcaag ggctggagtg gatgggcatc attaacccct ccggtggaag cacctcctat    180
gcgcaaaagt tccagggtcg cgtcaccatg actcgcgata cctccacttc cactgtgtac    240
atggaactga gctccctgag gtccgaggac accgccgtgt actactgcgc acgggatgga    300
ggcttgggcg gctacgaggc ttggggacag ggcaccctcg tgactgtgtc aagcggaggg    360
ggtggatccg gagggggagg atcaggcggt ggtggaagcg atatccagct acccagtcg    420
ccttccgcgc tgtctgcatc ggccggcgac agagtgacaa ttacctgtca agccagccag    480
```

```
gacatctcca actatctgaa ctggtaccag cagaagcccg gaaaggctcc gaagctgctg    540
atctacgacg ccagcaacct ggaacggggc gtgccatcac ggttctcggg atcagggtcg    600
ggcactgagt tcaccttcac catctcctcc ctccaacccg aggacattgc cacctactac    660
tgccagcagt acgacaacct cccgatcacc tttggacagg ggactcgcct ggaaatcaag    720
```

<210> SEQ ID NO 159
<211> LENGTH: 240
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 159

```
Glu Val Gln Leu Val Glu Thr Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Tyr Val His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Gly Leu Gly Gly Tyr Glu Ala Trp Gly Gln Gly Thr
            100                 105                 110

Leu Val Thr Val Ser Ser Gly Gly Gly Ser Gly Gly Gly Gly Ser
        115                 120                 125

Gly Gly Gly Gly Ser Asp Ile Gln Leu Thr Gln Ser Pro Ser Ala Leu
    130                 135                 140

Ser Ala Ser Ala Gly Asp Arg Val Thr Ile Thr Cys Gln Ala Ser Gln
145                 150                 155                 160

Asp Ile Ser Asn Tyr Leu Asn Trp Tyr Gln Gln Lys Pro Gly Lys Ala
                165                 170                 175

Pro Lys Leu Leu Ile Tyr Asp Ala Ser Asn Leu Glu Arg Gly Val Pro
            180                 185                 190

Ser Arg Phe Ser Gly Ser Gly Ser Gly Thr Glu Phe Thr Phe Thr Ile
        195                 200                 205

Ser Ser Leu Gln Pro Glu Asp Ile Ala Thr Tyr Tyr Cys Gln Gln Tyr
    210                 215                 220

Asp Asn Leu Pro Ile Thr Phe Gly Gln Gly Thr Arg Leu Glu Ile Lys
225                 230                 235                 240
```

<210> SEQ ID NO 160
<211> LENGTH: 759
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 160

```
gaagtgcaat tggtccagag cggaggagga cttgtgaagc caggcggatc cctgagattg    60
```

```
tcatgcgccg catcggggtt cacctttcc tcctactcca tgaactgggt cagacaggcg    120
cccggaaagg gacttgaatg ggtgtcgtcc atttcctcct cctcgtccta catctactac    180
gccgactccg tgaagggccg cttcaccatc tcccgggaca cgccaagaa cagcctgtat     240 ctccaaatga actccctgcg ggccgaagat actgctgtgt attactgcgc tcgggacttc    300
ccgtacgact catcgggcta ttactcggac gcgttcgata tctggggcca gggaactatg    360
gtcaccgtca gctctggtgg cggtggttcc ggagggggtg gatccggtgg cggaggatca    420
gagattgtgc tgacccagtc cccgctgtca ctgcccgtga ctccgggaga gcctgcctcg    480
atctcgtgtc ggtccagcca gtccctgctg cactcgaatg gtacaacta cctcgattgg    540 tacctccaaa agcctgggca gtcaccccaa ctgctgatct acctcgggag caacagagcc    600
agcggagtgc ctgaccgctt tagcggttcc ggatccggca ccgacttcac cctgaaaatc    660
agccgggtgg aagccgagga tgtcggcgtg tactactgca tgcaggcact gcagactctg    720
gggtacacct tcggccaggg cacgaagctc gagatcaag                            759
```

<210> SEQ ID NO 161
<211> LENGTH: 253
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 161

```
Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Asp Phe Pro Tyr Asp Ser Ser Gly Tyr Tyr Ser Asp Ala Phe
            100                 105                 110

Asp Ile Trp Gly Gln Gly Thr Met Val Thr Val Ser Ser Gly Gly Gly
        115                 120                 125

Gly Ser Gly Gly Gly Gly Ser Gly Gly Gly Gly Ser Glu Ile Val Leu
    130                 135                 140

Thr Gln Ser Pro Leu Ser Leu Pro Val Thr Pro Gly Glu Pro Ala Ser
145                 150                 155                 160

Ile Ser Cys Arg Ser Ser Gln Ser Leu Leu His Ser Asn Gly Tyr Asn
                165                 170                 175

Tyr Leu Asp Trp Tyr Leu Gln Lys Pro Gly Gln Ser Pro Gln Leu Leu
            180                 185                 190

Ile Tyr Leu Gly Ser Asn Arg Ala Ser Gly Val Pro Asp Arg Phe Ser
        195                 200                 205

Gly Ser Gly Ser Gly Thr Asp Phe Thr Leu Lys Ile Ser Arg Val Glu
    210                 215                 220

Ala Glu Asp Val Gly Val Tyr Tyr Cys Met Gln Ala Leu Gln Thr Leu
```

```
                    225                 230                 235                 240

Gly Tyr Thr Phe Gly Gln Gly Thr Lys Leu Glu Ile Lys
                245                 250

<210> SEQ ID NO 162
<211> LENGTH: 747
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 162
caagtgcaac tcgtccaatc cggtgccgaa gtcaagaagc tggttcctc cgtgaaagtg     60 tcgtgcaaag ccagcggcgg gactttagc tcctacgcga tcagctgggt cagacaggcc    120
cctggacaag gcctcgagtg gatgggcggc atcattccga ttttcggtac cgccaactac    180
gcccagaagt tccagggacg cgtgaccatt actaccgacg agagccactc aaccgcatac    240
atggaactgt ccagcctgcg ctccgaggac acggctgtgt actattgcgc cagacgggga    300
tggggaggat tctcctccgg ctccgcattc gacatctggg gacagggcac tatggtcact    360
gtgtcatccg ggggaggagg atcaggcggt ggaggatccg gtggtggcgg atccaacttc    420
atgctgaccc cagccccactc agtgtcggaa tcgcccggca caccgtgac atcagctgc     480 accggatcca gcgggaccat cggctctaat ttcgtgcagt ggtaccagca gtccccaggg    540
agagctccga ccctgttgat ctacgaggac acaaagcggc caagcggagt gccgcctaga    600
ttcgccggct ccgtggattc ctcgtccaac tcggcgtcgc tgaccatcag cggactcaag    660
actgaagatg aagccgacta ctactgtcag tcctacgact cgagcaactg ggtgtttggg    720
ggcgggacta agctgaccgt gcttgga                                        747

<210> SEQ ID NO 163
<211> LENGTH: 249
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 163

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Thr Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Trp Gly Gly Phe Ser Ser Gly Ser Ala Phe Asp Ile
            100                 105                 110

Trp Gly Gln Gly Thr Met Val Thr Val Ser Ser Gly Gly Gly Gly Ser
        115                 120                 125
```

Gly Gly Gly Gly Ser Gly Gly Gly Ser Asn Phe Met Leu Thr Gln
            130                 135                 140

Pro His Ser Val Ser Glu Ser Pro Gly Asn Thr Val Thr Ile Ser Cys
145                 150                 155                 160

Thr Gly Ser Ser Gly Thr Ile Gly Ser Asn Phe Val Gln Trp Tyr Gln
                165                 170                 175

Gln Ser Pro Gly Arg Ala Pro Thr Leu Leu Ile Tyr Glu Asp Thr Lys
            180                 185                 190

Arg Pro Ser Gly Val Pro Pro Arg Phe Ala Gly Ser Val Asp Ser Ser
        195                 200                 205

Ser Asn Ser Ala Ser Leu Thr Ile Ser Gly Leu Lys Thr Glu Asp Glu
210                 215                 220

Ala Asp Tyr Tyr Cys Gln Ser Tyr Asp Ser Ser Asn Trp Val Phe Gly
225                 230                 235                 240

Gly Gly Thr Lys Leu Thr Val Leu Gly
            245

<210> SEQ ID NO 164
<211> LENGTH: 735
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 164
gaagtccaat tggtgcagag cggatccgaa cttaagaaac ctggcgcgag cgtgaaagtg     60
tcctgcaagg cctccggagg gactttctcg tcgtacgcca ttagctgggt ccgccaagct    120
cctggccaag gctggagtg gatgggcggg attatcccca tcttcgggac tgcgaactac    180
gcccagaagt ttcagggccg ggtcactatc accgccgacg aatcaacctc gaccgcctac    240
atggaactgt cctcgcttcg gtccgaggat actgccgtgt actattgtgc ctcaacggcc    300
agacgcggat gggacaccgc tggtccgctc gattactggg gccagggaac cctcgtgacc    360
gtcagctccg gaggaggagg ctccggtggt ggaggatccg ggggtggtgg atccgacatc    420
caaatgaccc agtccccctc gtccctgagc gcctctgtgg gcgacagagt gacaattgca    480
tgcagggcct cacagactat ctcccgctac ctgaactggt accagcagaa gccaggaaag    540
gcccctaagc tgctcatcta cgctgcgtcc tcgctccaat ccggggtgtc ctcacggttt    600
tccggatcgg gttccggcac cgagttcacc ctgaccatca gcagcctgca gcccgaggac    660
ttcgcaacct acttctgcca gcaaacctac tccccgccga ttacgttcgg acaggggact    720
cggctggaaa tcaag                                                    735

<210> SEQ ID NO 165
<211> LENGTH: 245
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 165

Glu Val Gln Leu Val Gln Ser Gly Ser Glu Leu Lys Lys Pro Gly Ala
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Thr Ala Arg Arg Gly Trp Asp Thr Ala Gly Pro Leu Asp Tyr
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Ser Asp Ile Gln Met Thr Gln
    130                 135                 140

Ser Pro Ser Ser Leu Ser Ala Ser Val Gly Asp Arg Val Thr Ile Ala
145                 150                 155                 160

Cys Arg Ala Ser Gln Thr Ile Ser Arg Tyr Leu Asn Trp Tyr Gln Gln
                165                 170                 175

Lys Pro Gly Lys Ala Pro Lys Leu Leu Ile Tyr Ala Ala Ser Ser Leu
            180                 185                 190

Gln Ser Gly Val Ser Ser Arg Phe Ser Gly Ser Gly Ser Gly Thr Glu
        195                 200                 205

Phe Thr Leu Thr Ile Ser Ser Leu Gln Pro Glu Asp Phe Ala Thr Tyr
    210                 215                 220

Phe Cys Gln Gln Thr Tyr Ser Pro Pro Ile Thr Phe Gly Gln Gly Thr
225                 230                 235                 240

Arg Leu Glu Ile Lys
            245

<210> SEQ ID NO 166
<211> LENGTH: 729
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 166
gaagtgcaac tcgtcgaaac aggggcagaa gtgaaaaacc caggctcaag cgtgaaagtg      60
tcgtgcaagg cttcgggcgg aactctgtcc aactacgcca tctcctgggt ccgccaagct     120
ccgggaaagg gcctcgagtg gatgggcgga atcattccca ttttcgggac cgccaactac     180
gcgcaaaagt tccagggccg ggtcactatc accgcgacg aaagcaccag caccgcctac     240
atggaactgt cctccctgcg ctccgaggac actgccgtgt actattgcgc ccggaggtca     300
tcgtggtacc ccgagggctg cttccagcac tggggacagg gcactctcgt gaccgtgtcg     360
tcgggtggtg gtggatcagg aggggagga tccggaggag gcggaagcga tattcagctg     420
acccagtcac cgagctccct gtccgcctcc accggagaca gagtgaccat cacgtgtcgg     480
gcctcccaag ggatctcctc ctacctggcc tggtaccagc agaagcctgg aaaggcaccg     540
aagttgctga tctacgccgc gagcaccctt cagtccggag tgcctagccg cttctcgggt     600
tccggctctg gcactgactt cactctgacc attagctgcc tgcagtccga ggattttgcc     660
acctactact gccagcagta ctatagctac cccctgacct cgggggcgg aaccaagctc     720 gacatcaag                                                                729

<210> SEQ ID NO 167
<211> LENGTH: 243
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 167

Glu Val Gln Leu Val Glu Thr Gly Ala Glu Val Lys Asn Pro Gly Ser
1               5                   10                  15

Ser Val Lys Val Ser Cys Lys Ala Ser Gly Gly Thr Leu Ser Asn Tyr
            20                  25                  30

Ala Ile Ser Trp Val Arg Gln Ala Pro Gly Lys Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Ser Ser Trp Tyr Pro Glu Gly Cys Phe Gln His Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Asp Ile Gln Leu Thr Gln Ser Pro
    130                 135                 140

Ser Ser Leu Ser Ala Ser Thr Gly Asp Arg Val Thr Ile Thr Cys Arg
145                 150                 155                 160

Ala Ser Gln Gly Ile Ser Ser Tyr Leu Ala Trp Tyr Gln Gln Lys Pro
                165                 170                 175

Gly Lys Ala Pro Lys Leu Leu Ile Tyr Ala Ala Ser Thr Leu Gln Ser
            180                 185                 190

Gly Val Pro Ser Arg Phe Ser Gly Ser Gly Ser Gly Thr Asp Phe Thr
        195                 200                 205

Leu Thr Ile Ser Cys Leu Gln Ser Glu Asp Phe Ala Thr Tyr Tyr Cys
    210                 215                 220

Gln Gln Tyr Tyr Ser Tyr Pro Leu Thr Phe Gly Gly Thr Lys Leu
225                 230                 235                 240

Asp Ile Lys

<210> SEQ ID NO 168
<211> LENGTH: 732
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 168
gaagtgcaac tcgtccaatc tggtgccgaa gtcaagaagc ctggctcaag cgtgaaagtg     60
tcctgcaaag cgtcgggagg gaccttcagc tcctacgcca tttcctgggt ccgccaagca    120
ccaggacagg gcctggagtg gatgggcggc atcatcccga tcttcgggac tgccaactac    180

```
gcccagaagt tccaggggag agtgaccatt accgccgacg agtcgaccag cacggcctac    240
atggaactgt ccagcctgcg ctccgaggac actgccgtgt actactgcgc gagggccaga    300
ctcggtggag cgttcgacat ctggggacag ggcaccatgg tcaccgtgtc atccggtggc    360
ggaggatccg gtggtggcgg atcaggaggg ggaggatccc agtccgtgct gactcagcct    420
ccctccgtga gcgctgcacc gggacagaag gtcaccatct catgctcggg gggaagctcc    480
aacatcggga accactacgt gtcctggtac aacagttgc ctggtgccgc tccaaagctg    540
ctgatctatg acgataacaa gcggccgtcc ggaatccccg accggttctc ggggtctaga    600
tccggaacca gcgcaactct cggcattacc ggactgcaga gcggcgatga ggccgactac    660
tactgtggca catgggactc gtcgctggct gcccacgtgt ttggcactgg caccaaggtc    720
accgtgcttg ga                                                        732
```

<210> SEQ ID NO 169
<211> LENGTH: 244
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 169

```
Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Arg Leu Gly Gly Ala Phe Asp Ile Trp Gly Gln Gly Thr
            100                 105                 110

Met Val Thr Val Ser Ser Gly Gly Gly Ser Gly Gly Gly Gly Ser
        115                 120                 125

Gly Gly Gly Gly Ser Gln Ser Val Leu Thr Gln Pro Pro Ser Val Ser
    130                 135                 140

Ala Ala Pro Gly Gln Lys Val Thr Ile Ser Cys Ser Gly Ser Ser
145                 150                 155                 160

Asn Ile Gly Asn His Tyr Val Ser Trp Tyr Gln Gln Leu Pro Gly Ala
                165                 170                 175

Ala Pro Lys Leu Leu Ile Tyr Asp Asp Asn Lys Arg Pro Ser Gly Ile
            180                 185                 190

Pro Asp Arg Phe Ser Gly Ser Arg Ser Gly Thr Ser Ala Thr Leu Gly
        195                 200                 205

Ile Thr Gly Leu Gln Ser Gly Asp Glu Ala Asp Tyr Tyr Cys Gly Thr
    210                 215                 220

Trp Asp Ser Ser Leu Ala Ala His Val Phe Gly Thr Gly Thr Lys Val
225                 230                 235                 240

Thr Val Leu Gly
```

<210> SEQ ID NO 170
<211> LENGTH: 747
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 170

```
gaagtgcaac ttgtccagag cggagccgaa gtgaagaaac ctggatcctc cgtcaaagtg     60
tcgtgcaagg cttcgggcgg aaccttctcc tcgtacgcga tctcatgggt cagacaggca    120
cccggacagg gactggagtg gatgggcggc atcattccca tcttcggcac cgctaattac    180
gcccagaagt ttcaggggag agtgaccatc accgccgacg agtccacctc cactgcctac    240
atggaactgt cctcactgag gtccgaggat actgccgtgt actactgcgc gtcgcaaaag    300
gggggtggat ggtccattga cgccttcgat atttggggac aggggacgat ggtcacagtg    360
tcatccggcg gtggtggatc cggtggtggc ggatccggag gaggaggcag ccagtccgtg    420
ctgacccagc cgcctagcgt gtcggccgca tctgggcagc gcgtgaccat ttcctgttcc    480
gggtcctcgt ccaacatcgg caacaactac gcctcctggt accaacagct cccgggaatg    540
gcccctaagc tgctgatcta cgaggacaac aagcggccat ccgggatctc agaccggttc    600
agcggatccc agtccggcac ttccgcgagc ctcgccatca ccggactgca ggctgaggac    660
gaagccgact actactgcca atcatatgac agctcgctca gcggcgatgt ggtgttcggc    720
ggtggcacta agctgaccgt gttggga                                       747
```

<210> SEQ ID NO 171
<211> LENGTH: 249
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 171

```
Glu Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
Ala Ile Ser Trp Val Arg Gln Ala Pro Gly Gln Gly Leu Glu Trp Met
        35                  40                  45
Gly Gly Ile Ile Pro Ile Phe Gly Thr Ala Asn Tyr Ala Gln Lys Phe
    50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Ser Gln Lys Gly Gly Gly Trp Ser Ile Asp Ala Phe Asp Ile Trp
            100                 105                 110
Gly Gln Gly Thr Met Val Thr Val Ser Gly Gly Gly Ser Gly
        115                 120                 125
Gly Gly Gly Ser Gly Gly Gly Ser Gln Ser Val Leu Thr Gln Pro
    130                 135                 140
Pro Ser Val Ser Ala Ala Ser Gly Gln Arg Val Thr Ile Ser Cys Ser
145                 150                 155                 160
```

```
Gly Ser Ser Ser Asn Ile Gly Asn Asn Tyr Ala Ser Trp Tyr Gln Gln
            165                 170                 175

Leu Pro Gly Met Ala Pro Lys Leu Leu Ile Tyr Glu Asp Asn Lys Arg
        180                 185                 190

Pro Ser Gly Ile Ser Asp Arg Phe Ser Gly Ser Gln Ser Gly Thr Ser
    195                 200                 205

Ala Ser Leu Ala Ile Thr Gly Leu Gln Ala Glu Asp Glu Ala Asp Tyr
210                 215                 220

Tyr Cys Gln Ser Tyr Asp Ser Ser Leu Ser Gly Asp Val Val Phe Gly
225                 230                 235                 240

Gly Gly Thr Lys Leu Thr Val Leu Gly
                245
```

<210> SEQ ID NO 172
<211> LENGTH: 735
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 172

```
caagtccagt tgcaacaatg gggagcaggc cttctgaaac cgtccgagac actgagcctg     60
acgtgcgccg tctatggcgg atcgttctcc ggatactact ggtcgtggat cagacagcct    120
ccgggaaagg gtctggaatg gatcggcgaa atcaaccaca gcggcagcac caattacaac    180
ccgtcactga agtcaagggt caccattagc gtggacactt ccaagaacca gttctccctg    240
aaactgtcga gcgtgaccgc tgccgatact gccgtgtact actgtgcccg cggccaagtc    300
aagtatagct caagcctcgg ctactggggc cagggaaccc tcgtgaccgt gtcctcgggt    360
ggaggaggct ccggtggtgg aggatccggt ggcggaggat cgcagtccgt gctgacccag    420
cctcccctccg tgtctgctgc ccctgggcaa aaggtcacca tttcgtgctc cggctcatcg    480
tccaacatcg gaacaacttg tgtgtcctgg taccagcagc tgcccggtac tgccccaaag    540
ctgctgatct acgaggacaa caagcgccca tccgggattc cggatcggtt cagcggatca    600
cggtccggaa ctagcgcgac cctggggatc accgggctcc agactggcga cgaagcggac    660
tactactgcg aacttgggga ctcctccttg ggggcctggg tgttcggcgg agggaccaag    720
ctcaccgtgc ttgga                                                     735
```

<210> SEQ ID NO 173
<211> LENGTH: 245
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 173

```
Gln Val Gln Leu Gln Gln Trp Gly Ala Gly Leu Leu Lys Pro Ser Glu
1               5                  10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
```

```
                   50                  55                  60
Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Gly Gln Val Lys Tyr Ser Ser Leu Gly Tyr Trp Gly Gln Gly
            100                 105                 110

Thr Leu Val Thr Val Ser Ser Gly Gly Gly Gly Ser Gly Gly Gly Gly
            115                 120                 125

Ser Gly Gly Gly Gly Ser Gln Ser Val Leu Thr Gln Pro Pro Ser Val
130                 135                 140

Ser Ala Ala Pro Gly Gln Lys Val Thr Ile Ser Cys Ser Gly Ser Ser
145                 150                 155                 160

Ser Asn Ile Gly Asn Asn Phe Val Ser Trp Tyr Gln Gln Leu Pro Gly
                165                 170                 175

Thr Ala Pro Lys Leu Leu Ile Tyr Glu Asp Asn Lys Arg Pro Ser Gly
            180                 185                 190

Ile Pro Asp Arg Phe Ser Gly Ser Arg Ser Gly Thr Ser Ala Thr Leu
            195                 200                 205

Gly Ile Thr Gly Leu Gln Thr Gly Asp Glu Ala Asp Tyr Tyr Cys Gly
            210                 215                 220

Thr Trp Asp Ser Ser Leu Gly Ala Trp Val Phe Gly Gly Gly Thr Lys
225                 230                 235                 240

Leu Thr Val Leu Gly
                245

<210> SEQ ID NO 174
<211> LENGTH: 723
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 174
caagtccaac tcgtcgaaac tggtggtggc ctcgtgaagc ctggaggatc cctgcgcctt      60
tcctgtgccg cttccggctt tactttctcg tcgtactcca tgaactgggt cagacaggct    120
cccggaaagg gcctggaatg ggtgtcctcc atctcgtcct catcctccta catctattac    180
gcggactccg tgaagggcag attcaccatt tcccgggaca cgccaagaa cagcttgtac     240 ctccaaatga actccctgcg ggcagaggac accgccgtgt actactgcgc gagggatggg    300
gatttctgga gcggagccat cgactactgg ggccagggaa ctctcgtgac cgtcagctcc    360
ggtggtggtg gaagcggagg cggaggttct gggggggag atcagacat tcagctgacc     420 cagtcgccat cctccctgag cgcctcagtg ggggaccgcg tgactattac atgccaggcc    480
tcccaagata tctcgaacta cctgaactgg tatcagcaga agcctggaaa ggccccgaag    540
ctgttgatct acgatgccag caacctggag actggggtgc cttcccggtt ctcgggatca    600
ggctcgggca ccgatttcac cttcacgatc agcagcctgc agcccgagga cattgcaacc    660
tactactgcc agcagtacga caatctgccg ctttttgggg gaggcaccaa gctggaaatc    720
aaa                                                                  723

<210> SEQ ID NO 175
<211> LENGTH: 241
```

<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 175

```
Gln Val Gln Leu Val Glu Thr Gly Gly Gly Leu Val Lys Pro Gly Gly
1               5                   10                  15
Ser Leu Arg Leu Ser Cys Ala Ala Ser Gly Phe Thr Phe Ser Ser Tyr
            20                  25                  30
Ser Met Asn Trp Val Arg Gln Ala Pro Gly Lys Gly Leu Glu Trp Val
        35                  40                  45
Ser Ser Ile Ser Ser Ser Ser Tyr Ile Tyr Tyr Ala Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Asp Gly Asp Phe Trp Ser Gly Ala Ile Asp Tyr Trp Gly Gln
            100                 105                 110
Gly Thr Leu Val Thr Val Ser Ser Gly Gly Gly Gly Ser Gly Gly Gly
        115                 120                 125
Gly Ser Gly Gly Gly Gly Ser Asp Ile Gln Leu Thr Gln Ser Pro Ser
    130                 135                 140
Ser Leu Ser Ala Ser Val Gly Asp Arg Val Thr Ile Thr Cys Gln Ala
145                 150                 155                 160
Ser Gln Asp Ile Ser Asn Tyr Leu Asn Trp Tyr Gln Gln Lys Pro Gly
                165                 170                 175
Lys Ala Pro Lys Leu Leu Ile Tyr Asp Ala Ser Asn Leu Glu Thr Gly
            180                 185                 190
Val Pro Ser Arg Phe Ser Gly Ser Gly Thr Asp Phe Thr Phe
        195                 200                 205
Thr Ile Ser Ser Leu Gln Pro Glu Asp Ile Ala Thr Tyr Tyr Cys Gln
    210                 215                 220
Gln Tyr Asp Asn Leu Pro Leu Phe Gly Gly Gly Thr Lys Leu Glu Ile
225                 230                 235                 240
Lys
```

<210> SEQ ID NO 176
<211> LENGTH: 723
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 176

```
gaggtgcaat tggtgcagtc aggtggtgga gtggtgcagc caggaagatc ccttagactc      60
tcgtgtgcgg cgtcaggctt taccttctcc tcgtactcca tgaactgggt cagacaggca     120
ccgggaaagg gactggaatg ggtgtcctcc atctcgtcct cctcctccta catctactac     180
gccgatagcg tgaagggccg gttcaccatt tcgcgcgaca acgccaagaa caccctgtac     240
ctccaaatga attcgctgcg ggccgaagat accgctgtct attactcgcg ccgcgacaac     300
tggggctcgc tggactattg gggccaggga accctcgtca ccgtgtcaag cggagggggt     360
```

```
ggatccggag cggaggatcc ggtggaggg ggaagcgaca ttcagatgac tcagagcccg   420
tcctccctgt ctgcctccgt gggggatcgc gtgaccatca catgccaggc ctcacaagac   480
atcagcaatt acctgaactg gtaccagcag aagcctggaa aggcccccaa gctgctgatc   540
tacgatgcca gcaacctgga gactggggtg ccttcaaggt tctccggttc cggaagcggc   600
actgacttca ccttcactat ctcgagcctg caacccgagg acattgccac ctactactgc   660
cagcagtacg acaaccttcc gcacatgtac acgttcggcc agggcaccaa gctcgaaatc   720
aaa                                                                 723
```

```
<210> SEQ ID NO 177
<211> LENGTH: 241
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 177
```

```
Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Asn Trp Gly Ser Leu Asp Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Ser Asp Ile Gln Met Thr Gln Ser Pro Ser Ser Leu Ser
    130                 135                 140

Ala Ser Val Gly Asp Arg Val Thr Ile Thr Cys Gln Ala Ser Gln Asp
145                 150                 155                 160

Ile Ser Asn Tyr Leu Asn Trp Tyr Gln Gln Lys Pro Gly Lys Ala Pro
                165                 170                 175

Lys Leu Leu Ile Tyr Asp Ala Ser Asn Leu Glu Thr Gly Val Pro Ser
            180                 185                 190

Arg Phe Ser Gly Ser Gly Ser Gly Thr Asp Phe Thr Phe Thr Ile Ser
        195                 200                 205

Ser Leu Gln Pro Glu Asp Ile Ala Thr Tyr Tyr Cys Gln Gln Tyr Asp
    210                 215                 220

Asn Leu Pro His Met Tyr Thr Phe Gly Gln Gly Thr Lys Leu Glu Ile
225                 230                 235                 240

Lys
```

```
<210> SEQ ID NO 178
<211> LENGTH: 1548
<212> TYPE: DNA
<213> ORGANISM: Artificial Sequence
```

<220> FEATURE:
<221> NAME/KEY: source
<223> OTHER INFORMATION: /note="Description of Artificial Sequence:
      Synthetic polynucleotide"

<400> SEQUENCE: 178

| caggtacagc ttcaacaaag cggaccggga cttgttaagc attcccaaac cctttctctc | 60 |
| acgtgtgcaa ttagcggcga tagtgtatcc tctaattctg cggcctggaa ctggatacga | 120 |
| caatcaccaa gccggggact cgagtggttg ggccgaacct actatcggtc caaatggtat | 180 |
| aatgactacg cagtatccgt gaaatctcgc attacgatca atccagacac ctccaaaaat | 240 |
| caattttctc tgcagttgaa tagcgtgact cccgaggaca cggccgttta ctattgcgcc | 300 |
| caggaagttg aaccccacga tgcatttgat atttggggcc agggaaccat ggtgacagtg | 360 |
| agtagtgggg gtggaggatc tggaggaggc ggtagcggcg ggggcggcag tgatatccag | 420 |
| atgacgcagt caccttccag cgtgtatgcg agtgtggggg acaaggtcac cataacctgt | 480 |
| cgcgctagcc aagatgtcag cggggtggctg gcttggtacc agcagaaacc aggtttggct | 540 |
| cctcagcttt tgatctcagg agcgagcacg cttcagggtg aggtcccaag tcgctttagt | 600 |
| ggctctggct ccgggacaga cttcacgttg acgatcagca gtttgcagcc tgaggatttc | 660 |
| gcgacctact actgccagca agcgaaatat tttccgtaca ctttcggtca ggggaccaaa | 720 |
| ttggagatca aggtgggggg tggttcaggc ggcggaggct caggcggcgg cggtagcgga | 780 |
| ggaggcggaa gcggggggtgg cggatcagaa gtgcaactcg ttcagagtgg cgcggaggtt | 840 |
| aagaaacccg gtgcatctgt aaaggttagc tgtaaggcat caggatacac ttttaccagc | 900 |
| tattacatgc attgggtgag acaggctccc ggtcagggg tcgaatggat ggggttgatc | 960 |
| aacccgagtg gtggttcaac atcttacgcc cagaagtttc agggccgagt aacaatgact | 1020 |
| cgggacacgt ctacctcaac tgtgtatatg gagctttcca gcctgcgctc agaggataca | 1080 |
| gcagtctatt actgcgcacg gtcagacaga ggtataacgg ccactgatgc gttcgatatc | 1140 |
| tgggggacaag ggactatggt aactgtgtct tccggaggag gaggtagtgg aggggggagga | 1200 |
| agcggtgggg ggggctcaca gtccgttttg actcagccac caagcgtctc agtcgcaccg | 1260 |
| gggcgaatgg cgaaaattac ttgcggcggg agcgacatag caacaagaa tgtgcattgg | 1320 |
| taccaacaga aaccaggtca agcacctgtt ctcgtggtgt atgatgacta cgatcgccca | 1380 |
| agcgggatcc cggagcggtt ctctggatca aattctggtg atgcagccac tctgacaata | 1440 |
| tcaacggtgg aagtcggtga cgaggctgat tacttctgcc aagtatggga tggcagcgga | 1500 |
| gatccctact ggatgtttgg aggaggtact caactgacag ttctgggc | 1548 |

<210> SEQ ID NO 179
<211> LENGTH: 516
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 179

Gln Val Gln Leu Gln Gln Ser Gly Pro Gly Leu Val Lys His Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
 50                  55                  60

Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Gln Glu Val Glu Pro His Asp Ala Phe Asp Ile Trp
                100                 105                 110

Gly Gln Gly Thr Met Val Thr Val Ser Ser Gly Gly Gly Gly Ser Gly
            115                 120                 125

Gly Gly Gly Ser Gly Gly Gly Ser Asp Ile Gln Met Thr Gln Ser
130                 135                 140

Pro Ser Ser Val Tyr Ala Ser Val Gly Asp Lys Val Thr Ile Thr Cys
145                 150                 155                 160

Arg Ala Ser Gln Asp Val Ser Gly Trp Leu Ala Trp Tyr Gln Gln Lys
                165                 170                 175

Pro Gly Leu Ala Pro Gln Leu Leu Ile Ser Gly Ala Ser Thr Leu Gln
                180                 185                 190

Gly Glu Val Pro Ser Arg Phe Ser Gly Ser Gly Ser Gly Thr Asp Phe
            195                 200                 205

Thr Leu Thr Ile Ser Ser Leu Gln Pro Glu Asp Phe Ala Thr Tyr Tyr
    210                 215                 220

Cys Gln Gln Ala Lys Tyr Phe Pro Tyr Thr Phe Gly Gln Gly Thr Lys
225                 230                 235                 240

Leu Glu Ile Lys Gly Gly Gly Gly Ser Gly Gly Gly Ser Gly Gly
                245                 250                 255

Gly Gly Ser Gly Gly Gly Gly Ser Gly Gly Gly Ser Glu Val Gln
            260                 265                 270

Leu Val Gln Ser Gly Ala Glu Val Lys Lys Pro Gly Ala Ser Val Lys
    275                 280                 285

Val Ser Cys Lys Ala Ser Gly Tyr Thr Phe Thr Ser Tyr Tyr Met His
290                 295                 300

Trp Val Arg Gln Ala Pro Gly Gln Gly Leu Glu Trp Met Gly Leu Ile
305                 310                 315                 320

Asn Pro Ser Gly Gly Ser Thr Ser Tyr Ala Gln Lys Phe Gln Gly Arg
                325                 330                 335

Val Thr Met Thr Arg Asp Thr Ser Thr Ser Thr Val Tyr Met Glu Leu
                340                 345                 350

Ser Ser Leu Arg Ser Glu Asp Thr Ala Val Tyr Tyr Cys Ala Arg Ser
            355                 360                 365

Asp Arg Gly Ile Thr Ala Thr Asp Ala Phe Asp Ile Trp Gly Gln Gly
    370                 375                 380

Thr Met Val Thr Val Ser Ser Gly Gly Gly Gly Ser Gly Gly Gly Gly
385                 390                 395                 400

Ser Gly Gly Gly Gly Ser Gln Ser Val Leu Thr Gln Pro Pro Ser Val
                405                 410                 415

Ser Val Ala Pro Gly Arg Met Ala Lys Ile Thr Cys Gly Gly Ser Asp
                420                 425                 430

Ile Gly Asn Lys Asn Val His Trp Tyr Gln Gln Lys Pro Gly Gln Ala
            435                 440                 445

Pro Val Leu Val Val Tyr Asp Asp Tyr Asp Arg Pro Ser Gly Ile Pro
450                 455                 460

Glu Arg Phe Ser Gly Ser Asn Ser Gly Asp Ala Ala Thr Leu Thr Ile
465                 470                 475                 480

Ser Thr Val Glu Val Gly Asp Glu Ala Asp Tyr Phe Cys Gln Val Trp
                485                 490                 495

Asp Gly Ser Gly Asp Pro Tyr Trp Met Phe Gly Gly Gly Thr Gln Leu
            500                 505                 510

Thr Val Leu Gly
        515

<210> SEQ ID NO 180
<211> LENGTH: 732
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 180
caggtacagc tgcagcagtc aggtccagga ctggtgaagc actcgcagac cctctcactc      60
acctgtgcca tctccgggga cagtgtctct agcaacagtg ctgcttggaa ctggatcagg     120
cagtccccat cgagaggcct tgagtggctg gaaggacat actacaggtc caagtggtat      180
aatgattatg cagtatctgt gaaaagtcga ataaccatca cccagacac atccaagaac      240 cagttctccc tgcagttgaa ctctgtgact cccgaggaca cggctgtgta ttactgtgcc     300
caagaggtag aacctcatga tgcttttgat atctggggcc aagggacaat ggtcaccgtc     360
tcttcaggag gtggcgggtc tggcggtgga ggtagcggtg gtggcggatc cgacatccag     420
atgacccagt ctccatcttc cgtgtatgca tctgtaggag acaaagtcac catcacttgt     480
cgggcgagtc aggatgttag cggctggtta gcctggtatc agcagaaacc agggctagcc     540
cctcagctcc tgatctctgg tgcatccact ttgcaaggtg aagtcccatc aaggttcagc     600
ggcagtggat ctgggacaga ttttactctc accatcagca gcctgcagcc tgaagatttt     660
gccacttatt attgtcaaca ggctaaatat ttcccttaca cttttggcca ggggaccaag     720
ctggaaatca aa                                                          732

<210> SEQ ID NO 181
<211> LENGTH: 244
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 181

Gln Val Gln Leu Gln Gln Ser Gly Pro Gly Leu Val Lys His Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Gln Glu Val Glu Pro His Asp Ala Phe Asp Ile Trp
            100                 105                 110

Gly Gln Gly Thr Met Val Thr Val Ser Ser Gly Gly Gly Ser Gly
        115                 120                 125

Gly Gly Gly Ser Gly Gly Gly Ser Asp Ile Gln Met Thr Gln Ser
130                 135                 140

Pro Ser Ser Val Tyr Ala Ser Val Gly Asp Lys Val Thr Ile Thr Cys
145                 150                 155                 160

Arg Ala Ser Gln Asp Val Ser Gly Trp Leu Ala Trp Tyr Gln Gln Lys
                165                 170                 175

Pro Gly Leu Ala Pro Gln Leu Leu Ile Ser Gly Ala Ser Thr Leu Gln
            180                 185                 190

Gly Glu Val Pro Ser Arg Phe Ser Gly Ser Gly Ser Gly Thr Asp Phe
        195                 200                 205

Thr Leu Thr Ile Ser Ser Leu Gln Pro Glu Asp Phe Ala Thr Tyr Tyr
    210                 215                 220

Cys Gln Gln Ala Lys Tyr Phe Pro Tyr Thr Phe Gly Gln Gly Thr Lys
225                 230                 235                 240

Leu Glu Ile Lys

<210> SEQ ID NO 182
<211> LENGTH: 732
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 182
caggtacagc tgcagcagtc aggtccagga ctggtgaagc cctcgcagac cctctcactc      60
acctgtgcca tctcagggaa cagtgtctct agcaacagtg ctgcttggaa ctggatcagg     120
cagtccccat cgagaggcct gagtggctg ggaaggacat actacaggtc caagtggtat     180
aatgattatg cagtatctgt gaaaagtcga ataaccatca cccagacac atccaagaac     240 cagttctccc tgcagctgaa ctctgtgact cccgaggaca cggctgtgta ttactgtgcc     300
caagaggtag aacctcaaga tgcttttgat atctggggcc aagggacaat ggtcaccgtc     360
tcttcaggag gtggcgggtc tggcggtgga ggtagcggtg gtggcggatc cgacatccag     420
atgacccagt ctccatcttc cgtgtctgca tctgtaggag acaaagtcac catcacttgt     480
cgggcgagtc aggatgttag cggctggtta gcctggtatc agcagaaacc agggctagcc     540
cctcagctcc tgatctttgg tgcatccact ttgcaaggtg aagtcccatc aagattcagc     600
ggcggtggat ctgggacaga ttttactctc accatcagca gcctgcagcc tgaagatttt     660
gccacttatt attgtcaaca ggctaaatat ttcccttaca cttttggcca ggggaccaag     720
ctggaaatca aa                                                         732

<210> SEQ ID NO 183
<211> LENGTH: 244
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 183

-continued

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asn Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Gln Glu Val Glu Pro Gln Asp Ala Phe Asp Ile Trp
            100                 105                 110

Gly Gln Gly Thr Met Val Thr Val Ser Ser Gly Gly Gly Ser Gly
        115                 120                 125

Gly Gly Gly Ser Gly Gly Gly Ser Asp Ile Gln Met Thr Gln Ser
    130                 135                 140

Pro Ser Ser Val Ser Ala Ser Val Gly Asp Lys Val Thr Ile Thr Cys
145                 150                 155                 160

Arg Ala Ser Gln Asp Val Ser Gly Trp Leu Ala Trp Tyr Gln Gln Lys
                165                 170                 175

Pro Gly Leu Ala Pro Gln Leu Leu Ile Phe Gly Ala Ser Thr Leu Gln
            180                 185                 190

Gly Glu Val Pro Ser Arg Phe Ser Gly Gly Ser Gly Thr Asp Phe
        195                 200                 205

Thr Leu Thr Ile Ser Ser Leu Gln Pro Glu Asp Phe Ala Thr Tyr Tyr
    210                 215                 220

Cys Gln Gln Ala Lys Tyr Phe Pro Tyr Thr Phe Gly Gln Gly Thr Lys
225                 230                 235                 240

Leu Glu Ile Lys

<210> SEQ ID NO 184
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 184

Gly Ser Thr Ser Gly Ser Gly Lys Pro Gly Ser Gly Glu Gly Ser Thr
1               5                   10                  15

Lys Gly

<210> SEQ ID NO 185
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 185

Gly Gly Gly Gly Ser
1               5
```

```
<210> SEQ ID NO 186
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 186

Gly Phe Leu Gly
1

<210> SEQ ID NO 187
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 187

Gly Gly Gly Gly Ser Gly Gly Gly Gly Ser Gly Gly Gly Gly Ser
1               5                   10                  15

<210> SEQ ID NO 188
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 188

Arg Ala Lys Arg
1

<210> SEQ ID NO 189
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 189

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25
```

COMPOSITIONS AND METHODS FOR TREATING CANCER WITH SELF-DRIVING CHIMERIC ANTIGEN RECEPTORS

CROSS-REFERENCE TO RELATED APPLICATIONS

This application is a 371 U.S. National Phase Application of PCT/US2020/021320, filed on Mar. 6, 2020, which claims priority to U.S. Provisional Patent Application No. 62/954,161 filed on Dec. 27, 2019 and U.S. Provisional Patent Application No. 62/814,759 filed on Mar. 6, 2019. The entire contents of each of the foregoing applications is incorporated herein by reference.

SEQUENCE LISTING

This application contains a Sequence Listing that has been submitted electronically in ASCII format and is hereby incorporated by reference in its entirety. Said ASCII copy, created on Sep. 3, 2021, is named SequenceListing.txt and is 375 kilobytes in size.

FIELD OF THE DISCLOSURE

This application relates to the field of cancer, particularly to inducible promoters connected to therapeutic payloads and methods of use thereof.

BACKGROUND

Cancer is one of the most deadly threats to human health. In the U.S. alone, cancer affects nearly 1.3 million new patients each year, and is the second leading cause of death after cardiovascular disease, accounting for approximately 1 in 4 deaths. Solid tumors are responsible for most of those deaths. Although there have been significant advances in the medical treatment of certain cancers, the overall 5-year survival rate for all cancers has improved only by about 10% in the past 20 years. Cancers, or malignant tumors, metastasize and grow rapidly in an uncontrolled manner, making treatment extremely difficult.

Multiple myeloma ("MM") is a debilitating and often incurable disease, with over 30,000 new cases diagnosed in the U.S. every year (source: MM research foundation). MM is the second most prevalent blood cancer in the U.S., after Non-Hodgkin's Lymphoma ("NHL"), (Smith L, McCourt O, Henrich M, et al. Multiple myeloma and physical activity: a scoping review. BMJ Open. 2015; 5: e009576). MM impacts plasma cells in the bone marrow, and may lead to bone marrow failure and patient death (National Cancer Institute. A snapshot of myeloma. Nov. 5, 2014. see the world wide web at cancer.gov). Complications of myeloma include bone pain, bone loss, anemia, immunosuppression, kidney disfunction, neuropathy (Mayo Clinic staff. Diseases and conditions: multiple myeloma: treatments and drugs. Dec. 4, 2015).

First line therapy for MM includes proteasome inhibitors, immunomodulatory drugs, steroids, histone deacetylase ("HDAC") inhibitors, and chemotherapy. These approaches are aimed at killing MM cells, however, many of them are also associated with broad immunosuppression and systemic toxicities.

Chimeric antigen receptor T-cell (CAR T) technology has brought great advancement to the treatment of hematologic malignancies like MM, and holds great promise for the treatment of solid tumors. However, two presently unresolved drawbacks of this technology are insufficient CAR T potency and suboptimal responses on the one hand, and detrimental side effects stemming from excessive CAR T activation, such as cytokine release syndrome on the other hand. The purpose of this invention is to address both issues by creating CAR T moieties and other therapeutic payloads that can be naturally fine-tuned based on tumor burden and inflammatory milieu in the patient, at any given time in the course of treatment, and in any local microenvironment.

Chimeric Antigen Receptors (CARs) are hybrid molecules comprising three essential units: (1) an extracellular antigen-binding motif, (2) linking/transmembrane motifs, and (3) intracellular T-cell signaling motifs (Long A H, Haso W M, Orentas R J. Lessons learned from a highly-active CD22-specific chimeric antigen receptor. Oncoimmunology. 2013; 2 (4):e23621). The antigen-binding motif of a CAR is commonly fashioned after an single chain Fragment variable (ScFv), the minimal binding domain of an immunoglobulin (Ig) molecule. Alternate antigen-binding motifs, such as receptor ligands (e.g., IL-13 has been engineered to bind tumor expressed IL-13 receptor), intact immune receptors, library-derived peptides, and innate immune system effector molecules (such as NKG2D) also have been engineered. Alternate cell targets for CAR expression (such as NK or gamma-delta T cells) are also under development (Brown C E et al. Clin Cancer Res. 2012; 18(8):2199-209; Lehner M et al. PLoS One. 2012; 7 (2):e31210). There remains significant work with regard to defining the most active T-cell population to transduce with CAR vectors, determining the optimal culture and expansion techniques, and defining the molecular details of the CAR protein structure itself.

The linking motifs of a CAR can be a relatively stable structural domain, such as the constant domain of IgG, or designed to be an extended flexible linker. Structural motifs, such as those derived from IgG constant domains, can be used to extend the ScFv binding domain away from the T-cell plasma membrane surface. This may be important for some tumor targets where the binding domain is particularly close to the tumor cell surface membrane (such as for the disialoganglioside GD2; Orentas et al., unpublished observations). To date, the signaling motifs used in CARs always include the CD3-ζ chain because this core motif is the key signal for T cell activation. The first reported second-generation CARs featured CD28 signaling domains and the CD28 transmembrane sequence. This motif was used in third-generation CARs containing CD137 (4-1BB) signaling motifs as well (Zhao Y et al. J Immunol. 2009; 183 (9): 5563-74). With the advent of new technology, the activation of T cells with beads linked to anti-CD3 and anti-CD28 antibody, and the presence of the canonical "signal 2" from CD28 was no longer required to be encoded by the CAR itself using bead activation, third-generation vectors were found to be not superior to second-generation vectors in in vitro assays, and they provided no clear benefit over second-generation vectors in mouse models of leukemia (Haso W, Lee D W, Shah N N, Stetler-Stevenson M, Yuan C M, Pastan I H, Dimitrov D S, Morgan R A, FitzGerald D J, Barrett D M, Wayne A S, Mackall C L, Orentas R J. Anti-CD22-chimeric antigen receptors targeting B cell precursor acute lymphoblastic leukemia, Blood. 2013; 121 (7):1165-74; Kochenderfer J N et al. Blood. 2012; 119 (12):2709-20). This is borne out by the clinical success of CD19-specific CARs that are in a second generation CD28/CD3-ζ ((Lee D W et al. American Society of Hematology Annual Meeting. New Orleans, LA; Dec. 7-10, 2013) and a CD137/CD3-ζ signaling format (Porter D L et al. N Engl J Med. 2011; 365 (8): 725-33). In addition to CD137, other tumor necrosis factor receptor superfamily members such as OX40 also are able to provide important persistence signals in CAR-transduced T cells (Yvon E et al. Clin Cancer Res. 2009; 15(18):5852-60). Equally important are the culture conditions under which the CAR T-cell populations were cultured.

T-cell-based immunotherapy has become a new frontier in synthetic biology; multiple promoters and gene products are envisioned to steer these highly potent cells to the tumor microenvironment, where T cells can both evade negative regulatory signals and mediate effective tumor killing. The elimination of unwanted T cells through the drug-induced dimerization of inducible caspase 9 constructs with AP1903 demonstrates one way in which a powerful switch that can control T-cell populations can be initiated pharmacologically (Di Stasi A et al. N Engl J Med. 2011; 365(18):1673-83). The creation of effector T-cell populations that are immune to the negative regulatory effects of transforming growth factor-β by the expression of a dominant negative receptor further demonstrates that degree to which effector T cells can be engineered for optimal antitumor activity (Foster A E et al. J Immunother. 2008; 31(5):500-5). Thus, while it appears that CARs can trigger T-cell activation in a manner similar to an endogenous T-cell receptor, a major impediment to the clinical application of this technology to date has been limited in vivo expansion of $CAR^+$ T cells, rapid disappearance of the cells after infusion, and disappointing clinical activity.

To date, prior art CAR therapeutic approaches employ CAR T constructs under the control of a constitutive promoter such as human elongation factor 1 alpha (EF1α), phosphoglycerate kinase (PGK), murine leukemia virus (MuLV), murine stem cell virus (MSCV), or other constitutive promoters known in the art, which constitutive promoters are often expressed at a high level, or induced artificially (via small molecule or a soluble component). These approaches are maladjusted to the dynamics of antigen expression, which may lead to, on a cellular level, an excessive or insufficient effector cell response, and on an organism level, to undertreatment or over-treatment and toxicity for the patient.

Accordingly, there is an urgent and long felt need in the art for discovering novel compositions and methods for treatment of MM and CLL using an approach that can exhibit specific and efficacious anti-tumor effect without the aforementioned shortcomings (e.g. high toxicity, insufficient efficacy).

The present invention addresses these needs by providing compositions and therapeutic methods that can be used to treat cancers and other diseases and/or conditions. In particular, the present invention as disclosed and described herein provides inducible promoter-therapeutic payload constructs that may be used for the treatment of diseases, disorders or conditions associated with dysregulated expression of various antigens, for example and not by way of limitation, mesothelin, CD33, CD19, CD19/CD20, CD22, CD19/CD22, ROR1, CD123, or CD38, or a combination thereof, and which inducible promoter-therapeutic payload constructs contain antigen-specific binding domains that exhibit a high surface expression on transduced T cells, and exhibit a high degree of cytolysis and transduced T cell in vivo expansion and persistence. Furthermore, the present invention as disclosed and described herein provides for the self-driving regulation of such therapeutic payloads by utilizing a surface antigen-regulated inducible promoter which adjusts the level of expression of the one or more therapeutic payloads, dependent upon the level of expression of surface antigen on the target cell.

SUMMARY

The present invention as disclosed and described herein is based upon the unexpected discovery that modulation or adjustment of a surface antigen-regulated promoter's expression of a therapeutic payload construct can be directly correlated with the activity of the therapeutic payload, and therefore the level of expression of surface antigen in a target cell's milieu.

Novel self-driving inducible promoter-payload therapeutic constructs are provided herein comprising a therapeutic payload operably connected to a surface antigen-regulated inducible promoter which adjusts the level of expression of the one or more therapeutic payloads, dependent upon the level of expression of surface antigen on the target cell.

Without being limited to any particular mechanism of action, as used herein, a "self-driving" surface antigen-regulated inducible promoter refers to the utilization of a surface antigen-regulated inducible promoter to drive the therapeutic payloads to provide for a low basal level of the therapeutic payload surface expression in the absence of tumor target antigen expression. In the presence of activating target antigen on the surface of a target cell, the therapeutic payload is activated which triggers activation of the applicable signal transduction pathway(s), thereby activating the signal mediator(s) of the surface antigen-regulated inducible promoter thereby leading to increased expression of the therapeutic payload above the basal level of expression.

In this manner, a positive feed-back loop is created whereby higher expression of a given target antigen leads to higher expression of the therapeutic payload and vice versa thereby leading to efficient regulation of therapeutic payload expression to achieve a T-cell response precisely tailored to the level of target present at the specific site and time. Heightened therapeutic payload expression leads to an optimal anti-tumor activity and rapid elimination of target tumor cells. As tumor cells are reduced/removed in amount, the level of the therapeutic payload expression returns to its basal level of expression.

In one aspect, an isolated nucleic acid molecule is provided herein encoding a therapeutic payload operably connected to a surface antigen-regulated inducible promoter, and wherein said surface antigen-regulated inducible promoter adjusts the level of expression of the one or more therapeutic payloads, dependent upon the level of expression of surface antigen on the target cell thereby achieving a T-cell response precisely regulated to the level of target antigen present in the tumor milieu.

In one embodiment, an isolated nucleic acid molecule is provided herein encoding a therapeutic payload operably connected to a surface antigen-regulated inducible promoter comprising a nucleotide sequence comprising SEQ ID NO: 137 and 138, or a combination thereof, and wherein said surface antigen-regulated inducible promoter adjusts the level of expression of the one or more therapeutic payloads, dependent upon the level of expression of surface antigen on the target cell thereby achieving a T-cell response precisely regulated to the level of target antigen present in the tumor milieu.

In one aspect, self-driving surface antigen-regulated inducible promoter-therapeutic payload constructs comprising at least one therapeutic payload comprising chimeric antigen receptors (CARs), cytokines, chemokines, trafficking receptors, bispecific antibodies, neutralizing/blocking antibodies, T-cell stimulatory receptors, truncated inhibitory receptors, hybrid inhibitory/activating receptors, anti-apoptotic proteins, shRNA, or protease, or a combination thereof, operably connected to a surface antigen-regulated inducible promoter comprising a STAT5 response element, AP-1 response element, or NF kappa B response element, or a combination thereof, which surface antigen-regulated inducible promoter adjusts the level of expression of the one or more therapeutic payloads, dependent upon the level of expression of surface antigen on the target cell are provided herein, as well as host cells (e.g., T-cells) expressing the surface antigen-regulated inducible promoter-therapeutic payload constructs, and nucleic acid molecules encoding the surface antigen-regulated inducible promoter therapeutic payload constructs.

In one embodiment, the one or more therapeutic payloads (for example, and not by way of limitation, chimeric antigen receptors (CARs), cytokines, chemokines, trafficking receptors, bispecific antibodies, neutralizing/blocking antibodies, T-cell stimulatory receptors, truncated inhibitory receptors, hybrid inhibitory/activating receptors, anti-apoptotic proteins, shRNA, or protease-based) are expressed under the control of the surface antigen-regulated inducible promoter, with separation of the one or more therapeutic payloads by a 2A ribosomal skip sequence or an internal ribosome entry sequence (IRES) or a combination thereof.

In one aspect, the surface antigen-regulated inducible promoter-therapeutic payload constructs disclosed herein may comprise, for example, and not by way of limitation, a CAR, which may comprise either a single molecule expressed on the effector cell surface, or may comprise an effector cell-expressed signaling module and a soluble targeting module, such that when the soluble targeting module binds to the cell-expressed signaling module, a complete functional CAR is formed. The CARs exhibit a high surface expression on transduced T cells, with a high degree of cytolysis and transduced T cell expansion and persistence in vivo. Methods of using the disclosed CARs, host cells, and nucleic acid molecules are also provided, for example, to treat a cancer in a subject. Methods of using the disclosed surface antigen-regulated inducible promoter-therapeutic payload constructs, host cells, and nucleic acid molecules are also provided, for example, to regulate expression of the therapeutic payload.

In one aspect, an isolated polynucleotide encoding a CAR-based surface antigen-regulated inducible promoter-therapeutic payload is provided, wherein the therapeutic payload is operably connected to a surface antigen-regulated inducible promoter, and wherein the therapeutic payload comprises a CAR comprising a fragment selected from the group consisting of an Fab fragment, an F(ab')$_2$ fragment, an Fv fragment, and a single chain Fv (ScFv).

In one embodiment, an isolated nucleic acid molecule encoding the CAR-based surface antigen-regulated inducible promoter-therapeutic payload is provided wherein the encoded extracellular antigen binding domain comprises at least one single chain variable fragment of an antibody that binds to mesothelin, CD33, CD19, CD19/CD20, CD22, ROR1, CD123, or CD38 antigen binding domain, or a combination thereof.

In another embodiment, an isolated nucleic acid molecule encoding the CAR-based surface antigen-regulated inducible promoter-therapeutic payload is provided wherein the encoded extracellular antigen binding domain comprises at least one heavy chain variable region of an antibody that binds to mesothelin, CD33, CD19, CD19/CD20, CD22, ROR1, CD123, or CD38 antigen binding domain, or a combination thereof.

In one aspect, an isolated polynucleotide encoding a surface antigen-regulated inducible promoter-therapeutic payload construct is provided, wherein the therapeutic payload is operably connected to a surface antigen-regulated inducible promoter, and wherein the therapeutic payload comprises a CAR comprising, from N-terminus to C-terminus, at least one extracellular binding domain comprising a mesothelin, CD33, CD19, CD19/CD20, CD22, CD19/22, ROR1, CD123, or CD38 antigen binding domain, or a combination thereof; at least one transmembrane domain, and at least one intracellular signaling domain.

Thus, in one embodiment, an isolated polynucleotide encoding a CAR-based therapeutic payload operably connected to a surface antigen-regulated inducible promoter is provided wherein the at least one mesothelin, CD33, CD19, CD19/CD20, CD22, CD19/CD22, ROR1, CD123, or CD38 antigen binding domain of the CAR-based therapeutic payload comprises a nucleic acid sequence selected from the group consisting of SEQ ID NOs: 7, 9, 11, 15, 17, 19, 21, 23, 25, 87, 89, 91, 93, 95, 97, 115, 117, 119, 121, 123, 125, 127, 129, 131, 133, and 135.

In one embodiment, an isolated polynucleotide encoding a CAR-based therapeutic payload operably connected to at least one surface antigen-regulated inducible promoter is provided, wherein the at least one mesothelin, CD33, CD19, CD19/CD20, CD22, CD19/CD22, ROR1, CD123, or CD38 antigen binding domain of the CAR-based therapeutic payload comprises an amino acid sequence selected from the group consisting of SEQ ID NOs: 8, 10, 12, 16, 18, 20, 22, 24, 26, 88, 90, 92, 94, 98, 116, 118, 120, 122, 124, 126, 128, 130, 132, 134, and 136.

In one embodiment, an isolated polynucleotide encoding a CAR-based surface antigen-regulated inducible promoter-therapeutic payload construct is provided, wherein the therapeutic payload is operably connected to a surface antigen-regulated inducible promoter, and wherein the therapeutic payload comprises a CAR comprising, from N-terminus to C-terminus, at least one extracellular binding domain comprising a nucleic acid sequence selected from the group consisting of SEQ ID NOs: 7, 9, 11, 15, 17, 19, 21, 23, 25, 87, 89, 91, 93, 95, 97, 115, 117, 119, 121, 123, 125, 127, 129, 131, 133, and 135, or a combination thereof; at least one transmembrane domain, and at least one intracellular signaling domain.

In one embodiment, an isolated polynucleotide encoding a CAR-based surface antigen-regulated inducible promoter-therapeutic payload construct is provided, wherein the therapeutic payload is operably connected to a surface antigen-regulated inducible promoter, and wherein the therapeutic payload comprises a CAR comprising, from N-terminus to C-terminus, at least one extracellular binding domain comprising an amino acid sequence selected from the group consisting of SEQ ID NOs: 8, 10, 12, 16, 18, 20, 22, 24, 26, 88, 90, 92, 94, 98, 116, 118, 120, 122, 124, 126, 128, 130, 132, 134, and 136, or a combination thereof; at least one transmembrane domain, and at least one intracellular signaling domain.

In one embodiment, the targeting domain of the CAR-based surface antigen-regulated inducible promoter CAR-based therapeutic payload construct is expressed separately in the form of monoclonal antibody, ScFv Fab, Fab'2 and contains at least one mesothelin, CD33, CD19, CD19/CD20, CD22, CD19/CD22, ROR1, CD123, or CD38 antigen-targeting domain comprising a nucleic acid sequence selected from the group consisting of SEQ ID NOs: 7, 9, 11, 15, 17, 19, 21, 23, 25, 87, 89, 91, 93, 95, 97, 115, 117, 119, 121, 123, 125, 127, 129, 131, 133, and 135 coupled to an additional binding tag or epitope, wherein the effector-cell expressed component of the CAR contains a binding domain specifically directed to bind the tag or epitope expressed on the soluble CAR module, such as specific binding on the soluble component of the CAR to the cell bound component of the CAR forms the full functional CAR structure.

In another embodiment, the targeting domain of the CAR-based surface antigen-regulated inducible promoter-therapeutic payload construct is expressed separately in the form of a monoclonal antibody, ScFv Fab, Fab'2 and contains at least one mesothelin, CD33, CD19, CD19/CD20, CD22, CD19/CD22, ROR1, CD123, or CD38 antigen-targeting domain comprising a nucleic acid sequence selected from the group consisting of SEQ ID NOs: 7, 9, 11, 15, 17, 19, 21, 23, 25, 87, 89, 91, 93, 95, 97, 115, 117, 119, 121, 123, 125, 127, 129, 131, 133, and 135 and an additional ScFv, whereas the effector-cell expressed component of the CAR contains a tag or epitope specifically reactive with the additional ScFv expressed on the soluble CAR module, such as specific binding on the soluble component of the CAR to the cell bound component of the CAR forms the full functional CAR structure.

In yet another embodiment, an isolated nucleic acid molecule encoding the CAR-based surface antigen-regulated inducible promoter-therapeutic payload construct is provided wherein the encoded CAR extracellular antigen binding domain further comprises at least one lipocalin-based antigen binding antigen (anticalins) that binds to mesothelin, CD33, CD19, CD19/CD20, CD22, CD19/22, ROR1, CD123, or CD38 antigen binding domain, or a combination thereof.

In one embodiment, an isolated nucleic acid molecule encoding a CAR-based surface antigen-regulated inducible promoter-therapeutic payload construct is provided wherein the encoded extracellular mesothelin, CD33, CD19, CD19/CD20, CD22, CD19/22, ROR1, CD123, or CD38, antigen binding domain is connected to the transmembrane domain by a linker domain.

In another embodiment, an isolated nucleic acid molecule encoding a CAR-based surface antigen-regulated inducible promoter-therapeutic payload construct is provided wherein the encoded extracellular mesothelin, CD33, CD19, CD19/CD20, CD22, CD19/22, ROR1, CD123, or CD38 antigen binding domain is preceded by a sequence encoding a leader or signal peptide.

In yet another embodiment, an isolated nucleic acid molecule encoding a CAR-based surface antigen-regulated inducible promoter-therapeutic payload construct is provided comprising at least one antigen binding domain encoded by a nucleotide sequence comprising a nucleic acid sequence selected from the group consisting of SEQ ID NOs: 7, 9, 11, 15, 17, 19, 21, 23, 25, 87, 89, 91, 93, 95, 97, 115, 117, 119, 121, 123, 125, 127, 129, 131, 133, and 135, and wherein the CAR additionally encodes an extracellular antigen binding domain which targets an antigen that includes, but is not limited to, CD19, CD20, CD22, CD33, CD123, CD5, CD7, CD138, BCMA (CD269), ROR1, TSLPR, TEM-1, TEM-7, TEM-8, TEM-9, CD371, CD276, CD99, GPC2, GPC3, FGFR4, c-Met, PSMA, Glycolipid F77, EGFRvIII, GD-2, NY-ESO-1 TCR, MAGE A3 TCR, PRAME TCR, KRAS TCR or any combination thereof.

In certain embodiments, an isolated nucleic acid molecule encoding a CAR-based surface antigen-regulated inducible promoter-therapeutic payload construct is provided wherein the additionally encoded extracellular antigen binding domain comprises an anti-CD19 ScFv antigen binding domain, an anti-CD20 ScFv antigen binding domain, an anti-CD22 ScFv antigen binding domain, an anti-ROR1 ScFv antigen binding domain, an anti-mesothelin ScFv antigen binding domain, an anti-CD33 ScFv antigen binding domain, an anti-CD38 ScFv antigen binding domain, an anti-CD123 (IL3RA) ScFv antigen binding domain, an anti-CD138 ScFv antigen binding domain, an anti-BCMA (CD269) ScFv antigen binding domain, an anti-GPC2 ScFv antigen binding domain, an anti-GPC3 ScFv antigen binding domain, an anti-FGFR4 ScFv antigen binding domain, an anti-c-Met ScFv antigen binding domain, an anti-PMSA ScFv antigen binding domain, an anti-glycolipid F77 ScFv antigen binding domain, an anti-EGFRvIII ScFv antigen binding domain, an anti-GD-2 ScFv antigen binding domain, an anti-NY-ESo-1 TCR ScFv antigen binding domain, an anti-MAGE A3 TCR ScFv antigen binding domain, or an amino acid sequence with 85%, 90%, 95%, 96%, 97%, 98% or 99% identity thereof, or any combination thereof.

In one aspect, the CAR-based surface antigen-regulated inducible promoter-therapeutic payload constructs provided herein further comprise a linker or spacer domain.

In one embodiment, an isolated nucleic acid molecule encoding a CAR-based surface antigen-regulated inducible promoter-therapeutic payload construct is provided wherein the extracellular antigen binding domain comprising mesothelin, CD33, CD19, CD19/CD20, CD22, CD19/22, ROR1, CD123, or CD38, or a combination thereof; the intracellular signaling domain; or both are connected to the transmembrane domain by a linker or spacer domain.

In one embodiment, an isolated nucleic acid molecule encoding a CAR-based surface antigen-regulated inducible promoter-therapeutic payload construct is provided wherein the encoded linker domain is derived from the extracellular domain of CD8, TNFRSF19, or CD28, and is linked to a transmembrane domain.

In another embodiment, an isolated nucleic acid molecule encoding a CAR-based surface antigen-regulated inducible promoter-therapeutic payload construct is provided wherein the encoded CAR further comprises a transmembrane domain that comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, TNFRSF19 and CD154, or a combination thereof.

In yet another embodiment, an isolated nucleic acid molecule encoding a CAR-based surface antigen-regulated inducible promoter-therapeutic payload construct is provided wherein the encoded intracellular signaling domain further comprises a CD3 zeta intracellular domain.

In one embodiment, an isolated nucleic acid molecule encoding a CAR-based surface antigen-regulated inducible promoter-therapeutic payload construct is provided wherein the encoded intracellular signaling domain is arranged on a C-terminal side relative to the CD3 zeta intracellular domain.

In another embodiment, an isolated nucleic acid molecule encoding a CAR-based surface antigen-regulated inducible promoter-therapeutic payload construct is provided wherein the encoded at least one intracellular signaling domain comprises a costimulatory domain, a primary signaling domain, or a combination thereof.

In further embodiments, an isolated nucleic acid molecule encoding a CAR-based surface antigen-regulated inducible promoter-therapeutic payload construct is provided wherein the encoded at least one costimulatory domain comprises a functional signaling domain of OX40, CD70, CD27, CD28, CD5, ICAM-1, LFA-1 (CD11a/CD18), ICOS (CD278), DAP10, DAP12, and 4-1BB (CD137), or a combination thereof.

In one embodiment, an isolated nucleic acid molecule encoding a CAR-based surface antigen-regulated inducible promoter-therapeutic payload construct is provided that further contains a leader sequence or signal peptide wherein the leader or signal peptide nucleotide sequence comprises the nucleotide sequence of SEQ ID NO: 13, SEQ ID NO: 39, SEQ ID NO: 41, or SEQ ID NO: 43.

In yet another embodiment, an isolated nucleic acid molecule encoding a CAR-based surface antigen-regulated inducible promoter-therapeutic payload construct is provided wherein the encoded leader sequence comprises the amino acid sequence of SEQ ID NO: 14 SEQ ID NO: 40, SEQ ID NO: 42, or SEQ ID NO: 44.

In one aspect, a CAR-based surface antigen-regulated inducible promoter-therapeutic payload construct is provided herein comprising, from N-terminus to C-terminus, at least one antigen binding domain, at least one transmembrane domain, and at least one intracellular signaling domain.

In one embodiment, a CAR-based surface antigen-regulated inducible promoter-therapeutic payload construct is provided wherein the extracellular antigen binding domain comprises at least one single chain variable fragment of an antibody that binds to the antigen, or at least one heavy chain variable region of an antibody that binds to the antigen, or a combination thereof.

In another embodiment, a CAR-based surface antigen-regulated inducible promoter-therapeutic payload construct is provided wherein the at least one transmembrane domain comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154, or a combination thereof.

In some embodiments, a CAR-based surface antigen-regulated inducible promoter-therapeutic payload construct is provided wherein CAR additionally encodes an extracellular antigen binding domain comprising CD19, CD20, CD22, CD19/22, ROR1, mesothelin, CD33, CD38, CD123 (IL3RA), CD138, BCMA (CD269), GPC2, GPC3, FGFR4, c-Met, PSMA, Glycolipid F77, EGFRvIII, GD-2, NY-ESO-1 TCR, MAGE A3 TCR, or an amino acid sequence with 85%, 90%, 95%, 96%, 97%, 98% or 99% identity thereof, or any combination thereof.

In one embodiment, a CAR-based surface antigen-regulated inducible promoter-therapeutic payload construct is provided wherein the extracellular antigen binding domain comprises an anti-CD19 ScFv antigen binding domain, an anti-CD20 ScFv antigen binding domain, an anti-CD22 ScFv antigen binding domain, an anti-ROR1 ScFv antigen binding domain, an anti-mesothelin ScFv antigen binding domain, an anti-CD33 ScFv antigen binding domain, an anti-CD38 ScFv antigen binding domain, an anti-CD123 (IL3RA) ScFv antigen binding domain, an anti-CD138 ScFv antigen binding domain, an anti-BCMA (CD269) ScFv antigen binding domain, an anti-GPC2 ScFv antigen binding domain, an anti-GPC3 ScFv antigen binding domain, an anti-FGFR4 ScFv antigen binding domain, an anti-c-Met ScFv antigen binding domain, an anti-PMSA ScFv antigen binding domain, an anti-glycolipid F77 ScFv antigen binding domain, an anti-EGFRvIII ScFv antigen binding domain, an anti-GD-2 ScFv antigen binding domain, an anti-NY-ESo-1 TCR ScFv antigen binding domain, an anti-MAGE A3 TCR ScFv antigen binding domain, or an amino acid sequence with 85%, 90%, 95%, 96%, 97%, 98% or 99% identity thereof, or any combination thereof.

In another embodiment, a CAR-based surface antigen-regulated inducible promoter-therapeutic payload construct is provided wherein the extracellular antigen binding domain comprises an immunoglobulin variable heavy chain only (VH) anti-CD19 antigen binding domain, an anti-CD20 VH antigen binding domain, an anti-CD22 VH antigen binding domain, an anti-ROR1 VH antigen binding domain, an anti-mesothelin VH antigen binding domain, an anti-CD33 VH antigen binding domain, an anti-CD38 VH antigen binding domain, an anti-CD123 (IL3RA) VH antigen binding domain, an anti-CD138 VH antigen binding domain, an anti-BCMA (CD269) VH antigen binding domain, an anti-GPC2 VH antigen binding domain, an anti-GPC3 VH antigen binding domain, an anti-FGFR4 VH antigen binding domain, an anti-c-Met VH antigen binding domain, an anti-PMSA VH antigen binding domain, an anti-glycolipid F77 VH antigen binding domain, an anti-EGFRvIII VH antigen binding domain, an anti-GD-2 VH antigen binding domain, an anti-NY-ESO-1 TCR VH antigen binding domain, an anti-MAGE A3 TCR VH antigen binding domain, or an amino acid sequence with 85%, 90%, 95%, 96%, 97%, 98% or 99% identity thereof, or any combination thereof.

In another embodiment, a CAR-based surface antigen-regulated inducible promoter-therapeutic payload construct is provided wherein the extracellular antigen binding domain comprises a protein or a peptide (P) sequence capable of specifically binding target antigen, which may be derived from a natural or a synthetic sequence comprising anti-CD19 P antigen binding domain, an anti-CD20 P antigen binding domain, an anti-CD22 P antigen binding domain, an anti-ROR1 P antigen binding domain, an anti-mesothelin P antigen binding domain, an anti-CD33 P antigen binding domain, an anti-CD38 P antigen binding domain, an anti-CD123 (IL3RA) P antigen binding domain, an anti-CD138 P antigen binding domain, an anti-BCMA (CD269) P antigen binding domain, an anti-GPC2 P antigen binding domain, an anti-GPC3 P antigen binding domain, an anti-FGFR4 P antigen binding domain, an anti-c-Met P antigen binding domain, an anti-PMSA P antigen binding domain, an anti-glycolipid F77 P antigen binding domain, an anti-EGFRvIII P antigen binding domain, an anti-GD-2 P antigen binding domain, an anti-NY-ESO-1 TCR P antigen binding domain, an anti-MAGE A3 TCR P antigen binding domain, or an amino acid sequence with 85%, 90%, 95%, 96%, 97%, 98% or 99% identity thereof, or any combination thereof. In another embodiment, a CAR is provided wherein the at least one intracellular signaling domain comprises a costimulatory domain and a primary signaling domain.

In yet another embodiment, a CAR-based surface antigen-regulated inducible promoter-therapeutic payload construct is provided wherein the at least one intracellular signaling domain comprises a costimulatory domain comprising a functional signaling domain of a protein selected from the group consisting of OX40, CD70, CD27, CD28, CD5, ICAM-1, LFA-1 (CD11a/CD18), ICOS (CD278), DAP10, DAP12, and 4-1BB (CD137), or a combination thereof.

In another embodiment, the nucleic acid sequence encoding a CAR-based surface antigen-regulated inducible promoter-therapeutic payload construct comprises the nucleic acid sequence of SEQ ID NO: 139. In one embodiment, the nucleic acid sequence encodes a CAR-based promoter-therapeutic payload construct comprising the amino acid sequence of SEQ ID NO: 78.

In another embodiment, the nucleic acid sequence encoding a CAR-based surface antigen-regulated inducible promoter-therapeutic payload construct comprises the nucleic acid sequence of SEQ ID NO: 140. In one embodiment, the nucleic acid sequence encodes a CAR-based promoter-therapeutic payload construct comprising the amino acid sequence of SEQ ID NO: 78.

In another embodiment, the nucleic acid sequence encoding a CAR-based surface antigen-regulated inducible promoter-therapeutic payload construct comprises the nucleic acid sequence of SEQ ID NO: 77. In one embodiment, the nucleic acid sequence encodes a CAR-based promoter-therapeutic payload construct comprising the amino acid sequence of SEQ ID NO: 78.

In one aspect, the surface antigen-regulated inducible promoter CAR-based therapeutic payload constructs disclosed herein are modified to express or contain a detectable marker for use in diagnosis, monitoring, and/or predicting the treatment outcome such as progression free survival of cancer patients or for monitoring the progress of such treatment.

In one embodiment, the nucleic acid molecule encoding the CAR-based surface antigen-regulated inducible promoter-therapeutic payload constructs can be contained in a vector, such as a viral vector. The vector is a DNA vector, an RNA vector, a plasmid vector, a cosmid vector, a herpes virus vector, a measles virus vector, a lentivirus vector, adenoviral vector, or a retrovirus vector, or a combination thereof.

In yet another embodiment, the vector expressing the CAR-based surface antigen-regulated inducible promoter-therapeutic payload constructs construct can be further modified to include one or more operative elements to control the expression of CAR T cells, or to eliminate CAR-T cells by virtue of a suicide switch. The suicide switch can include, for example, an apoptosis inducing signaling cascade or a drug that induces cell death. In a preferred embodiment, the vector expressing the CAR can be further modified to express an enzyme such thymidine kinase (TK) or cytosine deaminase (CD).

In another aspect, host cells including the nucleic acid molecule encoding the CAR-based surface antigen-regulated inducible promoter-therapeutic payload constructs are also provided. In some embodiments, the host cell is a T cell, such as a primary T cell obtained from a subject. In one embodiment, the host cell is a CD8+ T cell.

In one aspect, a transduced T cell comprising an isolated nucleic acid molecule encoding a therapeutic payload operably connected to a surface antigen-regulated inducible promoter is provided herein, wherein the surface antigen-regulated inducible promoter therapeutic payload construct confers upon said transduced CAR T cell the ability to mount an antitumor response dependent upon the level of expression of surface antigen on the target cell thereby achieving a T-cell response precisely regulated to the level of target antigen present in the tumor milieu.

In another aspect, a transduced CAR T cell comprising an isolated nucleic acid molecule encoding a CAR operably connected to a surface antigen-regulated inducible promoter is provided herein, wherein the surface antigen-regulated inducible promoter CAR construct confers upon said transduced CAR T cell the ability to mount an antitumor response dependent upon the level of expression of corresponding surface antigen on the target cell thereby achieving a CAR T-cell response precisely regulated to the level of target surface antigen present in the tumor milieu, wherein i) in the absence of tumor target surface antigen expression, surface antigen-regulated inducible promoter confers a low basal level of CAR expression; ii) in the presence of activating target surface antigen on the surface of a target cell, the CAR is activated which triggers activation of the applicable signal transduction pathway(s), thereby activating the signal mediator(s) of the surface antigen-regulated inducible promoter thereby leading to increased expression of the CAR above the basal level of expression; iii) higher expression of a given target surface antigen leads to higher expression of the CAR and vice versa thereby leading to efficient regulation of CAR expression to achieve a CAR T-cell response precisely tailored to the level of target present at the specific site and time; iv) heightened CAR expression leads to an optimal anti-tumor activity and rapid elimination of target tumor cells; and v) as tumor cells are reduced/removed in amount, the level of the CAR expression returns to its basal level of expression.

In one embodiment, a transduced T cell with heightened CAR expression leads to an optimal anti-tumor activity and rapid elimination of target tumor cells such that as tumor cells are reduced/removed in amount, the level of the therapeutic payload expression returns to the basal level of expression (c.f, the pre-antitumor response expression level).

In one embodiment the transduced T cells are autologous. In another embodiment the transduced T cells are allogeneic.

In yet another aspect, a pharmaceutical composition is provided comprising an anti-tumor effective amount of a population of human T cells, wherein the T cells comprise a nucleic acid sequence that encodes a CAR-based surface antigen-regulated inducible promoter-therapeutic payload constructs, wherein the CAR comprises at least one extracellular antigen binding domain comprising an antigen binding domain comprising the amino acid sequence selected from the group consisting of SEQ ID NOs: 8, 10, 12, 16, 18, 20, 22, 24, 26, 88, 90, 92, 94, 98, 116, 118, 120, 122, 124, 126, 128, 130, 132, 134, and 136; at least one linker domain; at least one transmembrane domain; and at least one intracellular signaling domain, wherein the T cells are T cells of a human having a cancer. The cancer includes, inter alia, a hematological cancer such as leukemia (e.g., chronic lymphocytic leukemia (CLL), acute lymphocytic leukemia (ALL), or chronic myelogenous leukemia (CML), lymphoma (e.g., mantle cell lymphoma, non-Hodgkin's lymphoma or Hodgkin's lymphoma) or multiple myeloma (MM), or a combination thereof.

In one embodiment, a pharmaceutical composition is provided wherein the at least one transmembrane domain of the CAR-based surface antigen-regulated inducible promoter-therapeutic payload constructs contains a transmembrane domain of a protein selected from the group consisting of the alpha, beta or zeta chain of the T-cell receptor, CD28, CD3 epsilon, CD45, CD4, CD5, CD8, CD9, CD16, CD22, Mesothelin, CD33, CD37, CD64, CD80, CD86, CD134, CD137 and CD154, or a combination thereof.

In another embodiment, a pharmaceutical composition is provided wherein the human cancer includes an adult carcinoma comprising oral and pharynx cancer (tongue, mouth, pharynx, head and neck), digestive system cancers (esophagus, stomach, small intestine, colon, rectum, anus, liver, interhepatic bile duct, gallbladder, pancreas), respiratory system cancers (larynx, lung and bronchus), bones and joint cancers, soft tissue cancers, skin cancers (melanoma, basal and squamous cell carcinoma), pediatric tumors (neuroblastoma, rhabdomyosarcoma, osteosarcoma, Ewing's sarcoma), tumors of the central nervous system (brain, astrocytoma, glioblastoma, glioma), and cancers of the breast, the genital system (uterine cervix, uterine corpus, ovary, vulva, vagina, prostate, testis, penis, endometrium), the urinary system (urinary bladder, kidney and renal pelvis, ureter), the eye and orbit, the endocrine system (thyroid), and the brain and other nervous system, or any combination thereof.

In yet another embodiment, a pharmaceutical composition is provided comprising an anti-tumor effective amount of a population of human T cells of a human having a cancer wherein the cancer is a refractory cancer non-responsive to one or more chemotherapeutic agents. The cancer includes hematopoietic cancer, myelodysplastic syndrome pancreatic cancer, head and neck cancer, cutaneous tumors, minimal residual disease (MRD) in acute lymphoblastic leukemia (ALL), acute myeloid leukemia (AML), adult B cell malignancies including, CLL (Chronic lymphocytic leukemia), CML (chronic myelogenous leukemia), non-Hodgkin's lymphoma (NHL), pediatric B cell malignancies (including B lineage ALL (acute lymphocytic leukemia)), multiple myeloma (MM), lung cancer, breast cancer, ovarian cancer, prostate cancer, colon cancer, melanoma or other hematological cancer and solid tumors, or any combination thereof.

In yet another embodiment, a pharmaceutical composition is provided wherein the surface antigen-regulated inducible promoter-therapeutic payload constructs adjust the activity of the therapeutic payload by utilizing native effector cell pathways based on a native cell activation, mitogenic state, or a combination thereof.

In another aspect, methods of making CAR-containing T cells (hereinafter "CAR-T cells") are provided. The methods include transducing a T cell with a vector or nucleic acid molecule comprising a surface antigen-regulated inducible promoter-therapeutic payload encoding a disclosed CAR that specifically binds to mesothelin, CD33, CD19, CD19/CD20, CD22, CD19/22, ROR1, CD123, or CD38, or a combination thereof, thereby making the CAR-T cell.

In yet another aspect, a method of generating a population of RNA-engineered cells is provided that comprises introducing an in vitro transcribed RNA or synthetic RNA of a nucleic acid molecule comprising a surface antigen-regulated inducible promoter-therapeutic payload encoding a disclosed CAR into a cell of a subject, thereby generating a CAR T cell.

In yet another aspect, a method for diagnosing a disease, disorder or condition associated with the expression of a surface antigen-regulated inducible promoter-therapeutic payload construct in a cell comprising a nucleotide sequence selected from the group consisting of SEQ ID NOs: 139, 140, and 141, or a combination thereof, is provided comprising contacting the cell with a human anti-mesothelin, anti-CD33, anti-CD19, anti-CD19/CD20, anti-CD22, anti-ROR1, anti-CD123, or anti-CD38, antibody or fragment thereof, or a combination thereof, wherein the antibody or a fragment thereof comprises an amino acid sequence selected from the group consisting of SEQ ID NOs: 8, 10, 12, 16, 18, 20, 22, 24, 26, 88, 90, 92, 94, 98, 116, 118, 120, 122, 124, 126, 128, 130, 132, 134, and 136, or a combination thereof; and b) detecting the presence of the antigens mesothelin, CD33, CD19, CD19/CD20, CD22, ROR1, CD123, or CD38, or a combination thereof wherein the presence of mesothelin, CD33, CD19, CD19/CD20, CD22, ROR1, CD123, or CD38, or a combination thereof diagnoses for the disease, disorder or condition associated with the expression of mesothelin, CD33, CD19, CD19/CD20, CD22, ROR1, CD123, or CD38, or a combination thereof.

In one embodiment, the disease, disorder or condition associated with the expression of mesothelin, CD33, CD19, CD19/CD20, CD22, CD19/22, ROR1, CD123, or CD38, or a combination thereof, is cancer including hematopoietic cancer, myelodysplastic syndrome pancreatic cancer, head and neck cancer, cutaneous tumors, minimal residual disease (MRD) in acute lymphoblastic leukemia (ALL), acute myeloid leukemia (AML), adult B cell malignancies including, CLL (chronic lymphocytic leukemia), CML (chronic myelogenous leukemia), non-Hodgkin's lymphoma (NHL), pediatric B cell malignancies (including B lineage ALL (acute lymphocytic leukemia)), multiple myeloma (MM), lung cancer, breast cancer, ovarian cancer, prostate cancer, colon cancer, melanoma or other hematological cancer and solid tumors, or any combination thereof.

In another embodiment, a method of diagnosing, prognosing, or determining risk of a mesothelin-, CD33-, CD19-, CD19/CD20-, CD22-, CD19/22-, ROR1-, CD123-, or CD38- (or combination thereof) related disease in a mammal, is provided comprising detecting the expression of mesothelin, CD33, CD19, CD19/CD20, CD22, CD19/22, ROR1, CD123, or CD38, or a combination thereof, in a sample derived from the mammal comprising: a) contacting the sample with a surface antigen-regulated inducible promoter-therapeutic payload construct comprising human anti-mesothelin, anti-CD33, anti-CD19, anti-CD19/CD20, anti-CD22, anti-CD19/22, anti-ROR1, anti-CD123, or anti-CD38, (or a combination thereof) antibody or fragment thereof, wherein the antibody or a fragment thereof comprises an amino acid sequence selected from the group consisting of SEQ ID NOs: 8, 10, 12, 16, 18, 20, 22, 24, 26, 88, 90, 92, 94, 98, 116, 118, 120, 122, 124, 126, 128, 130, 132, 134, and 136; and b) detecting the presence of one or more antigens wherein the presence of said antigen diagnoses for a mesothelin, CD33-, CD19, CD19/CD20-, CD22-, CD19/22-, ROR1-, CD123-, or CD38-related disease in the mammal.

In another embodiment, a method of redirecting CAR antigen targets, is provided comprising contacting a cell with a surface antigen-regulated inducible promoter-therapeutic payload construct comprising human anti-mesothelin, anti-CD33, anti-CD19, anti-CD19/CD20, anti-CD22, anti-CD19/22, anti-ROR1, anti-CD123, or anti-CD38, antibody or fragment thereof, wherein the antibody or a fragment thereof comprises an amino acid sequence selected from the group consisting of SEQ ID NOs: 8, 10, 12, 16, 18, 20, 22, 24, 26, 88, 90, 92, 94, 98, 116, 118, 120, 122, 124, 126, 128, 130, 132, 134, and 136. In one embodiment, the cell is selected from the group consisting of a mesothelin, CD33, CD19, CD19/CD20, CD22, CD19/22, ROR1, CD123, or CD38-expressing tumor cell, a tumor-associated macrophage, and any combination thereof.

In another aspect, a method is provided for inducing an anti-tumor immunity in a mammal comprising administering to the mammal a therapeutically effective amount of a T cell transduced with a surface antigen-regulated inducible promoter-therapeutic payload construct comprising a vector or nucleic acid molecule encoding a disclosed therapeutic payload, for example, and not by way of limitation, a CAR, cytokine, chemokine, trafficking receptor, bispecific antibody, a neutralizing/blocking antibody, a T-cell stimulatory receptor, truncated inhibitory receptor, hybrid inhibitory/activating receptor, anti-apoptotic protein, shRNA, or protease, or a combination thereof.

In another embodiment, a method of treating or preventing cancer in a mammal is provided comprising administering to the mammal one or more of the disclosed surface antigen-regulated promoter-therapeutic payload constructs, in an amount effective to treat or prevent cancer in the mammal. The method includes administering to the subject a therapeutically effective amount of host cells expressing a disclosed CAR that specifically binds mesothelin, CD33, CD19, CD19/CD20, CD22, CD19/22, ROR1, CD123, or CD38 and/or one or more of the aforementioned antigens, under conditions sufficient to form an immune complex of the antigen binding domain on the CAR and the extracellular domain of mesothelin, CD33, CD19, CD19/CD20, CD22, CD19/22, ROR1, CD123, or CD38 and/or one or more of the aforementioned antigens in the subject.

In yet another embodiment, a method is provided for treating a mammal having a disease, disorder or condition associated with an elevated expression of a tumor antigen, the method comprising administering to the subject a pharmaceutical composition comprising one or more of the disclosed surface antigen-regulated inducible promoter-therapeutic payload constructs, comprising an anti-tumor effective amount of a population of T-cells, wherein the T-cells comprise a nucleic acid sequence that encodes a CAR, wherein the CAR includes at least one extracellular mesothelin, CD33, CD19, CD19/CD20, CD22, CD19/22, ROR1, CD123, or CD38 antigen binding domain comprising the amino acid sequence of SEQ ID NOs: 8, 10, 12, 16, 18, 20, 22, 24, 26, 88, 90, 92, 94, 98, 116, 118, 120, 122, 124, 126, 128, 130, 132, 134, and 136, or any combination thereof, at least one linker or spacer domain, at least one transmembrane domain, at least one intracellular signaling domain, and wherein the T-cells are T-cells of the subject having cancer.

In yet another embodiment, a method is provided for treating cancer in a subject in need thereof comprising administering to the subject a pharmaceutical composition comprising one or more of the disclosed surface antigen-regulated inducible promoter-therapeutic payload constructs, comprising an anti-tumor effective amount of a population of T-cells, wherein the T-cells comprise a nucleic acid sequence that encodes a chimeric antigen receptor (CAR), wherein the CAR comprises at least one mesothelin, CD33, CD19, CD19/CD20, CD22, CD19/22, ROR1, CD123, or CD38 antigen binding domain comprising the amino acid sequence of SEQ ID NOs: 8, 10, 12, 16, 18, 20, 22, 24, 26, 88, 90, 92, 94, 98, 116, 118, 120, 122, 124, 126, 128, 130, 132, 134, and 136, or any combination thereof, at least one linker or spacer domain, at least one transmembrane domain, at least one intracellular signaling domain, wherein the T-cells are T-cells of the subject having cancer. In some embodiments of the aforementioned methods, the at least one transmembrane domain comprises a transmembrane domain of the alpha, beta or zeta chain of the T-cell receptor, CD28, CD3 epsilon, CD45, CD4, CD5, CD8, CD9, CD16, CD22, Mesothelin, CD33, CD37, CD64, CD80, CD86, CD134, CD137 and CD154, or a combination thereof.

In yet another embodiment, a method is provided for generating a persisting population of genetically engineered T-cells in a human diagnosed with cancer. In one embodiment, the method comprises administering to a human a T-cell genetically engineered to express a surface antigen-regulated promoter-therapeutic payload construct (e.g. CAR-, cytokine-, chemokine-, trafficking receptor-, bispecific antibody-, a neutralizing/blocking antibody-, a T cell stimulatory receptor-, a truncated inhibitory receptor-, a hybrid inhibitory/activating receptor-, an anti-apoptotic protein-, an shRNA-, a protease-based) wherein the self-driving surface antigen-regulated promoter-therapeutic payload construct comprises at least one mesothelin, CD33, CD19, CD19/CD20, CD22, CD19/22, ROR1, CD123, or CD38 antigen binding domain comprising the amino acid sequence of SEQ ID NOs: 8, 10, 12, 16, 18, 20, 22, 24, 26, 88, 90, 92, 94, 98, 116, 118, 120, 122, 124, 126, 128, 130, 132, 134, and 136, or any combination thereof; at least one transmembrane domain; and at least one intracellular signaling domain wherein the persisting population of genetically engineered T-cells, or the population of progeny of the T-cells, persists in the human for at least one month, two months, three months, four months, five months, six months, seven months, eight months, nine months, ten months, eleven months, twelve months, two years, or three years after administration.

In one embodiment, the progeny T-cells in the human comprise a memory T-cell. In another embodiment, the T-cell is an autologous T-cell.

In all of the aspects and embodiments of methods described herein, any of the aforementioned cancers, diseases, disorders or conditions associated with an elevated expression of a tumor antigen that may be treated or prevented or ameliorated using one or more of the surface antigen-regulated promoter-therapeutic payload constructs disclosed herein.

For the avoidance of doubt, the specification and claims as disclosed herein specifically exclude by way of proviso the Syn-Notch constructs as set forth in U.S. Pat. No. 9,670,281, issued on Jun. 6, 2017 entitled Binding-triggered transcriptional switches and methods of use thereof and U.S. Pat. No. 9,834,608, issued on Dec. 5, 2017 (Wendell A. Lim et al.), respectively, and the NFAT-regulated expression of IL-12, as set forth in U.S. Pat. No. 8,556,882, issued on Oct. 15, 2013 (Richard A. Morgan et al.).

In yet another aspect, a kit is provided for making a surface antigen-regulated promoter-therapeutic payload construct in a T-cell as described supra or for preventing, treating, or ameliorating any of the cancers, diseases, disorders or conditions associated with an elevated expression of a tumor antigen in a subject as described supra, comprising a container comprising any one of the nucleic acid molecules, vectors, host cells, or compositions disclosed supra or any combination thereof, and instructions for using the kit.

It will be understood that the surface antigen-regulated promoter-therapeutic payload constructs, host cells, nucleic acids, and methods are useful beyond the specific aspects and embodiments that are described in detail herein. The foregoing features and advantages of the disclosure will become more apparent from the following detailed description, which proceeds with reference to the accompanying figures.

BRIEF DESCRIPTION OF THE FIGURES

(FIG. 5B) CAR LTG1563-dependent Raji cytotoxicity during Coculture 1. (FIG. 5C) CAR LTG1563-dependent T cell expansion during Cocultures 1&2. (FIG. 5B, FIG. 5C). n=3 donors (*: $p<0.05$, :$p<0.01$, *:$p<0.001$, ****:$p<0.0001$; 2-way ANOVA with Tukey's correction).

(FIG. 8A) Coculture time course diagram of a long-term killing assay. Cells were activated with TransAct reagent at D0, transduced at D1 with LV vectors (0.5% v/v), and washed and treated with either: 0 IU/mL IL-2 or 30 IU/mL IL2 from D2-D5 post-activation. From D5-D9 post-activation, CAR LTG1563 T cells were cocultured with Raji-GFP (CD19+) cells at an effector:target ratio of 1:3 in the presence or absence of 10 ng/mL TGF-β (Coculture 1); from D9-D13, cells were re-stimulated with Raji-GFP cells in the presence or absence of 10 ng/mL TGF-β (Coculture 2), and from D13-19, cells were re-stimulated with Raji-GFP cells in the presence or absence of 10 ng/mL TGF-β (Coculture 3). (FIG. 8B) CAR LTG1563-dependent T cell expansion during Cocultures 1-3. (FIG. 8C) CAR LTG1563-dependent Raji cytotoxicity during Cocultures 1-3. (FIG. 8B, FIG. 8C). n=2 donors.

(FIG. 9A) Coculture time course diagram of a long-term killing assay. Cells were activated with TransAct reagent at D0, transduced at D1 with LV vectors (0.5% v/v), and washed and treated with 30 IU/mL IL2 from D0-D8 post-activation. From D8-D14 post-activation, CAR LTG1563 T cells were cocultured with Raji-GFP (CD19+) cells at an effector:target ratio of 1:3 in the presence or absence of 10 ng/mL TGF-β (Coculture 1); from D14-D20, cells were re-stimulated with Raji-GFP cells at an effector:target ratio of 1:3 in the presence or absence of 10 ng/mL TGF-β (Coculture 2). (FIG. 9B) CAR LTG1563-dependent Raji cytotoxicity during Cocultures 1-2. (FIG. 9C) Quantification of CAR T exhaustion marker expression (PD1) at D20 post-activation (Coculture 2, D8) by flow cytometry at various time points pre- and post-coculture with CD19+ Raji-GFP cells (Cocultures 1&2). (FIG. 9B,FIG. 9C). *: $p<0.05$, : $p<0.01$, *:$p<0.001$, ****:$p<0.0001$. UTD=untransduced T cells. n=3 independent donors.

(FIG. 10A) Expression of PD-L1 on transduced and magnetically-sorted Raji-GFP-PDL1 NHL B cell lines. (FIG. 10B) Coculture time course diagram for the long-term killing assay: Cells were activated with TransAct reagent at D0, transduced at D1 with LV vectors (0.5% v/v), and washed and treated with 30 IU/mL IL2 from D0-D8 post-activation. From D8-D14 post-activation, CAR LTG1563 T cells were cocultured with Raji-GFP (CD19+, PDL1-) or Raji-GFP-PDL1 (CD19+, PDL1+) cells at an effector:target ratio of 1:3 in the presence or absence of 10 ng/mL TGF-β (Coculture 1); from D14-D20, cells were re-stimulated with Raji-GFP or Raji-GFP-PDL1 cells at an effector:target ratio of 1:3 in the presence or absence of 10 ng/mL TGF-β (Coculture 2). (FIG. 10C) CAR LTG1563-dependent Raji cytotoxicity at the final timepoint analyzed in Coculture 1 (D14 post-activation) and Coculture 2 (D20 post-activation). (FIG. 10D) CAR LTG1563-dependent T cell expansion during full T cell culture period, including Cocultures 1-2. (FIG. 10E) Quantification of CAR T IL-2 production by flow cytometry 24 hours post-coculture with CD19+ Raji-GFP or Raji-GFP-PDL1 cells (Cocultures 1&2). (FIGS. 10B-E). *: $p<0.05$, : $p<0.01$, *:$p<0.001$, ****: $p<0.0001$. UTD=untransduced T cells. n=3 independent donors.

DETAILED DESCRIPTION

Definitions

Figure 1:
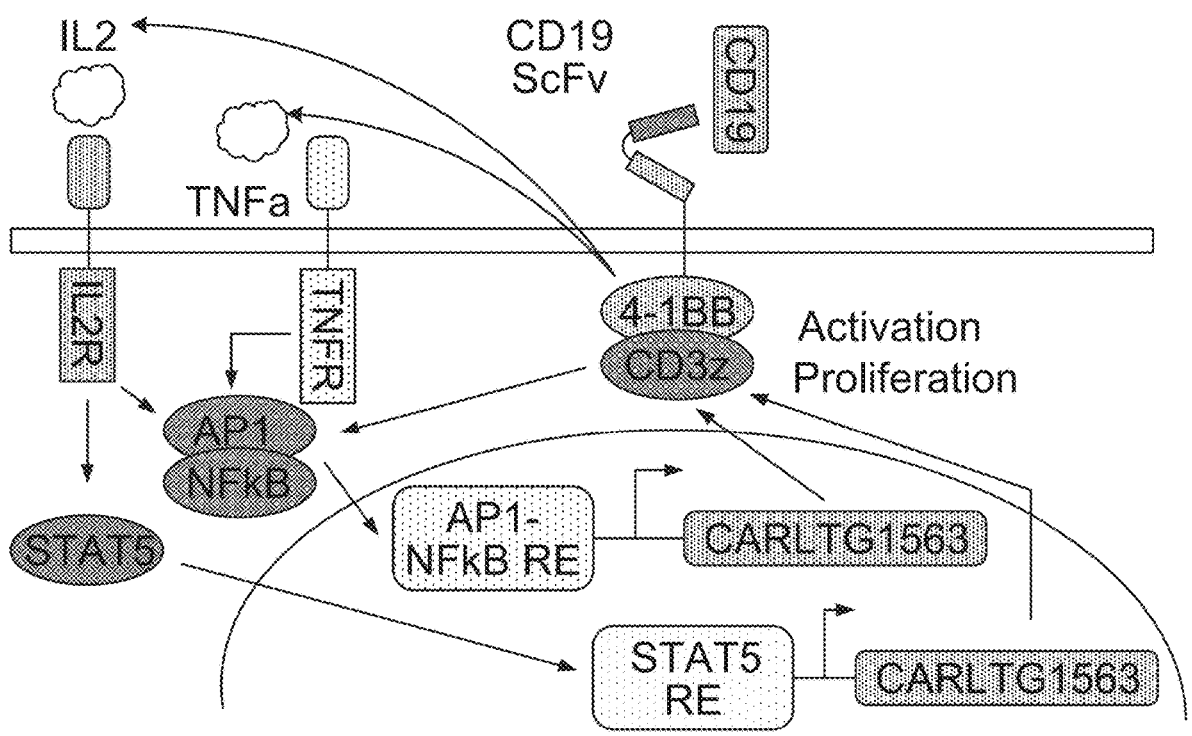
FIG. 1 depicts a Schematic Diagram of positive regulation of the self-driving STAT5 CAR via IL-2 pathway and AP1/NFκB CAR via cytokine/CAR stimulation pathways.

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen." As used herein, the term "comprises" means "includes." Thus, "comprising an antigen" means "including an antigen" without excluding other elements. The phrase "and/or" means "and" or "or." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the Materials, Methods, and Examples are illustrative only and not intended to be limiting. To facilitate review of the various embodiments, the following explanations of terms are provided:

The term "about" when referring to a measurable value such as an amount, a temporal duration, and the like, is meant to encompass variations of .+–0.20% or in some instances .+–0.10%, or in some instances .+–0.5%, or in some instances .+–0.1%, or in some instances .+–0.01% from the specified value, as such variations are appropriate to perform the disclosed methods.

Unless otherwise noted, the technical terms herein are used according to conventional usage. Definitions of common terms in molecular biology can be found in Benjamin Lewin, *Genes VII*, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnology: A Comprehensive Desk Reference*, published by VCH Publishers, Inc., 1995; and other similar references.

The present invention as disclosed and described herein is based upon the unexpected discovery that modulation or adjustment of a surface antigen-regulated promoter's expression of a therapeutic payload construct can be directly correlated with the activity of the therapeutic payload, and therefore the level of expression of surface antigen in a target cell's milieu.

The present disclosure provides for novel self-driving inducible promoter-therapeutic payload constructs comprising one or more therapeutic payloads operably connected to a surface antigen-regulated inducible promoter, which surface antigen-regulated inducible promoter adjusts the level of expression of the one or more therapeutic payloads, dependent upon the level of expression of surface antigen in a target cell's milieu, as well as host cells (e.g., T-cells) expressing the surface antigen-regulated inducible promoter therapeutic payload constructs, and nucleic acid molecules encoding the surface antigen-regulated inducible promoter-therapeutic payload constructs.

Without being limited to any particular mechanism of action, as used herein, a "self-driving" surface antigen-regulated inducible promoter refers to the utilization of a surface antigen-regulated inducible promoter to drive the therapeutic payloads to provide for a low basal level of the therapeutic payload surface expression in the absence of tumor target antigen expression. In the presence of activating target antigen on the surface of a target cell, the therapeutic payload is activated which triggers activation of the applicable signal transduction pathway(s), thereby activating the signal mediator(s) of the surface antigen-regulated inducible promoter thereby leading to increased expression of the therapeutic payload above the basal level of expression. In this manner, a positive feed-back loop is created whereby higher expression of a given target antigen leads to higher expression of the therapeutic payload and vice versa thereby leading to efficient regulation of therapeutic payload expression to achieve a T-cell response precisely tailored to the level of target present at the specific site and time. Heightened therapeutic payload expression leads to an optimal anti-tumor activity and rapid elimination of target tumor cells. As tumor cells are reduced/removed in amount, the level of the therapeutic payload expression returns to its basal level of expression.

This self-driving mode of activation will be repeated upon a subsequent re-exposure to antigen (for example and not by way of limitation, that occurring through a relapse of the tumor, a metastatic event, tumor migration/spreading, etc.). As a result, this control over the timing and magnitude of the self-driving therapeutic payload T-cell response affords improved treatment efficacy, reduced risk of tumor escape, and reduced toxicity of the treatment. This is akin to biologically or endogenously tailoring the treatment dose to the state of disease at the cellular level.

What follows is a detailed description of the self-driving surface antigen-regulated promoter-therapeutic payload constructs including a description of the surface antigen-regulated inducible promoters, the therapeutic payloads, along with a more detailed description of the self-driving CAR-based surface antigen-regulated promoter-therapeutic payload constructs, antibodies and antigen binding fragments thereof, conjugates, nucleotides, expression, vectors, and host cells, methods of treatment, compositions, and kits employing the disclosed self-driving CAR-based surface antigen-regulated promoter-therapeutic payload constructs.

A. Surface Antigen-Regulated Inducible Promoters

In one aspect, an isolated nucleic acid molecule is provided herein encoding a therapeutic payload operably connected to a surface antigen-regulated inducible promoter, and wherein said surface antigen-regulated inducible promoter adjusts the level of expression of the one or more therapeutic payloads, dependent upon the level of expression of surface antigen on the target cell thereby achieving a T-cell response precisely regulated to the level of target antigen present in the tumor milieu.

In one embodiment, an isolated nucleic acid molecule is provided herein encoding a therapeutic payload operably connected to a surface antigen-regulated inducible promoter comprising a nucleotide sequence comprising SEQ ID NO: 137 and 138, or a combination thereof, and wherein said surface antigen-regulated inducible promoter adjusts the level of expression of the one or more therapeutic payloads, dependent upon the level of expression of surface antigen on the target cell thereby achieving a T-cell response precisely regulated to the level of target antigen present in the tumor milieu.

In one embodiment, an isolated nucleic acid molecule is provided herein encoding a therapeutic payload operably connected to a surface antigen-regulated inducible promoter comprising a nucleotide sequence comprising SEQ ID NO: 137 and 138, or a combination thereof, or a sequence with 85%, 90%, 95%, 96%, 97%, 98% or 99% identity thereof, and wherein said surface antigen-regulated inducible promoter adjusts the level of expression of the one or more therapeutic payloads dependent upon the level of expression of surface antigen on the target cell thereby achieving a T-cell response precisely regulated to the level of target antigen present in the tumor milieu.

In another embodiment, an isolated nucleic acid molecule is provided herein encoding a therapeutic payload operably connected to a surface antigen-regulated inducible promoter comprising a nucleotide sequence comprising SEQ ID NO: 137 and 138, or a combination thereof, and wherein said surface antigen-regulated inducible promoter upregulates the level of expression of the one or more therapeutic payloads, dependent upon the level of expression of surface antigen on the target cell thereby achieving a T-cell response precisely regulated to the level of target antigen present in the tumor milieu.

In another embodiment, an isolated nucleic acid molecule is provided herein encoding a therapeutic payload operably connected to a surface antigen-regulated inducible promoter comprising a nucleotide sequence comprising SEQ ID NO: 137 and 138, or a combination thereof, or a sequence with 85%, 90%, 95%, 96%, 97%, 98% or 99% identity thereof, and wherein said surface antigen-regulated inducible promoter upregulates the level of expression of the one or more therapeutic payloads, dependent upon the level of expression of surface antigen on the target cell thereby achieving a T-cell response precisely regulated to the level of target antigen present in the tumor milieu.

In yet another embodiment, the level of expression of the surface antigen-regulated inducible promoter therapeutic payload constructs described herein may be upregulated for example, and not by way of limitation, from approximately 10-100%, 200%, 300%, 400%, and 500%. The ranges recited herein specifically includes all integer amounts therein as if specifically recited thereto.

In one embodiment, an isolated nucleic acid molecule is provided herein encoding a therapeutic payload operably connected to a surface antigen-regulated inducible promoter comprising a nucleotide sequence comprising SEQ ID NO: 137 and 138, or a combination thereof, and wherein said surface antigen-regulated inducible promoter downregulates the level of expression of the one or more therapeutic payloads, dependent upon the level of expression of surface antigen on the target cell thereby achieving a T-cell response precisely regulated to the level of target antigen present in the tumor milieu.

In another embodiment, an isolated nucleic acid molecule is provided herein encoding a therapeutic payload operably connected to a surface antigen-regulated inducible promoter comprising a nucleotide sequence comprising SEQ ID NO: 137 and 138, or a combination thereof, or a sequence with 85%, 90%, 95%, 96%, 97%, 98% or 99% identity thereof, and wherein said surface antigen-regulated inducible promoter downregulates the level of expression of the one or more therapeutic payloads, dependent upon the level of expression of surface antigen on the target cell thereby achieving a T-cell response precisely regulated to the level of target antigen present in the tumor milieu.

In yet another embodiment, the level of expression of the surface antigen-regulated inducible promoter therapeutic payload constructs described herein may be downregulated for example, and not by way of limitation, from approximately 10-100%, 200%, 300%, 400%, and 500%. The range recited herein specifically includes all integer amounts therein as if specifically recited thereto.

B. Therapeutic Payloads

In its broadest aspect, self-driving surface antigen-regulated inducible promoter-therapeutic payload constructs comprising at least one therapeutic payload comprising chimeric antigen receptors (CARs), cytokines, chemokines, trafficking receptors, bispecific antibodies, neutralizing/blocking antibodies, T-cell stimulatory receptors, truncated inhibitory receptors, hybrid inhibitory/activating receptors, anti-apoptotic proteins, shRNA, or protease, or a combination thereof, operably connected to a surface antigen-regulated inducible promoter comprising a STAT5 response element, AP-1 response element, or NF kappa B response element, or a combination thereof, which surface antigen-regulated inducible promoter adjusts the level of expression of the therapeutic payload, dependent upon the level of expression of surface antigen on the target cell are provided herein, as well as host cells (e.g., T-cells) expressing the surface antigen-regulated inducible promoter therapeutic payload constructs, and nucleic acid molecules encoding the surface antigen-regulated inducible promoter-therapeutic payload constructs.

In one aspect, self-driving surface antigen-regulated inducible promoter-therapeutic payload constructs comprising a therapeutic CAR and at least one therapeutic payload comprising a CAR, cytokines, chemokines, trafficking receptors, bispecific antibodies, neutralizing/blocking antibodies, T-cell stimulatory receptors, truncated inhibitory receptors, hybrid inhibitory/activating receptors, anti-apoptotic proteins, shRNA, or protease, or a combination thereof, operably connected to a surface antigen-regulated inducible promoter comprising a STAT5 response element, AP-1 response element, or NF kappa B response element, or a combination thereof, which surface antigen-regulated inducible promoter adjusts the level of expression of the therapeutic CAR and therapeutic payload, dependent upon the level of expression of surface antigen on the target cell are provided herein, as well as host cells (e.g., T-cells) expressing the surface antigen-regulated inducible promoter therapeutic payload constructs, and nucleic acid molecules encoding the surface antigen-regulated inducible promoter-therapeutic payload constructs.

In one embodiment, an isolated nucleic acid molecule is provided wherein the surface antigen-regulated inducible promoter-therapeutic payload construct further comprises a cytokine comprising IL-2, IL-15, IL-7, TNFa, IFN gamma, IFN beta, IFN alpha, IL-21, IL-33, IL-22, IL-6, IL-10, IL-9, IL-4, IL-12, TGF beta, IL-17, IL-18, or any combination thereof.

In another embodiment, an isolated nucleic acid molecule is provided wherein the surface antigen-regulated inducible promoter-therapeutic payload construct further comprises for example and not by way of limitation, a chemokine comprising, CCL2, CCL3, CCL4, CCL5, CCL19, CCL21, CCL25, CXCL9, CXCL10, CXCL11, CXCL12, CXCL13, CXCL16, or any combination thereof.

In another embodiment, an isolated nucleic acid molecule is provided wherein the surface antigen-regulated inducible promoter-therapeutic payload construct further comprises a trafficking receptor, such as a cytokine receptor, for example, and not by way of limitation, CCR2, CCR3, CCR4, CCR7, CCR8, CCR9, CXCR3, CXCR4, CXCR6, $S1P_1$ or any combination thereof, which trafficking receptor serves to aid in the trafficking of CAR T cells to the tumor site.

In another embodiment, an isolated nucleic acid molecule is provided wherein the surface antigen-regulated inducible promoter-therapeutic payload construct further comprises for example and not by way of limitation, a bispecific antibody, including a Bi-specific T cell engager (BiTE), for example, and not by way of limitation, anti-CD3 and anti CD19 targeting, or anti-CD3 and anti CD22 targeting, or anti-CD3 and anti CD20 targeting, or anti-CD3 and anti CD33 targeting, or anti-CD3 and anti CD123 targeting, or anti-CD3 and anti CD38 targeting, other multi-targeting antibody.

In another embodiment, an isolated nucleic acid molecule is provided wherein the surface antigen-regulated inducible promoter-therapeutic payload construct further comprises a neutralizing/blocking antibody, for example, and not by way of limitation, against PD-L1, PD-L2, CD95L, TRAIL receptor, IL-6R, IL-1R, TGF beta receptor, PD-1, LAG-3, Tim-3, TGF beta, IL-10, CTLA-4, VISTA, TIGIT, IL-1, IL-1R, expressed as an scFv, or as IgG, or scFvFc, or VHH, or F(ab), or F(ab)2, or a native ligand binding domain, or in other configurations, which neutralizing/blocking antibody serves to potentiate T cell lytic function, cytokine release, persistence, proliferation potential, prevent T cell checkpoint blockade, exhaustion, apoptosis, activation-induced cell death.

In another embodiment, an isolated nucleic acid molecule is provided wherein the surface antigen-regulated inducible promoter-therapeutic payload construct further comprises a T cell stimulatory receptor, for example, and not by way of limitation, IL-2R alpha, IL-15R alpha, IL-7R alpha, CXCR5, which stimulatory receptor serves to potentiate T cell anti-tumor function.

In another embodiment, an isolated nucleic acid molecule is provided wherein the surface antigen-regulated inducible promoter-therapeutic payload construct further comprises a truncated inhibitory receptor (dominant negative; "dn"), for example, and not by way of limitation, dn-TGF beta receptor II, dn-PD-1, dn-CTLA-4, dn-IL-10 receptor, dn-KLRGI, dn-CD160, dn-TIM3, dn-LAG3, dn-BTLA, dn-VISTA, which truncated inhibitory receptor serves to prevent inhibition of T cell function.

In another embodiment, an isolated nucleic acid molecule is provided wherein the surface antigen-regulated inducible promoter-therapeutic payload construct further comprises a hybrid inhibitory/activating receptor, for example, and not by way of limitation, ectodomain of PD-1 fused to endodomain of CD28, ectodomain of TGF beta receptor II fused to endodomain of gp130, ectodomain of IL-10 receptor fused to endodomain of 4-1BB, or IL-4 receptor fused to an endo-domain of IL-7 receptor, which hybrid inhibitory/activating receptor serves to transform T cell-inhibitory signal into T-cell activating signal.

In another embodiment, an isolated nucleic acid molecule is provided wherein the surface antigen-regulated inducible promoter-therapeutic payload construct further comprises an anti-apoptotic protein, for example, and not by way of limitation, BCL-2, MCL-1, CED9, Bfl-1, Brag-1, A-1, or BCL-XL, which anti-apoptotic protein serves to extend T cell persistence and prevent apoptosis.

In another embodiment, an isolated nucleic acid molecule is provided wherein the surface antigen-regulated inducible promoter-therapeutic payload construct further comprises an shRNA, for example, and not by way of limitation, for PD-1, CTLA-4, KLRG-1, CD160, TGF beta receptor II, IL-10R, which shRNA serves to downregulate T cell-inhibitory factors and potentiate T cell anti-tumor function.

In another embodiment, an isolated nucleic acid molecule is provided wherein the surface antigen-regulated inducible promoter-therapeutic payload construct further comprises a protease, such as MMP2, MMP4, which protease serves to digest tumor stroma and increase T cell penetration into tumor.

In another embodiment, an isolated nucleic acid molecule is provided wherein the surface antigen-regulated inducible promoter-therapeutic payload construct further comprises a peptide, such as iRGD peptide, which peptide serves to increase tumor penetration of anti-cancer drugs.

In another embodiment, an isolated nucleic acid molecule is provided wherein the surface antigen-regulated inducible promoter-therapeutic payload construct further comprises a second CAR T construct, which CAR T construct serves to target a second tumor antigen, or target an antigen expressed on the suppressor cells present in the tumor microenvironment, for example, and not by way of limitation, PD-L1, PD-L2, TRAIL receptor CD33, CD138, present on MDSC and inhibitory B cells.

In yet another embodiment, the one or more therapeutic payloads (for example, and not by way of limitation, chimeric antigen receptors (CARs), cytokines, chemokines, trafficking receptors, bispecific antibodies, neutralizing/blocking antibodies, T-cell stimulatory receptors, truncated inhibitory receptors, hybrid inhibitory/activating receptors, anti-apoptotic proteins, shRNA, or protease-based) are expressed under the control of the surface antigen-regulated inducible promoter, with separation of the one or more therapeutic payloads by a 2A ribosomal skip sequence or an internal ribosome entry sequence (IRES) or a combination thereof.

In yet another embodiment, an isolated nucleic acid molecule is provided wherein the surface antigen-regulated inducible promoter-therapeutic payload construct further comprises a cytokine comprising IL-2, IL-15, IL-7, TNFa, IFN gamma, IFN beta, IFN alpha, IL-21, IL-33, IL-22, IL-6, IL-10, IL-9, IL-4, IL-12, TGF beta, IL-17, IL-18, a chemokine comprising CCR4, CCR6, CXCR5, a trafficking receptor, such as a cytokine receptor, for example, and not by way of limitation, CCR4, CCR7, CCR2, a bispecific antibody, including a Bi-specific T cell engager (BiTE), for example, and not by way of limitation, anti-CD3 and anti CD19 targeting, or other multi-targeting antibody, a neutralizing/blocking antibody, for example, and not by way of limitation, against PD-L1, IL-6R, IL-1R, expressed as an scFv, or as IgG, or in other configurations, a T cell stimulatory receptor, a truncated inhibitory receptor, a hybrid inhibitory/activating receptor, for example, and not by way of limitation, ectodomain of PD-1, fused to endodomain of CD28, an anti-apoptotic protein, for example, and not by way of limitation, BCL-2, or BCL-XL, an shRNA, a protease, a second CAR T construct, or any combination thereof, each with their aforementioned biological properties as listed supra.

C. Chimeric Antigen Receptors (CARs)

In a narrower aspect, the present invention as disclosed and described herein is based upon the unexpected discovery that modulation or adjustment of a surface antigen-regulated promoter's expression of a therapeutic payload construct can be directly correlated with the activity of the therapeutic payload, and therefore the level of expression of surface antigen in a target cell's milieu.

In contrast to previously-existing CAR T constructs for which the expression is regulated by constitutive promoters, the CAR-based surface antigen-regulated inducible promoter-therapeutic payload constructs described herein possess certain advantages over the prior art, including, for example, and not by way of limitation: i) adjusting or tailoring the timing and magnitude of the anti-tumor response to the specific amount of the antigen expressed at that time by the tumor, allowing optimal execution of anti-tumor CAR functions; ii) preventing detrimental T cell over-activation (exhaustion, activation induced cell death, reduced metabolic capacity, rapid terminal differentiation); iii) reducing or eliminating the risk of toxicities associated with inappropriate CAR activation or overactivation; iv) reducing or eliminating CAR-associated cytokine release syndrome (CRS); or v) reducing or eliminating CAR-associated neurotoxicity; or any combination thereof.

Thus, in one aspect of the invention as disclosed and described herein, the at least one CAR-based therapeutic payload construct self-driven by the surface antigen-regulated inducible promoter provided herein comprises at least one chimeric antigen receptor operably connected to a surface antigen-regulated inducible promoter, which surface antigen-regulated inducible promoter adjusts the level of expression of the one or more therapeutic payloads, dependent upon the level of expression of surface antigen on the target cell.

In one embodiment, the self-driving CAR-based surface antigen-regulated promoter-therapeutic payload constructs provided herein comprise, for example and not by way of limitation, one or more CAR-based therapeutic payloads operably connected to a surface antigen-regulated inducible promoter, and wherein the CAR-based therapeutic payload comprises a CAR comprising, from N-terminus to C-terminus, at least one extracellular binding domain comprising a mesothelin, CD33, CD19, CD19/CD20, CD22, CD19/22, ROR1, CD123, or CD38 antigen binding domain, or a combination thereof; at least one transmembrane domain, and at least one intracellular signaling domain.

A CAR is an artificially constructed hybrid protein or polypeptide containing the antigen binding domains of an antibody (e.g., single chain variable fragment (ScFv)) linked to T-cell signaling domains via the transmembrane domain. Characteristics of CARs include their ability to redirect T-cell specificity and reactivity toward a selected target in a non-MHC-restricted manner, and exploiting the antigen-binding properties of monoclonal antibodies. The non-MIHC-restricted antigen recognition gives T cells expressing CARs the ability to recognize antigen independent of antigen processing, thus bypassing a major mechanism of tumor escape. Moreover, when expressed in T-cells, CARs advantageously do not dimerize with endogenous T cell receptor (TCR) alpha and beta chains.

The unique ability to combine functional moieties derived from different protein domains has been a key innovative feature of CARs. The choice of each of these protein domains is a key design feature, as is the way in which they are specifically combined. Each design domain is an essential component that can be used across different CAR platforms to engineer the function of lymphocytes. For example, the choice of the extracellular binding domain can make an otherwise ineffective CAR be effective.

The physico-chemical properties of the immunoglobulin-derived protein sequences used to create the extracellular antigen binding domain of a self-driving CAR-based surface antigen-regulated promoter-therapeutic payload construct can either be entirely neutral, or they can self-associate and drive the T-cell to a state of metabolic exhaustion, thus making the therapeutic T-cell expressing that self-driving CAR-based surface antigen-regulated promoter-therapeutic payload construct far less effective. This occurs independently of the antigen binding function of this CAR domain. Furthermore, the choice of the intracellular signaling domain(s) also can govern the activity and the durability of the therapeutic lymphocyte population used for immunotherapy. While the ability to bind target antigen and the ability to transmit an activation signal to the T-cell through these extracellular and intracellular domains, respectively, are important CAR design aspects, what has also become apparent is that the choice of the source of the extracellular antigen binding fragments can have a significant effect on the efficacy of the self-driving CAR-based surface antigen-regulated promoter-therapeutic payload construct and thereby have a defining role for the function and clinical utility of the self-driving CAR-based surface antigen-regulated promoter-therapeutic payload construct.

As disclosed herein, the intracellular T-cell signaling domains of the self-driving CAR-based surface antigen-regulated promoter-therapeutic payload constructs can include, for example, a T-cell receptor signaling domain, a T-cell costimulatory signaling domain, or both. The T-cell receptor signaling domain refers to a portion of the surface antigen-regulated promoter-therapeutic payload construct comprising the intracellular domain of a T-cell receptor, such as, for example, and not by way of limitation, the intracellular portion of the CD3 zeta protein. The costimulatory signaling domain refers to a portion of surface antigen-regulated promoter-therapeutic payload construct comprising the intracellular domain of a costimulatory molecule, which is a cell surface molecule other than an antigen receptor or their ligands that are required for an efficient response of lymphocytes to antigen.

What follows is a detailed description of the inventive self-driving CAR-based surface antigen-regulated promoter-therapeutic payload constructs including a description of their extracellular antigen binding domains, the transmembrane domain and the intracellular domain, along with additional description of the self-driving CAR-based surface antigen-regulated promoter-therapeutic payload constructs, antibodies and antigen binding fragments thereof, conjugates, nucleotides, expression, vectors, and host cells, methods of treatment, compositions, and kits employing the disclosed self-driving CAR-based surface antigen-regulated promoter-therapeutic payload constructs.

1. Extracellular Domain

In one embodiment, the CAR-based surface antigen-regulated promoter-therapeutic payload construct comprises a target-specific binding element otherwise referred to as an antigen binding domain or moiety. The choice of domain depends upon the type and number of ligands that define the surface of a target cell. For example, the antigen binding domain may be chosen to recognize a ligand that acts as a cell surface marker on target cells associated with a particular disease state. Thus, examples of cell surface markers that may act as ligands for the antigen binding domain of the therapeutic surface antigen target specific promoter-payload construct include those associated with viral, bacterial and parasitic infections, autoimmune disease and cancer cells.

In one embodiment, the surface antigen-regulated promoter-therapeutic payload construct can be engineered to target a tumor antigen of interest by way of engineering a desired antigen binding domain that specifically binds to an antigen on a tumor cell. Tumor antigens are proteins that are produced by tumor cells that elicit an immune response, particularly T-cell mediated immune responses. The selection of the antigen binding domain will depend on the particular type of cancer to be treated. Tumor antigens are well known in the art and include, for example, a glioma-associated antigen, carcinoembryonic antigen (CEA), .beta.-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and mesothelin. The tumor antigens disclosed herein are merely included by way of example. The list is not intended to be exclusive and further examples will be readily apparent to those of skill in the art.

In one embodiment, the tumor antigen comprises one or more antigenic cancer epitopes associated with a malignant tumor. Malignant tumors express a number of proteins that can serve as target antigens for an immune attack. These molecules include, but are not limited to, tissue-specific antigens such as MART-1, tyrosinase and GP 100 in melanoma and prostatic acid phosphatase (PAP) and prostate-specific antigen (PSA) in prostate cancer. Other target molecules belong to the group of transformation-related molecules such as the oncogene HER-2/Neu/ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD20 and CD37 are other candidates for target antigens in B-cell lymphoma. Some of these antigens (CEA, HER-2, CD19, CD20, idiotype) have been used as targets for passive immunotherapy with monoclonal antibodies with limited success.

The type of tumor antigen may also be a tumor-specific antigen (TSA) or a tumor-associated antigen (TAA). A TSA is unique to tumor cells and does not occur on other cells in the body. A TAA is not unique to a tumor cell and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development when the immune system is immature and unable to respond or they may be antigens that are normally present at extremely low levels on normal cells but which are expressed at much higher levels on tumor cells.

Non-limiting examples of TSAs or TAAs include the following: Differentiation antigens such as MART-1/MelanA (MART-I), gp100 (Pmel 17), tyrosinase, TRP-1, TRP-2 and tumor-specific multi-lineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3CA 27.29BCAA, CA 195, CA 242, CA-50, CAM43, CD68P1, CO-029, FGF-5, G250, Ga733EpCAM, HTgp-175, M344, MA-50, MG7-Ag, MOV18, NB/70K, NY-CO-1, RCAS1, SDCCAG16, TA-90Mac-2 binding proteincyclophilin C-associated protein, TAAL6, TAG72, TLP, and TPS.

Moreover, in certain embodiments, the use of a human extracellular antigen binding domain, instead of a mouse-derived binding domain, results in generation of a self-driving CAR-based surface antigen-regulated promoter-therapeutic payload construct that functions better in vivo, while avoiding the induction of anti-CAR immunity in the host immune response and the killing of the CAR-T cell population that is associated with murine-based antigen binding domains.

The self-driving CAR-based surface antigen-regulated promoter-therapeutic payload constructs expressing the entirely human extracellular ScFv antigen binding domain exhibit superior activities/properties including i) prevention of poor CAR-T persistence and function as seen with mouse-derived binding sequences; ii) lack of requirement for regional delivery of the self-driving CAR-based surface antigen-regulated promoter-therapeutic payload construct to be efficacious; and iii) ability to generate CAR-T cell designs based both on binders with high and low affinity to a respective antigen. This latter property allows investigators to better tune efficacy versus toxicity, and/or tissue specificity of the CAR-T product, since lower-affinity binders may have higher specificity to tumors versus normal tissues due to higher expression of certain antigens on tumors than normal tissue, which may prevent on-target off tumor toxicity and bystander cell killing.

In a preferred embodiment, the antigen binding domain portion of the CAR-based surface antigen-regulated promoter-therapeutic payload construct targets an antigen that includes but is not limited to CD19, CD20, CD22, ROR1, Mesothelin, CD33, c-Met, PSMA, Glycolipid F77, EGFRvIII, GD-2, MY-ESO-1 TCR, MAGE A3 TCR, and the like.

In one embodiment, the extracellular antigen binding domain in the CAR-based surface antigen-regulated promoter-therapeutic payload constructs may comprise, for example, the scFV binders as disclosed in Applicant's issued U.S. Pat. No. 10,183,993, entitled Compositions and Methods for Treating Cancer with Anti-Mesothelin Immunotherapy, first filed as Provisional Patent Application No. 62/444,201 on Jan. 9, 2017, and issued on Jan. 22, 2019, and assigned Lentigen Technology, Inc. matter number LEN_017.

In one preferred embodiment, the isolated nucleic acid molecule encoding the extracellular mesothelin antigen binding domain comprises the nucleotide sequence of SEQ ID NO: 87, or a sequence with 85%, 90%, 95%, 96%, 97%, 98% or 99% identity thereof. In one embodiment, an isolated nucleic acid molecule is provided wherein the encoded extracellular mesothelin antigen binding domain comprises an amino acid sequence of SEQ ID NO: 88 or an amino acid sequence with 85%, 90%, 95%, 96%, 97%, 98% or 99% identity to an amino acid sequence of SEQ ID NO: 88.

In another embodiment, the nucleic acid sequence encoding a CAR comprises the nucleic acid sequence of SEQ ID NO: 89 or a sequence with 85%, 90%, 95%, 96%, 97%, 98% or 99% identity thereof, and encodes the CAR comprising the amino acid sequence as set forth in SEQ ID NO: 90 or a sequence with 85%, 90%, 95%, 96%, 97%, 98% or 99% identity thereof. In addition to scFv sequences that may be used as the extracellular antigen binding domain in the CAR-based surface antigen-regulated promoter-therapeutic payload constructs may comprise, single chain antigen binders (as opposed to scFv) can be incorporated can be incorporated into a functional CAR.

For example, the CD33-specific heavy chain only binder, as disclosed in Applicant's co-pending Non-Provisional patent application Ser. No. 15/934,770 (Provisional Patent No. 62/476,438), entitled Compositions and Methods For Treating Cancer With Anti-CD33 Immunotherapy, as filed on Mar. 24, 2018, and assigned Lentigen Technology, Inc. matter number LEN_018.

In one embodiment, the isolated nucleic acid molecule encoding the extracellular CD33 antigen binding domain comprises a nucleotide sequence of SEQ ID NO: 91, or a sequence with 85%, 90%, 95%, 96%, 97%, 98% or 99% identity thereof. In one embodiment, an isolated nucleic acid molecule is provided wherein the encoded extracellular CD33 antigen binding domain comprises an amino acid sequence of SEQ ID NO: 92 or an amino acid sequence with 85%, 90%, 95%, 96%, 97%, 98% or 99% identity to an amino acid sequence of SEQ ID NO: 92.

In another embodiment, the nucleic acid sequence encoding a functional CAR LTG1906 that targets CD33-expressing malignancies comprises the nucleic acid sequence of SEQ ID NO: 93 or a sequence with 85%, 90%, 95%, 96%, 97%, 98% or 99% identity thereof, and encodes the CAR comprising the amino acid sequence as set forth in SEQ ID NO: 94 or a sequence with 85%, 90%, 95%, 96%, 97%, 98% or 99% identity thereof.

In one embodiment, the extracellular antigen binding domain in the CAR-based surface antigen-regulated promoter-therapeutic payload constructs may comprise, for example, the scFV binders as disclosed in Applicant's Provisional Patent Application No. 62/773,940, entitled Compositions and Methods for Treating Cancer with Anti-CD38 Immunotherapy, as filed on Nov. 30, 2018, and assigned Lentigen Technology, Inc. matter number LEN_026.

In one embodiment, the isolated nucleic acid molecule encoding the extracellular CD38 antigen binding domain M3803 comprises a nucleotide sequence of SEQ ID NO: 144, or a sequence with 85%, 90%, 95%, 96%, 97%, 98% or 99% identity thereof. In one embodiment, an isolated nucleic acid molecule is provided wherein the encoded extracellular CD38 antigen binding domain comprises an amino acid sequence of SEQ ID NO: 145 or an amino acid sequence with 85%, 90%, 95%, 96%, 97%, 98% or 99% identity to an amino acid sequence of SEQ ID NO: 145.

In one embodiment, the isolated nucleic acid molecule encoding the extracellular CD38 antigen binding domain M3804 comprises a nucleotide sequence of SEQ ID NO: 146, or a sequence with 85%, 90%, 95%, 96%, 97%, 98% or 99% identity thereof. In one embodiment, an isolated nucleic acid molecule is provided wherein the encoded extracellular CD38 antigen binding domain comprises an amino acid sequence of SEQ ID NO: 147 or an amino acid sequence with 85%, 90%, 95%, 96%, 97%, 98% or 99% identity to an amino acid sequence of SEQ ID NO: 147.

In one embodiment, the isolated nucleic acid molecule encoding the extracellular CD38 antigen binding domain M3809 comprises a nucleotide sequence of SEQ ID NO: 148, or a sequence with 85%, 90%, 95%, 96%, 97%, 98% or 99% identity thereof. In one embodiment, an isolated nucleic acid molecule is provided wherein the encoded extracellular CD38 antigen binding domain comprises an amino acid sequence of SEQ ID NO: 149 or an amino acid sequence with 85%, 90%, 95%, 96%, 97%, 98% or 99% identity to an amino acid sequence of SEQ ID NO: 149.

In one embodiment, the isolated nucleic acid molecule encoding the extracellular CD38 antigen binding domain M3811 comprises a nucleotide sequence of SEQ ID NO: 150, or a sequence with 85%, 90%, 95%, 96%, 97%, 98% or 99% identity thereof. In one embodiment, an isolated nucleic acid molecule is provided wherein the encoded extracellular CD38 antigen binding domain comprises an amino acid sequence of SEQ ID NO: 151 or an amino acid sequence with 85%, 90%, 95%, 96%, 97%, 98% or 99% identity to an amino acid sequence of SEQ ID NO: 151. In another embodiment, the nucleic acid sequence encoding a functional CAR LTG 2091 that targets CD38-expressing malignancies comprises the nucleic acid sequence of SEQ ID NO: 7 or a sequence with 85%, 90%, 95%, 96%, 97%, 98% or 99% identity thereof, and encodes the CAR comprising the amino acid sequence as set forth in SEQ ID NO: 8 or a sequence with 85%, 90%, 95%, 96%, 97%, 98% or 99% identity thereof.

In another embodiment, the nucleic acid sequence encoding a functional CAR LTG 2092 that targets CD38-expressing malignancies comprises the nucleic acid sequence of SEQ ID NO: 9 or a sequence with 85%, 90%, 95%, 96%, 97%, 98% or 99% identity thereof, and encodes the CAR comprising the amino acid sequence as set forth in SEQ ID NO: 10 or a sequence with 85%, 90%, 95%, 96%, 97%, 98% or 99% identity thereof.

In another embodiment, the nucleic acid sequence encoding a functional CAR LTG 2095 that targets CD38-expressing malignancies comprises the nucleic acid sequence of SEQ ID NO: 11 or a sequence with 85%, 90%, 95%, 96%, 97%, 98% or 99% identity thereof, and encodes the CAR comprising the amino acid sequence as set forth in SEQ ID NO: 12 or a sequence with 85%, 90%, 95%, 96%, 97%, 98% or 99% identity thereof.

In another embodiment, the nucleic acid sequence encoding a functional CAR LTG 2097 that targets CD38-expressing malignancies comprises the nucleic acid sequence of SEQ ID NO: 15 or a sequence with 85%, 90%, 95%, 96%, 97%, 98% or 99% identity thereof, and encodes the CAR comprising the amino acid sequence as set forth in SEQ ID NO: 16 or a sequence with 85%, 90%, 95%, 96%, 97%, 98% or 99% identity thereof.

In one embodiment, the extracellular antigen binding domain in the CAR-based surface antigen-regulated promoter-therapeutic payload constructs may comprise, for example, the scFV binders as disclosed in Applicant's co-pending Non-Provisional patent application Ser. No. 16/179,364, entitled Compositions and Methods for Treating Cancer with Anti-ROR1 Immunotherapy, as filed on Nov. 2, 2018, and assigned Lentigen Technology, Inc. matter number LEN_022.

In one embodiment, the isolated nucleic acid molecule encoding the extracellular ROR1 antigen binding domain comprises a nucleotide sequence of SEQ ID NO: 152, or a sequence with 85%, 90%, 95%, 96%, 97%, 98% or 99% identity thereof. In one embodiment, an isolated nucleic acid molecule is provided wherein the encoded extracellular ROR1 antigen binding domain comprises an amino acid sequence of SEQ ID NO: 153 or an amino acid sequence with 85%, 90%, 95%, 96%, 97%, 98% or 99% identity to an amino acid sequence of SEQ ID NO: 153.

In one embodiment, the isolated nucleic acid molecule encoding the extracellular ROR1 antigen binding domain comprises a nucleotide sequence of SEQ ID NO: 154, or a sequence with 85%, 90%, 95%, 96%, 97%, 98% or 99% identity thereof. In one embodiment, an isolated nucleic acid molecule is provided wherein the encoded extracellular ROR1 antigen binding domain comprises an amino acid sequence of SEQ ID NO: 155 or an amino acid sequence with 85%, 90%, 95%, 96%, 97%, 98% or 99% identity to an amino acid sequence of SEQ ID NO: 155.

In one embodiment, the isolated nucleic acid molecule encoding the extracellular ROR1 antigen binding domain comprises a nucleotide sequence of SEQ ID NO: 156, or a sequence with 85%, 90%, 95%, 96%, 97%, 98% or 99% identity thereof. In one embodiment, an isolated nucleic acid molecule is provided wherein the encoded extracellular ROR1 antigen binding domain comprises an amino acid sequence of SEQ ID NO: 157 or an amino acid sequence with 85%, 90%, 95%, 96%, 97%, 98% or 99% identity to an amino acid sequence of SEQ ID NO: 157.

In another embodiment, the nucleic acid sequence encoding a functional CAR LTG 1941 that targets ROR1-expressing malignancies comprises the nucleic acid sequence of SEQ ID NO: 17 or a sequence with 85%, 90%, 95%, 96%, 97%, 98% or 99% identity thereof, and encodes the CAR comprising the amino acid sequence as set forth in SEQ ID NO: 18 or a sequence with 85%, 90%, 95%, 96%, 97%, 98% or 99% identity thereof.

In another embodiment, the nucleic acid sequence encoding a functional CAR LTG 1942 that targets ROR1-expressing malignancies comprises the nucleic acid sequence of SEQ ID NO: 19 or a sequence with 85%, 90%, 95%, 96%, 97%, 98% or 99% identity thereof, and encodes the CAR comprising the amino acid sequence as set forth in SEQ ID NO: 20 or a sequence with 85%, 90%, 95%, 96%, 97%, 98% or 99% identity thereof.

In another embodiment, the nucleic acid sequence encoding a functional CAR LTG 1943 that targets ROR1-expressing malignancies comprises the nucleic acid sequence of SEQ ID NO: 21 or a sequence with 85%, 90%, 95%, 96%, 97%, 98% or 99% identity thereof, and encodes the CAR comprising the amino acid sequence as set forth in SEQ ID NO: 22 or a sequence with 85%, 90%, 95%, 96%, 97%, 98% or 99% identity thereof.

In one embodiment, the extracellular antigen binding domain in the CAR-based surface antigen-regulated promoter-therapeutic payload constructs may comprise, for example, the scFV binders as disclosed in Applicant's Provisional Patent Application No. 62/734,106, entitled Compositions and Methods for Treating Cancer with Anti-CD123 Immunotherapy, as filed on Sep. 20, 2018, and assigned Lentigen Technology, Inc. matter number LEN_024.

In one embodiment, the isolated nucleic acid molecule encoding the extracellular CD123 antigen binding domain M12303 comprises a nucleotide sequence of SEQ ID NO: 158, or a sequence with 85%, 90%, 95%, 96%, 97%, 98% or 99% identity thereof. In one embodiment, an isolated nucleic acid molecule is provided wherein the encoded extracellular CD123 antigen binding domain comprises an amino acid sequence of SEQ ID NO: 159 or an amino acid sequence with 85%, 90%, 95%, 96%, 97%, 98% or 99% identity to an amino acid sequence of SEQ ID NO: 159.

In one embodiment, the isolated nucleic acid molecule encoding the extracellular CD123 antigen binding domain M12304 comprises a nucleotide sequence of SEQ ID NO: 160, or a sequence with 85%, 90%, 95%, 96%, 97%, 98% or 99% identity thereof. In one embodiment, an isolated nucleic acid molecule is provided wherein the encoded extracellular CD123 antigen binding domain comprises an amino acid sequence of SEQ ID NO: 161 or an amino acid sequence with 85%, 90%, 95%, 96%, 97%, 98% or 99% identity to an amino acid sequence of SEQ ID NO: 161.

In one embodiment, the isolated nucleic acid molecule encoding the extracellular CD123 antigen binding domain M12305 comprises a nucleotide sequence of SEQ ID NO: 162, or a sequence with 85%, 90%, 95%, 96%, 97%, 98% or 99% identity thereof. In one embodiment, an isolated nucleic acid molecule is provided wherein the encoded extracellular CD123 antigen binding domain comprises an amino acid sequence of SEQ ID NO: 163 or an amino acid sequence with 85%, 90%, 95%, 96%, 97%, 98% or 99% identity to an amino acid sequence of SEQ ID NO: 163.

In one embodiment, the isolated nucleic acid molecule encoding the extracellular CD123 antigen binding domain M12306 comprises a nucleotide sequence of SEQ ID NO: 164, or a sequence with 85%, 90%, 95%, 96%, 97%, 98% or 99% identity thereof. In one embodiment, an isolated nucleic acid molecule is provided wherein the encoded extracellular CD123 antigen binding domain comprises an amino acid sequence of SEQ ID NO: 165 or an amino acid sequence with 85%, 90%, 95%, 96%, 97%, 98% or 99% identity to an amino acid sequence of SEQ ID NO: 165.

In one embodiment, the isolated nucleic acid molecule encoding the extracellular CD123 antigen binding domain M12308 comprises a nucleotide sequence of SEQ ID NO: 166, or a sequence with 85%, 90%, 95%, 96%, 97%, 98% or 99% identity thereof. In one embodiment, an isolated nucleic acid molecule is provided wherein the encoded extracellular CD123 antigen binding domain comprises an amino acid sequence of SEQ ID NO: 167 or an amino acid sequence with 85%, 90%, 95%, 96%, 97%, 98% or 99% identity to an amino acid sequence of SEQ ID NO: 167.

In one embodiment, the isolated nucleic acid molecule encoding the extracellular CD123 antigen binding domain M12311 comprises a nucleotide sequence of SEQ ID NO: 168, or a sequence with 85%, 90%, 95%, 96%, 97%, 98% or 99% identity thereof. In one embodiment, an isolated nucleic acid molecule is provided wherein the encoded extracellular CD123 antigen binding domain comprises an amino acid sequence of SEQ ID NO: 169 or an amino acid sequence with 85%, 90%, 95%, 96%, 97%, 98% or 99% identity to an amino acid sequence of SEQ ID NO: 169.

In one embodiment, the isolated nucleic acid molecule encoding the extracellular CD123 antigen binding domain M12313 comprises a nucleotide sequence of SEQ ID NO: 170, or a sequence with 85%, 90%, 95%, 96%, 97%, 98% or 99% identity thereof. In one embodiment, an isolated nucleic acid molecule is provided wherein the encoded extracellular CD123 antigen binding domain comprises an amino acid sequence of SEQ ID NO: 171 or an amino acid sequence with 85%, 90%, 95%, 96%, 97%, 98% or 99% identity to an amino acid sequence of SEQ ID NO: 171.

In one embodiment, the isolated nucleic acid molecule encoding the extracellular CD123 antigen binding domain M12315 comprises a nucleotide sequence of SEQ ID NO: 172, or a sequence with 85%, 90%, 95%, 96%, 97%, 98% or 99% identity thereof. In one embodiment, an isolated nucleic acid molecule is provided wherein the encoded extracellular CD123 antigen binding domain comprises an amino acid sequence of SEQ ID NO: 173 or an amino acid sequence with 85%, 90%, 95%, 96%, 97%, 98% or 99% identity to an amino acid sequence of SEQ ID NO: 173.

In one embodiment, the isolated nucleic acid molecule encoding the extracellular CD123 antigen binding domain M12317 comprises a nucleotide sequence of SEQ ID NO: 174, or a sequence with 85%, 90%, 95%, 96%, 97%, 98% or 99% identity thereof. In one embodiment, an isolated nucleic acid molecule is provided wherein the encoded extracellular CD123 antigen binding domain comprises an amino acid sequence of SEQ ID NO: 175 or an amino acid sequence with 85%, 90%, 95%, 96%, 97%, 98% or 99% identity to an amino acid sequence of SEQ ID NO: 175.

In one embodiment, the isolated nucleic acid molecule encoding the extracellular CD123 antigen binding domain M12318 comprises a nucleotide sequence of SEQ ID NO: 176, or a sequence with 85%, 90%, 95%, 96%, 97%, 98% or 99% identity thereof. In one embodiment, an isolated nucleic acid molecule is provided wherein the encoded extracellular CD123 antigen binding domain comprises an amino acid sequence of SEQ ID NO: 177 or an amino acid sequence with 85%, 90%, 95%, 96%, 97%, 98% or 99% identity to an amino acid sequence of SEQ ID NO: 177.

In another embodiment, the nucleic acid sequence encoding a functional CAR LTG 2075 that targets CD123-expressing malignancies comprises the nucleic acid sequence of SEQ ID NO: 23 or a sequence with 85%, 90%, 95%, 96%, 97%, 98% or 99% identity thereof, and encodes the CAR comprising the amino acid sequence as set forth in SEQ ID NO: 24 or a sequence with 85%, 90%, 95%, 96%, 97%, 98% or 99% identity thereof.

In another embodiment, the nucleic acid sequence encoding a functional CAR LTG 2076 that targets CD123-expressing malignancies comprises the nucleic acid sequence of SEQ ID NO: 25 or a sequence with 85%, 90%, 95%, 96%, 97%, 98% or 99% identity thereof, and encodes the CAR comprising the amino acid sequence as set forth in SEQ ID NO: 26 or a sequence with 85%, 90%, 95%, 96%, 97%, 98% or 99% identity thereof.

In another embodiment, the nucleic acid sequence encoding a functional CAR LTG 2077 that targets CD123-expressing malignancies comprises the nucleic acid sequence of SEQ ID NO: 115 or a sequence with 85%, 90%, 95%, 96%, 97%, 98% or 99% identity thereof, and encodes the CAR comprising the amino acid sequence as set forth in SEQ ID NO: 116 or a sequence with 85%, 90%, 95%, 96%, 97%, 98% or 99% identity thereof.

In another embodiment, the nucleic acid sequence encoding a functional CAR LTG 2078 that targets CD123-expressing malignancies comprises the nucleic acid sequence of SEQ ID NO: 117 or a sequence with 85%, 90%, 95%, 96%, 97%, 98% or 99% identity thereof, and encodes the CAR comprising the amino acid sequence as set forth in SEQ ID NO: 118 or a sequence with 85%, 90%, 95%, 96%, 97%, 98% or 99% identity thereof.

In another embodiment, the nucleic acid sequence encoding a functional CAR LTG 2079 that targets CD123-expressing malignancies comprises the nucleic acid sequence of SEQ ID NO: 119 or a sequence with 85%, 90%, 95%, 96%, 97%, 98% or 99% identity thereof, and encodes the CAR comprising the amino acid sequence as set forth in SEQ ID NO: 120 or a sequence with 85%, 90%, 95%, 96%, 97%, 98% or 99% identity thereof.

In another embodiment, the nucleic acid sequence encoding a functional CAR LTG 2082 that targets CD123-expressing malignancies comprises the nucleic acid sequence of SEQ ID NO: 121 or a sequence with 85%, 90%, 95%, 96%, 97%, 98% or 99% identity thereof, and encodes the CAR comprising the amino acid sequence as set forth in SEQ ID NO: 122 or a sequence with 85%, 90%, 95%, 96%, 97%, 98% or 99% identity thereof.

In another embodiment, the nucleic acid sequence encoding a functional CAR LTG 2083 that targets CD123-expressing malignancies comprises the nucleic acid sequence of SEQ ID NO: 123 or a sequence with 85%, 90%, 95%, 96%, 97%, 98% or 99% identity thereof, and encodes the CAR comprising the amino acid sequence as set forth in SEQ ID NO: 124 or a sequence with 85%, 90%, 95%, 96%, 97%, 98% or 99% identity thereof.

In another embodiment, the nucleic acid sequence encoding a functional CAR LTG 2085 that targets CD123-expressing malignancies comprises the nucleic acid sequence of SEQ ID NO: 125 or a sequence with 85%, 90%, 95%, 96%, 97%, 98% or 99% identity thereof, and encodes the CAR comprising the amino acid sequence as set forth in SEQ ID NO: 126 or a sequence with 85%, 90%, 95%, 96%, 97%, 98% or 99% identity thereof.

In another embodiment, the nucleic acid sequence encoding a functional CAR LTG 2087 that targets CD123-expressing malignancies comprises the nucleic acid sequence of SEQ ID NO: 127 or a sequence with 85%, 90%, 95%, 96%, 97%, 98% or 99% identity thereof, and encodes the CAR comprising the amino acid sequence as set forth in SEQ ID NO: 128 or a sequence with 85%, 90%, 95%, 96%, 97%, 98% or 99% identity thereof.

In another embodiment, the nucleic acid sequence encoding a functional CAR LTG 2088 that targets CD123-expressing malignancies comprises the nucleic acid sequence of SEQ ID NO: 129 or a sequence with 85%, 90%, 95%, 96%, 97%, 98% or 99% identity thereof, and encodes the CAR comprising the amino acid sequence as set forth in SEQ ID NO: 130 or a sequence with 85%, 90%, 95%, 96%, 97%, 98% or 99% identity thereof.

In one embodiment, the extracellular antigen binding domain in the CAR-based surface antigen-regulated promoter-therapeutic payload constructs may comprise, for example, the scFV binders as disclosed in Applicant's Provisional Patent Application No. 62/736,955, entitled Compositions and Methods for Treating Cancer with Human Anti-CD19/22 Immunotherapy, as filed on Sep. 26, 2018, and assigned Lentigen Technology, Inc. matter number LEN_025.

In one embodiment, the isolated nucleic acid molecule encoding the extracellular CD19/CD22 antigen binding domain comprises a nucleotide sequence SEQ ID NO: 178, or a sequence with 85%, 90%, 95%, 96%, 97%, 98% or 99% identity thereof. In one embodiment, an isolated nucleic acid molecule is provided wherein the encoded extracellular mesothelin antigen binding domain comprises an amino acid sequence of SEQ ID NO: 179 or an amino acid sequence with 85%, 90%, 95%, 96%, 97%, 98% or 99% identity to an amino acid sequence of SEQ ID: 179.

In another embodiment, the nucleic acid sequence encoding a functional CAR LTG 2737 that targets CD19/CD22-expressing malignancies comprises the nucleic acid sequence of SEQ ID NO: 131 or a sequence with 85%, 90%, 95%, 96%, 97%, 98% or 99% identity thereof, and encodes the CAR comprising the amino acid sequence as set forth in SEQ ID NO: 132 or a sequence with 85%, 90%, 95%, 96%, 97%, 98% or 99% identity thereof.

In one embodiment, the extracellular antigen binding domain in the CAR-based surface antigen-regulated promoter-therapeutic payload constructs may comprise, for example, the scFV binders as disclosed in Applicant's co-pending Non-Provisional patent application Ser. No. 16/161,542, entitled Compositions and Methods for Treating Cancer with Human Anti-CD22 Immunotherapy, as filed on Oct. 16, 2018, and assigned Lentigen Technology, Inc. matter number LEN_021.

In one embodiment, the isolated nucleic acid molecule encoding the extracellular CD22 antigen binding domain 16P17 comprises a nucleotide sequence SEQ ID NO: 180, or a sequence with 85%, 90%, 95%, 96%, 97%, 98% or 99% identity thereof. In one embodiment, an isolated nucleic acid molecule is provided wherein the encoded extracellular mesothelin antigen binding domain comprises an amino acid sequence of SEQ ID NO: 181 or an amino acid sequence with 85%, 90%, 95%, 96%, 97%, 98% or 99% identity to an amino acid sequence of SEQ ID: 181.

In one embodiment, the isolated nucleic acid molecule encoding the extracellular CD22 antigen binding domain 16P13 comprises a nucleotide sequence SEQ ID NO: 182, or a sequence with 85%, 90%, 95%, 96%, 97%, 98% or 99% identity thereof. In one embodiment, an isolated nucleic acid molecule is provided wherein the encoded extracellular mesothelin antigen binding domain comprises an amino acid sequence of SEQ ID NO: 183 or an amino acid sequence with 85%, 90%, 95%, 96%, 97%, 98% or 99% identity to an amino acid sequence of SEQ ID: 183.

In another embodiment, the nucleic acid sequence encoding a functional CAR LTG 2209 that targets CD22-expressing malignancies comprises the nucleic acid sequence of SEQ ID NO: 133 or a sequence with 85%, 90%, 95%, 96%, 97%, 98% or 99% identity thereof, and encodes the CAR comprising the amino acid sequence as set forth in SEQ ID NO: 134 or a sequence with 85%, 90%, 95%, 96%, 97%, 98% or 99% identity thereof.

In another embodiment, the nucleic acid sequence encoding a functional CAR LTG 2219 that targets CD22-expressing malignancies comprises the nucleic acid sequence of SEQ ID NO: 135 or a sequence with 85%, 90%, 95%, 96%, 97%, 98% or 99% identity thereof, and encodes the CAR comprising the amino acid sequence as set forth in SEQ ID NO: 136 or a sequence with 85%, 90%, 95%, 96%, 97%, 98% or 99% identity thereof.

In one embodiment, the extracellular antigen binding domain in the CAR-based surface antigen-regulated promoter-therapeutic payload constructs may comprise, for example, the scFV binders as disclosed in Applicant's co-pending Non-Provisional patent application Ser. No. 16/050,754, entitled Compositions and Methods for Treating Cancer with Anti-CD19/20 Immunotherapy, as filed on Jul. 31, 2018, and assigned Lentigen Technology, Inc. matter number LEN_019.

In one embodiment, the isolated nucleic acid molecule encoding the extracellular CD19/CD20 antigen binding domain comprises a nucleotide sequence SEQ ID NO: 141, or a sequence with 85%, 90%, 95%, 96%, 97%, 98% or 99% identity thereof. In one embodiment, an isolated nucleic acid molecule is provided wherein the encoded extracellular mesothelin antigen binding domain comprises an amino acid sequence of SEQ ID NO: 112 or an amino acid sequence with 85%, 90%, 95%, 96%, 97%, 98% or 99% identity to an amino acid sequence of SEQ ID: 112.

In one embodiment, the isolated nucleic acid molecule encoding the extracellular CD19/CD20 antigen binding domain comprises a nucleotide sequence SEQ ID NO: 113, or a sequence with 85%, 90%, 95%, 96%, 97%, 98% or 99% identity thereof. In one embodiment, an isolated nucleic acid molecule is provided wherein the encoded extracellular mesothelin antigen binding domain comprises an amino acid sequence of SEQ ID NO: 114 or an amino acid sequence with 85%, 90%, 95%, 96%, 97%, 98% or 99% identity to an amino acid sequence of SEQ ID: 114.

In another embodiment, the nucleic acid sequence encoding a functional CAR LTG 1496 that targets CD19/CD20-expressing malignancies comprises the nucleic acid sequence of SEQ ID NO: 95 or a sequence with 85%, 90%, 95%, 96%, 97%, 98% or 99% identity thereof, and encodes the CAR comprising the amino acid sequence as set forth in SEQ ID NO: 96 or a sequence with 85%, 90%, 95%, 96%, 97%, 98% or 99% identity thereof.

In another embodiment, the nucleic acid sequence encoding a functional CAR LTG 1497 that targets CD19/CD20-expressing malignancies comprises the nucleic acid sequence of SEQ ID NO: 97 or a sequence with 85%, 90%, 95%, 96%, 97%, 98% or 99% identity thereof, and encodes the CAR comprising the amino acid sequence as set forth in SEQ ID NO: 98 or a sequence with 85%, 90%, 95%, 96%, 97%, 98% or 99% identity thereof.

In yet another embodiment, the nucleic acid sequence encoding a CAR-based surface antigen-regulated promoter-therapeutic payload construct comprises one or more of the nucleic acid sequences disclosed in Applicant's co-pending Continuation-In-Part Patent application Ser. No. 16/134,735, filed Sep. 18, 2018, entitled Compositions and Methods for Treating Cancer with DuoCARs, which claims priority to PCT Application No. PCT/US17/49923, filed Sep. 1, 2017, which in turn claims the benefit of priority under 35 U.S.C. Section 119(e) to U.S. Provisional Patent Application No. 62/382,791 filed on Sep. 2, 2016, the entire contents of each of which are incorporated herein by reference.

Thus, in one embodiment, variant single specificity-based CAR structures that are known to be compatible in Applicant's DuoCAR setting may also utilized to generate the CAR-based surface antigen-regulated promoter-therapeutic payload constructs. Specific examples of the single specificity therapeutic surface antigen-regulated promoter-payload constructs (e.g. CAR-based) on which a DuoCAR-based surface antigen-regulated promoter-therapeutic payload construct technology may be based include the single CD20 targeting vector LTG1495, nucleotide sequence SEQ ID NO: 142 and amino acid sequence SEQ ID NO: 143. A second example is the single specificity CAR LTG2200, specific for CD22, nucleotide sequence SEQ ID NO: 69 and amino acid sequence SEQ ID NO: 70.

In yet another embodiment, variant CAR structures that are known to be compatible in the DuoCAR setting a may also utilized to generate the CAR-based surface antigen-regulated promoter-therapeutic payload constructs included within the scope of this disclosure. These include the CD19-specific CAR LTG1494 described in nucleotide sequence SEQ ID NO: 71 and amino acid sequence SEQ ID NO: 72, respectively. This sequence includes the well-described linker that joins the heavy and light chains of the scFv referred to as the Whitlow linker (amino acid sequence GSTSGSGKPGSGEGSTKG (SEQ ID NO: 184), see Whitlow M., et al., 1993, Protein Eng. 6:989-995). In some cases the Whitlow linker was substituted for a (GGGGS)n linker (SEQ ID NO: 185), for example in a CD19 CAR format, as in LTG1538, nucleotide sequence SEQ ID NO: 73 and amino acid sequence SEQ ID NO: 74, respectively. In another example CARs were created that have alternate transmembrane domains. The anti-CD19 CAR LTG1562, nucleotide sequence SEQ ID NO: 75 and amino acid sequence SEQ ID NO: 76, respectively, utilizes the CD4 (as opposed to CD8) transmembrane domain. Similarly the anti-CD19 CAR LTG1563 has an alternate transmembrane derived from TNFRSF19, nucleotide sequence SEQ ID NO: 77 and amino acid sequence SEQ ID NO: 78, respectively.

In yet another embodiment, another example of a therapeutic application would be the treatment of leukemia that expresses the CD19, CD20, and TSLPR antigens with DuoCAR-based surface antigen-regulated promoter-therapeutic payload constructs of the present invention. In particular, a DuoCAR-based surface antigen-regulated promoter-therapeutic payload construct(s) comprises LTG1496 or LTG 1497 (SEQ ID NOs: 95, 97, respectively) combined with a TSLPR-specific CAR (LTG1789), SEQ ID NO: 101 and amino acid sequence SEQ ID NO: 102, respectively, that has been created from TSLPR-specific scFV domains, nucleotide sequence SEQ ID NO: 99 and amino acid sequence SEQ ID NO: 100.

In one embodiment, each of the aforementioned DuoCAR-based surface antigen-regulated promoter-therapeutic payload constructs, the respective CAR constructs are self-driven by a single surface antigen-regulated promoter with separation of the CAR constructs by a ribosome 2A skip site therebetween.

In another embodiment, each of the aforementioned DuoCAR-based surface antigen-regulated promoter-therapeutic payload constructs, the respective CAR constructs are self-driven by separate surface antigen-regulated promoters.

In certain embodiments, as used herein, a non-limiting example of an anti-cd19 CAR construct includes the anti-cd19 CAR construct encoded by the nucleotide sequence referred to herein as LTG1563 (c.f., SEQ ID NO. 77) and which encodes the anti-cd19 CAR construct identified herein as CAR-LTG1563 (c.f., SEQ ID NO. 78).

In one embodiment, the construction of a surface antigen-regulated inducible promoter-therapeutic payload construct comprising the nucleic acid sequence of SEQ ID NO: 139 and encoding the CAR-based promoter-therapeutic payload construct comprising the amino acid sequence of SEQ ID NO: 78 (CAR LTG1563) is described in Example 1 infra.

In one embodiment, the construction of a surface antigen-regulated inducible promoter-therapeutic payload construct comprising the nucleic acid sequence of SEQ ID NO: 140 and encoding the CAR-based promoter-therapeutic payload construct comprising the amino acid sequence of SEQ ID NO: 78 (CAR LTG1563) is described in Example 1 infra.

In one embodiment, the construction of a surface antigen-regulated inducible promoter-therapeutic payload construct comprising the nucleic acid sequence of SEQ ID NO: 77 and encoding the CAR-based promoter-therapeutic payload construct comprising the amino acid sequence of SEQ ID NO: 78 (CAR LTG1563) is described in Example 1 infra.

Without being intended to limit to any particular mechanism of action, it is believed that possible reasons for the enhanced therapeutic function associated with the exemplary surface antigen-regulated promoter-therapeutic payload constructs of the invention include, for example, and not by way of limitation, a) improved lateral movement within the plasma membrane allowing for more efficient signal transduction, b) superior location within plasma membrane microdomains, such as lipid rafts, and greater ability to interact with transmembrane signaling cascades associated with T cell activation, c) superior location within the plasma membrane by preferential movement away from dampening or down-modulatory interactions, such as less proximity to or interaction with phosphatases such as CD45, and d) superior assembly into T cell receptor signaling complexes (e.g. the immune synapse), or any combination thereof.

Depending on the desired antigen to be targeted, the surface antigen-regulated promoter-therapeutic payload construct can be engineered to include the appropriate antigen binding domain that is specific to the desired antigen target. For example, and not by way of limitation, if CD19 is the desired antigen that is to be targeted, an antibody for CD19 can be used as the antigen binding domain incorporated into the surface antigen-regulated promoter-therapeutic payload construct.

In one exemplary embodiment, the antigen binding domain portion of the CAR-based surface antigen-regulated promoter-therapeutic payload construct targets CD19. Preferably, the extracellular antigen binding domain in the surface antigen-regulated promoter-therapeutic payload construct is anti-CD19 scFV, wherein the nucleic acid sequence of the extracellular anti-CD19 scFV comprises the sequence set forth in SEQ ID NO: 37 or a sequence with 85%, 90%, 95%, 96%, 97%, 98% or 99% identity thereof. In one embodiment, the extracellular anti-CD19 scFV comprises the nucleic acid sequence that encodes the amino acid sequence of SEQ ID NO: 38 or a sequence with 85%, 90%, 95%, 96%, 97%, 98% or 99% identity thereof. In another embodiment, the extracellular anti-CD19 scFV portion of the CAR comprises the amino acid sequence set forth in SEQ ID NO: 38 or a sequence with 85%, 90%, 95%, 96%, 97%, 98% or 99% identity thereof.

In one aspect of the present invention, there is provided a surface antigen-regulated promoter-therapeutic payload construct capable of binding to a non-TSA or non-TAA including, for example and not by way of limitation, an antigen derived from Retroviridae (e.g. human immunodeficiency viruses such as HIV-1 and HIV-LP), Picornaviridae (e.g. poliovirus, hepatitis A virus, enterovirus, human coxsackievirus, rhinovirus, and echovirus), rubella virus, coronavirus, vesicular stomatitis virus, rabies virus, ebola virus, parainfluenza virus, mumps virus, measles virus, respiratory syncytial virus, influenza virus, hepatitis B virus, parvovirus, Adenoviridae, Herpesviridae (e.g. type 1 and type 2 herpes simplex virus (HSV), varicella-zoster virus, cytomegalovirus (CMV), and herpes virus), Poxviridae (e.g. smallpox virus, vaccinia virus, and pox virus), or hepatitis C virus, or any combination thereof.

In another aspect of the present invention, there is provided a surface antigen-regulated promoter-therapeutic payload construct capable of binding to an antigen derived from a bacterial strain of Staphylococci, *Streptococcus*, *Escherichia coli*, *Pseudomonas*, or *Salmonella*. Particularly, there is provided a surface antigen-regulated promoter-therapeutic payload construct capable of binding to an antigen derived from an infectious bacterium, for example, *Helicobacter pyloris*, *Legionella pneumophilia*, a bacterial strain of *Mycobacteria* sps. (e.g. *M. tuberculosis*, *M. avium*, *M. intracellulare*, *M. kansaii*, or *M. gordonea*), *Staphylococcus aureus*, *Neisseria gonorrhoeae*, *Neisseria meningitides*, *Listeria monocytogenes*, *Streptococcus pyogenes*, Group A *Streptococcus*, Group B *Streptococcus* (*Streptococcus agalactiae*), *Streptococcus pneumoniae*, or *Clostridium tetani*, or a combination thereof.

2. Transmembrane Domain

With respect to the transmembrane domain, the CAR-based surface antigen-regulated promoter-therapeutic payload construct comprises one or more TNFRSF transmembrane domains fused to the extracellular domain of the surface antigen-regulated promoter-therapeutic payload construct.

In one embodiment, the TNFRSF transmembrane domain comprises at least one TNFRSF19 transmembrane domain. In one embodiment, an isolated nucleic acid molecule is provided wherein the encoded TNFRSF transmembrane domain comprises a TNFRSF19 transmembrane domain.

In one embodiment, the isolated nucleic acid molecule encoding the TNFRSF19 transmembrane domain comprises a nucleotide sequence of SEQ ID NO: 51, or a sequence with 85%, 90%, 95%, 96%, 97%, 98% or 99% identity thereof. In one embodiment, an isolated nucleic acid molecule is provided wherein the encoded TNFRSF19 transmembrane domain comprises an amino acid sequence of SEQ ID NO: 52, or an amino acid sequence with 85%, 90%, 95%, 96%, 97%, 98% or 99% identity to an amino acid sequence of SEQ ID NO: 52.

The transmembrane domain may be derived either from a natural or from a synthetic source. Where the source is natural, the domain may be derived from any membrane-bound or transmembrane protein.

Transmembrane regions of particular use in the surface antigen-regulated promoter-therapeutic payload construct described herein may be derived from (i.e. comprise) at least the transmembrane region(s) of) the alpha, beta or zeta chain of the T-cell receptor, CD28, CD3 epsilon, CD45, CD4, CD5, CD8, CD9, CD16, CD22, mesothelin, CD33, CD37, CD64, CD80, CD86, CD134, CD137, CD154. Alternatively, the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligoor polypeptide linker, preferably between 2 and 10 amino acids in length may form the linkage between the transmembrane domain and the cytoplasmic signaling domain of the surface antigen-regulated promoter-therapeutic payload construct. A glycine-serine doublet provides a particularly suitable linker.

In one embodiment, the transmembrane domain that naturally is associated with one of the domains in the surface antigen-regulated promoter-therapeutic payload construct is used in addition to the transmembrane domains described supra.

In some instances, the transmembrane domain can be selected by amino acid substitution to avoid binding of such domains to the transmembrane domains of the same or different surface membrane proteins to minimize interactions with other members of the receptor complex.

In one embodiment, the transmembrane domain in the surface antigen-regulated promoter-therapeutic payload construct of the invention is the CD8 transmembrane domain. In one embodiment, the CD8 transmembrane domain comprises the nucleic acid sequence of SEQ ID NO: 27. In one embodiment, the CD8 transmembrane domain comprises the nucleic acid sequence that encodes the amino acid sequence of SEQ ID NO: 28. In another embodiment, the CD8 transmembrane domain comprises the amino acid sequence of SEQ ID NO: 28.

In one embodiment, the encoded transmembrane domain comprises an amino acid sequence having at least one, two or three modifications (e.g., substitutions) but not more than 20, 10 or 5 modifications (e.g., substitutions) of an amino acid sequence of SEQ ID NO: 28, or a sequence with 95-99% identity to an amino acid sequence of SEQ ID NO: 28.

In some instances, the transmembrane domain of the CAR comprises the CD8.alpha.hinge domain. In one embodiment, the CD8 hinge domain comprises the nucleic acid sequence of SEQ ID NO: 29. In one embodiment, the CD8 hinge domain comprises the nucleic acid sequence that encodes the amino acid sequence of SEQ ID NO: 30. In another embodiment, the CD8 hinge domain comprises the amino acid sequence of SEQ ID NO: 30, or a sequence with 95-99% identify thereof.

In one embodiment, an isolated nucleic acid molecule is provided wherein the encoded linker domain is derived from the extracellular domain of CD8, and is linked to the transmembrane CD8 domain, the transmembrane CD28 domain, or a combination thereof.

In one embodiment of the patient-specific autologous anti-tumor lymphocyte cell population(s) as disclosed herein, non-limiting exemplary transmembrane domains for use in the CAR-based surface antigen-regulated promoter-therapeutic payload constructs disclosed herein include the TNFRSF16 and TNFRSF19 transmembrane domains may be used to derive the TNFRSF transmembrane domains and/or linker or spacer domains as disclosed in Applicant's co-pending patent application Ser. No. 15/767,076, entitled CHIMERIC ANTIGEN RECEPTORS AND METHODS OF USE, as filed on Apr. 9, 2018, and assigned Lentigen Technology, Inc. matter number LEN_015 (US), including, in particular, those other TNFRSF members listed within the tumor necrosis factor receptor superfamily as listed in Table I therein.

In one embodiment, the transmembrane domain in the CAR of the invention is the TNFRSF19 transmembrane domain. In one embodiment, the TNFRSF19 transmembrane domain comprises the nucleic acid sequence of SEQ ID NO: 51. In one embodiment, the TNFRSF19 transmembrane domain comprises the nucleic acid sequence that encodes the amino acid sequence of SEQ ID NO: 52. In another embodiment, the TNFRSF19 transmembrane domain comprises the amino acid sequence of SEQ ID NO: 52.

In one embodiment, the encoded transmembrane domain comprises an amino acid sequence having at least one, two or three modifications (e.g., substitutions) but not more than 20, 10 or 5 modifications (e.g., substitutions) of an amino acid sequence of SEQ ID NO: 52, or a sequence with 95-99% identity to an amino acid sequence of SEQ ID NO: 52.

3. Spacer Domain

In the CAR-based surface antigen-regulated promoter-therapeutic payload construct, a spacer domain can be arranged between the extracellular domain and the TNFRSF transmembrane domain, or between the intracellular domain and the TNFRSF transmembrane domain. The spacer domain means any oligopeptide or polypeptide that serves to link the TNFRSF transmembrane domain with the extracellular domain and/or the TNFRSF transmembrane domain with the intracellular domain. The spacer domain comprises up to 300 amino acids, preferably 10 to 100 amino acids, and most preferably 25 to 50 amino acids.

In several embodiments, the linker can include a spacer element, which, when present, increases the size of the linker such that the distance between the effector molecule or the detectable marker and the antibody or antigen binding fragment is increased. Exemplary spacers are known to the person of ordinary skill, and include those listed in U.S. Pat. Nos. 7,964,566, 7,498,298, 6,884,869, 6,323,315, 6,239,104, 6,034,065, 5,780,588, 5,665,860, 5,663,149, 5,635,483, 5,599,902, 5,554,725, 5,530,097, 5,521,284, 5,504,191, 5,410,024, 5,138,036, 5,076,973, 4,986,988, 4,978,744, 4,879,278, 4,816,444, and 4,486,414, as well as U.S. Pat. Pub. Nos. 20110212088 and 20110070248, each of which is incorporated by reference herein in its entirety.

The spacer domain preferably has a sequence that promotes binding of a CAR-based surface antigen-regulated promoter-therapeutic payload construct with an antigen and enhances signaling into a cell. Examples of an amino acid that is expected to promote the binding include cysteine, a charged amino acid, and serine and threonine in a potential glycosylation site, and these amino acids can be used as an amino acid constituting the spacer domain.

As the spacer domain, the entire or a part of amino acid numbers 118 to 178 (SEQ ID NO: 31) which is a hinge region of CD8.alpha. (NCBI RefSeq: NP.sub.-001759.3), amino acid numbers 135 to 195 of CD8.beta. (GenBank: AAA35664.1), amino acid numbers 315 to 396 of CD4 (NCBI RefSeq: NP.sub.-000607.1), or amino acid numbers 137 to 152 of CD28 (NCBI RefSeq: NP.sub.-006130.1) can be used. Also, as the spacer domain, a part of a constant region of an antibody H chain or L chain (CHI region or CL region, for example, a peptide having an amino acid sequence shown in SEQ ID NO: 32) can be used. Further, the spacer domain may be an artificially synthesized sequence.

In addition, an entire or a part of amino acids comprising the constant region of a human IgG4 (UniProt ID: P01861), including CHI, (amino acid numbers 1-98), hinge, SEQ ID NO: 80, and the corresponding nucleotide SEQ ID NO:79, (amino acid numbers 99-110), CH2, amino acid SEQ ID NO: 81 and corresponding nucleotide SEQ ID NO: 80, (amino acid numbers 111-220) and CH3, SEQ ID NO:84 and corresponding nucleotide SEQ ID NO: 83, (amino acid numbers 221-327) or a combination thereof, such as IgG4

Hinge CH2 CH3 domain, SEQ ID NO: 86, and the corresponding nucleotide SEQ ID NO: 85, can be used.

In one embodiment, the spacer domain of the CAR comprises the TNFRSF19 hinge domain which comprises the nucleic acid sequence of SEQ ID NO: 53. In one embodiment, the TNFRSF19 hinge domain comprises the nucleic acid sequence that encodes the amino acid sequence of SEQ ID NO: 54. In another embodiment, the TNFRSF19 hinge domain comprises the amino acid sequence of SEQ ID NO: 54, or a sequence with 95-99% identify thereof.

In one embodiment, the spacer domain of the CAR comprises the TNFRSF19 truncated hinge domain comprises the nucleic acid sequence of SEQ ID NO: 55. In one embodiment, the TNFRSF19 truncated hinge domain comprises the nucleic acid sequence that encodes the amino acid sequence of SEQ ID NO: 56. In another embodiment, the TNFRSF19 truncated hinge domain comprises the amino acid sequence of SEQ ID NO: 56, or a sequence with 95-99% identify thereof.

In one embodiment, the TNFRSF19 hinge and transmembrane domains comprise the nucleic acid sequence of SEQ ID NO: 49. In one embodiment, the TNFRSF19 hinge and transmembrane domains comprise the nucleic acid sequence that encodes the amino acid sequence of SEQ ID NO: 50. In another embodiment, the TNFRSF19 hinge and transmembrane domains comprise the amino acid sequence of SEQ ID NO: 50, or a sequence with 95-99% identify thereof.

In one embodiment, a CD8a hinge domain is fused to a TNFRSF19 transmembrane domain comprising the nucleic acid sequence of SEQ ID NO: 57. In one embodiment, the CD8a hinge domain is fused to a TNFRSF19 transmembrane domain comprises the nucleic acid sequence that encodes the amino acid sequence of SEQ ID NO: 58. In another embodiment, the CD8a hinge domain is fused to a TNFRSF19 transmembrane domain comprises the amino acid sequence of SEQ ID NO: 58, or a sequence with 95-99% identify thereof.

Further, in the surface antigen-regulated promoter-therapeutic payload construct, a signal peptide sequence, also termed leader peptide, can be linked to the N-terminus. The signal peptide sequence exists at the N-terminus of many secretory proteins and membrane proteins, and has a length of 15 to 30 amino acids. Since many of the protein molecules mentioned above as the intracellular domain have signal peptide sequences, the signal peptides can be used as a signal peptide for the surface antigen-regulated promoter-therapeutic payload construct. In one embodiment, the signal peptide comprises the amino acid sequence shown in SEQ ID NO: 14).

In one embodiment, the CD8 alpha leader peptide, is comprising the nucleic acid sequence of SEQ ID NO: 43. In one embodiment, CD8 alpha leader peptide comprises the nucleic acid sequence that encodes the amino acid sequence of SEQ ID NO: 44. In another embodiment, the CD8a hinge domain is fused to a TNFRSF19 transmembrane domain comprises the amino acid sequence of SEQ ID NO: 44, or a sequence with 95-99% identify thereof.

In another embodiment, the GMCSF leader peptide, is comprising the nucleic acid sequence of SEQ ID NO: 39. In one embodiment, the GMCSF leader peptide, comprises the nucleic acid sequence that encodes the amino acid sequence of SEQ ID NO: 40. In another embodiment, the CD8a hinge domain is fused to a TNFRSF19 transmembrane domain comprises the amino acid sequence of SEQ ID NO: 40, or a sequence with 95-99% identify thereof.

In another embodiment, the TNFRSF19 leader peptide is comprising the nucleic acid sequence of SEQ ID NO: 41. In one embodiment, TNFRSF19 leader peptide, and CD8 alpha leader peptide comprises the nucleic acid sequence that encodes the amino acid sequence of SEQ ID NO: 42. In another embodiment, the CD8a hinge domain is fused to a TNFRSF19 transmembrane domain comprises the amino acid sequence of SEQ ID NO: 42, or a sequence with 95-99% identify thereof.

In one embodiment, a tag sequence encoding a truncated sequence of epidermal growth factor receptor (tEGFR) is comprising the nucleic acid sequence of SEQ ID NO: 67. In one embodiment, tEGFR comprises the nucleic acid sequence that encodes the amino acid sequence of SEQ ID NO: 68. In another embodiment, the tEGFR tag comprises the amino acid sequence of SEQ ID NO: 68, or a sequence with 95-99% identify thereof.

In one embodiment, a furin recognition site and downstream T2A self-cleaving peptide sequence, designed for simultaneous bicistronic expression of the tag sequence and the therapeutic payload sequence, is comprising the nucleic acid sequence of SEQ ID NO: 65. In one embodiment, furin and T2A sequence comprises the nucleic acid sequence that encodes the amino acid sequence of SEQ ID NO: 66. In another embodiment, the tEGFR tag comprises the amino acid sequence of SEQ ID NO: 66 or a sequence with 95-99% identify thereof.

In one embodiment, an upstream furin recognition site and T2A self-cleaving peptide sequence and a furin recognition downstream site, designed for simultaneous bicistronic expression of the tag sequence and the CAR sequence, is comprising the nucleic acid sequence of SEQ ID NO: 67. In one embodiment, furin and T2A sequence comprises the nucleic acid sequence that encodes the amino acid sequence of SEQ ID NO: 68. In another embodiment, the tEGFR tag comprises the amino acid sequence of SEQ ID NO: 68 or a sequence with 95-99% identify thereof.

In one embodiment, the targeting domain of the CAR-based surface antigen-regulated promoter-therapeutic payload construct is expressed separately in the form of monoclonal antibody, ScFv Fab, Fab'2 and is containing at binding tag or epitope, whereas the effector-cell expressed component of the surface antigen-regulated promoter-therapeutic payload construct contains a binding domain specifically directed to bind the tag or epitope expressed on the soluble CAR module, such as specific binding on the soluble component of the CAR to the cell bound component forms the full functional CAR structure.

4. Intracellular Domain

The cytoplasmic domain or otherwise the intracellular signaling domain of the CAR is responsible for activation of at least one of the normal effector functions of the immune cell in which the CAR has been placed in. The term "effector function" refers to a specialized function of a cell. Effector function of a T cell, for example, may be cytolytic activity or helper activity including the secretion of cytokines. Thus, the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Preferred examples of intracellular signaling domains for use in the CAR include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the CARs disclosed herein include those derived from TCR zeta (CD3 Zeta), FcR gamma, FcR beta, CD3 gamma, CD3 delta, CD3 epsilon, CD5, CD22, CD79a, CD79b, and CD66d. Specific, non-limiting examples, of the ITAM include peptides having sequences of amino acid numbers 51 to 164 of CD3.zeta. (NCBI RefSeq: NP.sub.-932170.1), amino acid numbers 45 to 86 of Fc.epsilon.RI.gamma. (NCBI RefSeq: NP.sub.-004097.1), amino acid numbers 201 to 244 of Fc.epsilon.RI.beta. (NCBI RefSeq: NP.sub.-000130.1), amino acid numbers 139 to 182 of CD3.gamma. (NCBI RefSeq: NP.sub.-000064.1), amino acid numbers 128 to 171 of CD3 delta. (NCBI RefSeq: NP.sub.-000723. 1), amino acid numbers 153 to 207 of CD3.epsilon. (NCBI RefSeq: NP.sub.-000724.1), amino acid numbers 402 to 495 of CD5 (NCBI RefSeq: NP.sub.-055022.2), amino acid numbers 707 to 847 of 0022 (NCBI RefSeq: NP.sub.-001762.2), amino acid numbers 166 to 226 of CD79a (NCBI RefSeq: NP.sub.-001774.1), amino acid numbers 182 to 229 of CD79b (NCBI RefSeq: NP.sub.-000617. 1), and amino acid numbers 177 to 252 of CD66d (NCBI RefSeq: NP.sub.-001806.2), and their variants having the same function as these peptides have. The amino acid number based on amino acid sequence information of NCBI RefSeq ID or GenBank described herein is numbered based on the full length of the precursor (comprising a signal peptide sequence etc.) of each protein. In one embodiment, the cytoplasmic signaling molecule in the CAR comprises a cytoplasmic signaling sequence derived from CD3 zeta.

In a preferred embodiment, the intracellular domain of the CAR can be designed to comprise the CD3-zeta signaling domain by itself or combined with any other desired cytoplasmic domain(s) useful in the context of the CAR. For example, the intracellular domain of the CAR can comprise a CD3 zeta chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such costimulatory molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. Specific, non-limiting examples, of such costimulatory molecules include peptides having sequences of amino acid numbers 236 to 351 of CD2 (NCBI RefSeq: NP.sub.-001758.2), amino acid numbers 421 to 458 of CD4 (NCBI RefSeq: NP.sub.-000607.1), amino acid numbers 402 to 495 of CD5 (NCBI RefSeq: NP.sub.-055022.2), amino acid numbers 207 to 235 of CD8.alpha. (NCBI RefSeq: NP.sub.-001759.3), amino acid numbers 196 to 210 of CD83 (GenBank: AAA35664.1), amino acid numbers 181 to 220 of CD28 (NCBI RefSeq: NP.sub.-006130.1), amino acid numbers 214 to 255 of CD137 (4-1BB, NCBI RefSeq: NP.sub.-001552.2), amino acid numbers 241 to 277 of CD134 (OX40, NCBI RefSeq: NP.sub.-003318.1), and amino acid numbers 166 to 199 of ICOS (NCBI RefSeq: NP.sub.-036224.1), and their variants having the same function as these peptides have. Thus, while the disclosure herein is exemplified primarily with 4-1BB as the co-stimulatory signaling element, other costimulatory elements are within the scope of the disclosure.

The cytoplasmic signaling sequences within the cytoplasmic signaling portion of the CAR may be linked to each other in a random or specified order. Optionally, a short oligo- or polypeptide linker, preferably between 2 and 10 amino acids in length may form the linkage. A glycine-serine doublet provides a particularly suitable linker.

In one embodiment, the intracellular domain is designed to comprise the signaling domain of CD3-zeta and the signaling domain of CD28. In another embodiment, the intracellular domain is designed to comprise the signaling domain of CD3-zeta and the signaling domain of 4-1BB. In yet another embodiment, the intracellular domain is designed to comprise the signaling domain of CD3-zeta and the signaling domain of CD28 and 4-1BB.

In one embodiment, the intracellular domain in the CAR is designed to comprise the signaling domain of 4-1BB and the signaling domain of CD3-zeta, wherein the signaling domain of 4-1BB comprises the nucleic acid sequence set forth in SEQ ID NO: 33, SEQ ID NO: 45, or SEQ ID NO: 59, respectively and the signaling domain of CD3-zeta comprises the nucleic acid sequence set forth in SEQ ID NO: 35, SEQ ID NO: 47, or SEQ ID NO: 61, respectively.

In one embodiment, the intracellular domain in the CAR is designed to comprise the signaling domain of 4-1BB and the signaling domain of CD3-zeta, wherein the signaling domain of 4-1BB comprises the nucleic acid sequence that encodes the amino acid sequence of SEQ ID NO: 34, SEQ ID NO: 46, or SEQ ID NO: 60, respectively and the signaling domain of CD3-zeta comprises the nucleic acid sequence that encodes the amino acid sequence of SEQ ID NO: 36, or SEQ ID NO: 48, or SEQ ID NO: 62.

In one embodiment, the intracellular domain in the CAR is designed to comprise the signaling domain of 4-1BB and the signaling domain of CD3-zeta, wherein the signaling domain of 4-1BB comprises the amino acid sequence set forth in SEQ ID NO: 34, SEQ ID NO: 46, or SEQ ID NO: 60, respectively and the signaling domain of CD3-zeta comprises the amino acid sequence set forth in SEQ ID NO: 36, SEQ ID NO: 48, or SEQ ID NO: 62, respectively.

In one embodiment, the intracellular domain in the CAR is designed to comprise the signaling domain of CD28 and the signaling domain of CD3-zeta, wherein the signaling domain of CD28 comprises the nucleic acid sequence set forth in SEQ ID NO: 45, or SEQ ID NO: 59, respectively, and the signaling domain of CD3-zeta comprises the nucleic acid sequence set forth in SEQ ID NO: 35, SEQ ID NO: 47, or SEQ ID NO: 61, respectively.

In one embodiment, the intracellular domain in the CAR is designed to comprise the signaling domain of CD28 and the signaling domain of CD3-zeta, wherein the signaling domain of CD28 comprises the nucleic acid sequence that encodes the amino acid sequence of SEQ ID NO: 46, or SEQ ID NO: 60, respectively and the signaling domain of CD3-zeta comprises the nucleic acid sequence that encodes the amino acid sequence of SEQ ID NO: 36, or SEQ ID NO: 48, or SEQ ID NO: 62.

In one embodiment, the intracellular domain in the CAR is designed to comprise the signaling domain of CD28 and the signaling domain of CD3-zeta, wherein the signaling domain of CD28 comprises the amino acid sequence set forth in SEQ ID NO: 46, or SEQ ID NO: 60, respectively and the signaling domain of CD3-zeta comprises the amino acid sequence set forth in SEQ ID NO: 36, SEQ ID NO: 48, or SEQ ID NO: 62, respectively.

5. CARs with Additional Auxiliary Components

In another embodiment, the construction of a surface antigen-regulated inducible promoter-therapeutic payload construct comprising additional auxiliary components comprising dominant negative receptors lacking the intracellular signaling domains of either TGFBRII (TGFBRIIdn) and/or PD1 (PD1dn) which were co-expressed with the CAR LTG1563 construct, via ribosomal skipping sites (P2A) to generate a surface antigen-regulated inducible promoter-therapeutic payload construct comprising the nucleic acid sequence of SEQ ID NO: 103, 105, 107, or a combination thereof, and encoding the CAR-based promoter-therapeutic payload construct comprising the amino acid sequence of SEQ ID NO: 104, 106, 108, or a combination thereof, is described in Example 2 infra.

In another embodiment, the surface antigen-regulated inducible promoter-therapeutic payload construct comprising additional auxiliary components comprising dominant negative receptors lacking the intracellular signaling domains of either TGFBRII (TGFBRIIdn) or PD1 (PD1dn) which are co-expressed with the CAR LTG1563 construct, via skipping sites (P2A) to generate a surface antigen-regulated inducible promoter-therapeutic payload construct comprising the nucleic acid sequence of SEQ ID NO: 103, 105, 107, or a combination thereof, and encoding the CAR-based promoter-therapeutic payload construct comprising the amino acid sequence of SEQ ID NO: 104, 106, 108, or a combination thereof, such that use of the dominant negative receptors dnTGFb and dnPD1 confers prevention of the auto-immunity toxicity typically associated with the use of constitutive activation of the dominant negative receptors, while simultaneously benefiting from the reduced immunosuppression of T cell function when the CAR is expressed and functional, or confers greater resistance to immunosuppression of CAR T cells by tumor microenvironment that each dn receptor alone, or a combination thereof.

In yet another embodiment, an isolated nucleic acid molecule is provided wherein the surface antigen-regulated inducible promoter-therapeutic payload construct comprises the nucleic acid sequence of SEQ ID NO: 103, and encodes the CAR LTG1563 with a dominant negative version of inhibitory TGF-beta receptor comprising the amino acid sequence as set forth in SEQ ID NO: 104, or an amino acid sequence with 85%, 90%, 95%, 96%, 97%, 98% or 99% identity thereof.

In yet another embodiment, an isolated nucleic acid molecule is provided wherein the surface antigen-regulated inducible promoter-therapeutic payload construct comprises the nucleic acid sequence of SEQ ID NO: 105, and encodes the CAR LTG1563 with a dominant negative version of PD1 comprising the amino acid sequence as set forth in SEQ ID NO: 106, or an amino acid sequence with 85%, 90%, 95%, 96%, 97%, 98% or 99% identity thereof.

In yet another embodiment, an isolated nucleic acid molecule is provided wherein the surface antigen-regulated inducible promoter-therapeutic payload construct with the AP1-NFκB_RE promoter with the dominant negative version of inhibitory TGF-beta receptor and the dominant negative version of PD1 co-expressed with the CAR LTG1563 construct, separated by ribosomal skipping sites (P2A) comprising the nucleic acid sequence of SEQ ID NO: 107 (the construct with the dominant negative version of inhibitory TGF-beta receptor and the dominant negative version of PD1 co-expressed with the CAR LTG1563 construct, separated by ribosomal skipping sites (P2A) and encodes the CAR comprising the amino acid sequence as set forth in SEQ ID NO: 108 or an amino acid sequence with 85%, 90%, 95%, 96%, 97%, 98% or 99% identity thereof.

In yet another embodiment, an isolated nucleic acid molecule is provided wherein the surface antigen-regulated inducible promoter-therapeutic payload construct with the STAT5_RE promoter comprises the nucleic acid sequence of SEQ ID NO: 109 and encodes the CAR LTG1563 with a dominant negative version of inhibitory TGF-beta comprising the amino acid sequence as set forth in SEQ ID NO: 104, or an amino acid sequence with 85%, 90%, 95%, 96%, 97%, 98% or 99% identity thereof.

In yet another embodiment, an isolated nucleic acid molecule is provided wherein the surface antigen-regulated inducible promoter-therapeutic payload construct with the STAT5_RE promoter comprises the nucleic acid sequence of SEQ ID NO: 110 and encodes the CAR LTG1563 with the dominant negative version of PD1 comprising the amino acid sequence as set forth in SEQ ID NO: 106, or an amino acid sequence with 85%, 90%, 95%, 96%, 97%, 98% or 99% identity thereof.

In another embodiment, an isolated nucleic acid molecule is provided wherein the surface antigen-regulated inducible promoter-therapeutic payload construct with the STAT5_RE promoter with the dominant negative version of inhibitory TGF-beta receptor and the dominant negative version of PD1 are co-expressed with the CAR LTG1563 construct, separated by ribosomal skipping sites (P2A) comprising the nucleic acid sequence of SEQ ID NO: 111 and encodes the CAR comprising the amino acid sequence as set forth in SEQ ID NO: 108 or an amino acid sequence with 85%, 90%, 95%, 96%, 97%, 98% or 99% identity thereof.

In yet another embodiment, an isolated nucleic acid molecule is provided wherein the constitutive promoter-therapeutic payload construct with the EF1a promoter with the dominant negative version of inhibitory TGF-beta receptor is co-expressed with the CAR LTG1563 construct, wherein the constitutive EF1a promoter is used to express the additional protein with the co-expressed CAR LTG1563 construct.

In yet another embodiment, an isolated nucleic acid molecule is provided wherein the constitutive promoter-therapeutic payload construct with the EF1a promoter with the dominant negative version of PD1 is co-expressed with the CAR LTG1563 construct, wherein the constitutive EF1a promoter is used to express the additional protein with the co-expressed CAR LTG1563 construct.

In yet another embodiment, an isolated nucleic acid molecule is provided wherein the constitutive promoter-therapeutic payload construct with the EF1a promoter with the dominant negative version of inhibitory TGF-beta receptor and the dominant negative version of PD1 is co-expressed with the CAR LTG1563 construct and are separated by ribosomal skipping sites (P2A) wherein the constitutive EF1a promoter is used to successfully express the additional proteins with the co-expressed CAR LTG1563 construct.

6. Additional Description of CARs

Also expressly included within the scope of the invention are functional portions of the surface antigen-regulated promoter-therapeutic payload constructs disclosed herein (e.g. CAR-, cytokine-, chemokine-, trafficking receptor-, bispecific antibody-, a neutralizing/blocking antibody-, a T cell stimulatory receptor-, a truncated inhibitory receptor-, a hybrid inhibitory/activating receptor-, an anti-apoptotic protein-, an shRNA-, a protease-based). The term "functional portion" when used in reference to a CAR refers to any part or fragment of one or more of the CARs disclosed herein, which part or fragment retains the biological activity of the CAR of which it is a part (the parent CAR). Functional portions encompass, for example, those parts of a CAR that retain the ability to recognize target cells, or detect, treat, or prevent a disease, to a similar extent, the same extent, or to a higher extent, as the parent CAR. In reference to the parent CAR, the functional portion can comprise, for instance, about 10%, 25%, 30%, 50%, 68%, 80%, 90%, 95%, or more, of the parent CAR.

The functional portion can comprise additional amino acids at the amino or carboxy terminus of the portion, or at both termini, which additional amino acids are not found in the amino acid sequence of the parent CAR. Desirably, the additional amino acids do not interfere with the biological function of the functional portion (e.g., recognize target cells, detect cancer, treat or prevent cancer, etc.). More desirably, the additional amino acids enhance the biological activity, as compared to the biological activity of the parent CAR.

Included in the scope of the disclosure are functional variants of the CARs disclosed herein. The term "functional variant" as used herein refers to a CAR, polypeptide, or protein having substantial or significant sequence identity or similarity to a parent CAR, which functional variant retains the biological activity of the CAR of which it is a variant. Functional variants encompass, for example, those variants of the CAR described herein (the parent CAR) that retain the ability to recognize target cells to a similar extent, the same extent, or to a higher extent, as the parent CAR. In reference to the parent CAR, the functional variant can, for instance, be at least about 30%, 50%, 75%, 80%, 90%, 98% or more identical in amino acid sequence to the parent CAR.

A functional variant can, for example, comprise the amino acid sequence of the parent CAR with at least one conservative amino acid substitution. Alternatively or additionally, the functional variants can comprise the amino acid sequence of the parent CAR with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent CAR.

Amino acid substitutions of the CARs are preferably conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a nonpolar side chain (e.g., Ala, Gly, Val, He, Leu, Met, Phe, Pro, Trp, Cys, Val, etc.), a basic/positively charged polar amino acid substituted for another basic/positively charged polar amino acid (e.g. Lys, His, Arg, etc.), an uncharged amino acid with a polar side chain substituted for another uncharged amino acid with a polar side chain (e.g., Asn, Gin, Ser, Thr, Tyr, etc.), an amino acid with a beta-branched side-chain substituted for another amino acid with a beta-branched side-chain (e.g., He, Thr, and Val), an amino acid with an aromatic side-chain substituted for another amino acid with an aromatic side chain (e.g., His, Phe, Trp, and Tyr), etc.

The CAR can consist essentially of the specified amino acid sequence or sequences described herein, such that other components, e.g., other amino acids, do not materially change the biological activity of the functional variant.

The CARs (including functional portions and functional variants) can be of any length, i.e., can comprise any number of amino acids, provided that the CARs (or functional portions or functional variants thereof) retain their biological activity, e.g., the ability to specifically bind to antigen, detect diseased cells in a mammal, or treat or prevent disease in a mammal, etc. For example, the CAR can be about 50 to about 5000 amino acids long, such as 50, 70, 75, 100, 125, 150, 175, 200, 300, 400, 500, 600, 700, 800, 900, 1000 or more amino acids in length.

The CARs (including functional portions and functional variants of the invention) can comprise synthetic amino acids in place of one or more naturally-occurring amino acids. Such synthetic amino acids are known in the art, and include, for example, aminocyclohexane carboxylic acid, norleucine, -amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, a-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, -aminocyclopentane carboxylic acid, a-aminocyclohexane carboxylic acid, a-aminocycloheptane carboxylic acid, a-(2-amino-2-norbomane)-carboxylic acid, γ-diaminobutyric acid, β-diaminopropionic acid, homophenylalanine, and a-tert-butylglycine.

The CARs (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

The CARs (including functional portions and functional variants thereof) can be obtained by methods known in the art. The CARs may be made by any suitable method of making polypeptides or proteins. Suitable methods of de novo synthesizing polypeptides and proteins are described in references, such as Chan et al., Fmoc Solid Phase Peptide Synthesis, Oxford University Press, Oxford, United Kingdom, 2000; Peptide and Protein Drug Analysis, ed. Reid, R., Marcel Dekker, Inc., 2000; Epitope Mapping, ed. Westwood et al., Oxford University Press, Oxford, United Kingdom, 2001; and U.S. Pat. No. 5,449,752. Also, polypeptides and proteins can be recombinantly produced using the nucleic acids described herein using standard recombinant methods. See, for instance, Sambrook et al., Molecular Cloning: A Laboratory Manual, 3rd ed., Cold Spring Harbor Press, Cold Spring Harbor, NY 2001; and Ausubel et al., Current Protocols in Molecular Biology, Greene Publishing Associates and John Wiley & Sons, NY, 1994. Further, some of the CARs (including functional portions and functional variants thereof) can be isolated and/or purified from a source, such as a plant, a bacterium, an insect, a mammal, e.g., a rat, a human, etc. Methods of isolation and purification are well-known in the art. Alternatively, the CARs described herein (including functional portions and functional variants thereof) can be commercially synthesized by companies. In this respect, the CARs can be synthetic, recombinant, isolated, and/or purified.

In each of the aforementioned recitations in Section A above, in addition to the CAR-based surface antigen-regulated promoter-therapeutic payload constructs described supra, the surface antigen-regulated promoter-therapeutic payload constructs may further comprise various other therapeutic modalities or auxiliary components comprising one or more of the following: a cytokine comprising IL-2, IL-15, IL-7, TNFa, IFN gamma, IFN beta, IFN alpha, IL-21, IL-33, IL-22, IL-6, IL-10, IL-9, IL-4, IL-12, TGF beta, IL-17, IL-18, a chemokine comprising CCR4, CCR6, CXCR5, a trafficking receptor, such as a cytokine receptor, for example, and not by way of limitation, CCR4, CCR7, CCR2, a bispecific antibody, including a Bi-specific T cell engager (BiTE), for example, and not by way of limitation, anti-CD3 and anti CD19 targeting, or other multi-targeting antibody, a neutralizing/blocking antibody, for example, and not by way of limitation, against PD-L1, IL-6R, IL-1R, expressed as an scFv, or as IgG, or in other configurations, a T cell stimulatory receptor, a truncated inhibitory receptor, a hybrid inhibitory/activating receptor, for example, and not by way of limitation, ectodomain of PD-1, fused to endodomain of CD28, an anti-apoptotic protein, for example, and not by way of limitation, BCL-2, or BCL-XL, an shRNA, a protease, a second CAR T construct, or any combination thereof, each with their aforementioned biological properties as listed supra.

D. Antibodies and Antigen Binding Fragments

One embodiment further provides a CAR-based surface antigen-regulated promoter-therapeutic payload construct, for example and not by way of limitation, a T-cell expressing a CAR, an antibody, or antigen binding domain or portion thereof, which specifically binds to one or more of the antigens disclosed herein. As used herein, a "T-cell expressing a CAR," or a "CAR T cell" means a T-cell expressing a CAR, and has antigen specificity determined by, for example, the antibody-derived targeting domain of the CAR.

As used herein, "antigen binding domain" can include an antibody and antigen binding fragments thereof. The term "antibody" is used herein in the broadest sense and encompasses various antibody structures, including but not limited to monoclonal antibodies, polyclonal antibodies, multi-specific antibodies (e.g., bispecific antibodies), and antigen binding fragments thereof, so long as they exhibit the desired antigen-binding activity. Non-limiting examples of antibodies include, for example, intact immunoglobulins and variants and fragments thereof known in the art that retain binding affinity for the antigen.

A "monoclonal antibody" is an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. The modifier "monoclonal" indicates the character of the antibody as being obtained from a substantially homogeneous population of antibodies, and is not to be construed as requiring production of the antibody by any particular method. In some examples, a monoclonal antibody is an antibody produced by a single clone of B lymphocytes or by a cell into which nucleic acid encoding the light and heavy variable regions of the antibody of a single antibody (or an antigen binding fragment thereof) have been transfected, or a progeny thereof. In some examples monoclonal antibodies are isolated from a subject. Monoclonal antibodies can have conservative amino acid substitutions which have substantially no effect on antigen binding or other immunoglobulin functions. Exemplary methods of production of monoclonal antibodies are known, for example, see Harlow & Lane, Antibodies, A Laboratory Manual, 2nd ed. Cold Spring Harbor Publications, New York (2013).

Typically, an immunoglobulin has heavy (H) chains and light (L) chains interconnected by disulfide bonds. Immunoglobulin genes include the kappa, lambda, alpha, gamma, delta, epsilon and mu constant region genes, as well as the myriad immunoglobulin variable domain genes. There are two types of light chain, lambda ($\lambda$) and kappa ($\kappa$). There are five main heavy chain classes (or isotypes) which determine the functional activity of an antibody molecule: IgM, IgD, IgG, IgA and IgE.

Each heavy and light chain contains a constant region (or constant domain) and a variable region (or variable domain; see, e.g., Kindt et al. Kuby Immunology, $6^{th}$ ed., W.H. Freeman and Co., page 91 (2007).) In several embodiments, the heavy and the light chain variable regions combine to specifically bind the antigen. In additional embodiments, only the heavy chain variable region is required. For example, naturally occurring camelid antibodies consisting of a heavy chain only are functional and stable in the absence of light chain (see, e.g., Hamers-Casterman et al., Nature, 363:446-448, 1993; Sheriff et al., Nat. Struct. Biol., 3:733-736, 1996). References to "VH" or "VH" refer to the variable region of an antibody heavy chain, including that of an antigen binding fragment, such as Fv, ScFv, dsFv or Fab. References to "VL" or "VL" refer to the variable domain of an antibody light chain, including that of an Fv, ScFv, dsFv or Fab.

Light and heavy chain variable regions contain a "framework" region interrupted by three hypervariable regions, also called "complementarity-determining regions" or "CDRs" (see, e.g., Kabat et al., Sequences of Proteins of Immunological Interest, U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The amino acid sequence boundaries of a given CDR can be readily determined using any of a number of well-known schemes, including those described by Kabat et al. ("Sequences of Proteins of Immunological Interest," $5^{th}$ Ed. Public Health Service, National Institutes of Health, Bethesda, M D, 1991; "Kabat" numbering scheme), A1-Lazikani et al., (JMB 273,927-948, 1997; "Chothia" numbering scheme), and Lefranc et al. ("IMGT unique numbering for immunoglobulin and T cell receptor variable domains and Ig superfamily V-like domains," Dev.

Comp. Immunol., 27:55-77, 2003; "IMGT" numbering scheme). The CDRs of each chain are typically referred to as CDR1, CDR2, and CDR3 (from the N-terminus to C-terminus), and are also typically identified by the chain in which the particular CDR is located. Thus, a VH CDR3 is the CDR3 from the variable domain of the heavy chain of the antibody in which it is found, whereas a VL CDR1 is the CDR1 from the variable domain of the light chain of the antibody in which it is found. Light chain CDRs are sometimes referred to as LCDR1, LCDR2, and LCDR3. Heavy chain CDRs are sometimes referred to as HCDR1, HCDR2, and HCDR3.

An "antigen binding fragment" is a portion of a full length antibody that retains the ability to specifically recognize the cognate antigen, as well as various combinations of such portions. Non-limiting examples of antigen binding fragments include Fv, Fab, Fab', Fab'-SH, F(ab')2; diabodies; linear antibodies; single-chain antibody molecules (e.g. ScFv); and multi-specific antibodies formed from antibody fragments. Antibody fragments include antigen binding fragments either produced by the modification of whole antibodies or those synthesized de novo using recombinant DNA methodologies (see, e.g., Kontermann and Dubel (Ed), Antibody Engineering, Vols. 1-2, 2nd Ed., Springer Press, 2010).

A single-chain antibody (ScFv) is a genetically engineered molecule containing the VH and VL domains of one or more antibody(ies) linked by a suitable polypeptide linker as a genetically fused single chain molecule (see, for example, Bird et al., Science, 242:423 426, 1988; Huston et al., Proc. Natl. Acad. Sci., 85:5879 5883, 1988; Ahmad et al., Clin. Dev. Immunol., 2012, doi:10.1155/2012/980250; Marbry, IDrugs, 13:543-549, 2010). The intramolecular orientation of the VH-domain and the VL-domain in a ScFv, is typically not decisive for ScFvs. Thus, ScFvs with both possible arrangements (VH-domain-linker domain-VL-domain; VL-domain-linker domain-VH-domain) may be used.

In a dsFv, the heavy and light chain variable chains have been mutated to introduce a disulfide bond to stabilize the association of the chains. Diabodies also are included, which are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, for example, Holliger et al., Proc. Natl. Acad. Sci., 90:6444 6448, 1993; Poljak et al., Structure, 2:1121 1123, 1994).

Antibodies also include genetically engineered forms such as chimeric antibodies (such as humanized murine antibodies) and heteroconjugate antibodies (such as bispecific antibodies). See also, Pierce Catalog and Handbook, 1994-1995 (Pierce Chemical Co., Rockford, IL); Kuby, J., Immunology, 3rd Ed., W.H. Freeman & Co., New York, 1997.

Non-naturally occurring antibodies can be constructed using solid phase peptide synthesis, can be produced recombinantly, or can be obtained, for example, by screening combinatorial libraries consisting of variable heavy chains and variable light chains as described by Huse et al., Science 246:1275-1281 (1989), which is incorporated herein by reference. These and other methods of making, for example, chimeric, humanized, CDR-grafted, single chain, and bifunctional antibodies, are well known to those skilled in the art (Winter and Harris, Immunol. Today 14:243-246 (1993); Ward et al., Nature 341:544-546 (1989); Harlow and Lane, supra, 1988; Hilyard et al., Protein Engineering: A practical approach (IRL Press 1992); Borrabeck, Antibody Engineering, 2d ed. (Oxford University Press 1995); each of which is incorporated herein by reference).

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. Antibody competition assays are known, and an exemplary competition assay is provided herein.

A "humanized" antibody or antigen binding fragment includes a human framework region and one or more CDRs from a non-human (such as a mouse, rat, or synthetic) antibody or antigen binding fragment. The non-human antibody or antigen binding fragment providing the CDRs is termed a "donor," and the human antibody or antigen binding fragment providing the framework is termed an "acceptor." In one embodiment, all the CDRs are from the donor immunoglobulin in a humanized immunoglobulin. Constant regions need not be present, but if they are, they can be substantially identical to human immunoglobulin constant regions, such as at least about 85-90%, such as about 95% or more identical. Hence, all parts of a humanized antibody or antigen binding fragment, except possibly the CDRs, are substantially identical to corresponding parts of natural human antibody sequences.

A "chimeric antibody" is an antibody which includes sequences derived from two different antibodies, which typically are of different species. In some examples, a chimeric antibody includes one or more CDRs and/or framework regions from one human antibody and CDRs and/or framework regions from another human antibody.

A "fully human antibody" or "human antibody" is an antibody which includes sequences from (or derived from) the human genome, and does not include sequence from another species. In some embodiments, a human antibody includes CDRs, framework regions, and (if present) an Fc region from (or derived from) the human genome. Human antibodies can be identified and isolated using technologies for creating antibodies based on sequences derived from the human genome, for example by phage display or using transgenic animals (see, e.g., Barbas et al. Phage display: A Laboratory Manuel. 1st Ed. New York: Cold Spring Harbor Laboratory Press, 2004. Print; Lonberg, Nat. Biotech., 23: 1117-1125, 2005; Lonenberg, Curr. Opin. Immunol., 20:450-459, 2008).

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a bispecific or bifunctional antibody has two different binding sites.

Methods of testing antibodies for the ability to bind to any functional portion of the CAR are known in the art and include any antibody-antigen binding assay, such as, for example, radioimmunoassay (RIA), ELISA, Western blot, immunoprecipitation, and competitive inhibition assays (see, e.g., Janeway et al., infra, U.S. Patent Application Publication No. 2002/0197266 A1, and U.S. Pat. No. 7,338, 929).

Also, a CAR, a T cell expressing a CAR, an antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

In each of the aforementioned recitation in Section B above, in addition to the CAR-based surface antigen-regulated promoter-therapeutic payload constructs described supra, the surface antigen-regulated promoter-therapeutic payload constructs may further comprise various other therapeutic modalities comprising one or more of the following: a cytokine comprising IL-2, IL-15, IL-7, TNFa, IFN gamma, IFN beta, IFN alpha, IL-21, IL-33, IL-22, IL-6, IL-10, IL-9, IL-4, IL-12, TGF beta, IL-17, IL-18, a chemokine comprising CCR4, CCR6, CXCR5, a trafficking receptor, such as a cytokine receptor, for example, and not by way of limitation, CCR4, CCR7, CCR2, a bispecific antibody, including a Bi-specific T cell engager (BiTE), for example, and not by way of limitation, anti-CD3 and anti CD19 targeting, or other multi-targeting antibody, a neutralizing/blocking antibody, for example, and not by way of limitation, against PD-L1, IL-6R, IL-1R, expressed as an scFv, or as IgG, or in other configurations, a T cell stimulatory receptor, a truncated inhibitory receptor, a hybrid inhibitory/activating receptor, for example, and not by way of limitation, ectodomain of PD-1, fused to endodomain of CD28, an anti-apoptotic protein, for example, and not by way of limitation, BCL-2, or BCL-XL, an shRNA, a protease, a second CAR T construct, or any combination thereof, each with their aforementioned biological properties as listed supra.

E. Conjugates

A surface antigen-regulated promoter-therapeutic payload construct (e.g., CAR-, cytokine-chemokine-, trafficking receptor-, bispecific antibody-, a neutralizing/blocking antibody-, a T-cell stimulatory receptor-, a truncated inhibitory receptor-, a hybrid inhibitory/activating receptor-, an anti-apoptotic protein-, an shRNA-, a protease-based), expressing, for example, a CAR or monoclonal antibodies, or antigen binding fragments thereof, specific for one or more of the antigens disclosed herein, can be conjugated to an agent, such as an effector molecule or detectable marker, using any number of means known to those of skill in the art. Both covalent and noncovalent attachment means may be used. Conjugates include, but are not limited to, molecules in which there is a covalent linkage of an effector molecule or a detectable marker to an antibody or antigen binding fragment that specifically binds one or more of the antigens disclosed herein. One of skill in the art will appreciate that various effector molecules and detectable markers can be used, including (but not limited to) chemotherapeutic agents, anti-angiogenic agents, toxins, radioactive agents such as $^{125}$I, $^{32}$P, $^{14}$C, $^{3}$H and $^{35}$S and other labels, target moieties and ligands, etc.

The choice of a particular effector molecule or detectable marker depends on the particular target molecule or cell, and the desired biological effect. Thus, for example, the effector molecule can be a cytotoxin that is used to bring about the death of a particular target cell (such as a tumor cell).

The procedure for attaching an effector molecule or detectable marker to an antibody or antigen binding fragment varies according to the chemical structure of the effector. Polypeptides typically contain a variety of functional groups; such as carboxylic acid (COOH), free amine (—NH$_2$) or sulfhydryl (—SH) groups, which are available for reaction with a suitable functional group on an antibody to result in the binding of the effector molecule or detectable marker. Alternatively, the antibody or antigen binding fragment is derivatized to expose or attach additional reactive functional groups. The derivatization may involve attachment of any of a number of known linker molecules such as those available from Pierce Chemical Company, Rockford, IL. The linker can be any molecule used to join the antibody or antigen binding fragment to the effector molecule or detectable marker. The linker is capable of forming covalent bonds to both the antibody or antigen binding fragment and to the effector molecule or detectable marker. Suitable linkers are well known to those of skill in the art and include, but are not limited to, straight or branched-chain carbon linkers, heterocyclic carbon linkers, or peptide linkers. Where the antibody or antigen binding fragment and the effector molecule or detectable marker are polypeptides, the linkers may be joined to the constituent amino acids through their side groups (such as through a disulfide linkage to cysteine) or to the alpha carbon amino and carboxyl groups of the terminal amino acids.

In several embodiments, the linker can include a spacer element, which, when present, increases the size of the linker such that the distance between the effector molecule or the detectable marker and the antibody or antigen binding fragment is increased. Exemplary spacers are known to the person of ordinary skill, and include those listed in U.S. Pat. Nos. 7,964,566, 7,498,298, 6,884,869, 6,323,315, 6,239,104, 6,034,065, 5,780,588, 5,665,860, 5,663,149, 5,635,483, 5,599,902, 5,554,725, 5,530,097, 5,521,284, 5,504,191, 5,410,024, 5,138,036, 5,076,973, 4,986,988, 4,978,744, 4,879,278, 4,816,444, and 4,486,414, as well as U.S. Pat. Pub. Nos. 20110212088 and 20110070248, each of which is incorporated by reference herein in its entirety.

In some embodiments, the linker is cleavable under intracellular conditions, such that cleavage of the linker releases the effector molecule or detectable marker from the antibody or antigen binding fragment in the intracellular environment. In yet other embodiments, the linker is not cleavable and the effector molecule or detectable marker is released, for example, by antibody degradation. In some embodiments, the linker is cleavable by a cleaving agent that is present in the intracellular environment (for example, within a lysosome or endosome or caveolea). The linker can be, for example, a peptide linker that is cleaved by an intracellular peptidase or protease enzyme, including, but not limited to, a lysosomal or endosomal protease. In some embodiments, the peptide linker is at least two amino acids long or at least three amino acids long. However, the linker can be 4, 5, 6, 7, 8, 9, 10, 11, 12, 13, 14 or 15 amino acids long, such as 1-2, 1-3, 2-5, 3-10, 3-15, 1-5, 1-10, 1-15 amino acids long. Proteases can include cathepsins B and D and plasmin, all of which are known to hydrolyze dipeptide drug derivatives resulting in the release of active drug inside target cells (see, for example, Dubowchik and Walker, 1999, Pharm. Therapeutics 83:67-123). For example, a peptide linker that is cleavable by the thiol-dependent protease cathepsin-B, can be used (for example, a Phenylalanine-Leucine or a Glycine-Phenylalanine-Leucine-Glycine linker (SEQ ID NO: 186)). Other examples of such linkers are described, for example, in U.S. Pat. No. 6,214,345, incorporated herein by reference. In a specific embodiment, the peptide linker cleavable by an intracellular protease is a Valine-Citruline linker or a Phenylalanine-Lysine linker (see, for example, U.S. Pat. No. 6,214,345, which describes the synthesis of doxorubicin with the Valine-Citruline linker).

In other embodiments, the cleavable linker is pH-sensitive, i.e., sensitive to hydrolysis at certain pH values. Typically, the pH-sensitive linker is hydrolyzable under acidic conditions. For example, an acid-labile linker that is hydrolyzable in the lysosome (for example, a hydrazone, semicarbazone, thiosemicarbazone, cis-aconitic amide, orthoester, acetal, ketal, or the like) can be used. (See, for example, U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, for example, a thioether attached to the therapeutic agent via an acylhydrazone bond (see, for example, U.S. Pat. No. 5,622,929).

In other embodiments, the linker is cleavable under reducing conditions (for example, a disulfide linker). A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene)-, SPDB and SMPT. (See, for example, Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987); Phillips et al., Cancer Res. 68:92809290, 2008). See also U.S. Pat. No. 4,880,935.)

In yet other specific embodiments, the linker is a malonate linker (Johnson et al., 1995, Anticancer Res. 15:1387-93), a maleimidobenzoyl linker (Lau et al., 1995, Bioorg-Med-Chem. 3(10):1299-1304), or a 3'-N-amide analog (Lau et al., 1995, Bioorg-Med-Chem. 3(10):1305-12).

In yet other embodiments, the linker is not cleavable and the effector molecule or detectable marker is released by antibody degradation. (See U.S. Publication No. 2005/0238649 incorporated by reference herein in its entirety).

In several embodiments, the linker is resistant to cleavage in an extracellular environment. For example, no more than about 20%, no more than about 15%, no more than about 10%, no more than about 5%, no more than about 3%, or no more than about 1% of the linkers, in a sample of conjugate, are cleaved when the conjugate is present in an extracellular environment (for example, in plasma). Whether or not a linker is resistant to cleavage in an extracellular environment can be determined, for example, by incubating the conjugate containing the linker of interest with plasma for a predetermined time period (for example, 2, 4, 8, 16, or 24 hours) and then quantitating the amount of free effector molecule or detectable marker present in the plasma. A variety of exemplary linkers that can be used in conjugates are described in WO 2004-010957, U.S. Publication No. 2006/0074008, U.S. Publication No. 20050238649, and U.S. Publication No. 2006/0024317, each of which is incorporated by reference herein in its entirety.

In several embodiments, a surface antigen-regulated promoter-therapeutic payload construct conjugate (e.g., CAR-, cytokine-, chemokine-, trafficking receptor-, bispecific antibody-, a neutralizing/blocking antibody-, a T-cell stimulatory receptor-, a truncated inhibitory receptor-, a hybrid inhibitory/activating receptor-, an anti-apoptotic protein-, an shRNA-, a protease-based), expressing, for example, a CAR, an antibody, or antigen binding portion thereof, and one or more small molecule toxins, such as a calicheamicin, maytansinoids, dolastatins, auristatins, a trichothecene, and CC1065, and the derivatives of these toxins that have toxin activity, are provided.

Maytansine compounds suitable for use as maytansinoid toxin moieties are well known in the art, and can be isolated from natural sources according to known methods, produced using genetic engineering techniques (see Yu et al. (2002) PNAS 99:7968-7973), or maytansinol and maytansinol analogues prepared synthetically according to known methods. Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, each of which is incorporated herein by reference. Conjugates containing maytansinoids, methods of making same, and their therapeutic use are disclosed, for example, in U.S. Pat. Nos. 5,208,020; 5,416,064; 6,441,163 and European Patent EP 0 425 235 B1, the disclosures of which are hereby expressly incorporated by reference.

Additional toxins can be employed with a surface antigen-regulated promoter-therapeutic payload construct conjugate (e.g., CAR-, cytokine-, chemokine-, trafficking receptor-, bispecific antibody-, a neutralizing/blocking antibody-, a T-cell stimulatory receptor-, a truncated inhibitory receptor-, a hybrid inhibitory/activating receptor-, an anti-apoptotic protein-, an shRNA-, a protease-based), expressing, for example CAR, a T cell expressing a CAR, an antibody, or antigen binding portion thereof. Exemplary toxins include *Pseudomonas* exotoxin (PE), ricin, abrin, diphtheria toxin and subunits thereof, ribotoxin, ribonuclease, saporin, and calicheamicin, as well as botulinum toxins A through F. These toxins are well known in the art and many are readily available from commercial sources (for example, Sigma Chemical Company, St. Louis, MO). Contemplated toxins also include variants of the toxins (see, for example, U.S. Pat. Nos. 5,079,163 and 4,689,401).

Saporin is a toxin derived from *Saponaria officinalis* that disrupts protein synthesis by inactivating the 60S portion of the ribosomal complex (Stirpe et al., Bio/Technology, 10:405-412, 1992). However, the toxin has no mechanism for specific entry into cells, and therefore requires conjugation to an antibody or antigen binding fragment that recognizes a cell-surface protein that is internalized in order to be efficiently taken up by cells.

Diphtheria toxin is isolated from *Corynebacterium diphtheriae*. Typically, diphtheria toxin for use in immunotoxins is mutated to reduce or to eliminate non-specific toxicity. A mutant known as CRM107, which has full enzymatic activity but markedly reduced non-specific toxicity, has been known since the 1970's (Laird and Groman, J. Virol. 19:220, 1976), and has been used inhuman clinical trials. See, U.S. Pat. Nos. 5,792,458 and 5,208,021.

Ricin is the lectin RCA60 from *Ricinus communis* (Castor bean). For examples of ricin, see, U.S. Pat. Nos. 5,079,163 and 4,689,401. *Ricinus communis* agglutinin (RCA) occurs in two forms designated $RCA_{60}$ and $RCA_{120}$ according to their molecular weights of approximately 65 and 120 kD, respectively (Nicholson & Blaustein, J. Biochim. Biophys. Acta 266:543, 1972). The A chain is responsible for inactivating protein synthesis and killing cells. The B chain binds ricin to cell-surface galactose residues and facilitates transport of the A chain into the cytosol (Olsnes et al., Nature 249:627-631, 1974 and U.S. Pat. No. 3,060,165).

Ribonucleases have also been conjugated to targeting molecules for use as immunotoxins (see Suzuki et al., Nat. Biotech. 17:265-70, 1999). Exemplary ribotoxins such as α-sarcin and restrictocin are discussed in, for example Rathore et al., Gene 190:31-5, 1997; and Goyal and Batra, Biochem. 345 Pt 2:247-54, 2000. Calicheamicins were first isolated from *Micromonospora echinospora* and are members of the enediyne antitumor antibiotic family that cause double strand breaks in DNA that lead to apoptosis (see, for example Lee et al., J. Antibiot. 42:1070-87,1989). The drug is the toxic moiety of an immunotoxin in clinical trials (see, for example, Gillespie et al., Ann. Oncol. 11:735-41, 2000).

Abrin includes toxic lectins from *Abrus precatorius*. The toxic principles, abrin a, b, c, and d, have a molecular weight of from about 63 and 67 kD and are composed of two disulfide-linked polypeptide chains A and B. The A chain inhibits protein synthesis; the B chain (abrin-b) binds to D-galactose residues (see, Funatsu et al., Agr. Biol. Chem. 52:1095, 1988; and Olsnes, Methods Enzymol. 50:330-335, 1978).

A surface antigen-regulated promoter-therapeutic payload construct (e.g., CAR-, cytokine-chemokine-, trafficking receptor-, bispecific antibody-, a neutralizing/blocking antibody-, a T-cell stimulatory receptor-, a truncated inhibitory receptor-, a hybrid inhibitory/activating receptor-, an anti-apoptotic protein-, an shRNA-, a protease-based), expressing, for example, a CAR, monoclonal antibodies, antigen binding fragments thereof, specific for one or more of the antigens disclosed herein, can also be conjugated with a detectable marker; for example, a detectable marker capable of detection by ELISA, spectrophotometry, flow cytometry, microscopy or diagnostic imaging techniques (such as computed tomography (CT), computed axial tomography (CAT) scans, magnetic resonance imaging (MRI), nuclear magnetic resonance imaging NMRI), magnetic resonance tomography (MTR), ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). For example, useful detectable markers include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, Green fluorescent protein (GFP), Yellow fluorescent protein (YFP). A CAR, a T cell expressing a CAR, an antibody, or antigen binding portion thereof, can also be conjugated with enzymes that are useful for detection, such as horseradish peroxidase, β-galactosidase, luciferase, alkaline phosphatase, glucose oxidase and the like. When a CAR, a T cell expressing a CAR, an antibody, or antigen binding portion thereof, is conjugated with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. A CAR, a T cell expressing a CAR, an antibody, or antigen binding portion thereof, may also be conjugated with biotin, and detected through indirect measurement of avidin or streptavidin binding. It should be noted that the avidin itself can be conjugated with an enzyme or a fluorescent label.

A surface antigen-regulated promoter-therapeutic payload construct (e.g., CAR-, cytokine-chemokine-, trafficking receptor-, bispecific antibody-, a neutralizing/blocking antibody-, a T-cell stimulatory receptor-, a truncated inhibitory receptor-, a hybrid inhibitory/activating receptor-, an anti-apoptotic protein-, an shRNA-, a protease-based), expressing, for example, a CAR, an antibody, or antigen binding portion thereof, may be conjugated with a paramagnetic agent, such as gadolinium. Paramagnetic agents such as superparamagnetic iron oxide are also of use as labels. Antibodies can also be conjugated with lanthanides (such as europium and dysprosium), and manganese. An antibody or antigen binding fragment may also be labeled with a predetermined polypeptide epitopes recognized by a secondary reporter (such as leucine zipper pair sequences, binding sites for secondary antibodies, metal binding domains, epitope tags).

A surface antigen-regulated promoter-therapeutic payload construct (e.g., CAR-, cytokine-chemokine-, trafficking receptor-, bispecific antibody-, a neutralizing/blocking antibody-, a T-cell stimulatory receptor-, a truncated inhibitory receptor-, a hybrid inhibitory/activating receptor-, an anti-apoptotic protein-, an shRNA-, a protease-based), expressing, for example, a CAR, an antibody, or antigen binding portion thereof, can also be conjugated with a radiolabeled amino acid. The radiolabel may be used for both diagnostic and therapeutic purposes. For instance, the radiolabel may be used to detect one or more of the antigens disclosed herein and antigen expressing cells by x-ray, emission spectra, or other diagnostic techniques. Further, the radiolabel may be used therapeutically as a toxin for treatment of tumors in a subject, for example for treatment of a neuroblastoma. Examples of labels for polypeptides include, but are not limited to, the following radioisotopes or radionucleotides: $^{3}H$, $^{14}C$, $^{15}N$, $^{35}S$, $^{90}Y$, $^{99}Tc$, $^{111}In$, $^{125}I$, $^{131}I$.

Means of detecting such detectable markers are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

In each of the aforementioned recitations in Section C above, in addition to the CAR-based surface antigen-regulated promoter-therapeutic payload conjugate constructs described supra, the surface antigen-regulated promoter-therapeutic payload conjugate constructs may further comprise various other therapeutic modalities comprising one or more of the following: a cytokine comprising IL-2, IL-15, IL-7, TNFa, IFN gamma, IFN beta, IFN alpha, IL-21, IL-33, IL-22, IL-6, IL-10, IL-9, IL-4, IL-12, TGF beta, IL-17, IL-18, a chemokine comprising CCR4, CCR6, CXCR5, a trafficking receptor, such as a cytokine receptor, for example, and not by way of limitation, CCR4, CCR7, CCR2, a bispecific antibody, including a Bi-specific T cell engager (BiTE), for example, and not by way of limitation, anti-CD3 and anti CD19 targeting, or other multi-targeting antibody, a neutralizing/blocking antibody, for example, and not by way of limitation, against PD-L1, IL-6R, IL-1R, expressed as an scFv, or as IgG, or in other configurations, a T cell stimulatory receptor, a truncated inhibitory receptor, a hybrid inhibitory/activating receptor, for example, and not by way of limitation, ectodomain of PD-1, fused to endodomain of CD28, an anti-apoptotic protein, for example, and not by way of limitation, BCL-2, or BCL-XL, an shRNA, a protease, a second CAR T construct, or any combination thereof, each with their aforementioned biological properties as listed supra.

F. Nucleotides, Expression, Vectors, and Host Cells

Further provided by an embodiment of the invention is a nucleic acid comprising a nucleotide sequence encoding any of surface antigen-regulated promoter-therapeutic payload constructs (e.g., CAR-, cytokine-, chemokine-, trafficking receptor-, bispecific antibody-, a neutralizing/blocking antibody-, a T-cell stimulatory receptor-, a truncated inhibitory receptor-, a hybrid inhibitory/activating receptor-, an anti-apoptotic protein-, an shRNA-, a protease-based), an antibody, or antigen binding portion thereof, described herein (including functional portions and functional variants thereof). The nucleic acids of the invention may comprise a nucleotide sequence encoding any of the leader sequences, antigen binding domains, transmembrane domains, and/or intracellular T cell signaling domains described herein.

In some embodiments, the nucleotide sequence may be codon-modified. Without being bound to a particular theory, it is believed that codon optimization of the nucleotide sequence increases the translation efficiency of the mRNA transcripts. Codon optimization of the nucleotide sequence may involve substituting a native codon for another codon that encodes the same amino acid, but can be translated by tRNA that is more readily available within a cell, thus increasing translation efficiency. Optimization of the nucleotide sequence may also reduce secondary mRNA structures that would interfere with translation, thus increasing translation efficiency.

In an embodiment of the invention, the nucleic acid may comprise a codon-modified nucleotide sequence that encodes the antigen binding domain of the inventive CAR. In another embodiment of the invention, the nucleic acid may comprise a codon-modified nucleotide sequence that encodes any of the CARs described herein (including functional portions and functional variants thereof).

"Nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In some embodiments, the nucleic acid does not comprise any insertions, deletions, inversions, and/or substitutions. However, it may be suitable in some instances, as discussed herein, for the nucleic acid to comprise one or more insertions, deletions, inversions, and/or substitutions.

A recombinant nucleic acid may be one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques, such as those described in Sambrook et al., supra. The nucleic acids can be constructed based on chemical synthesis and/or enzymatic ligation reactions using procedures known in the art. See, for example, Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3—(3-amino-3-N-2-carboxypropyl) uracil, and 2,6-diaminopurine. Alternatively, one or more of the nucleic acids of the invention can be purchased from companies, such as Integrated DNA Technologies (Coralville, IA, USA).

The nucleic acid can comprise any isolated or purified nucleotide sequence which encodes any of the CARs or functional portions or functional variants thereof. Alternatively, the nucleotide sequence can comprise a nucleotide sequence which is degenerate to any of the sequences or a combination of degenerate sequences.

An embodiment also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions may hybridize under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive CARs. It is generally appreciated that conditions can be rendered more stringent by the addition of increasing amounts of formamide.

Also provided is a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein.

In an embodiment, the nucleic acids can be incorporated into a recombinant expression vector. In this regard, an embodiment provides recombinant expression vectors comprising any of the nucleic acids. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors are not naturally-occurring as a whole.

However, parts of the vectors can be naturally-occurring. The recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. Preferably, the non-naturally occurring or altered nucleotides or internucleotide linkages do not hinder the transcription or replication of the vector.

In an embodiment, the recombinant expression vector can be any suitable recombinant expression vector, and can be used to transform or transfect any suitable host cell. Suitable vectors include those designed for propagation and expansion or for expression or both, such as plasmids and viruses. The vector can be selected from the group consisting of the pUC series (Fermentas Life Sciences, Glen Burnie, MD), the pBluescript series (Stratagene, LaJolla, CA), the pET series (Novagen, Madison, WI), the pGEX series (Pharmacia Biotech, Uppsala, Sweden), and the pEX series (Clontech, Palo Alto, CA).

Bacteriophage vectors, such as λvTIO, λvTI 1, λZapII (Stratagene), EMBL4, and λNMI 149, also can be used. Examples of plant expression vectors include pBIOl, pBI101.2, pBHOl 0.3, pBI121 and pBIN19 (Clontech). Examples of animal expression vectors include pEUK-Cl, pMAM, and pMAMneo (Clontech). The recombinant expression vector may be a viral vector, e.g., a retroviral vector or a lentiviral vector. A lentiviral vector is a vector derived from at least a portion of a lentivirus genome, including especially a self-inactivating lentiviral vector as provided in Milone et al., Mol. Ther. 17(8): 1453-1464 (2009). Other examples of lentivirus vectors that may be used in the clinic, include, for example, and not by way of limitation, the LENTIVECTOR® gene delivery technology from Oxford BioMedica plc, the LENTIMAX™ vector system from Lentigen and the like. Nonclinical types of lentiviral vectors are also available and would be known to one skilled in the art.

A number of transfection techniques are generally known in the art (see, e.g., Graham et al., Virology, 52: 456-467 (1973); Sambrook et al., supra; Davis et al., Basic Methods in Molecular Biology, Elsevier (1986); and Chu et al, Gene, 13: 97 (1981).

Transfection methods include calcium phosphate co-precipitation (see, e.g., Graham et al., supra), direct micro injection into cultured cells (see, e.g., Capecchi, Cell, 22: 479-488 (1980)), electroporation (see, e.g., Shigekawa et al., BioTechniques, 6: 742-751 (1988)), liposome mediated gene transfer (see, e.g., Mannino et al., BioTechniques, 6: 682-690 (1988)), lipid mediated transduction (see, e.g., Feigner et al., Proc. Natl. Acad. Sci. USA, 84: 7413-7417 (1987)), and nucleic acid delivery using high velocity microprojectiles (see, e.g., Klein et al, Nature, 327: 70-73 (1987)).

In an embodiment, the recombinant expression vectors can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColE1, 2μ plasmid, λ, SV40, bovine papilloma virus, and the like.

The recombinant expression vector may comprise regulatory sequences, such as transcription and translation initiation and termination codons, which are specific to the type of host cell (e.g., bacterium, fungus, plant, or animal) into which the vector is to be introduced, as appropriate, and taking into consideration whether the vector is DNA- or RNA-based. The recombinant expression vector may comprise restriction sites to facilitate cloning.

The recombinant expression vector can include one or more marker genes, which allow for selection of transformed or transfected host cells. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the CAR (including functional portions and functional variants thereof), or to the nucleotide sequence which is complementary to or which hybridizes to the nucleotide sequence encoding the CAR. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, or a promoter found in the long-terminal repeat of the murine stem cell virus.

The recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art (see, for example, Suicide Gene Therapy: Methods and Reviews, Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine daminase, purine nucleoside phosphorylase, and nitroreductase.

An embodiment further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5a E. coli cells, Chinese hamster ovarian cells, monkey VERO cells, COS cells, HEK293 cells, and the like. For purposes of amplifying or replicating the recombinant expression vector, the host cell may be a prokaryotic cell, e.g., a DH5a cell. For purposes of producing a recombinant CAR, the host cell may be a mammalian cell. The host cell may be a human cell. While the host cell can be of any cell type, can originate from any type of tissue, and can be of any developmental stage, the host cell may be a peripheral blood lymphocyte (PBL) or a peripheral blood mononuclear cell (PBMC). The host cell may be a T cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. The T cell may be a human T cell. The T cell may be a T cell isolated from a human. The T cell can be any type of T cell and can be of any developmental stage, including but not limited to, CD4$^+$/CD8$^+$ double positive T cells, CD4$^+$ helper T cells, e.g., Th1 and Th2 cells, CD8$^+$ T cells (e.g., cytotoxic T cells), tumor infiltrating cells, memory T cells, memory stem cells, i.e. Tscm, naive T cells, and the like. The T cell may be a CD8$^+$ T cell or a CD4$^+$ T cell.

In an embodiment, the surface antigen-regulated promoter-therapeutic payload constructs as described herein can be used in suitable non-T cells. Such cells are those with an immune-effector function, such as, for example, NK cells, and T-like cells generated from pluripotent stem cells.

Also provided by an embodiment is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cell, a muscle cell, a brain cell, etc. Alternatively, the population of cells can be a substantially homogeneous population, in which the population comprises mainly host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

CARs (including functional portions and variants thereof), nucleic acids, recombinant expression vectors, host cells (including populations thereof), and antibodies (including antigen binding portions thereof), can be isolated and/or purified. For example, a purified (or isolated) host cell preparation is one in which the host cell is more pure than cells in their natural environment within the body. Such host cells may be produced, for example, by standard purification techniques. In some embodiments, a preparation of a host cell is purified such that the host cell represents at least about 50%, for example at least about 70%, of the total cell content of the preparation. For example, the purity can be at least about 50%, can be greater than about 60%, about 70% or about 80%, or can be about 100%.

In each of the aforementioned recitations in Section D above, in addition to the CAR-based surface antigen-regulated promoter-therapeutic payload construct nucleotides, expression, vectors, and host cells described supra, the surface antigen-regulated promoter-therapeutic payload constructs may further comprise various other therapeutic modalities comprising one or more of the following: a cytokine comprising IL-2, IL-15, IL-7, TNFa, IFN gamma, IFN beta, IFN alpha, IL-21, IL-33, IL-22, IL-6, IL-10, IL-9, IL-4, IL-12, TGF beta, IL-17, IL-18, a chemokine comprising CCR4, CCR6, CXCR5, a trafficking receptor, such as a cytokine receptor, for example, and not by way of limitation, CCR4, CCR7, CCR2, a bispecific antibody, including a Bi-specific T cell engager (BiTE), for example, and not by way of limitation, anti-CD3 and anti CD19 targeting, or other multi-targeting antibody, a neutralizing/blocking antibody, for example, and not by way of limitation, against PD-L1, IL-6R, IL-1R, expressed as an scFv, or as IgG, or in other configurations, a T cell stimulatory receptor, a truncated inhibitory receptor, a hybrid inhibitory/activating receptor, for example, and not by way of limitation, ectodomain of PD-1, fused to endodomain of CD28, an anti-apoptotic protein, for example, and not by way of limitation, BCL-2, or BCL-XL, an shRNA, a protease, a second CAR T construct, or any combination thereof, each with their aforementioned biological properties as listed supra.

G. Methods of Treatment

It is contemplated that the surface antigen-regulated promoter-therapeutic payload constructs (e.g., CAR-, cytokine-, chemokine-, trafficking receptor-, bispecific antibody-, a neutralizing/blocking antibody-, a T-cell stimulatory receptor-, a truncated inhibitory receptor-, a hybrid inhibitory/activating receptor-, an anti-apoptotic protein-, an shRNA-, a protease-based) disclosed herein can be used in methods of treating or preventing a disease in a mammal. In this regard, an embodiment provides a method of treating or preventing cancer in a mammal, comprising administering to the mammal the CARs, the nucleic acids, the recombinant expression vectors, the host cells, the population of cells, the antibodies and/or the antigen binding portions thereof, and/or the pharmaceutical compositions in an amount effective to treat or prevent cancer in the mammal.

An embodiment further comprises lymphodepleting the mammal prior to administering the CARs disclosed herein. Examples of lymphodepletion include, but may not be limited to, nonmyeloablative lymphodepleting chemotherapy, myeloablative lymphodepleting chemotherapy, total body irradiation, etc.

For purposes of the methods, wherein host cells or populations of cells are administered, the cells can be cells that are allogeneic or autologous to the mammal. Preferably, the cells are autologous to the mammal. As used herein, allogeneic means any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically. As used herein, "autologous" means any material derived from the same individual to whom it is later to be re-introduced into the individual.

The mammal referred to herein can be any mammal. As used herein, the term "mammal" refers to any mammal, including, but not limited to, mammals of the order Rodentia, such as mice and hamsters, and mammals of the order Lagomorpha, such as rabbits. The mammals may be from the order Carnivora, including Felines (cats) and Canines (dogs). The mammals may be from the order Artiodactyla, including Bovines (cows) and Swine (pigs) or of the order Perissodactyla, including Equines (horses). The mammals may be of the order Primates, Ceboids, or Simoids (monkeys) or of the order Anthropoids (humans and apes). Preferably, the mammal is a human.

With respect to the methods, the cancer can be any cancer, including any of acute lymphocytic cancer, acute myeloid leukemia, alveolar rhabdomyosarcoma, bladder cancer (e.g., bladder carcinoma), bone cancer, brain cancer (e.g., medulloblastoma), breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, fibrosarcoma, gastrointestinal carcinoid tumor, head and neck cancer (e.g., head and neck squamous cell carcinoma), Hodgkin lymphoma, hypopharynx cancer, kidney cancer, larynx cancer, leukemia, liquid tumors, liver cancer, lung cancer (e.g., non-small cell lung carcinoma and lung adenocarcinoma), lymphoma, mesothelioma, mastocytoma, melanoma, multiple myeloma, nasopharynx cancer, non-Hodgkin lymphoma, B-chronic lymphocytic leukemia, hairy cell leukemia, acute lymphocytic leukemia (ALL), and Burkitt's lymphoma, ovarian cancer, pancreatic cancer, peritoneum, omentum, and mesentery cancer, pharynx cancer, prostate cancer, rectal cancer, renal cancer, skin cancer, small intestine cancer, soft tissue cancer, solid tumors, synovial sarcoma, gastric cancer, testicular cancer, thyroid cancer, and ureter cancer.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the methods can provide any amount or any level of treatment or prevention of cancer in a mammal.

Furthermore, the treatment or prevention provided by the method can include treatment or prevention of one or more conditions or symptoms of the disease, e.g., cancer, being treated or prevented. Also, for purposes herein, "prevention" can encompass delaying the onset of the disease, or a symptom or condition thereof.

Another embodiment provides a method of detecting the presence of cancer in a mammal, comprising: (a) contacting a sample comprising one or more cells from the mammal with the CARs, the nucleic acids, the recombinant expression vectors, the host cells, the population of cells, the antibodies, and/or the antigen binding portions thereof, or the pharmaceutical compositions, thereby forming a complex, (b) and detecting the complex, wherein detection of the complex is indicative of the presence of cancer in the mammal.

The sample may be obtained by any suitable method, e.g., biopsy or necropsy. A biopsy is the removal of tissue and/or cells from an individual. Such removal may be to collect tissue and/or cells from the individual in order to perform experimentation on the removed tissue and/or cells. This experimentation may include experiments to determine if the individual has and/or is suffering from a certain condition or disease-state. The condition or disease may be, e.g., cancer.

With respect to an embodiment of the method of detecting the presence of a proliferative disorder, e.g., cancer, in a mammal, the sample comprising cells of the mammal can be a sample comprising whole cells, lysates thereof, or a fraction of the whole cell lysates, e.g., a nuclear or cytoplasmic fraction, a whole protein fraction, or a nucleic acid fraction. If the sample comprises whole cells, the cells can be any cells of the mammal, e.g., the cells of any organ or tissue, including blood cells or endothelial cells.

The contacting can take place in vitro or in vivo with respect to the mammal. Preferably, the contacting is in vitro.

Also, detection of the complex can occur through any number of ways known in the art. For instance, the CARs disclosed herein, polypeptides, proteins, nucleic acids, recombinant expression vectors, host cells, populations of cells, or antibodies, or antigen binding portions thereof, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles) as disclosed supra.

Methods of testing a CAR for the ability to recognize target cells and for antigen specificity are known in the art. For instance, Clay et al., J. Immunol, 163: 507-513 (1999), teaches methods of measuring the release of cytokines (e.g., interferon-γ, granulocyte/monocyte colony stimulating factor (GM-CSF), tumor necrosis factor a (TNF-a) or interleukin 2 (IL-2)). In addition, CAR function can be evaluated by measurement of cellular cytotoxicity, as described in Zhao et al, J. Immunol, 174: 4415-4423 (2005).

Another embodiment provides for the use of the CARs, nucleic acids, recombinant expression vectors, host cells, populations of cells, antibodies, or antigen binding portions thereof, and/or pharmaceutical compositions of the invention, for the treatment or prevention of a proliferative disorder, e.g., cancer, in a mammal. The cancer may be any of the cancers described herein.

Any method of administration can be used for the disclosed therapeutic agents, including local and systemic administration. For example, topical, oral, intravascular such as intravenous, intramuscular, intraperitoneal, intranasal, intradermal, intrathecal and subcutaneous administration can be used. The particular mode of administration and the dosage regimen will be selected by the attending clinician, taking into account the particulars of the case (for example the subject, the disease, the disease state involved, and whether the treatment is prophylactic). In cases in which more than one agent or composition is being administered, one or more routes of administration may be used; for example, a chemotherapeutic agent may be administered orally and an antibody or antigen binding fragment or conjugate or composition may be administered intravenously. Methods of administration include injection for which the CAR, CAR T Cell, conjugates, antibodies, antigen binding fragments, or compositions are provided in a nontoxic pharmaceutically acceptable carrier such as water, saline, Ringer's solution, dextrose solution, 5% human serum albumin, fixed oils, ethyl oleate, or liposomes. In some embodiments, local administration of the disclosed compounds can be used, for instance by applying the antibody or antigen binding fragment to a region of tissue from which a tumor has been removed, or a region suspected of being prone to tumor development. In some embodiments, sustained intra-tumoral (or near-tumoral) release of the pharmaceutical preparation that includes a therapeutically effective amount of the antibody or antigen binding fragment may be beneficial. In other examples, the conjugate is applied as an eye drop topically to the cornea, or intravitreally into the eye.

The disclosed therapeutic agents can be formulated in unit dosage form suitable for individual administration of precise dosages. In addition, the disclosed therapeutic agents may be administered in a single dose or in a multiple dose schedule. A multiple dose schedule is one in which a primary course of treatment may be with more than one separate dose, for instance 1-10 doses, followed by other doses given at subsequent time intervals as needed to maintain or reinforce the action of the compositions. Treatment can involve daily or multi-daily doses of compound(s) over a period of a few days to months, or even years. Thus, the dosage regime will also, at least in part, be determined based on the particular needs of the subject to be treated and will be dependent upon the judgment of the administering practitioner.

Typical dosages of the antibodies or conjugates can range from about 0.01 to about 30 mg/kg, such as from about 0.1 to about 10 mg/kg.

In particular examples, the subject is administered a therapeutic composition that includes one or more of the conjugates, antibodies, compositions, CARs, CAR T cells or additional agents, on a multiple daily dosing schedule, such as at least two consecutive days, 10 consecutive days, and so forth, for example for a period of weeks, months, or years. In one example, the subject is administered the conjugates, antibodies, compositions or additional agents for a period of at least 30 days, such as at least 2 months, at least 4 months, at least 6 months, at least 12 months, at least 24 months, or at least 36 months.

In some embodiments, the disclosed methods include providing surgery, radiation therapy, and/or chemotherapeutics to the subject in combination with a disclosed antibody, antigen binding fragment, conjugate, CAR or T cell expressing a CAR (for example, sequentially, substantially simultaneously, or simultaneously). Methods and therapeutic dosages of such agents and treatments are known to those skilled in the art, and can be determined by a skilled clinician. Preparation and dosing schedules for the additional agent may be used according to manufacturer's instructions or as determined empirically by the skilled practitioner. Preparation and dosing schedules for such chemotherapy are also described in Chemotherapy Service, (1992) Ed., M. C. Perry, Williams & Wilkins, Baltimore, MD.

In some embodiments, the combination therapy can include administration of a therapeutically effective amount of an additional cancer inhibitor to a subject. Non-limiting examples of additional therapeutic agents that can be used with the combination therapy include microtubule binding agents, DNA intercalators or cross-linkers, DNA synthesis inhibitors, DNA and RNA transcription inhibitors, antibodies, enzymes, enzyme inhibitors, gene regulators, and angiogenesis inhibitors. These agents (which are administered at a therapeutically effective amount) and treatments can be used alone or in combination. For example, any suitable anti-cancer or anti-angiogenic agent can be administered in combination with the CARS, CAR-T cells, antibodies, antigen binding fragment, or conjugates disclosed herein. Methods and therapeutic dosages of such agents are known to those skilled in the art, and can be determined by a skilled clinician.

Additional chemotherapeutic agents include, but are not limited to alkylating agents, such as nitrogen mustards (for example, chlorambucil, chlormethine, cyclophosphamide, ifosfamide, and melphalan), nitrosoureas (for example, carmustine, fotemustine, lomustine, and streptozocin), platinum compounds (for example, carboplatin, cisplatin, oxaliplatin, and BBR3464), busulfan, dacarbazine, mechlorethamine, procarbazine, temozolomide, thiotepa, and uramustine; antimetabolites, such as folic acid (for example, methotrexate, pemetrexed, and raltitrexed), purine (for example, cladribine, clofarabine, fludarabine, mercaptopurine, and tioguanine), pyrimidine (for example, capecitabine), cytarabine, fluorouracil, and gemcitabine; plant alkaloids, such as *podophyllum* (for example, etoposide, and teniposide), taxane (for example, docetaxel and paclitaxel), *vinca* (for example, vinblastine, vincristine, vindesine, and vinorelbine); cytotoxic/antitumor antibiotics, such as anthracycline family members (for example, daunorubicin, doxorubicin, epirubicin, idarubicin, mitoxantrone, and valrubicin), bleomycin, rifampicin, hydroxyurea, and mitomycin; topoisomerase inhibitors, such as topotecan and irinotecan; monoclonal antibodies, such as alemtuzumab, bevacizumab, cetuximab, gemtuzumab, rituximab, panitumumab, pertuzumab, and trastuzumab; photosensitizers, such as aminolevulinic acid, methyl aminolevulinate, porfimer sodium, and verteporfin; and other agents, such as alitretinoin, altretamine, amsacrine, anagrelide, arsenic trioxide, asparaginase, axitinib, bexarotene, bevacizumab, bortezomib, celecoxib, denileukin diftitox, erlotinib, estramustine, gefitinib, hydroxycarbamide, imatinib, lapatinib, pazopanib, pentostatin, masoprocol, mitotane, pegaspargase, tamoxifen, sorafenib, sunitinib, vemurafinib, vandetanib, and tretinoin. Selection and therapeutic dosages of such agents are known to those skilled in the art, and can be determined by a skilled clinician.

The combination therapy may provide synergy and prove synergistic, that is, the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation, a synergistic effect may be attained when the compounds are administered or delivered sequentially, for example by different injections in separate syringes. In general, during alternation, an effective dosage of each active ingredient is administered sequentially, i.e. serially, whereas in combination therapy, effective dosages of two or more active ingredients are administered together.

In one embodiment, an effective amount of an antibody or antigen binding fragment that specifically binds to one or more of the antigens disclosed herein or a conjugate thereof is administered to a subject having a tumor following anti-cancer treatment. After a sufficient amount of time has elapsed to allow for the administered antibody or antigen binding fragment or conjugate to form an immune complex with the antigen expressed on the respective cancer cell, the immune complex is detected. The presence (or absence) of the immune complex indicates the effectiveness of the treatment. For example, an increase in the immune complex compared to a control taken prior to the treatment indicates that the treatment is not effective, whereas a decrease in the immune complex compared to a control taken prior to the treatment indicates that the treatment is effective.

In each of the aforementioned recitations in Section E above, in addition to the CAR-based surface antigen-regulated promoter-therapeutic payload construct methods of treatment described supra, the surface antigen-regulated promoter-therapeutic payload constructs may further comprise various other therapeutic modalities comprising one or more of the following: a cytokine comprising IL-2, IL-15, IL-7, TNFa, IFN gamma, IFN beta, IFN alpha, IL-21, IL-33, IL-22, IL-6, IL-10, IL-9, IL-4, IL-12, TGF beta, IL-17, IL-18, a chemokine comprising CCR4, CCR6, CXCR5, a trafficking receptor, such as a cytokine receptor, for example, and not by way of limitation, CCR4, CCR7, CCR2, a bispecific antibody, including a Bi-specific T cell engager (BiTE), for example, and not by way of limitation, anti-CD3 and anti CD19 targeting, or other multi-targeting antibody, a neutralizing/blocking antibody, for example, and not by way of limitation, against PD-L1, IL-6R, IL-1R, expressed as an scFv, or as IgG, or in other configurations, a T cell stimulatory receptor, a truncated inhibitory receptor, a hybrid inhibitory/activating receptor, for example, and not by way of limitation, ectodomain of PD-1, fused to endodomain of CD28, an anti-apoptotic protein, for example, and not by way of limitation, BCL-2, or BCL-XL, an shRNA, a protease, a second CAR T construct, or any combination thereof, each with their aforementioned biological properties as listed supra.

H. Biopharmaceutical Compositions

Biopharmaceutical or biologics compositions (hereinafter, "compositions") are provided herein for use in gene therapy, immunotherapy and/or cell therapy that include one or more of the disclosed surface antigen-regulated promoter-therapeutic payload constructs (e.g., CAR-, cytokine-, chemokine-, trafficking receptor-, bispecific antibody-, a neutralizing/blocking antibody-, a T-cell stimulatory receptor-, a truncated inhibitory receptor-, a hybrid inhibitory/activating receptor-, an anti-apoptotic protein-, an shRNA-, a protease-based), or T cells expressing a CAR, antibodies, antigen binding fragments, conjugates, CARs, or T cells expressing a CAR that specifically bind to one or more antigens disclosed herein, in a carrier (such as a pharmaceutically acceptable carrier). The compositions can be prepared in unit dosage forms for administration to a subject. The amount and timing of administration are at the discretion of the treating clinician to achieve the desired outcome. The compositions can be formulated for systemic (such as intravenous) or local (such as intra-tumor) administration. In one example, a disclosed CARs, or T cells expressing a CAR, antibody, antigen binding fragment, conjugate, is formulated for parenteral administration, such as intravenous administration. Compositions including a CAR, or T cell expressing a CAR, a conjugate, antibody or antigen binding fragment as disclosed herein are of use, for example, for the treatment and detection of a tumor, for example, and not by way of limitation, a neuroblastoma. In some examples, the compositions are useful for the treatment or detection of a carcinoma. The compositions including a CAR, or T cell expressing a CAR, a conjugate, antibody or antigen binding fragment as disclosed herein are also of use, for example, for the detection of pathological angiogenesis.

The compositions for administration can include a solution of the CAR, or T cell expressing a CAR, conjugate, antibody or antigen binding fragment dissolved in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents, adjuvant agents, and the like, for example, sodium acetate, sodium chloride, potassium chloride, calcium chloride, sodium lactate and the like. The concentration of a CAR, or T cell expressing a CAR, antibody or antigen binding fragment or conjugate in these formulations can vary widely, and will be selected primarily based on fluid volumes, viscosities, body weight and the like in accordance with the particular mode of administration selected and the subject's needs. Actual methods of preparing such dosage forms for use in in gene therapy, immunotherapy and/or cell therapy are known, or will be apparent, to those skilled in the art.

A typical composition for intravenous administration includes about 0.01 to about 30 mg/kg of antibody or antigen binding fragment or conjugate per subject per day (or the corresponding dose of a CAR, or T cell expressing a CAR, conjugate including the antibody or antigen binding fragment). Actual methods for preparing administrable compositions will be known or apparent to those skilled in the art and are described in more detail in such publications as *Remington's Pharmaceutical Science*, 19th ed., Mack Publishing Company, Easton, PA (1995).

A CAR, or T cell expressing a CAR, antibodies, antigen binding fragments, or conjugates may be provided in lyophilized form and rehydrated with sterile water before administration, although they are also provided in sterile solutions of known concentration. The CARs, or T cells expressing a CAR, antibody or antigen binding fragment or conjugate solution is then added to an infusion bag containing 0.9% sodium chloride, USP, and in some cases administered at a dosage of from 0.5 to 15 mg/kg of body weight. Considerable experience is available in the art in the administration of antibody or antigen binding fragment and conjugate drugs; for example, antibody drugs have been marketed in the U.S. since the approval of RITUXAN® in 1997. A CAR, or T cell expressing a CAR, antibodies, antigen binding fragments and conjugates thereof can be administered by slow infusion, rather than in an intravenous push or bolus. In one example, a higher loading dose is administered, with subsequent, maintenance doses being administered at a lower level. For example, an initial loading dose of 4 mg/kg antibody or antigen binding fragment (or the corresponding dose of a conjugate including the antibody or antigen binding fragment) may be infused over a period of some 90 minutes, followed by weekly maintenance doses for 4-8 weeks of 2 mg/kg infused over a 30 minute period if the previous dose was well tolerated.

Controlled release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, PA, (1995). Particulate systems include microspheres, microparticles, microcapsules, nanocapsules, nanospheres, and nanoparticles. Microcapsules contain the therapeutic protein, such as a cytotoxin or a drug, as a central core. In microspheres, the therapeutic is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly. See, for example, Kreuter, J., *Colloidal Drug Delivery Systems*, J. Kreuter, ed., Marcel Dekker, Inc., New York, NY, pp. 219-342 (1994); and Tice & Tabibi, *Treatise on Con-*

*trolled Drug Delivery*, A. Kydonieus, ed., Marcel Dekker, Inc. New York, NY, pp. 315-339, (1992).

Polymers can be used for ion-controlled release of the CARs, or T cells expressing a CAR, antibody or antigen binding fragment or conjugate compositions disclosed herein. Various degradable and nondegradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, PA (1993)). Numerous additional systems for controlled delivery of therapeutic proteins are known (see U.S. Pat. Nos. 5,055,303; 5,188,837; 4,235,871; 4,501,728; 4,837,028; 4,957,735; 5,019,369; 5,055,303; 5,514,670; 5,413,797; 5,268,164; 5,004,697; 4,902,505; 5,506,206; 5,271,961; 5,254,342 and 5,534,496).

In each of the aforementioned recitations in Section F above, in addition to the CAR-based surface antigen-regulated promoter-therapeutic payload construct compositions described supra, the surface antigen-regulated promoter-therapeutic payload constructs may further comprise various other therapeutic modalities comprising one or more of the following: a cytokine comprising IL-2, IL-15, IL-7, TNFa, IFN gamma, IFN beta, IFN alpha, IL-21, IL-33, IL-22, IL-6, IL-10, IL-9, IL-4, IL-12, TGF beta, IL-17, IL-18, a chemokine comprising CCR4, CCR6, CXCR5, a trafficking receptor, such as a cytokine receptor, for example, and not by way of limitation, CCR4, CCR7, CCR2, a bispecific antibody, including a Bi-specific T cell engager (BiTE), for example, and not by way of limitation, anti-CD3 and anti CD19 targeting, or other multi-targeting antibody, a neutralizing/blocking antibody, for example, and not by way of limitation, against PD-L1, IL-6R, IL-1R, expressed as an scFv, or as IgG, or in other configurations, a T cell stimulatory receptor, a truncated inhibitory receptor, a hybrid inhibitory/activating receptor, for example, and not by way of limitation, ectodomain of PD-1, fused to endodomain of CD28, an anti-apoptotic protein, for example, and not by way of limitation, BCL-2, or BCL-XL, an shRNA, a protease, a second CAR T construct, or any combination thereof, each with their aforementioned biological properties as listed supra.

I. Kits

In one aspect, kits employing the surface antigen-regulated promoter-therapeutic payload constructs (e.g., CAR-, cytokine-, chemokine-, trafficking receptor-, bispecific antibody-, a neutralizing/blocking antibody-, a T-cell stimulatory receptor-, a truncated inhibitory receptor-, a hybrid inhibitory/activating receptor-, an anti-apoptotic protein-, an shRNA-, a protease-based) disclosed herein are also provided. For example, kits for treating a tumor in a subject, or making a CAR T cell that expresses one or more of the CARs disclosed herein. The kits will typically include a disclosed antibody, antigen binding fragment, conjugate, nucleic acid molecule, CAR or T cell expressing a CAR as disclosed herein. More than one of the disclosed antibodies, antigen binding fragments, conjugates, nucleic acid molecules, CARs or T cells expressing a CAR can be included in the kit.

The kit can include a container and a label or package insert on or associated with the container. Suitable containers include, for example, bottles, vials, syringes, etc. The containers may be formed from a variety of materials such as glass or plastic. The container typically holds a composition including one or more of the disclosed antibodies, antigen binding fragments, conjugates, nucleic acid molecules, CARs or T cells expressing a CAR. In several embodiments the container may have a sterile access port (for example the container may be an intravenous solution bag or a vial having a stopper pierceable by a hypodermic injection needle). A label or package insert indicates that the composition is used for treating the particular condition.

The label or package insert typically will further include instructions for use of a disclosed antibodies, antigen binding fragments, conjugates, nucleic acid molecules, CARs or T cells expressing a CAR, for example, in a method of treating or preventing a tumor or of making a CAR T cell. The package insert typically includes instructions customarily included in commercial packages of therapeutic products that contain information about the indications, usage, dosage, administration, contraindications and/or warnings concerning the use of such therapeutic products. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

In each of the aforementioned recitations in Section G above, in addition to the CAR-based surface antigen-regulated promoter-therapeutic payload constructs described supra, the surface antigen-regulated promoter-therapeutic payload constructs may further comprise various other therapeutic modalities comprising one or more of the following: a cytokine comprising IL-2, IL-15, IL-7, TNFa, IFN gamma, IFN beta, IFN alpha, IL-21, IL-33, IL-22, IL-6, IL-10, IL-9, IL-4, IL-12, TGF beta, IL-17, IL-18, a chemokine comprising CCR4, CCR6, CXCR5, a trafficking receptor, such as a cytokine receptor, for example, and not by way of limitation, CCR4, CCR7, CCR2, a bispecific antibody, including a Bi-specific T cell engager (BiTE), for example, and not by way of limitation, anti-CD3 and anti CD19 targeting, or other multi-targeting antibody, a neutralizing/blocking antibody, for example, and not by way of limitation, against PD-L1, IL-6R, IL-1R, expressed as an scFv, or as IgG, or in other configurations, a T cell stimulatory receptor, a truncated inhibitory receptor, a hybrid inhibitory/activating receptor, for example, and not by way of limitation, ectodomain of PD-1, fused to endodomain of CD28, an anti-apoptotic protein, for example, and not by way of limitation, BCL-2, or BCL-XL, an shRNA, a protease, a second CAR T construct, or any combination thereof, each with their aforementioned biological properties as listed supra.

EXAMPLES

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

Example 1

Generation of a Self-Driving Car Construct Targeting the Cd19 Antigen

Despite clinical success of anti-CD19-based (e.g. CAR LTG1563) cancer therapy, suboptimal CAR activation and persistence on the one hand, and CAR over-activation and the associated toxicity (CRS, neurotoxicity) on the other hand, present a problem. In order to improve the safety and efficacy of CAR T therapy, a self-driving CAR was created.

Figure 3:
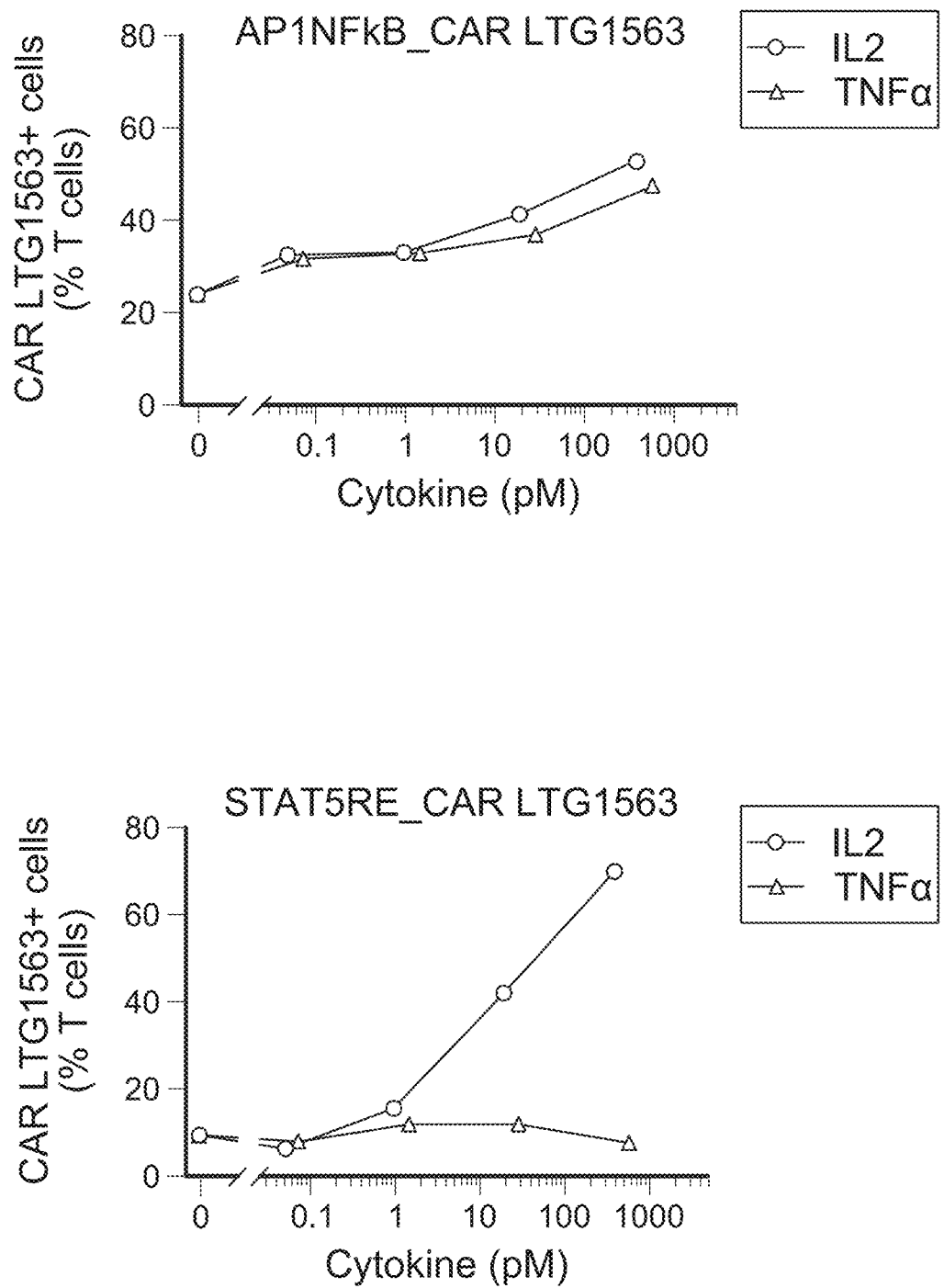
FIG. 3 depicts induction of CAR expression by cytokine—driven positive feedback loop in STAT5 and AP1/NFκB inducible CAR LTG1563 in one healthy donor (representative of 2 donors). T cells were treated with varying concentrations of IL2 and TNFα for 18 h, 5 days post-activation (4 days post-transduction).
Figure 4:
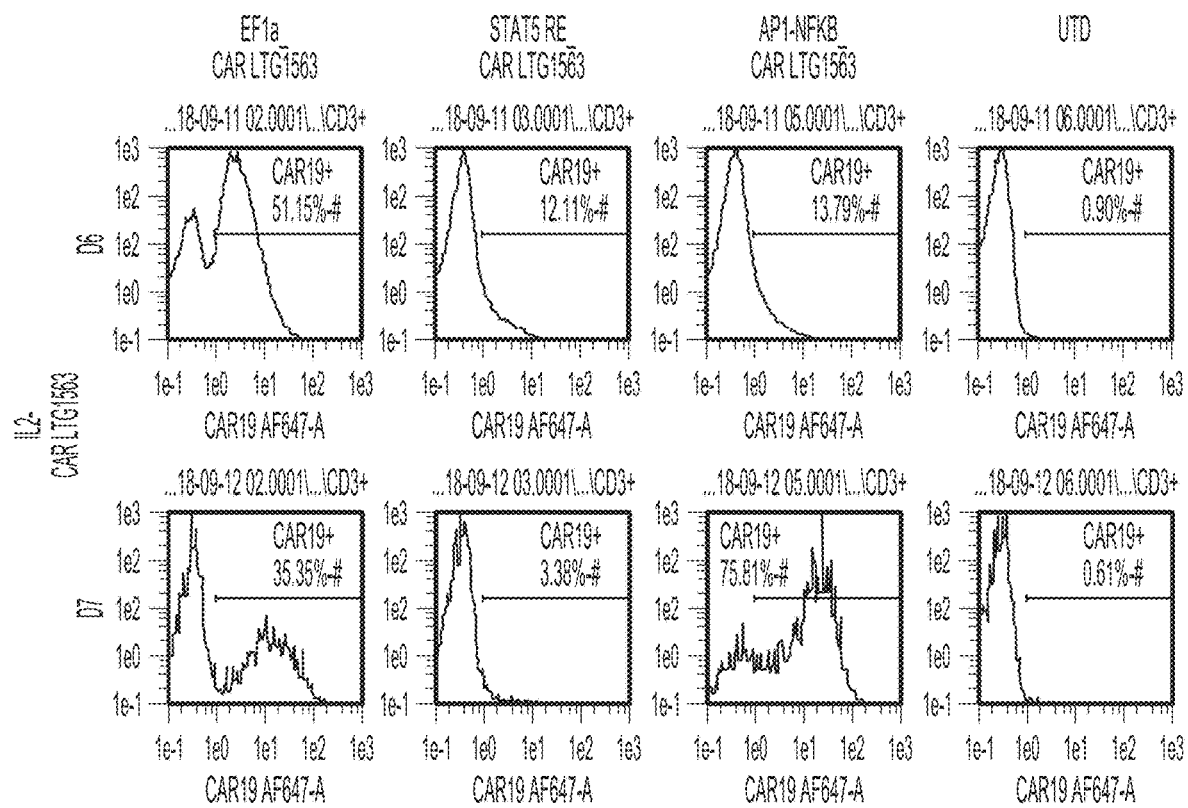
FIG. 4 depicts AP1/NFκB-regulated self-driving CAR LTG1563 exhibits rapid recovery of CAR expression following antigen exposure, as compared to the EF1α-driven constitutive CAR. The expression in self-driving CAR constructs regulated by the inducible STAT5 & AP1/NFκB promoters, and in EF1α-driven constitutive CAR construct, following initial coculture with Raji cells in 2 healthy donors. Cells were activated with TransAct reagent at D0, transduced at D1 with LV vectors at an MOI of 10, and washed and treated with either: 0 IU/mL IL-2 or 30 IU/mL IL2 from D2-D6 post-activation. From D6 post-activation, CAR LTG1563 T cells were cocultured with Raji-GFP (CD19+) cells at an effector:target ratio of 1:3. CAR expression prior to coculture (D6) and 1 day after coculture (D7) is shown, one representative donor of 2.
Figure 4:
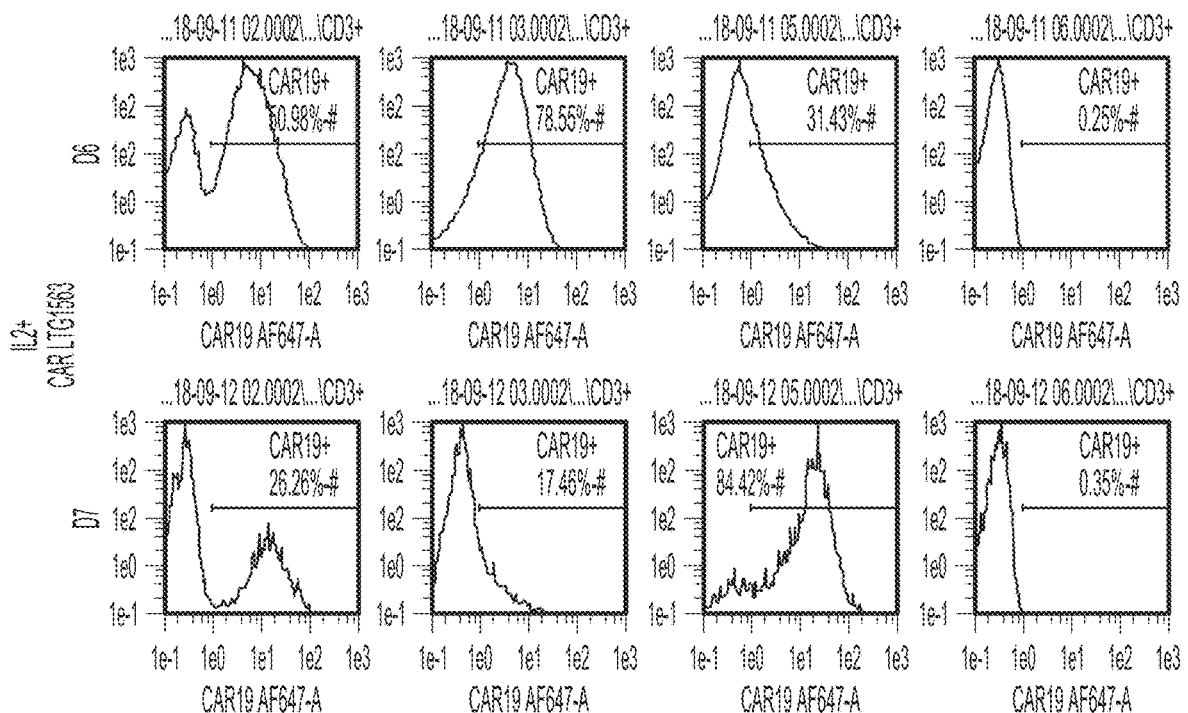

In this Example, CAR T cells are described that utilize CAR signaling to regulate its own expression and the expression of co-regulated transgenes via two mechanisms, and the use of these mechanisms beyond CAR expression:

1. Positive regulation of CAR T expression by cytokine (e.g. IL-2/IL-15/IL-7)-driven STAT5 response element (STAT5_RE), which induce the expression of a CAR molecule (e.g. anti-CD19 CAR LTG1563). When CAR T detects tumor antigen, a slow positive feedback-loop is activated which increases CAR expression on CAR T cells. Once the tumors have been eliminated, the positive feedback loop gradually diminishes and shuts down, naturally reducing CAR surface expression and bringing it back to surveillance state (FIG. 1).
2. Positive regulation of CAR T expression by a combination of cytokine (e.g. IL-2/IL-15/IL-7/TNFα)-driven and CAR/TCR-driven AP1/NFκB response elements (AP1/NFκB_RE), which induce the expression of a CAR molecule (e.g. CAR LTG1563). When CAR T detects tumor antigen, a rapid positive feedback-loop is activated which increases CAR expression on CAR-T cells. Over time, the AP1/NFκB-driven CAR LTG1563 demonstrates greater CD19-dependent killing activity, increased cytokine secretion, decreased exhaustion, and overall fitness of CAR T cells relative to constitutively-expressed CARs. Once the tumors have been eliminated, the positive feedback loop gradually diminishes and shuts down, naturally reducing CAR surface expression and bringing it back to surveillance state (FIG. 1).
3. Expression of additional proteins in the presence of CAR antigens to modulate CAR T function, including but not limited to: evasion of negative T cell regulation (dominant negative TGFBRII receptor, anti-PD1 antibody, etc.), positive regulators of T cell growth (IL15, IL12, etc.), T cell homing to tumors (chemokine receptors), and greater access to the tumor microenvironment (matrix metalloproteinases), or one constitutive CAR and a second inducible CAR, such as both CARs are encoded by the same lentiviral vector, and such as the inducible CAR is expressed as a result of the activation of the constitutive CAR. The second CAR may be targeting a second tumor antigen, or an antigen expressed on myeloid-derived suppressor cells (MDSC) (e.g. CD33, mesothelin), or on inhibitory B cells (e.g., CD19). In each case, these inducible proteins will be expressed in the presence of CAR stimulation and downregulated following termination of CAR signaling.
4. The STAT5_RE versus the AP1/NFκB_RE promoters can be used to modulate either self-expression of CAR proteins, or T cell function modulator proteins, in defined fashions. The greater cytokine (IL2)-dependent response of the STAT5_RE (FIG. 3) can be used to express proteins in CAR-T cells not directly responding to antigen, in a paracrine fashion near tumors. Alternatively, proteins can be expressed specifically in CAR T cells responding to tumors via AP1/NFκB_RE, due to the requirement for CAR signaling for the maximal response through this element (FIG. 4).

Materials and Methods:

Creation of Chimeric Antigen Receptor (CAR)—Expressing Vectors

In order to generate the novel transmembrane domain of CAR LTG1563, the single chain variable fragment (scFv) derived from FMC-63 mouse hybridoma (FMC-63: AA 1-267, GenBank ID: HM852952.1) in orientation VL to VH and connected by the (GGGGS)3 flexible intrachain linker (SEQ ID NO: 187) was used. The resulting targeting domain was then linked in frame to human CD8 hinge (AA 138-179, Ref sequence ID NP_001759.3), human TNF receptor Superfamily 19 transmembrane domain (TNFRSF19, AA 167-196, UntProt sequence ID: Q9NS68), human 4-1BB co-stimulatory domain (CD137, AA 214-255, UniProt sequence ID: Q07011) and human CD3 zeta signaling domain (CD247, AA 52-163, Ref sequence ID: NP_000725.1.). Leader sequence from human granulocyte macrophage colony stimulating factor receptor alpha subunit (AA 1-22, GenBank ID: EAW98673.1) was included to facilitate CAR expression at cell surface. CAR sequence was codon-optimized and cloned into a third generation lentiviral plasmid backbone under the regulation of surface antigen-regulated inducible promoters described below, or constitutive MSCV or EF1α promoter as a control.

Cell Lines Used to Demonstrate CAR Activity

The Burkitt lymphoma cell line Raji cell line, the chronic myelogenous leukemia line K562 line and reagents were purchased from American Tissue Culture Collection (ATCC, Manassass, VA), unless otherwise noted. Cells were cultured in RPMI-1640 medium supplemented with 10% heat-inactivated fetal bovine serum (FBS, Hyclone, Logan, UT) and 2 mM L-Glutamax (Thermo Fisher Scientific, Grand Island, NY). Human Embryonic kidney line 293T was purchased from ATCC and propagated in CD FortiCho medium (Gibco/Thermo Fisher Scientific, Grand Island, NY). Single-cell clones of luciferase-expressing cell lines were generated by stably transducing wild-type tumor lines with lentiviral vector encoding firefly luciferase (Lentigen Technology, Inc., Gaithersburg, MD), followed by cloning and selection of luciferase-positive clones.

Primary Human T Cells Used to Demonstrate CAR Activity

Whole blood was collected from healthy volunteers at Oklahoma Blood Institute (OBI) with donors' written consent. Processed buffy coats were purchased from OBI (Oklahoma City, OK). The CD4-positive and CD8-positive human T cells were purified from buffy coats via positive selection using a 1:1 mixture of CD4– and CD8– MicroBeads (Miltenyi Biotec, Bergisch Gladbach, Germany) according to manufacturer's protocol.

Primary T Cell Transduction

Human primary CD4+ and CD8+ T cells from normal donors were cultivated in TexMACS medium at a density of 1×106 cells/ml, activated with CD3/CD28 MACS® GMP T Cell TransAct reagent on day 0 (all reagents from Miltenyi Biotec), and transduced on day 1/2 with LV encoding CAR constructs overnight, and media exchanged on day 2/3. Supplementation with cytokines (IL-2, TNFα; Miltenyi Biotec, Bergisch Gladbach, Germany) was performed as described. Cultures were propagated until harvest on day 5-6 for co-incubation analysis.

Immune Effector Assays (CTL and Cytokine)

For long-term co-incubation assays, CAR T effector and GFP-expressing target cells were propagated as above, and flow cytometric analysis was utilized to determine the extent of target cell population killing, and CAR T population survival and expansion. Cells were gated based on forward and side scatter, and viable (7AAD-negative) cells. Percentages of surviving cells post in co-cultures were determined based on GFP positivity for Raji targets and CD3 for CAR T effectors. In addition, CAR T expression in live CD3 positive cells was determined by staining with CD19 Fc peptide, followed by anti-Fc (Fab')2-FL reagent.

Results:

Fully human CAR T constructs targeting the CD19 antigen were designed by combining in frame the sequences of leader peptide derived from GMCSFR, fully human anti-human CD19 ScFv sequence, CD8 hinge, TNFRSF19 transmembrane domain, 4-1BB costimulatory domain and CD3z activation domain.

Figure 2:
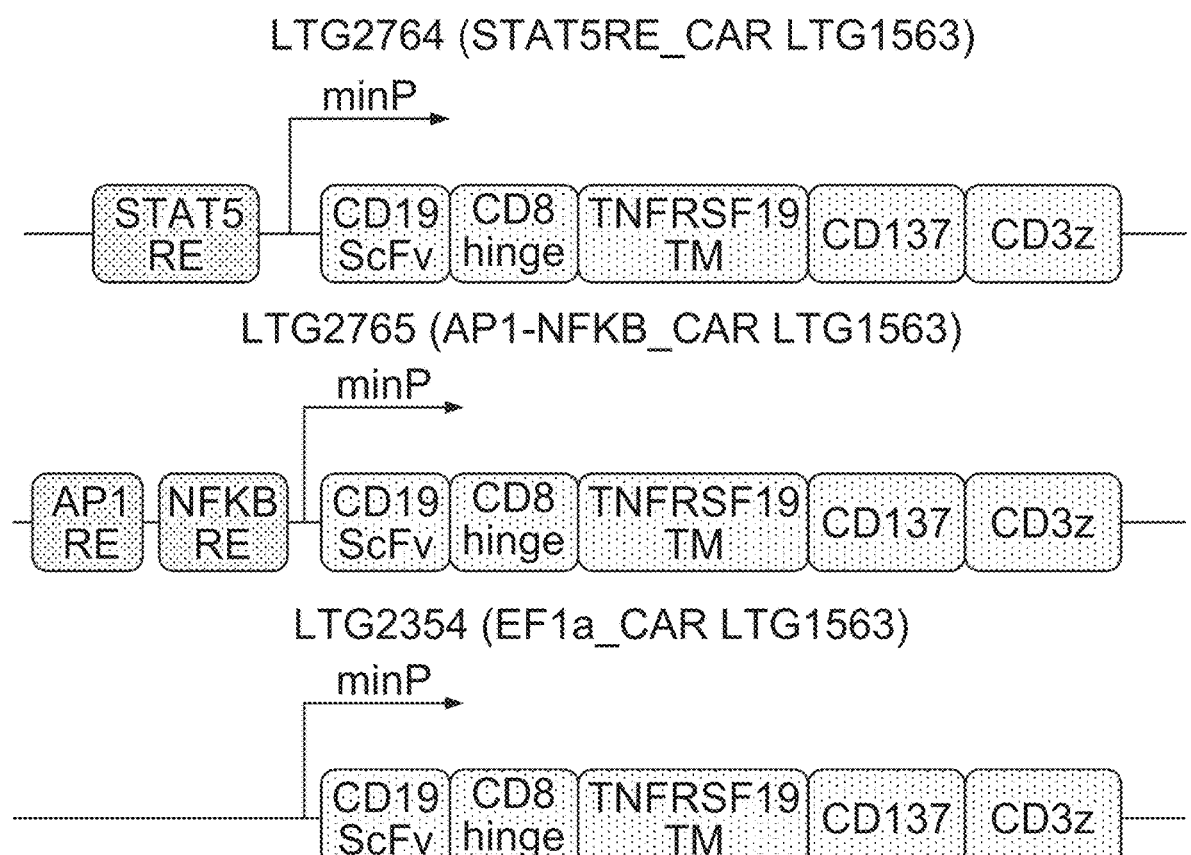
FIG. 2 depicts the structure of STAT5 and AP1/NFκB inducible CAR LTG1563, and constitutive EF1α-driven CAR LTG1563.

CAR positive regulation loop was designed by placing CAR LTG1563 expression under the control of a tandem STAT5 response element followed by a minimal promoter sequence. When IL-2 binds native IL-2 receptor on T cell surface, Jak/STAT signaling is initiated, STAT 5 translocates to the CAR promoter's regulatory region and enhances CAR expression. Constitutively-expressed EF1α-promoter driven CAR LTG1563 was constructed as a control and tested in parallel with STAT-5 and AP1/NFκB regulated CARs. Schema for positive CAR regulation via (1) IL-2 driven Stat5 and (2) IL-2/TNFα and CAR-driven AP1/NFκB-mediated mechanisms are depicted in FIG. 1, and the architecture of each of these constructs is depicted in FIG. 2.

T cells were purified from blood of two unrelated healthy donors by immunogenic selection using a 1:1 mixture of CD4 and CD8 beads (Miltenyi Biotec). Cells were transduced with CAR LTG1563 constructs in the absence of cytokine supplementation, as described in the materials and methods. The experimental groups included CD19 CAR driven by EF1α promoter at MOI 10, or with STAT5_RE CAR LTG1563 and AP1/NFκB_RE CAR LTG1563, positively regulated self-driving CARs at 0.25% vol/vol LV preparation (FIG. 3). Untransduced cells (UTD) cultured under same conditions were used as a negative control. On day 5, select groups received IL-2 or TNFα supplementation, and 20 h later CAR expression was detected by flow cytometry. EF1α-driven CAR expression was 30-40% depending on transducing MOI, and did not change due to IL-2/TNFα supplementation. By contrast, STAT5_RE CAR expression was greatly enhanced by IL-2 supplementation, but not by TNFα, as expected (FIG. 3). AP1/NFκB_RE CAR expression was enhanced by both IL-2 and TNFα, but to a lesser extent than IL-2 driven STAT5_RE CAR LTG1563 expression.

Further, in this experiment, the self-driving characteristic of both the STAT5 and AP1/NFκB response elements to drive CAR LTG1563 expression were assessed by CD19 antigen stimulation (FIG. 4). This was performed using CAR T cells from Donor A and Donor B in coculture with CD19 positive Raji NHL tumor cells stably expressing GFP. Strikingly, CAR expression was strongly induced in the AP1/NFκB_RE-driven CAR LTG1563 T cells within 20 h post-stimulation (FIG. 4B), demonstrating the integration of both CAR signaling and CAR-dependent cytokine expression when these response elements were used to drive CAR expression. The stimulation was much greater than could be observed simply by stimulating these cells with cytokines, indicating a stronger direct response to CAR signaling. This rapid AP1/NFκB-dependent CAR upregulation was in marked contrast to the constitutively-expressing EF1α-driven CAR LTG1563, which was transiently decreased by CD19 antigen-mediated stimulation of the CAR (likely due to internalization of these receptors). By contrast, the STAT5_RE-driven CAR LTG1563 was induced by coculture with CD19+ Raji cells, but on a much longer time scale than that observed for the AP1/NFκB-driven CAR LTG1563. This likely reflects an intermediate step required for the functionality of the STAT5 response element, the production of IL2 by CAR T cells and concomitant STAT5 signaling. IL2 supplementation of these cells from D3-D5 post-activation greatly increased the induction of CAR LTG1563 expression through the STAT5 element, likely by priming STAT-mediated signaling.

Notably, the expression of the AP1-NFκB CAR LTG1563 could be re-induced across multiple stimulations with CD19+ Raji cells (D6-D22 post-activation), indicating that the CAR T cells retain AP1/NFκB signaling responsiveness even during prolonged ex vivo cultures (data not shown). Importantly, the degree of CAR expression under the control of the AP1/NFκB promoter correlated quite well temporally with the number of Raji cells in the cocultures (data not shown). These results indicate that the AP1/NFκB element rapidly drives CAR LTG1563 expression in the presence of the cognate CD19 antigen, and that CAR LTG1563 is rapidly downregulated in the absence of antigen.

In the next experiment, T cells were purified from blood of three unrelated healthy donors by immunogenic selection using a 1:1 mixture of CD4 and CD8 beads (Miltenyi Biotec). Cells were transduced at D1 post-activation with CAR LTG1563 constructs in the absence of cytokine supplementation, as described in the materials and methods. The experimental groups included CD19 CAR driven by constitutive EF1α-derived CAR, STAT5 RE CAR LTG1563, and AP1-NFκB CAR LTG1563 were transduced with LV at an MOI of 10 (FIG. 3). In a subset of samples, IL2 supplementation (30 IU/mL) was carried out from D3-D6 post-activation, to prime expression of both the STAT5 RE CAR LTG1563 and AP1/NFκB CAR LTG1563. The CAR LTG1563-dependent cytotoxicity was assessed by coculture of CAR T cells with CD19+ Raji NHL cells stably expressing GFP. A very low effector to target ratio was used (1:3 CAR T:Raji cells), and CD19-dependent cytotoxicity was assessed by flow cytometric enumeration of the GFP+ Raji cells from D6-D13 post-activation (Coculture 1). Long-term function and expansion of the CAR T cells was assessed by re-stimulation of the cells at a similar effector to target ratio (1:3 Coculture 1:Raji cells) from D13-D20 post-activation (Coculture 2).

Figure 5A:
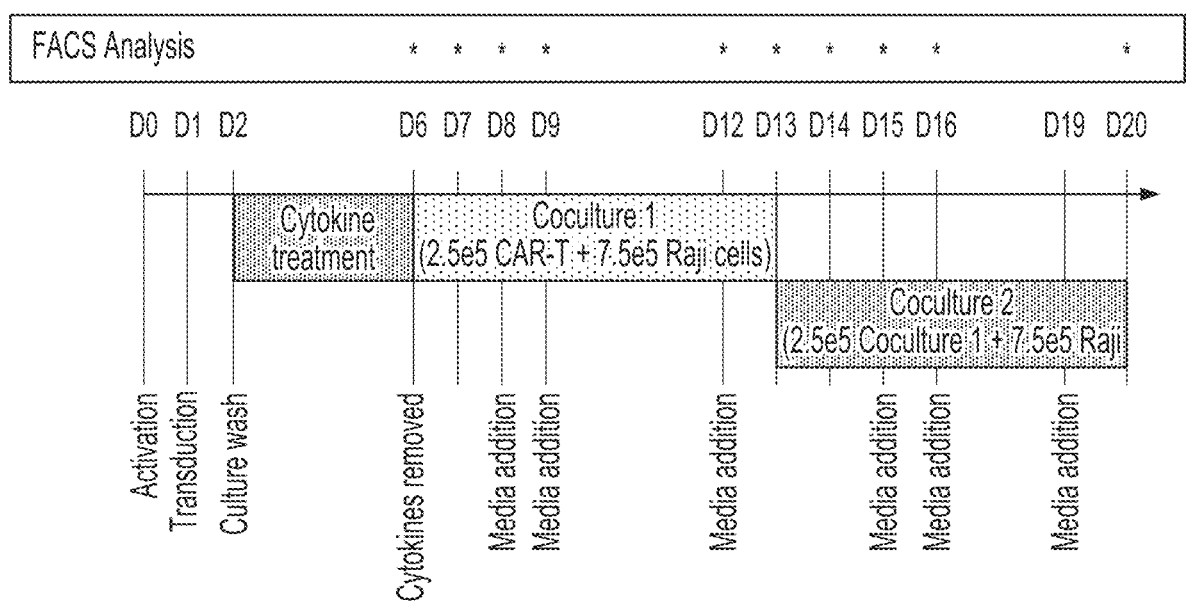
FIGS. 5A-5C depict superior Raji tumor killing and T cell expansion with CAR LTG1563 T cells regulated by AP1-NFκB-positive feedback loop (FIG. 5A) Long-term killing assay: Coculture time course diagram. Cells were activated with TransAct reagent at D0, transduced at D1 with LV vectors at an MOI of 10, and washed and treated with either: 0 IU/mL IL-2 or 30 IU/mL IL2 from D2-D6 post-activation. From D6-D13 post-activation, CAR LTG1563 T cells were cocultured with Raji-GFP (CD19+) cells at an effector:target ratio of 1:3 (Coculture 1), and from D13-D20, cells were re-stimulated with Raji-GFP cells.
Figure 5B:
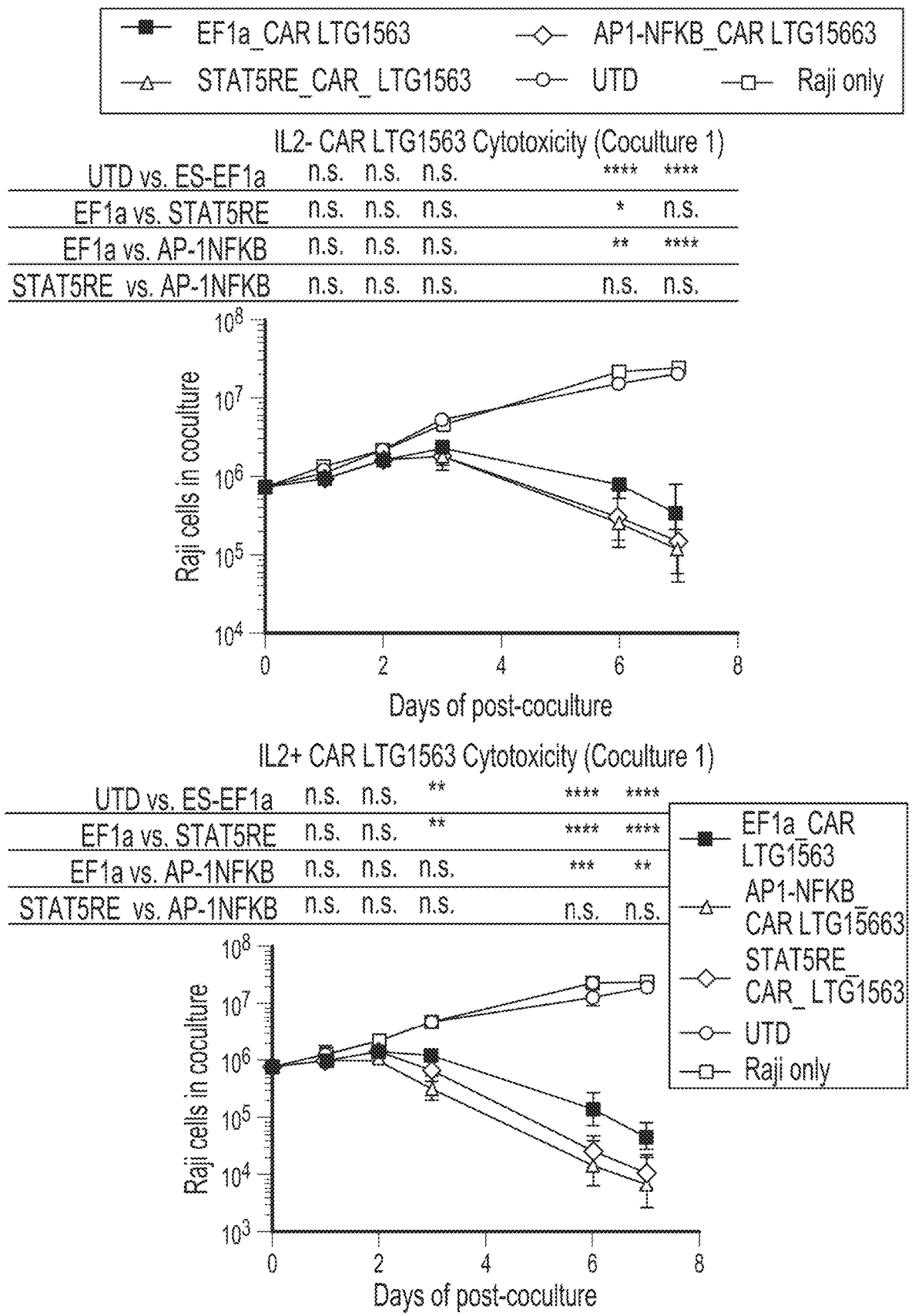

CAR T co-incubation with target cells was examined for a total of fourteen days (Coculture 1&2), during this time the numbers of viable Raji and T cells were enumerated by flow cytometric analysis (FIG. 5). Whereas Raji cells in Raji only and UTD control groups proceeded to grow unhindered to experimental day 8, CAR LTG1563 T cells strongly suppressed Raji expansion in all groups, regardless of IL2 priming. Of note, both STAT5 RE and AP1/NFκB CAR LTG1563 were superior to EF1α CAR LTG1563 in tumor killing throughout the initial coculture (Coculture 1), as measured on days 1, 2, 3, 6, and 7 after Raji addition (FIG. 5B). Strikingly, despite the low initial CAR LTG1563 expression in the IL2-cultures, both STAT5RE and AP1/NFκB outperformed the EF1α constitutively-expressing CAR LTG1563 construct (FIG. 5B). This potentially indicates that constitutive expression of CAR in the absence of a cognate antigen even for a short period (D2-D6 post-activation) may negatively affect the efficacy of CAR T cells, perhaps due to tonic signaling.

Figure 5C:
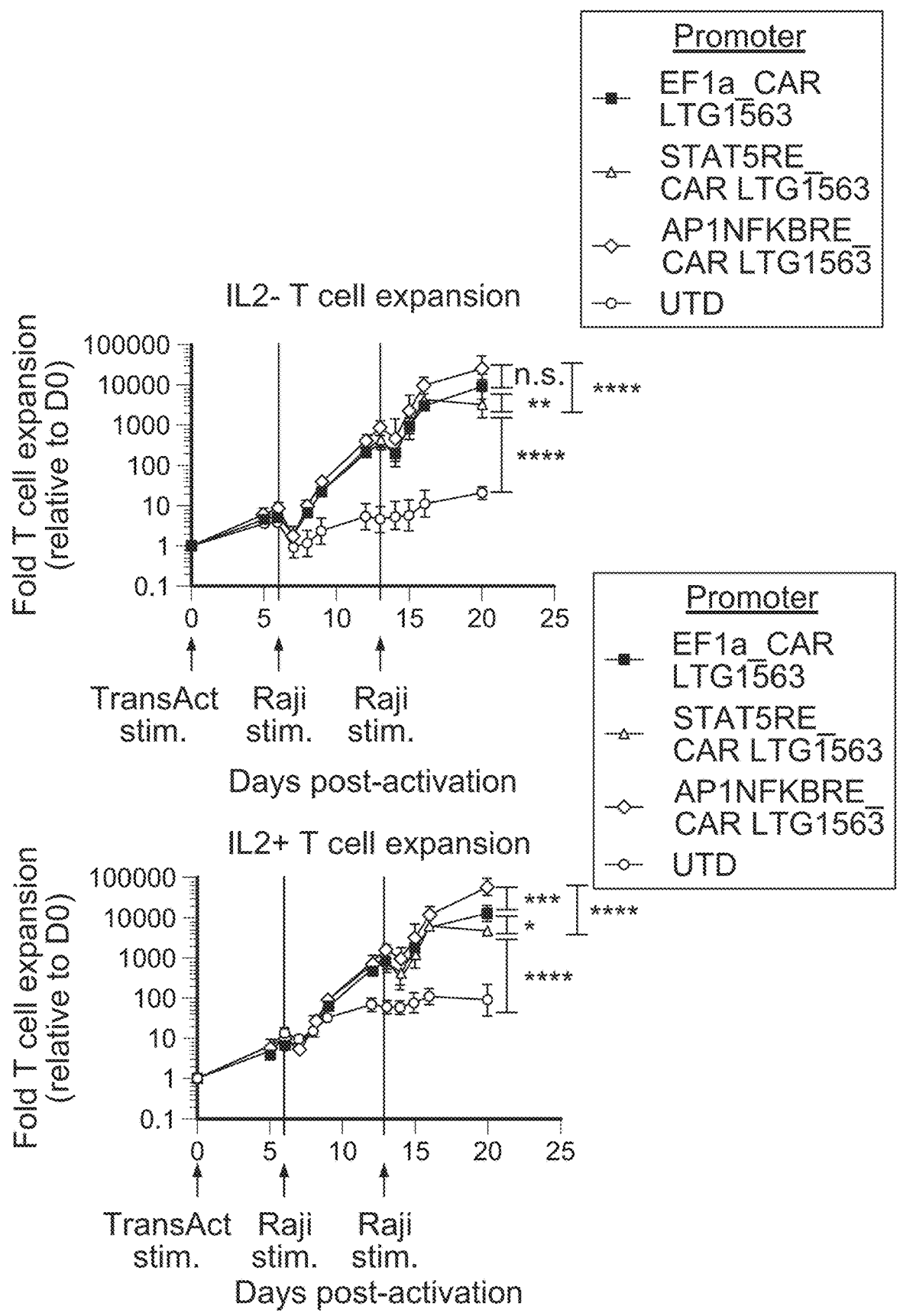

Further long-term analysis of CAR LTG1563-dependent cytotoxicity was assessed by re-stimulating the CAR T cells with CD19+ Raji cells. All CAR groups again demonstrated effective suppression of Raji expansion (data not shown), with AP1/NFκB-driven CAR LTG1563 showing superior tumor killing function as compared to constitutively-expressed EF1α_CAR LTG1563 (Figure. 5B). AP1/NFκB_CAR LTG1563-expressing T cells expanded to a greater extent throughout the culture period than either STAT5RE_CAR LTG1563 or EF1α_CAR LTG1563-expressing T cells (FIG. 5C). This is likely due to CAR signaling being present only when target CD19+ cells are also present, preserving the overall health of these cells and leading to concomitantly greater T cell expansion.

Overall, the results demonstrate the superiority of inducible, self-driving AP1/NFκB RE CAR LTG1563, which was manifested in lower unstimulated CAR expression, and lower susceptibility to exhaustion, low level priming by cytokine supplementation, and rapid upregulation and sustained expression in the presence of tumor Raji cells. Additionally, superior CTL function was observed as compared to same CAR construct under the control of constitutive EF1α promoter in initial activity. This correlated with a greater overall expansion of these AP1/NFκB CAR T cells due to antigen stimulation relative to all other tested constructs.

Example 2

Extension of Self-Driving Expression to Auxiliary Proteins

Given the success of the inducible AP1/NFκB promoter in self-driving the high-level CAR LTG1563 expression specifically in the presence of the cognate CAR antigen (CD19), it was desired to extend the functionality of this promoter to auxiliary proteins, which provide additional functionality to CAR-T cells. The advantage of the CAR antigen-inducible AP1/NFκB promoter is that any proteins under the control of this promoter will be highly expressed only when the CAR tumor antigen is present. Therefore, the AP1/NFκB promoter was used to express proteins that allow CAR-T cells to escape immunosuppression, e.g., dominant-negative TGF-beta receptor (TGFBRIIdn) and dominant-negative programmed cell death protein 1 (PD1dn). These dominant-negative receptors were expected to allow the CAR-T cells to evade immunosuppression by either TGF-β or PD-L1, respectively. The expected advantage of using the AP1/NFκB promoter is that TGF-β/PD-L1 immunosuppression plays an important role under normal conditions in patients to prevent development of T cell-mediated autoimmunity. However, the microenvironment of many cancers are characterized by overexpression of TGF-β and/or PD-L1, which can prevent T cell or CAR-T cell-mediated anti-tumor immune responses. Therefore, it would be highly advantageous to express these dominant negative receptors specifically under conditions where tumor cells are present.

Materials and Methods:

Creation of Dominant Negative Receptor(s)—Expressing Vectors

In order to generate the dominant negative receptors TGFBRIIdn and PD1dn, the proteins were linked in-frame to the CAR LTG1563-expressing vector (LTG1563). Downstream of the CAR LTG1563 sequence, a cleaved ribosome skip site (FP2AF) was introduced consisting of: a consensus furin cleavage site (amino acids: RAKR (SEQ ID NO: 188)) fused to a ribosome skip site (P2A) derived from the porcine teschovirus-1 polyprotein (AA 976-997, GenBank ID: CAB40546.1, mutated residue P977S) fused to a consensus furin cleavage sequence (amino acids: RAKR (SEQ ID NO: 188)). In TGFBRIIdn single-expressing vectors (LTG2864 and LTG2867), the resulting CAR LTG1563-FP2AF sequence was co-expressed with a dominant-negative TGF-beta receptor II sequence (TGFBRII: AA 1-191, Uniprot ID: P37173). In PD1dn single-expressing vectors (LTG2864 and LTG2867), the resulting CAR LTG1563-FP2AF sequence was co-expressed with a dominant-negative PD1 receptor (PD1: AA 1-199, Uniprot ID: Q15116).

In CAR-FP2AF-PD1dn-P2AF-TGFBRIIdn expressing vectors, CAR LTG1563-FP2AF was co-expressed with a dominant-negative PD1 receptor (PD1: AA 1-199, Uniprot ID: Q15116), followed by a consensus furin cleavage sequence (amino acids: RAKR (SEQ ID NO: 188)) fused to a ribosome skip site (P2A) derived from the porcine teschovirus-1 polyprotein (AA 976-997, GenBank ID: CAB40546.1, mutated residue P977S), and which in turn was co-expressed with a dominant-negative TGF-beta receptor II sequence (TGFBRII: AA 1-191, Uniprot ID: P37173). Protein sequences were codon-optimized and cloned into a third generation lentiviral plasmid backbone under the regulation of surface antigen-regulated inducible promoters AP1/NFκB, or constitutive EF1α promoter as a control.

Cell Lines Used to Demonstrate CAR Activity

The Burkitt lymphoma cell line Raji cell line, the chronic myelogenous leukemia line K562 line and reagents were purchased from American Tissue Culture Collection (ATCC, Manassass, VA), unless otherwise noted. Cells were cultured in RPMI-1640 medium supplemented with 10% heat-inactivated fetal bovine serum (FBS, Hyclone, Logan, UT) and 2 mM L-Glutamax (Thermo Fisher Scientific, Grand Island, NY). Human Embryonic kidney line 293T was purchased from ATCC and propagated in CD FortiCho medium (Gibco/Thermo Fisher Scientific, Grand Island, NY). Single-cell clones of luciferase-expressing cell lines were generated by stably transducing wild-type tumor lines with lentiviral vector encoding firefly luciferase (Lentigen Technology, Inc., Gaithersburg, MD), followed by cloning and selection of luciferase-positive clones.

Primary Human T Cells Used to Demonstrate CAR Activity

Whole blood was collected from healthy volunteers at Oklahoma Blood Institute (OBI) with donors' written consent. Processed buffy coats were purchased from OBI (Oklahoma City, OK). The CD4-positive and CD8-positive human T cells were purified from buffy coats via positive selection using a 1:1 mixture of CD4–and CD8–MicroBeads (Miltenyi Biotec, Bergisch Gladbach, Germany) according to manufacturer's protocol.

Primary T Cell Transduction

Human primary CD4+ and CD8+ T cells from normal donors were cultivated in TexMACS medium at a density of 1×106 cells/ml, activated with CD3/CD28 MACS® GMP T Cell TransAct reagent on day 0 (all reagents from Miltenyi Biotec), and transduced on day 1/2 with LV encoding CAR constructs overnight, and media exchanged on day 2/3. Supplementation with cytokines (IL-2, TGFβ; Miltenyi Biotec, Bergisch Gladbach, Germany) was performed as described. Cultures were propagated until harvest on day 5-6 for co-incubation analysis.

Immune Effector Assays (CTL and Cytokine)

For long-term co-incubation assays, CAR T effector and GFP-expressing target cells were propagated as above, and flow cytometric analysis was utilized to determine the extent of target cell population killing, and CAR T population survival and expansion. Cells were gated based on forward and side scatter, and viable (7AAD-negative) cells. Percentages of surviving cells post in co-cultures were determined based on GFP positivity for Raji targets and CD3 for CAR T effectors. In addition, CAR-T expression in live CD3 positive cells was determined by staining with CD19 Fc peptide, followed by anti-Fc (Fab')2-FL reagent. PD1 and TGFBRII expression was also determined (encompassing both the transgenes PD1dn and TGFBRIIdn as well as the native PD1 and TGFBRII proteins).

Results:

The self-driving capacity of the CAR LTG1563 constructs was extended to include auxiliary components to add additional functionality to the CAR-T cells, or CARs. In this case, dominant negative receptors lacking the intracellular signaling domains of either TGFBRII (TGFBRIIdn) or PD1 (PD1dn) were co-expressed with the CAR LTG1563 construct, via ribosomal skipping sites (P2A). Constitutively-expressed EF1α-promoter driven CAR LTG1563 was constructed as a control and tested in parallel with AP1/NFκB regulated CARs with auxiliary components. The architecture of each of these CAR constructs with auxiliary components is depicted in FIG. 6.

T cells were purified from blood of two unrelated healthy donors by immunogenic selection using a 1:1 mixture of CD4 and CD8 beads (Miltenyi Biotec). Cells were transduced with CAR LTG1563 constructs with auxiliary components in the absence of cytokine supplementation, as described in the materials and methods. The experimental groups included CAR LTG1563, CAR LTG1563-TGFBRIIdn, CAR LTG1563-PD1dn, or CAR LTG1563-PD1dn-TGFBRIIdn driven by the EF1α promoter, or with AP1/NFκB_RE-driven CAR LTG1563, CAR LTG1563-TGFBRIIdn, CAR LTG1563-PD1dn, or CAR LTG1563-PD1dn-TGFBRIIdn positively regulated self-driving CARs with auxiliary components at 0.5% vol/vol LV preparation (FIG. 6). Untransduced cells (UTD) cultured under same conditions were used as a negative control. The expression of CAR LTG1563 and the auxiliary components (TGFBRII, PD1) was assessed by flow cytometric enumeration; however, the expression of auxiliary components also reflects the expression of the native, full-length versions of these proteins on the CAR-T cells. Under the control of the constitutive EF1α promoter, a substantial increase in the expression of these TGFBRII and PD1 proteins was observed for the EF1a-CAR LTG1563-TGFBRIIdn and EF1a-CAR LTG1563-PD1dn constructs, respectively (FIG. 6B-6C), demonstrating that expression of the auxiliary transgenes was detectable above the native expression of these proteins.

Figure 6:
FIG. 6 depicts the structure of AP1/NFκB inducible and constitutive EF1α-driven CARs with additional auxiliary components (for example, dominant negative receptors): CAR LTG1563-TGFBRIIdn, CAR LTG1563-PD1dn, and CAR LTG1563-PD1dn-TGFBRIIdn.
Figure 6:
Figure 6:
Figure 6:
Figure 6:
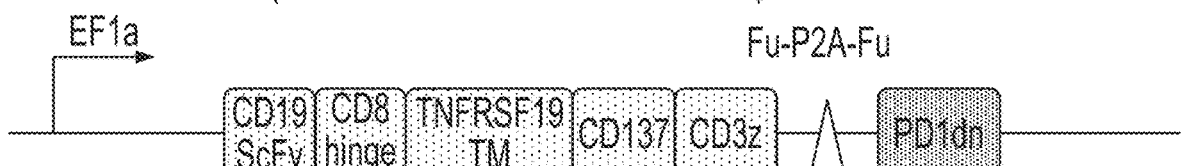
Figure 6:

Further, in this experiment, the self-driving characteristic of both the AP1/NFκB response elements to drive CAR LTG1563 expression were assessed by CD19 antigen stimulation (FIG. 6). This was performed using CAR T cells from Donor A and Donor B in coculture with CD19 positive Raji NHL tumor cells stably expressing GFP. Strikingly, CAR (FIG. 6A) and TGFBRII (FIG. 6B) expression was strongly induced in the AP1/NFκB_RE-CAR LTG1563-TGFBRIIdn T cells within 20 h post-stimulation. This indicates that the AP1/NFκB promoter can be used to induce proteins other than CARs in the presence of antigen signaling through a cognate CAR receptor.

Further, in this experiment, the CAR LTG1563-dependent cytotoxicity was assessed by coculture of CAR T cells with CD19+ Raji NHL cells stably expressing GFP, in the presence or absence of the immunosuppressive cytokine TGFβ (10 ng/mL). A very low effector to target ratio was used (1:3 CAR T:Raji cells), and CD19-dependent cytotoxicity was assessed by flow cytometric enumeration of the GFP+ Raji cells from D5-D9 post-activation (Coculture 1). Long-term function and expansion of the CAR T cells was assessed by a secondary re-stimulation of the cells at a similar effector to target ratio (1:3 Coculture 1:Raji cells) from D9-D13 post-activation (Coculture 2), and a tertiary re-stimulation (1:3 Coculture 2:Raji cells) from D13-D19 post-activation.

Figure 7A:
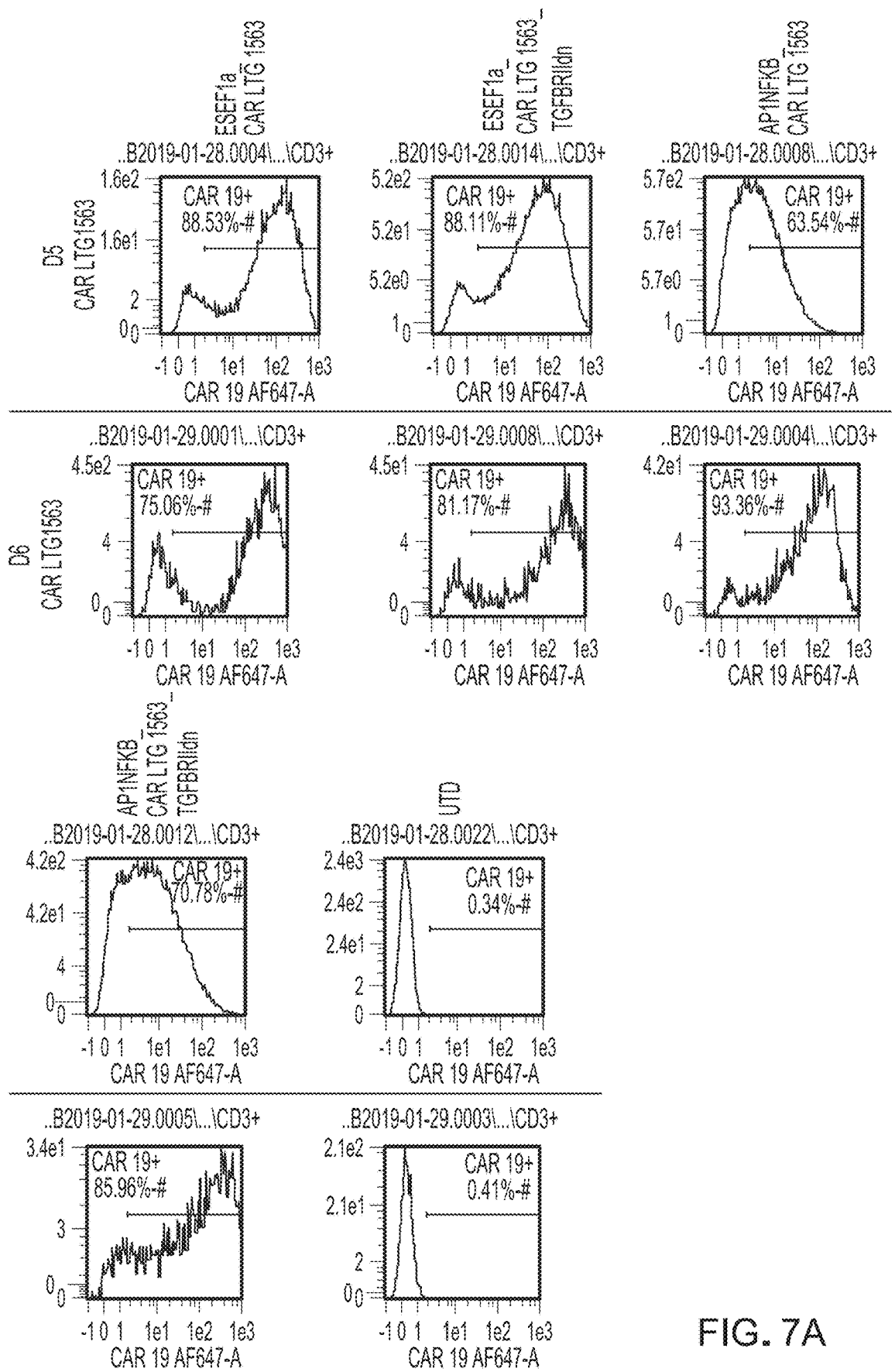
FIGS. 7A-C depict AP1/NFKB-regulated self-driving CAR LTG 1563 with additional auxiliary components, which exhibits rapid induction of the payload (CAR and the associated auxiliary components: TGFBRIIdn, PD1dn) expression following antigen exposure, as compared to the EF1α-driven constitutive CAR. The expression in self-driving CAR constructs regulated by the inducible AP1/NFκB promoters, and in EF1α-driven constitutive CAR construct, following initial coculture with Raji cells in 2 healthy donors. Cells were activated with TransAct reagent at D0, transduced at D1 with LV vectors at an MOI of 10, and washed and treated with 30 IU/mL IL2 from D2-D5 post-activation. From D5 post-activation, CAR LTG1563 T cells were cocultured with Raji-GFP (CD19+) cells at an effector:target ratio of 1:3. CAR, TGFBRII, and PD1 expression prior to coculture (D5) and 1 day after coculture (D6) are shown, one representative donor of 2.
Figure 7B:
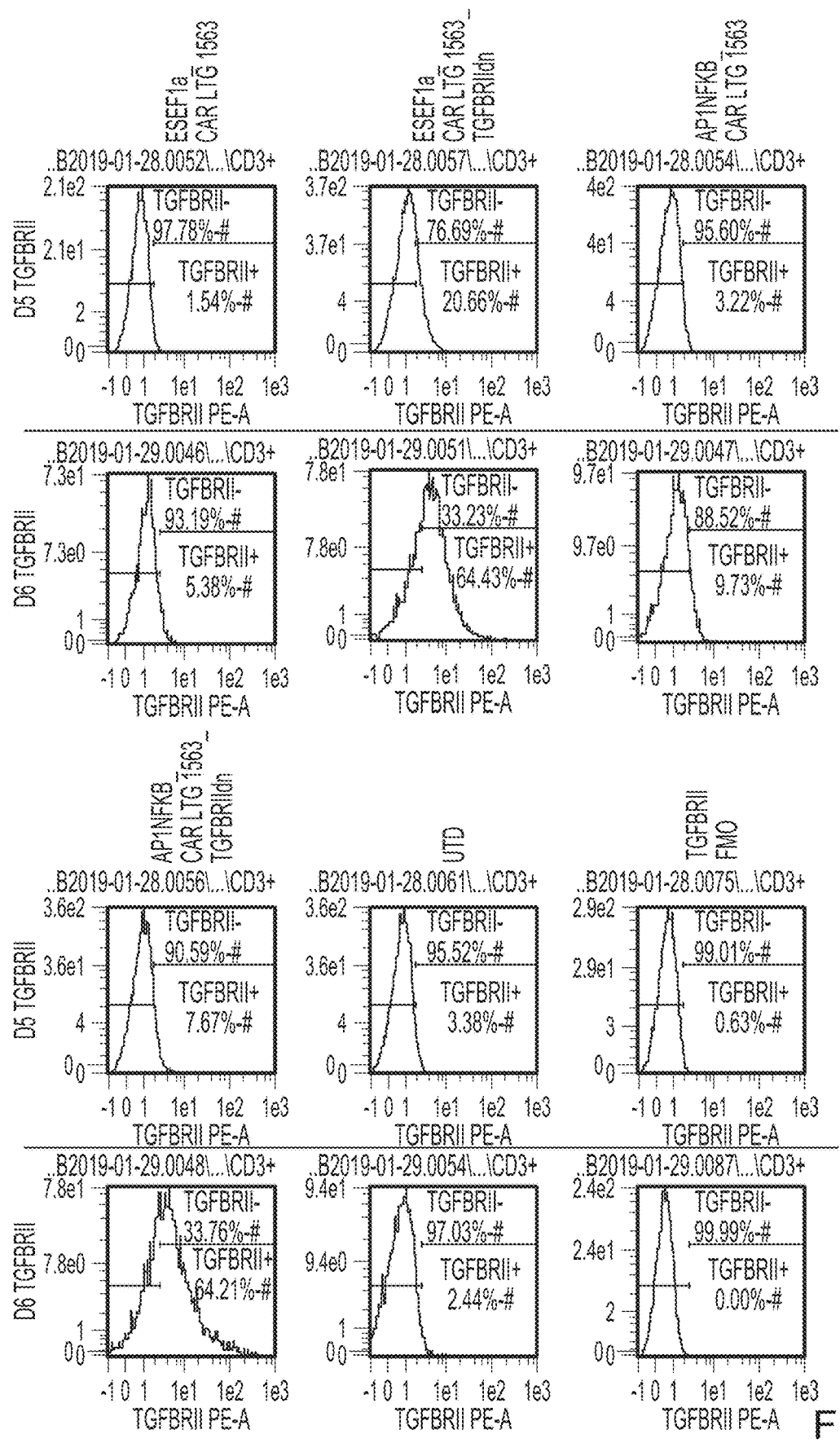
Figure 7C:
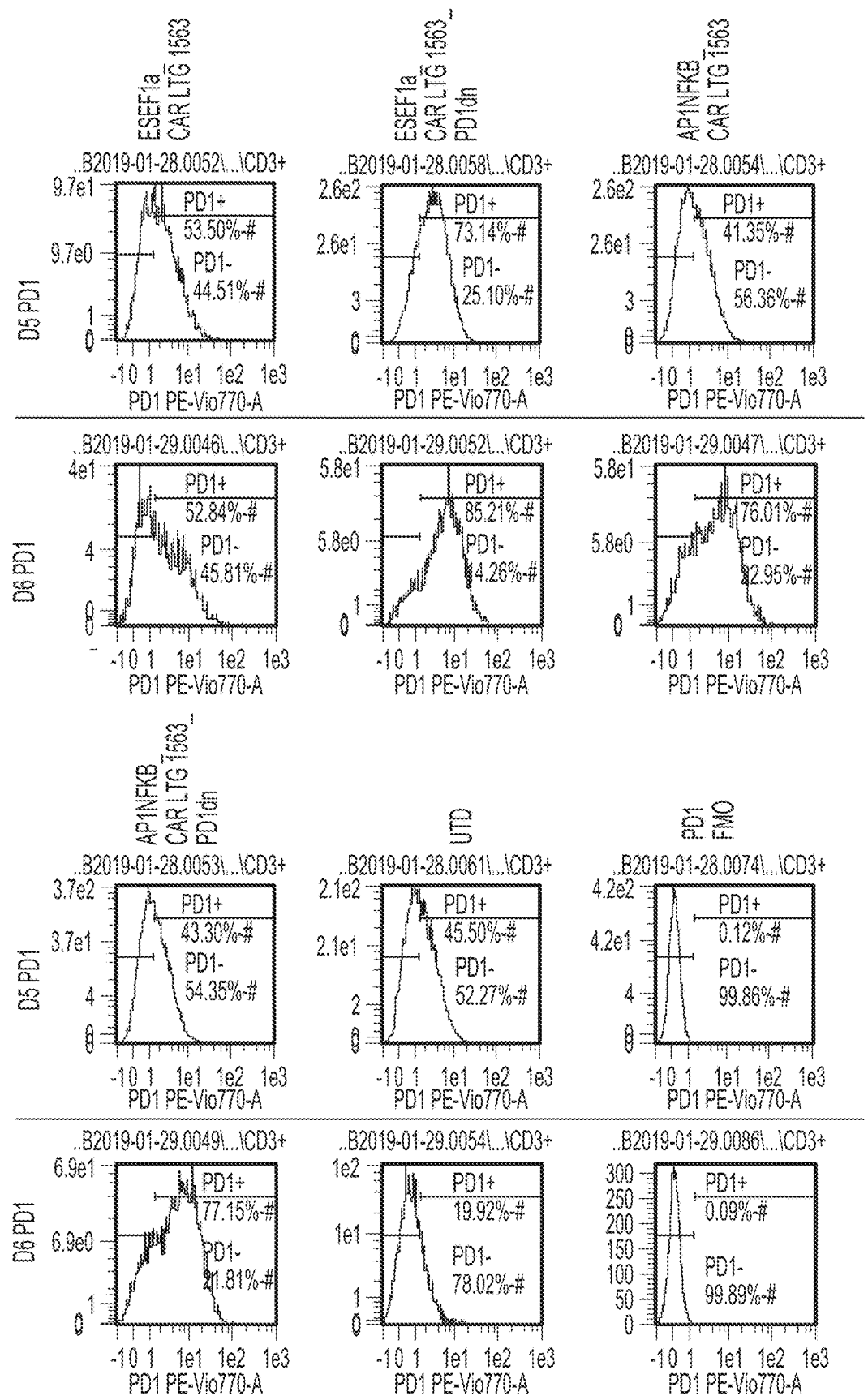
Figure 8A:
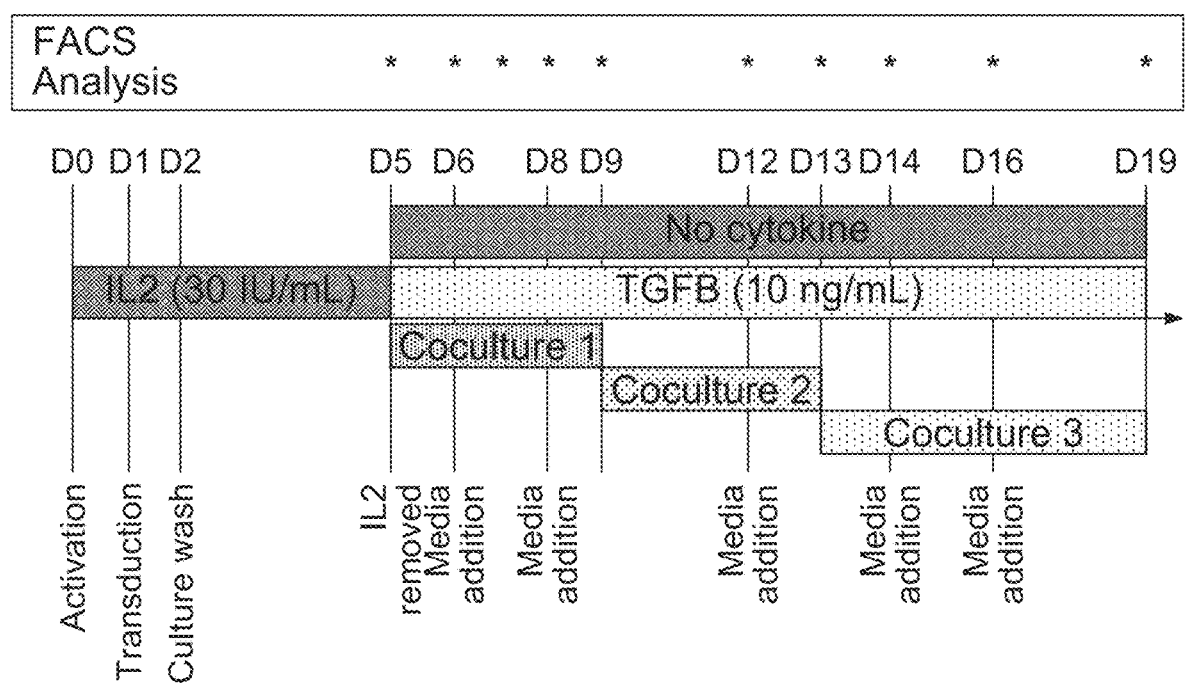
FIGS. 8A-8C depict superior Raji tumor killing and T cell expansion with CAR LTG 1563 (with additional auxiliary components) T cells protected from TGF-β suppression.
Figure 8B:
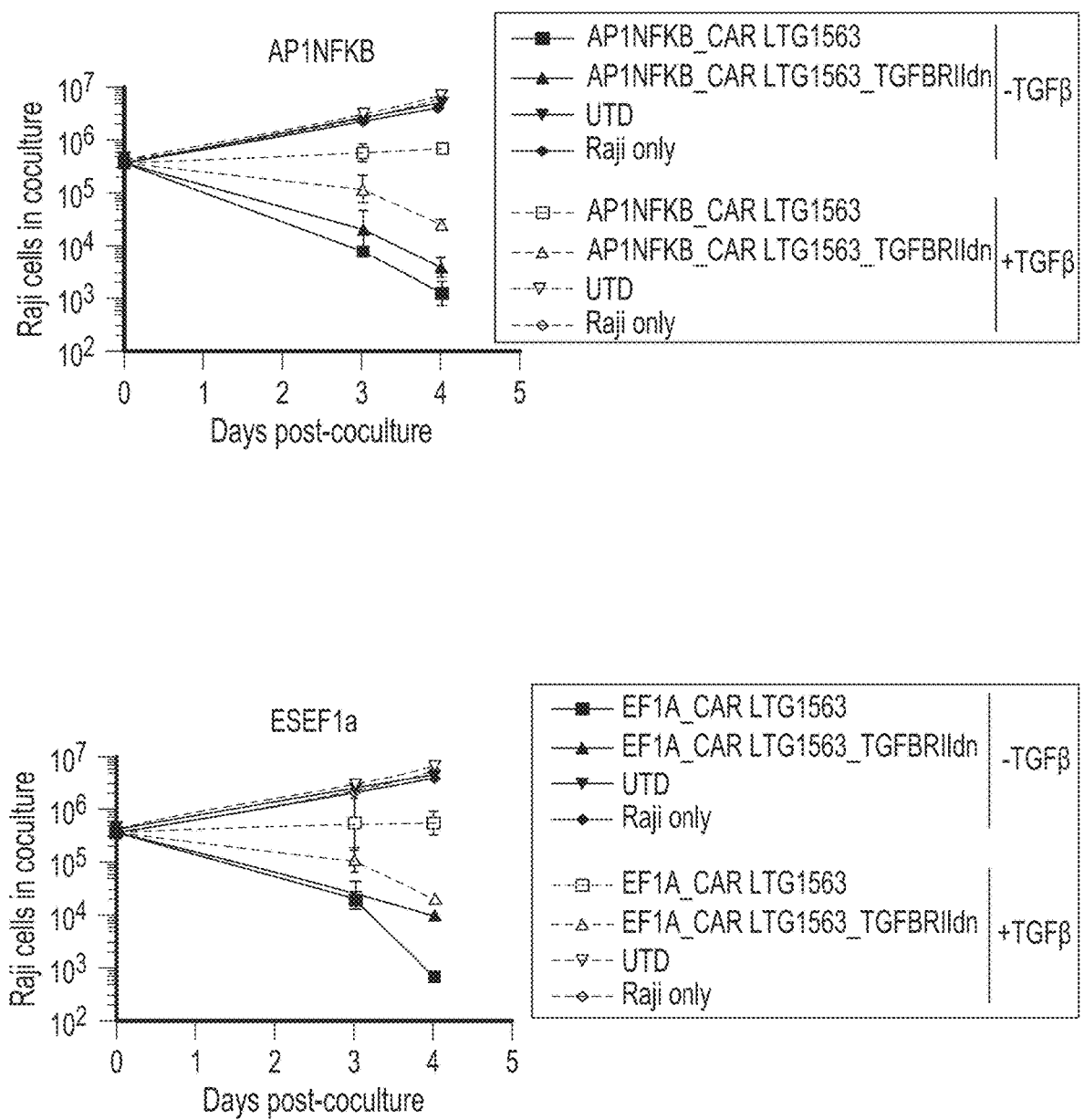
Figure 8C:
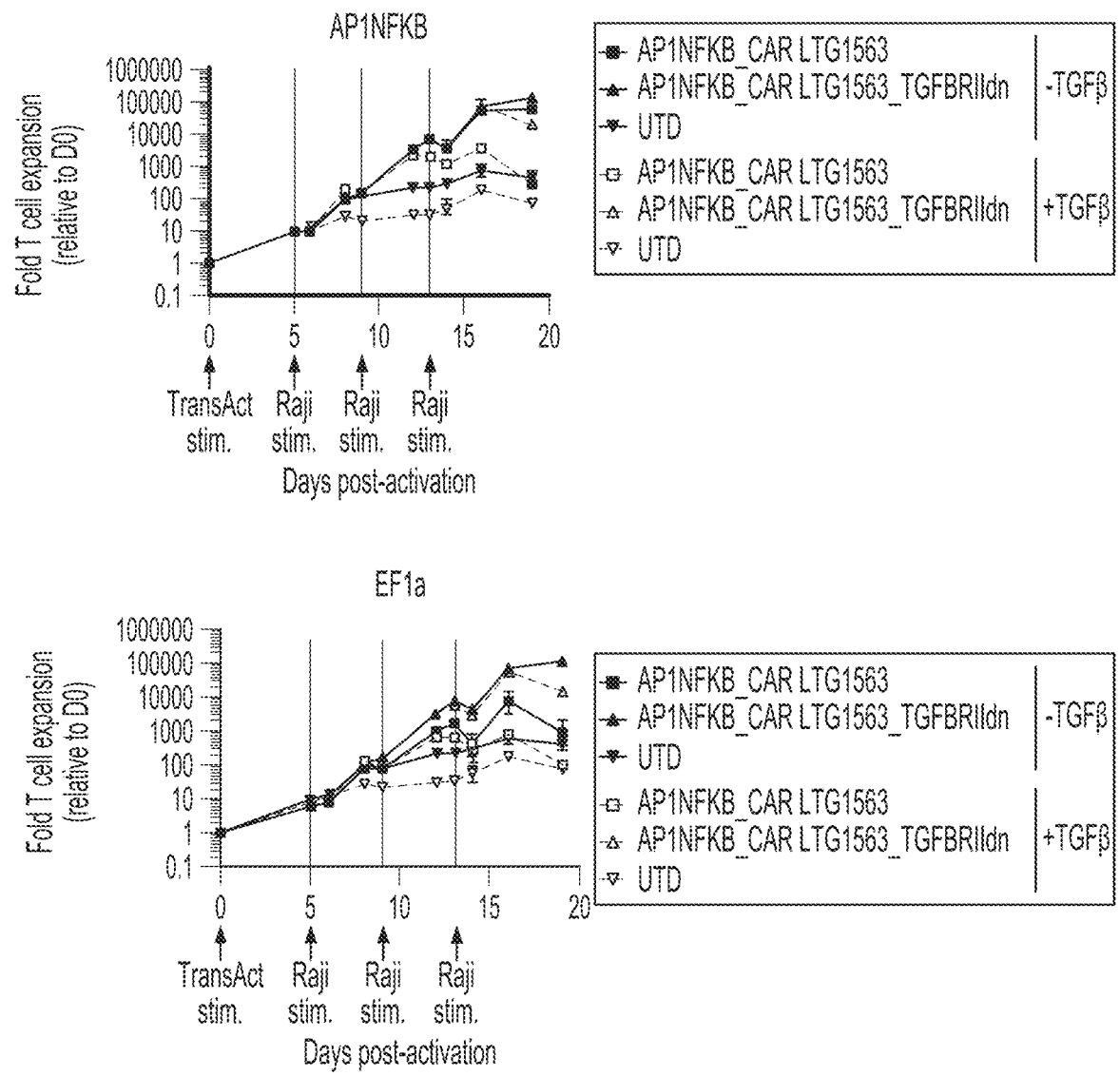

CAR T co-incubation with target cells was examined for a total of fifteen days (Coculture 1-3), during this time the numbers of viable Raji and T cells were enumerated by flow cytometric analysis (FIG. 8A). Whereas Raji cells in Raji only and UTD control groups proceeded to grow unhindered, CAR LTG1563 T cells strongly suppressed Raji expansion with all vectors in the absence of TGFβ, while the AP1NFKB-CAR LTG1563 and EF1a-CAR LTG1563 vectors displayed poor cytotoxicity of Raji cells in the presence of TGFβ. Strikingly, in the vector EF1a-CAR LTG1563-TGFBRIIdn, the dominant negative receptor TGFBRIIdn restored CAR-dependent cytotoxicity to a great extent in the presence of TGFβ (FIG. 8B). Similar restoration of CAR-dependent cytotoxicity was also observed for the AP1NFKB-CAR LTG1563-TGFBRIIdn vector, despite initially lower TGFBRII expression in these vectors (FIG. 7B). This indicates that the inducible nature of the AP1-NFKB promoter can be used to successfully express additional proteins beyond CARs, in a manner regulated by the antigen signaling through the CAR. The restoration of cytotoxicity in the presence of TGFβ for the EF1a-CAR LTG1563-TGFBRIIdn and AP1NFKB-CAR LTG1563-TGFBRIIdn vectors was also associated with a marked increase in CAR LTG1563-dependent T cell expansion throughout Cocultures 1-3 (FIG. 8C). Overall, this demonstrates successful use and induction of CARs with auxiliary components as a single-vector system using the inducible AP1-NFKB promoter.

Example 3

Characterization of CAR19 LTG1563 with TGFBRIIdn and PD-1dn Decoy Components in the Presence of TGFβ or PD-L1 Ligands Materials and Methods:

Cell Lines Used to Demonstrate CAR Activity

The Burkitt lymphoma cell line Raji cell line, the chronic myelogenous leukemia line K562 line and reagents were purchased from American Tissue Culture Collection (ATCC, Manassass, VA), unless otherwise noted. Cells were cultured in RPMI-1640 medium supplemented with 10% heat-inactivated fetal bovine serum (FBS, Hyclone, Logan, UT) and 2 mM L-Glutamax (Thermo Fisher Scientific, Grand Island, NY). Human Embryonic kidney line 293T was purchased from ATCC and propagated in CD FortiCho medium (Gibco/Thermo Fisher Scientific, Grand Island, NY).

Single-cell clones of luciferase-expressing cell lines were generated by stably transducing wild-type tumor lines with lentiviral vector encoding firefly luciferase (Lentigen Technology, Inc., Gaithersburg, MD), followed by cloning and selection of luciferase-positive clones. GFP- and PDL1-expressing cell lines by stably transducing luciferase-enabled tumor lines with lentiviral vector encoding GFP and/or PD-L1 (PDL1: AA 1-290, Uniprot ID: Q9NZQ7), followed by magnetic or FACS-based separation of GFP+ and PD-L1+ cells.

Primary Human T Cells Used to Demonstrate CAR Activity

Whole blood was collected from healthy volunteers at Oklahoma Blood Institute (OBI) with donors' written consent. Processed buffy coats were purchased from OBI (Oklahoma City, OK). The CD4-positive and CD8-positive human T cells were purified from buffy coats via positive selection using a 1:1 mixture of CD4- and CD8- Micro-Beads (Miltenyi Biotec, Bergisch Gladbach, Germany) according to manufacturer's protocol.

Primary T Cell Transduction

Human primary CD4+ and CD8+ T cells from normal donors were cultivated in TexMACS medium at a density of 1×106 cells/ml, activated with CD3/CD28 MACS® GMP T Cell TransAct reagent on day 0 (all reagents from Miltenyi Biotec), and transduced on day 1 with LV encoding CAR constructs overnight, and media exchanged on day 3. Supplementation with cytokines (IL-2, TGFβ; Miltenyi Biotec, Bergisch Gladbach, Germany) was performed as described. Cultures were propagated until harvest on day 8 for co-incubation analysis.

Immune Effector Assays (CTL and Cytokine)

For long-term co-incubation assays, CAR T effector and GFP-expressing target cells were propagated as above, and flow cytometric analysis was utilized to determine the extent of target cell population killing, and CAR T population survival and expansion. Cells were gated based on forward and side scatter, and viable (7AAD-negative) cells. Percentages of surviving cells post in co-cultures were determined based on GFP positivity for Raji targets and CD3 for CAR T effectors. In addition, CAR-T expression in live CD3 positive cells was determined by staining with CD19 Fc peptide, followed by anti-Fc (Fab')2-FL reagent. PD1 and TGFBRII expression was also determined by flow cytometry.

Figure 9A:
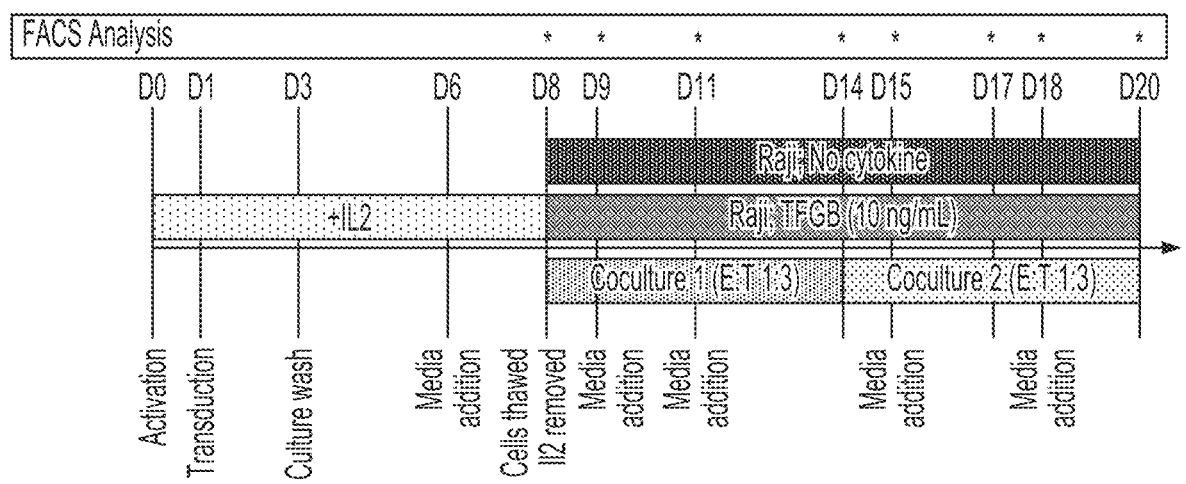
FIGS. 9A-C depict superior Raji tumor killing and less T cell exhaustion with CAR LTG 1563 (with additional auxiliary components) T cells protected from TGF-β suppression.

Results:

Prior experiments (FIG. 8) with CAR LTG1563 constructs expressing the auxiliary component TGFBRIIdn demonstrated significant protection from the anti-inflammatory effects of the immunosuppressive cytokine TGFβ. Therefore, these results were extended to include additional T cell donors and analysis of additional parameters of CAR T efficacy (cytokine production, activation marker expression, and exhaustion marker expression). Briefly, T cells were purified from blood of three unrelated healthy donors by immunogenic selection using a 1:1 mixture of CD4 and CD8 beads (Miltenyi Biotec). Cells were transduced with CAR LTG1563 constructs with auxiliary components in the presence of IL2 supplementation, as described in the materials and methods. The experimental groups included CAR LTG1563 or CAR LTG1563-TGFBRIIdn driven by the EF1α promoter, or with AP1/NFκB_RE-driven CAR LTG1563, CAR LTG1563-TGFBRIIdn regulated self-driving CARs with auxiliary components at 0.5% vol/vol LV preparation (FIG. 9A). Untransduced cells (UTD) cultured under same conditions were used as a negative control. The expression of CAR LTG1563 and the auxiliary components (TGFBRIIdn) was assessed by flow cytometric enumeration both prior to and after CD19 antigen stimulation with Raji NHL tumor cells, which displayed similar characteristics to prior experiments (FIG. 8 and data not shown).

Figure 9B:
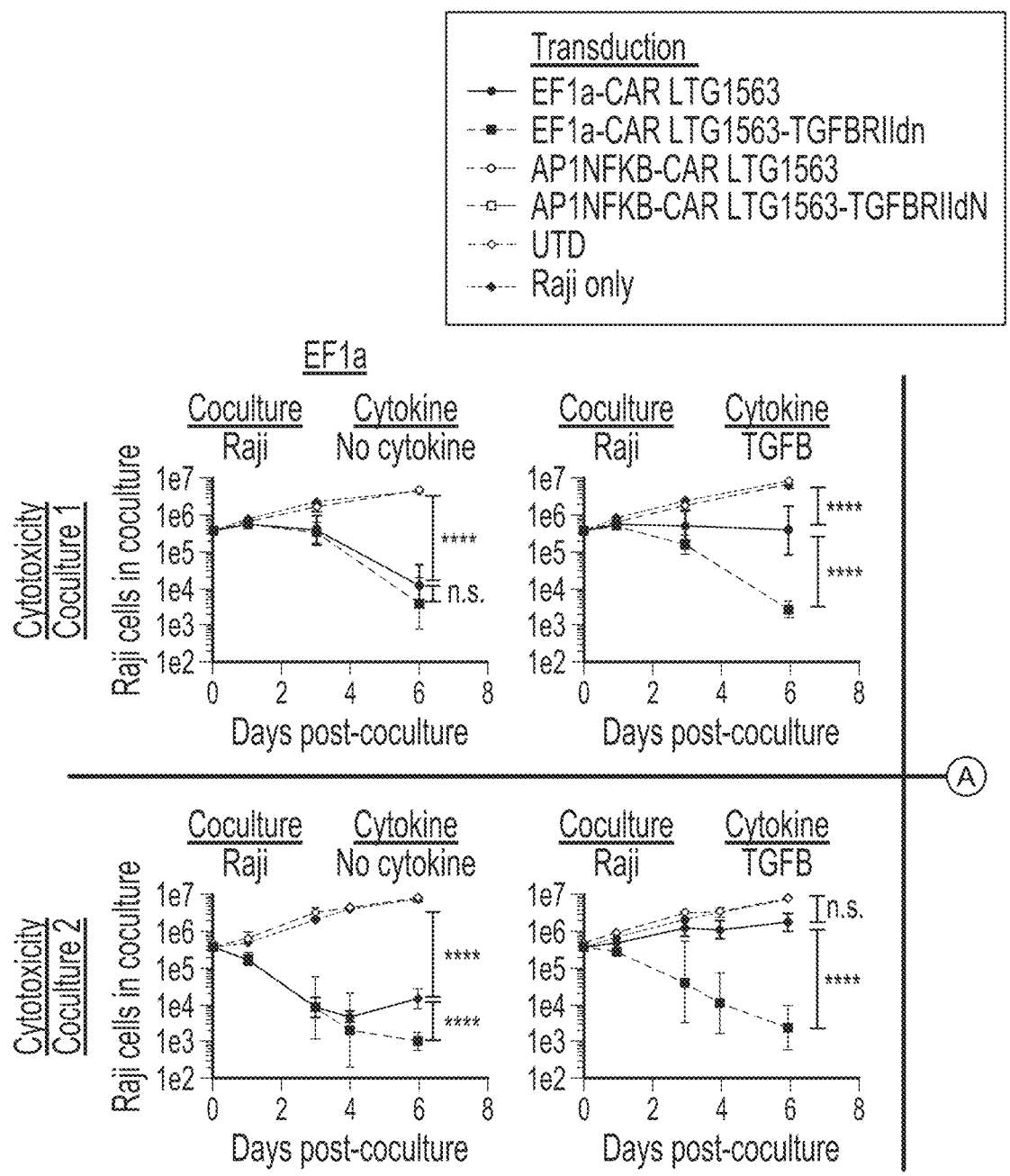
Figure 9B:
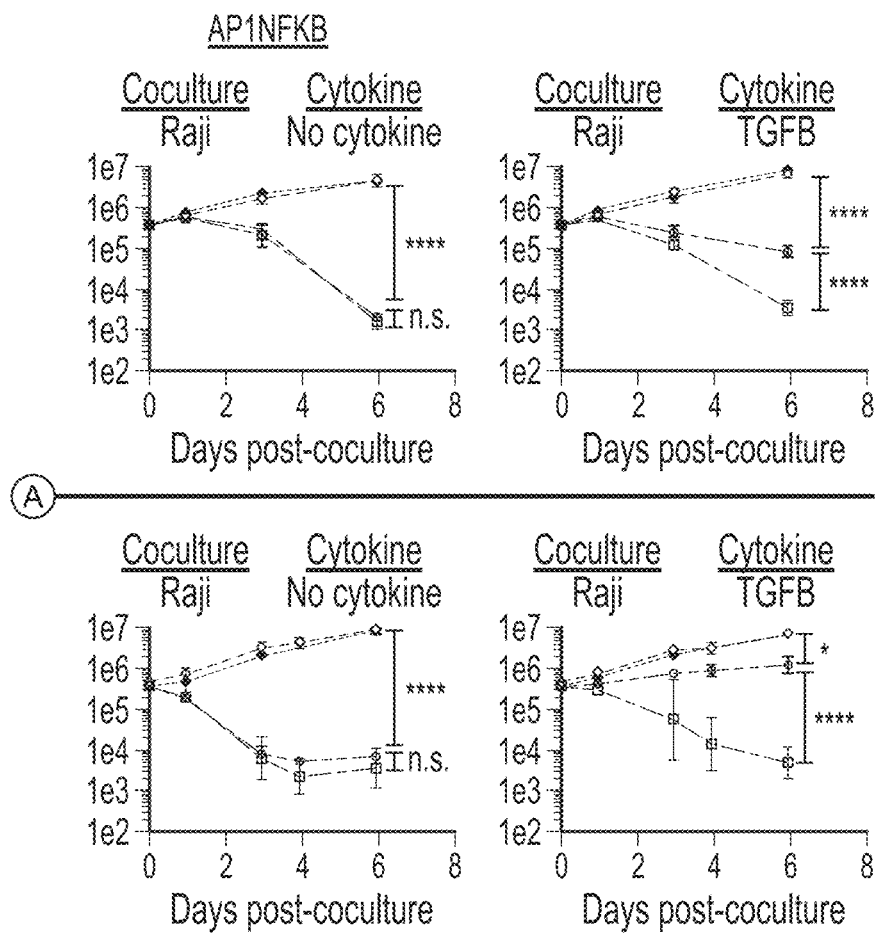

Further, in this experiment, the CAR LTG1563-dependent cytotoxicity was assessed by coculture of CAR T cells with CD19+ Raji NHL cells stably expressing GFP, in the presence or absence of the immunosuppressive cytokine TGFβ (10 ng/mL). A very low effector to target ratio was used (1:3 CAR T:Raji cells), and CD19-dependent cytotoxicity was assessed by flow cytometric enumeration of the GFP+ Raji cells from D8-D14 post-activation (Coculture 1, FIG. 9A). Long-term function and expansion of the CAR T cells was assessed by a secondary re-stimulation of the cells at a similar effector to target ratio (1:3 Coculture 1:Raji cells) from D14-D20 post-activation (Coculture 2). CAR T co-incubation with target cells was examined for a total of fourteen days (Coculture 1-2), during this time the numbers of viable Raji and T cells were enumerated by flow cytometric analysis (FIG. 9B). Whereas Raji cells in Raji only and UTD control groups proceeded to grow unhindered, CAR LTG1563 T cells strongly suppressed Raji expansion with all vectors in the absence of TGFβ, while the AP1NFKB-CAR LTG1563 and EF1a-CAR LTG1563 transduced T cells displayed poor cytotoxicity of Raji cells in the presence of TGFβ. Strikingly, in the vector EF1a-CAR LTG1563-TGFBRIIdn, the dominant negative receptor TGFBRIIdn restored CAR-dependent cytotoxicity to a great extent in the presence of TGFβ (FIG. 8B). Similar restoration of CAR-dependent cytotoxicity was also observed for the AP1NFKB-CAR LTG1563-TGFBRIIdn vector, despite initially lower TGFBRII expression in these vectors (data not shown). These results extend prior findings that the inducible nature of the AP1-NFKB promoter can be used to successfully express additional proteins beyond CARS, in a manner regulated by the antigen signaling through the CAR.

Figure 9C:
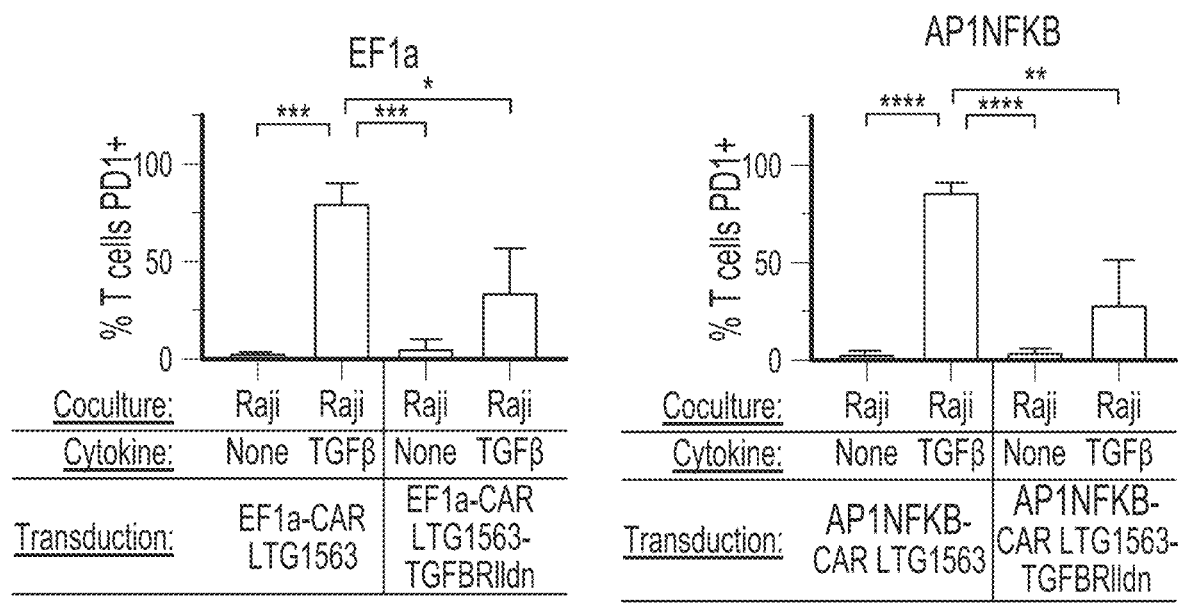

Additional T cell parameters were assessed in the course of the experiment. In the presence of TGFβ, the expression of the auxiliary component TGFBRIIdn restored high-level production of pro-inflammatory cytokines such as IL2 and expression of activation markers such as CD25 (data not shown). TGFβ supplementation of CAR T cocultures lead to markedly high expression levels of the exhaustion marker PD1 (FIG. 9C), as measured at the end of Coculture 2 (D20 post-activation). Of note, a significant decrease was observed in expression of the exhaustion marker PD1 in both AP1NFKB-CAR LTG1563-TGFBRIIdn and EF1a-CAR LTG1563-TGFBRIIdn-expressing CAR T cells in the presence of TGFβ relative to AP1NFKB-CAR LTG1563 and EF1a-CAR LTG1563-expressing CAR T cells under the same conditions (FIG. 9C). The reduced TGFβ-dependent expression of PD1 lead to the hypothesis that TGFBRIIdn expression could protect CAR-T cells not only from the anti-inflammatory effects of TGFβ, but also from the negative effects of PD-1 signaling.

Figure 10A:
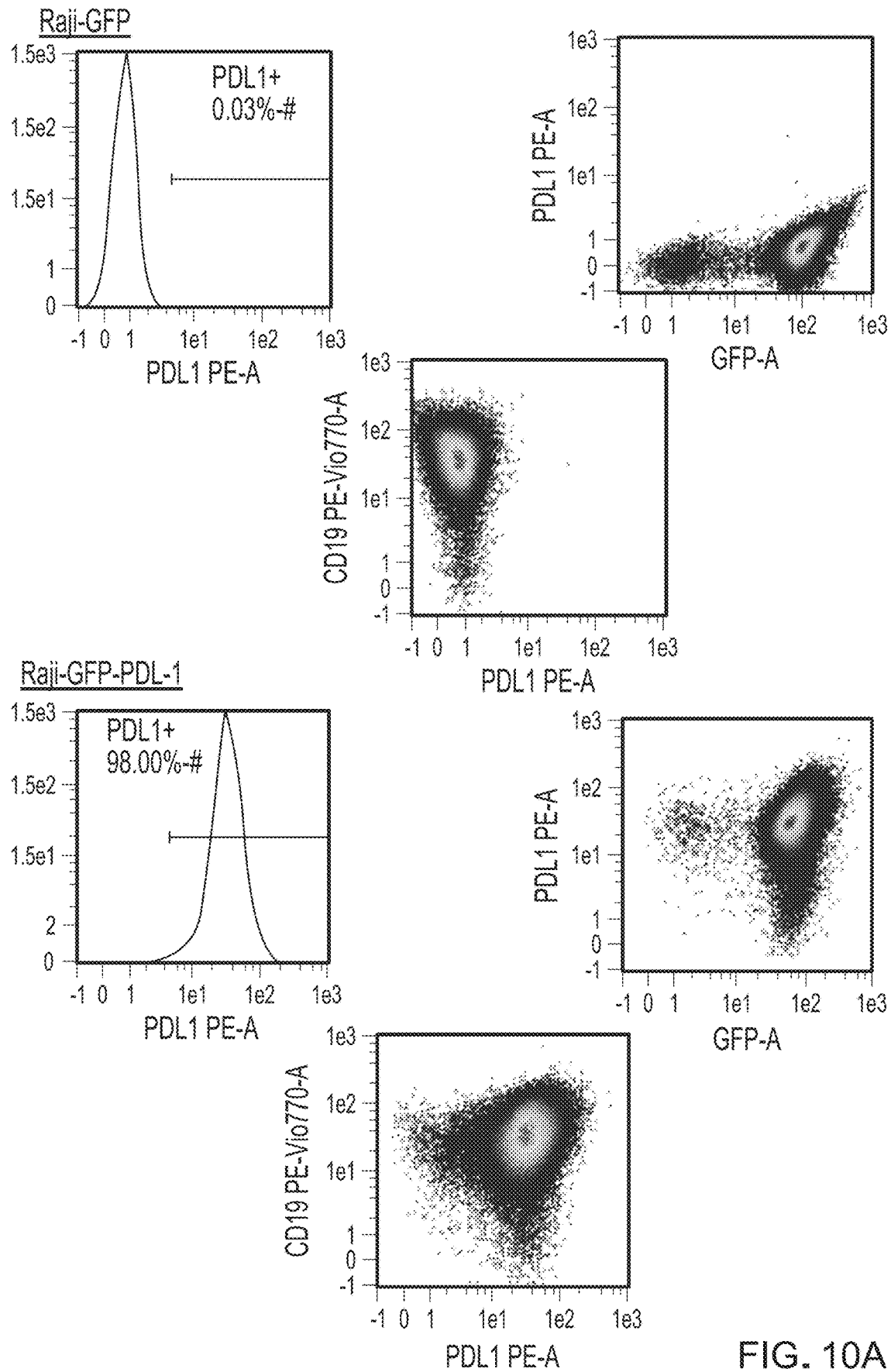
FIGS. 10A-E depicts superior Raji tumor killing, increased T cell expansion, and increased T cell cytokine production with CAR LTG 1563 (with additional auxiliary components) T cells protected from both TGF-β and PD-L1 suppression.
Figure 10B:
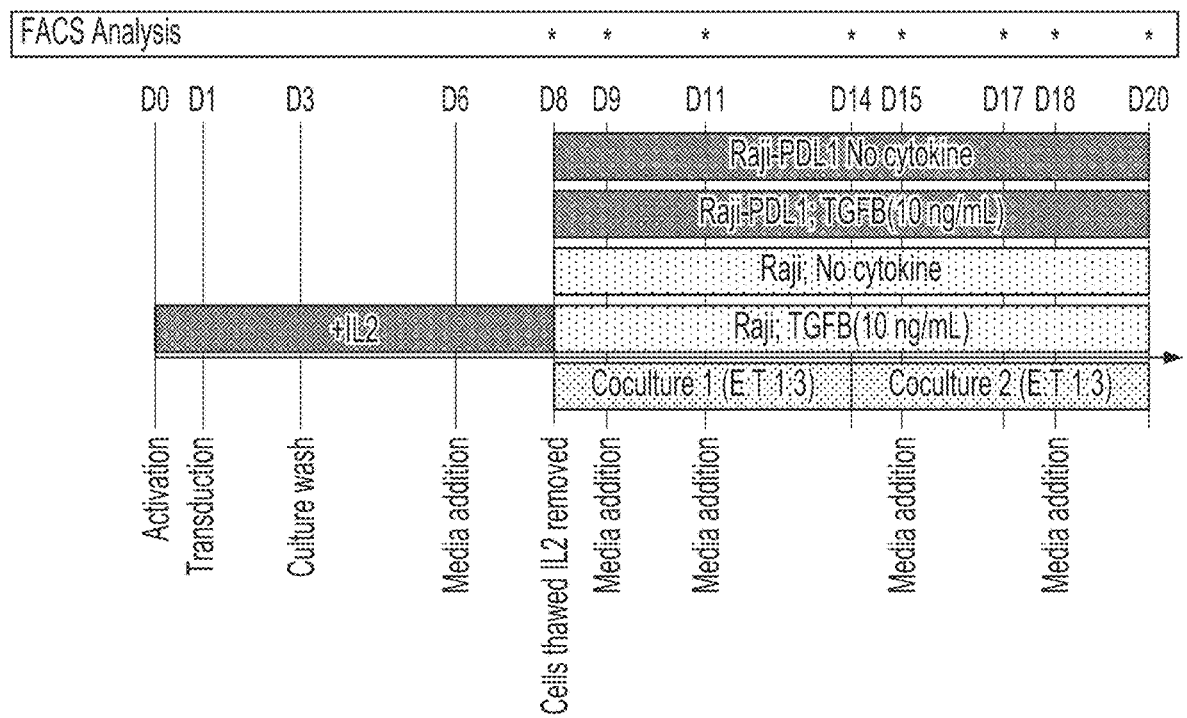
Figure 10C:
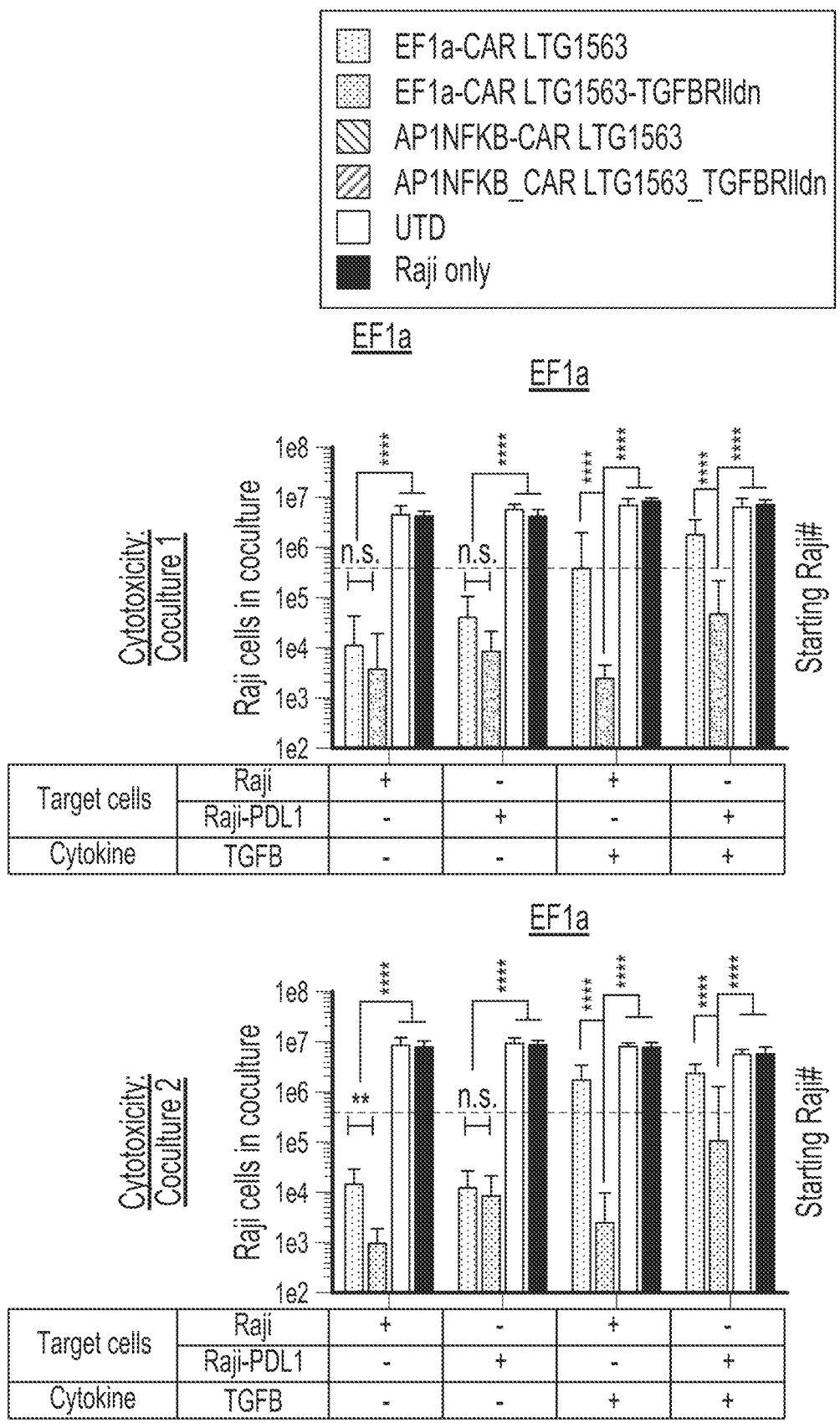
Figure 10C:
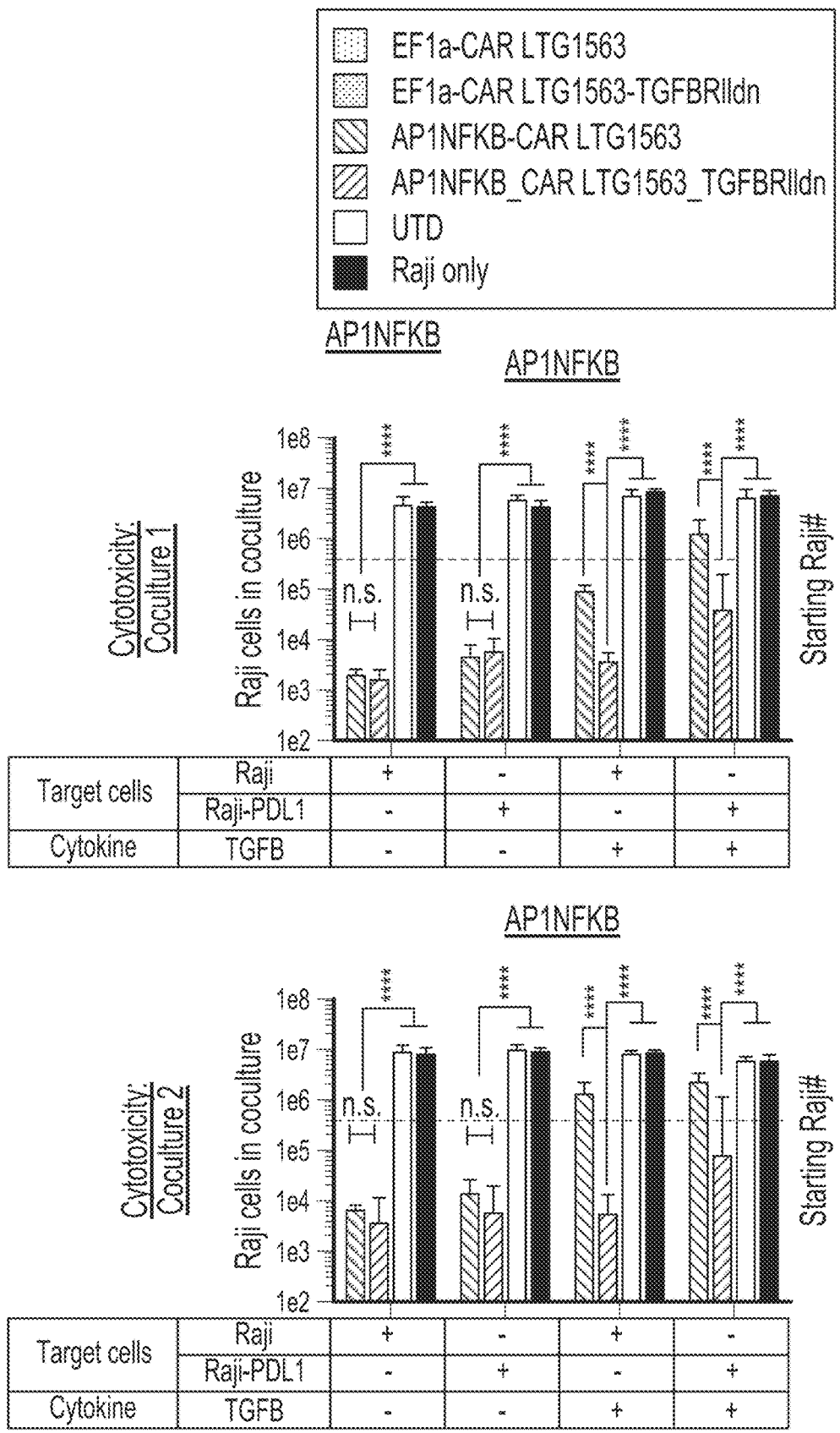
Figure 10D:
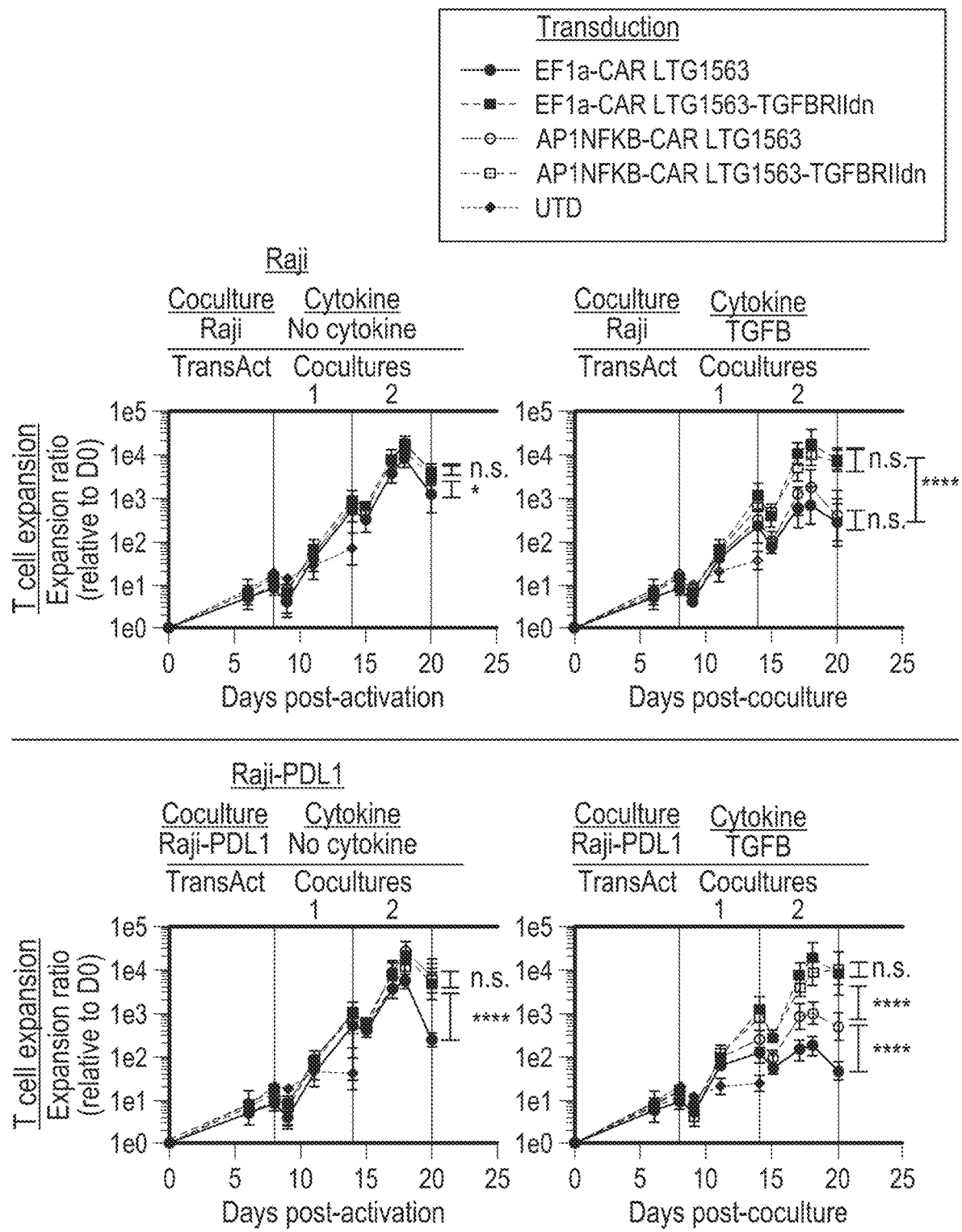
Figure 10E:
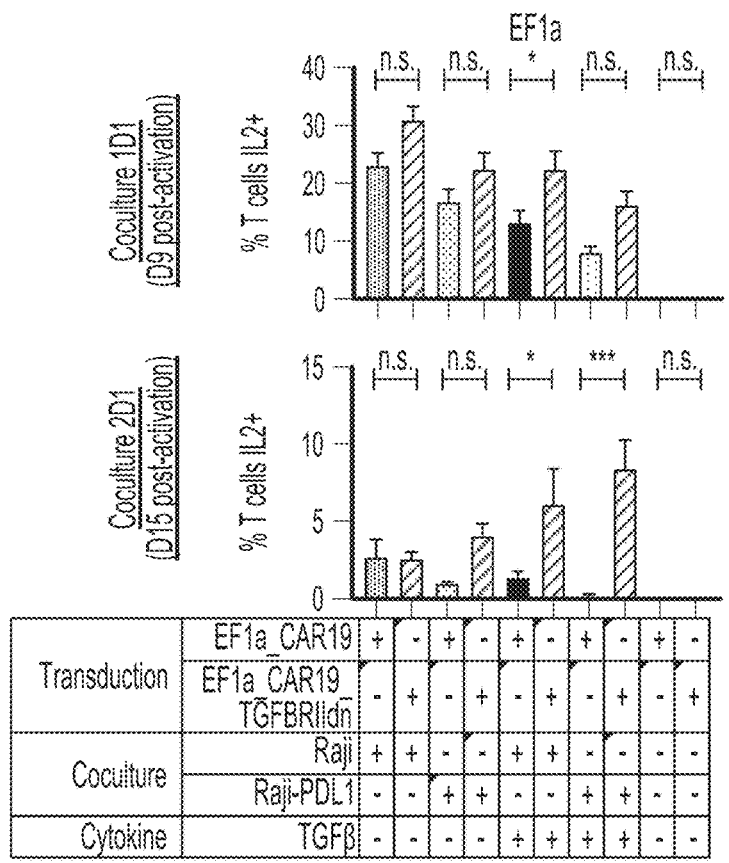
Figure 10E:
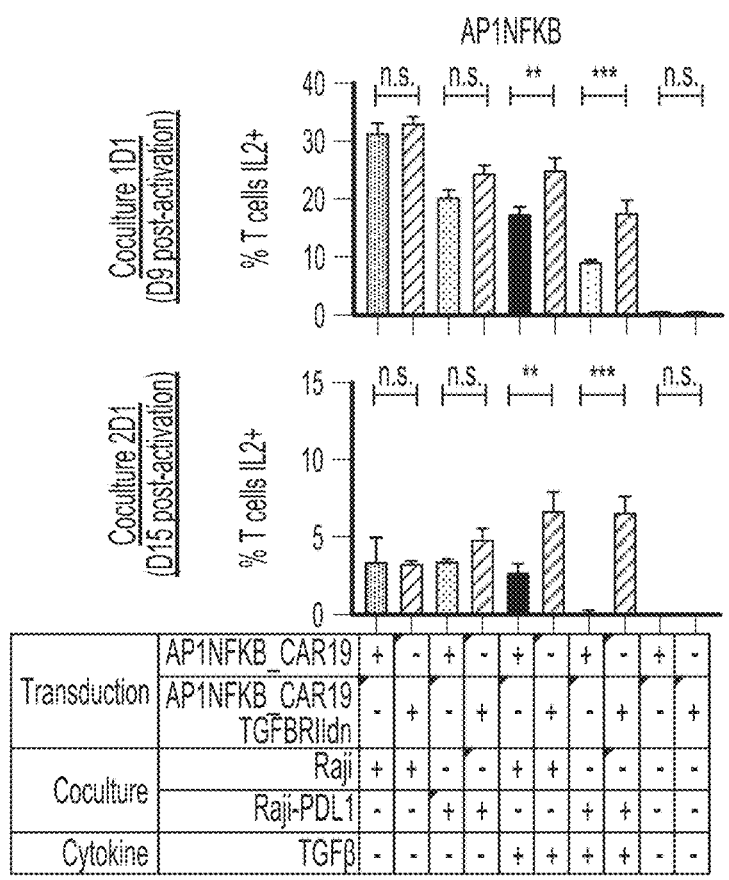

Consequently, the ability of the auxiliary CAR component TGFBRIIdn to protect from the immunosuppressive effects of PD-1/PD-L1 signaling was assessed by transducing CD19+ target Raji-GFP NHL cells with a lentivector stably expressing PD-L1 to create the cell line Raji-GFP-PDL1. Magnetic selection of PDL1 cells was performed, and stable expression of PDL1 over a period of weeks on Raji-GFP-PDL1 cells was assessed by flow cytometry (data not shown). As previously, T cells were purified from blood of three unrelated healthy donors by immunogenic selection using a 1:1 mixture of CD4 and CD8 beads (Miltenyi Biotec). Cells were transduced with CAR LTG1563 constructs with auxiliary components in the presence of IL2 supplementation, as described in the materials and methods. The experimental groups included CAR LTG1563 or CAR LTG1563-TGFBRIIdn driven by the EF1α promoter, or with AP1/NFκB_RE-driven CAR LTG1563, CAR LTG1563-TGFBRIIdn regulated self-driving CARs with auxiliary components at 0.5% vol/vol LV preparation (FIG. 9A). Untransduced cells (UTD) cultured under same conditions were used as a negative control. CAR LTG1563-dependent cytotoxicity was assessed by coculture of CAR T cells with CD19+ Raji-GFP or CD19+ Raji-GFP-PDL1 NHL cells, in the presence or absence of the immunosuppressive cytokine TGFβ (10 ng/mL). A very low effector to target ratio was used (1:3 CAR T:Raji cells), and CD19-dependent cytotoxicity was assessed by flow cytometric enumeration of the GFP+ Raji cells from D8-D14 post-activation (Coculture 1, FIG. 10C). Long-term function and expansion of the CAR T cells was assessed by a secondary re-stimulation of the cells at a similar effector to target ratio (1:3 Coculture 1:Raji cells) from D14-D20 post-activation (Coculture 2). CAR T co-incubation with target cells was examined for a total of fourteen days (Coculture 1-2), during this time the numbers of viable Raji and T cells were enumerated by flow cytometric analysis (FIG. 10C).

While PD-L1 expression alone on target Raji NHL cells was not sufficient to significantly affect CAR LTG1563-dependent cytotoxicity (FIG. 10A), a synergistic decrease was observed in the cytotoxic ability of AP1NFKB-CAR LTG1563 and EF1a-CAR LTG1563-expressing CAR T cells in the presence of both target PD-L1 expression and TGFβ supplementation. Notably, the co-expression of the auxiliary component TGFBRIIdn was able to restore the CD19-dependent killing capacity of CAR T cells in the presence of both target PD-L1 expression and TGFβ supplementation, although not to the degree observed in the absence of both PD-1/PD-L1 and TGFβ signaling. This is in agreement with the partial, but not complete, prevention of TGFβ-induced PD-1 expression observed in the presence of TGFBRIIdn expression (FIG. 9C).

The effects of the TGFBRIIdn transgene on CAR LTG1563-dependent T cell expansion were also assessed in the course of this experiment. Prior results were recapitulated (FIG. 5C) demonstrating that AP1NFKB-CAR LTG1563 demonstrated superior CD19 antigen-dependent T cell expansion relative to EF1a-CAR LTG1563 (FIG. 9C, 1st panel from left). Notably, the greater CAR19-dependent T cell expansion previously observed with AP1-NFKB_CAR19 relative to EF1α_CAR19 became more pronounced when Raji-PDL1 targets were used in coculture, even in the absence of TGFβ (FIG. 9C, 3rd panel from left). It is possible that any negative effects of tonic CAR signaling, as would potentially be the case during constitutive CAR expression (FIG. 4), become more apparent under conditions where PD1 checkpoint signaling occurs, which would be the case in coculture with Raji-PDL1 cells. In all circumstances, in the presence of both TGFβ supplementation and target cell PDL1 expression, the expression of the TGFBRIIdn transgene significantly increased the CAR19-dependent T cell expansion (FIG. 9C, 4th panel from the left), indicating protection from anti-inflammatory PD1/PD-L1 signaling by reducing TGFβ signaling.

What is claimed is:

1. A method of treating a hematological cancer in a human subject in need thereof, the method comprising administering to the human subject a pharmaceutical composition comprising an anti-tumor effective amount of a population of autologous T cells, wherein each cell of the population of autologous T cells comprises a nucleic acid sequence that encodes a chimeric antigen receptor (CAR) comprising the amino acid sequence of SEQ ID NO: 78, wherein the nucleic acid comprises a surface antigen-regulated inducible promoter comprising the nucleotide sequence of SEQ ID NO: 138 or a sequence with 85%, 90%, 95%, 96%, 97%, 98% or 99% identity thereof, operably linked to the CAR encoding sequence, wherein the surface antigen-regulated inducible promoter adjusts its level of transcription dependent upon the level of expression of surface antigen on a target cell, thereby treating the hematological cancer of the human subject.

2. The method of claim 1, wherein the surface antigen-regulated inducible promoter comprises a nucleic sequence comprising SEQ ID NO: 138.

3. The method of claim 1, wherein the hematological cancer is leukemia, lymphoma, or multiple myeloma.

4. The method of claim 3, wherein the leukemia is acute myeloid leukemia (AML), blastic plasmacytoid dendritic cell neoplasm (BPDCN), chronic myelogenous leukemia (CML), chronic lymphocytic leukemia (CLL), acute lymphoblastic T cell leukemia (T-ALL), or acute lymphoblastic B cell leukemia (B-ALL).

5. The method of claim 3, wherein the lymphoma is mantle cell lymphoma, non-Hodgkin's lymphoma or Hodgkin's lymphoma.

\* \* \* \* \*